US012721818B2

(12) United States Patent
Ramunas et al.

(10) Patent No.: US 12,721,818 B2
(45) Date of Patent: Sep. 1, 2026

(54) COMPOSITIONS AND METHODS FOR DELIVERY OF RNA

(71) Applicant: Rejuvenation Technologies Inc., Mountain View, CA (US)

(72) Inventors: John Ramunas, Sunnyvale, CA (US); Glenn Jeremy Markov, Mountain View, CA (US); William Gillis Olsen, Menlo Park, CA (US); Kyle Daniel Brewer, East Palo Alto, CA (US)

(73) Assignee: Rejuvenation Technologies, Inc., Mountain View, CA (US)

( * ) Notice: Subject to any disclaimer, the term of this patent is extended or adjusted under 35 U.S.C. 154(b) by 610 days.

(21) Appl. No.: 17/709,108

(22) Filed: Mar. 30, 2022

(65) Prior Publication Data

US 2022/0347112 A1 Nov. 3, 2022

Related U.S. Application Data

(60) Provisional application No. 63/169,118, filed on Mar. 31, 2021.

(51) Int. Cl.

| | |
|---|---|
| ***C12N 9/12*** | (2006.01) |
| ***A61K 9/51*** | (2006.01) |
| ***A61K 38/00*** | (2006.01) |
| ***A61K 38/45*** | (2006.01) |
| ***A61K 47/54*** | (2017.01) |
| ***A61K 48/00*** | (2006.01) |
| ***A61P 11/00*** | (2006.01) |

(52) U.S. Cl.

CPC ............ *A61K 9/5123* (2013.01); *A61K 38/45* (2013.01); *A61K 48/0033* (2013.01); *A61P 11/00* (2018.01); *C12Y 207/07049* (2013.01)

(58) Field of Classification Search

None

See application file for complete search history.

(56) References Cited

U.S. PATENT DOCUMENTS

2018/0333457 A1* 11/2018 Heartlein ............... A61K 47/26
2020/0215094 A1 7/2020 Ramunas et al.
2021/0023008 A1* 1/2021 Nakai ................. A61K 9/1271

FOREIGN PATENT DOCUMENTS

WO 2019188867 10/2019
WO WO-2020051220 A1 * 3/2020 ........... A61K 7/6929
WO 2020142725 7/2020

OTHER PUBLICATIONS

Bernardes de Jesus B, Vera E, Schneeberger K, et al. Telomerase gene therapy in adult and old mice delays aging and increases longevity without increasing cancer.2012. EMBO Mol Med. 4(8):691-704. doi:10.1002/emmm.201200245 (Year: 2012).*
Povedano JM, Martinez P, Serrano R, et al. Therapeutic effects of telomerase in mice with pulmonary fibrosis induced by damage to the lungs and short telomeres.2018. Elife.7:e31299. Published Jan. 30, 2018. doi:10.7554/eLife.31299 (Year: 2018).*
Tanaka, et al. "Self-Degradable Lipid-Like Materials Based on 'Hydrolysis accelerated by the intra-Particle Enrichment of Reactant (HyPER)' for Messenger RNA Delivery" (2020) Adv. Funct. Mater. 30, 1910575.

* cited by examiner

*Primary Examiner* — Tracy Vivlemore
*Assistant Examiner* — Fatimah Khalaf Matalkah
(74) *Attorney, Agent, or Firm* — Rimon PC

(57) ABSTRACT

The lipid nanoparticle compositions provided herein preferentially deliver and/or transfect the lung. Also provided herein are therapeutic polynucleotides, e.g. TERT mRNA, which may be delivered with the LNP formulations for the treatment of lung disease and fibrosis.

32 Claims, 28 Drawing Sheets
(9 of 28 Drawing Sheet(s) Filed in Color)
Specification includes a Sequence Listing.

| Run | Eff. Diam. (nm) | Half Width (nm) | Polydispersity | Baseline Index |
|---|---|---|---|---|
| 1 | 100.1 | 47.7 | 0.226 | 9.9 |
| 2 | 101.4 | 46.8 | 0.213 | 9.0 |
| 3 | 101.5 | 46.8 | 0.214 | 9.4 |
| Mean | 101.0 | 47.1 | 0.218 | 9.4 |
| Std. Error | 0.4 | 0.3 | 0.004 | 0.2 |
| Combined | 101.2 | 47.0 | 0.216 | 9.3 |

Organs

Cells mRNA reporter

Untreated control 0 mg/kg 0.1 mg/kg 0.3 mg/kg 0.6 mg/kg 2.0 mg/kg

Lung mean radiance
Photons/s/cm^2/sr
1×10^5
8×10^4
6×10^4
4×10^4
2×10^4
0
6% PEG
7% PEG
PBS
Lung mean radiance
Photons/s/cm^2/sr
1×10^7
8×10^6
6×10^6
4×10^6
2×10^6
0
0.5% PEG
1.2% PEG
3.5% PEG
6% PEG
7% PEG
PBS

SEQUENCE LISTING

```
<160> NUMBER OF SEQ ID NOS: 40

<210> SEQ ID NO 1
<211> LENGTH: 3399
<212> TYPE: DNA
<213> ORGANISM: Artificial
<220> FEATURE:
<223> OTHER INFORMATION: Synthetic

<400> SEQUENCE: 1

atgcccagag cccccagatg cagagccgtg agaagcctgc tgagaagcca ctacagagag     60

gtgctgcccc tggccacctt cgtgagaaga ctgggccccc agggctggag actggtgcag    120

agaggcgacc ccgccgcctt cagagccctg gtggcccagt gcctggtgtg cgtgccctgg    180

gacgccagac cccctcccgc cgcccccagc ttcagacagg tgagctgcct gaaggagctg    240

gtggccagag tgctgcagag actgtgcgag agaggcgcca agaacgtgct ggccttcggc    300

ttcgccctgc tggacggcgc cagaggcggc cctcccgagg ccttcaccac cagcgtgaga    360

agctacctgc ccaacaccgt gaccgacgcc ctgagaggca gcggcgcctg gggcctgctg    420
```

```
ctgagaagag tgggcgacga cgtgctggtg cacctgctgg ccagatgcgc cctgttcgtg    480
ctggtggccc ccagctgcgc ctaccaggtg tgcggccctc ccctgtacca gctgggcgcc    540
gccacccagg ccagaccccc tccccacgcc agcggcccca gaagaagact gggctgcgag    600
agagcctgga accacagcgt gagagaggcc ggcgtgcccc tgggcctgcc cgcccccggc    660
gccagaagaa gaggcggcag cgccagcaga agcctgcccc tgcccaagag acccagaaga    720
ggcgccgccc ccgagcccga gagaaccccc gtgggccagg gcagctgggc ccaccccggc    780
agaaccagag gccccagcga cagaggcttc tgcgtggtga gccccgccag acccgccgag    840
gaggccacca gcctggaggg cgccctgagc ggcaccagac acagccaccc cagcgtgggc    900
agacagcacc acgccggccc tcccagcacc agcagacctc ccagaccctg ggacaccccc    960
tgccctcccg tgtacgccga gaccaagcac ttcctgtaca gcagcggcga caaggagcag   1020
ctgagaccca gcttcctgct gagcagcctg agacccagcc tgaccggcgc cagaagactg   1080
gtggagacca tcttcctggg cagcagaccc tggatgcccg gcacccccag aagactgccc   1140
agactgcccc agagatactg gcagatgaga cccctgttcc tggagctgct gggcaaccac   1200
gcccagtgcc cctacggcgt gctgctgaag acccactgcc ccctgagagc cgccgtgacc   1260
cccgccgccg gcgtgtgcgc cagagagaag ccccagggca gcgtggccgc ccccgaggag   1320
gaggacaccg accccagaag actggtgcag ctgctgagac agcacagcag cccctggcag   1380
gtgtacggct tcgtgagagc ctgcctgaga agactggtgc ctcccggcct gtggggcagc   1440
agacacaacg agagaagatt cctgagaaac accaagaagt tcatcagcct gggcaagcac   1500
gccaagctga gcctgcagga gctgacctgg aagatgagcg tgagagactg cgcctggctg   1560
agaagaagcc ccggcgtggg ctgcgtgccc gccgccgagc acagactgag agaggagatc   1620
ctggccaagt tcctgcactg gctgatgagc gtgtacgtgg tggagctgct gagaagcttc   1680
ttctacgtga ccgagaccac cttccagaag aacagactgt tcttctacag aaagagcgtg   1740
tggagcaagc tgcagagcat cggcatcaga cagcacctga agagagtgca gctgagagag   1800
ctgagcgagg ccgaggtgag acagcacaga gaggccagac ccgccctgct gaccagcaga   1860
ctgagattca tccccaagcc cgacggcctg agacccatcg tgaacatgga ctacgtggtg   1920
ggcgccagaa ccttcagaag agagaagaga gccgagagac tgaccagcag agtgaaggcc   1980
ctgttcagcg tgctgaacta cgagagagcc agaagacccg gcctgctggg cgccagcgtg   2040
ctgggcctgg acgacatcca cagagcctgg agaaccttcg tgctgagagt gagagcccag   2100
gatcccccctc ccgagctgta cttcgtgaag gtggacgtga ccggcgccta cgacaccatc   2160
cccaggaca gactgaccga ggtgatcgcc agcatcatca agccccagaa cacctactgc   2220
gtgagaagat acgccgtggt gcagaaggcc gcccacggcc acgtgagaaa ggccttcaag   2280
agccacgtga gcaccctgac cgacctgcag ccctacatga gacagttcgt ggcccacctg   2340
caggagacca gcccccctgag agacgccgtg gtgatcgagc agagcagcag cctgaacgag   2400
gccagcagcg gcctgttcga cgtgttcctg agattcatgt gccaccacgc cgtgagaatc   2460
agaggcaaga gctacgtgca gtgccagggc atcccccagg gcagcatcct gagcaccctg   2520
ctgtgcagcc tgtgctacgg cgacatggag aacaagctgt tcgccggcat cagaagagac   2580
ggcctgctgc tgagactggt ggacgacttc ctgctggtga caccccacct gacccacgcc   2640
aagaccttcc tgagaaccct ggtgagaggc gtgcccgagt acggctgcgt ggtgaacctg   2700
agaaagaccg tggtgaactt ccccgtggag gacgaggccc tgggcggcac cgccttcgtg   2760
```

-continued

```
cagatgcccg cccacggcct gttcccctgg tgcggcctgc tgctggacac cagaaccctg   2820

gaggtgcaga gcgactacag cagctacgcc agaaccagca tcagagccag cctgaccttc   2880

aacagaggct tcaaggccgg cagaaacatg agaagaaagc tgttcggcgt gctgagactg   2940

aagtgccaca gcctgttcct ggacctgcag gtgaacagcc tgcagaccgt gtgcaccaac   3000

atctacaaga tcctgctgct gcaggcctac agattccacg cctgcgtgct gcagctgccc   3060

ttccaccagc aggtgtggaa gaaccccacc ttcttcctga gagtgatcag cgacaccgcc   3120

agcctgtgct acagcatcct gaaggccaag aacgccggca tgagcctggg cgccaagggc   3180

gccgccggcc ccctgcccag cgaggccgtg cagtggctgt gccaccaggc cttcctgctg   3240

aagctgacca gacacagagt gacctacgtg cccctgctgg gcagcctgag aaccgcccag   3300

acccagctga gcagaaagct gcccggcacc accctgaccg ccctggaggc cgccgccaac   3360

cccgccctgc ccagcgactt caagaccatc ctggactga                          3399
```

```
<210> SEQ ID NO 2
<211> LENGTH: 3399
<212> TYPE: DNA
<213> ORGANISM: Artificial
<220> FEATURE:
<223> OTHER INFORMATION: Synthetic

<400> SEQUENCE: 2

atgccgcgcg ctccccgctg ccgagccgtg cgctccctgc tgcgcagcca ctaccgcgag     60

gtgctgccgc tggccacgtt cgtgcggcgc ctggggcccc agggctggcg gctggtgcag    120

cgcggggacc cggcggcttt ccgcgcgctg gtggcccagt gcctggtgtg cgtgccctgg    180

gacgcacggc cgcccccgc cgccccctcc ttccgccagg tgtcctgcct gaaggagctg     240

gtggcccgag tgctgcagag gctgtgcgag cgcggcgcga agaacgtgct ggccttcggc    300

ttcgcgctgc tggacggggc ccgcgggggc ccccccgagg ccttcaccac cagcgtgcgc    360

agctacctgc ccaacacggt gaccgacgca ctgcggggga gcggggcgtg gggctgctg     420

ctgcgccgcg tgggcgacga cgtgctggtt cacctgctgg cacgctgcgc gctctttgtg    480

ctggtggctc ccagctgcgc ctaccaggtg tgcgggccgc cgctgtacca gctcggcgct    540

gccactcagg cccggccccc gccacacgct agtggacccc gaaggcgtct gggatgcgaa    600

cgggcctgga accatagcgt cagggaggcc ggggtccccc tgggcctgcc agccccgggt    660

gcgaggaggc gcgggggcag tgccagccga agtctgccgt tgcccaagag gcccaggcgt    720

ggcgctgccc ctgagccgga gcggacgccc gttgggcagg ggtcctgggc ccacccgggc    780

aggacgcgtg gaccgagtga ccgtggtttc tgtgtggtgt cacctgccag acccgccgaa    840

gaagccacct ctttggaggg tgcgctctct ggcacgcgcc actcccaccc atccgtgggc    900

cgccagcacc acgcgggccc ccatccaca tcgcggccac cacgtccctg ggacacgcct     960

tgtcccccgg tgtacgccga gaccaagcac ttcctctact cctcaggcga caaggagcag   1020

ctgcggccct ccttcctact cagctctctg aggcccagcc tgactggcgc tcggaggctc   1080

gtggagacca tctttctggg ttccaggccc tggatgccag ggactccccg caggttgccc   1140

cgcctgcccc agcgctactg gcaaatgcgg cccctgtttc tggagctgct tgggaaccac   1200

gcgcagtgcc cctacggggt gctcctcaag acgcactgcc cgctgcgagc tgcggtcacc   1260

ccagcagccg gtgtctgtgc ccgggagaag ccccagggct ctgtggcggc ccccgaggag   1320

gaggacacag acccccgtcg cctggtgcag ctgctccgcc agcacagcag cccctggcag   1380

gtgtacggct tcgtgcgggc ctgcctgcgc cggctggtgc ccccaggcct ctggggctcc   1440
```

aggcacaacg aacgccgctt cctcaggaac accaagaagt tcatctccct ggggaagcat 1500
gccaagctct cgctgcagga gctgacgtgg aagatgagcg tgcgggactg cgcttggctg 1560
cgcaggagcc caggggttgg ctgtgttccg gccgcagagc accgtctgcg tgaggagatc 1620
ctggccaagt tcctgcactg gctgatgagt gtgtacgtcg tcgagctgct caggtctttc 1680
ttttatgtca cggagaccac gtttcaaaag aacaggctct tttctaccg gaagagtgtc 1740 tggagcaagt tgcaaagcat tggaatcaga cagcacttga agagggtgca gctgcgggag 1800
ctgtcggaag cagaggtcag gcagcatcgg gaagccaggc ccgccctgct gacgtccaga 1860
ctccgcttca tccccaagcc tgacgggctg cggccgattg tgaacatgga ctacgtcgtg 1920
ggagccagaa cgttccgcag agaaaagagg gccgagcgtc tcacctcgag ggtgaaggca 1980
ctgttcagcg tgctcaacta cgagcgggcg cggcgccccg gcctcctggg cgcctctgtg 2040
ctgggcctgg acgatatcca cagggcctgg cgcaccttcg tgctgcgtgt gcgggcccag 2100
gacccgccgc ctgagctgtt ctttgtcaag gtggatgtga cgggcgcgta cgacaccatc 2160
ccccaggaca ggctcacgga ggtcatcgcc agcatcatca aaccccagaa cacgtactgc 2220
gtgcgtcggt atgccgtggt ccagaaggcc gcccatgggc acgtccgcaa ggccttcaag 2280
agccacgtct ctaccttgac agacctccag ccgtacatgc gacagttcgt ggctcacctg 2340
caggagacca gcccgctgag ggatgccgtc gtcatcgagc agagctcctc cctgaatgag 2400
gccagcagtg gcctcttcga cgtcttccta cgcttcatgt gccaccacgc cgtgcgcatc 2460
aggggcaagt cctacgtcca gtgccagggg atcccgcagg gctccatcct ctccacgctg 2520
ctctgcagcc tgtgctacgg cgacatggag aacaagctgt ttgcggggat tcggcgggac 2580
gggctgctcc tgcgtttggt ggatgatttc ttgttggtga cacctcacct cacccacgcg 2640
aaaaccttcc tcaggaccct ggtccgaggt gtccctgagt atggctgcgt ggtgaacttg 2700
cggaagacag tggtgaactt ccctgtagaa gacgaggccc tgggtggcac ggcttttgtt 2760
cagatgccgg cccacggcct attcccctgg tgcggcctgc tgctggatac ccggaccctg 2820
gaggtgcaga gcgactactc cagctatgcc cggacctcca tcagagccag tctcaccttc 2880
aaccgcggct tcaaggctgg gaggaacatg cgtcgcaaac tctttggggt cttgcggctg 2940
aagtgtcaca gcctgtttct ggatttgcag gtgaacagcc tccagacggt gtgcaccaac 3000
atctacaaga tcctcctgct gcaggcgtac aggtttcacg catgtgtgct gcagctccca 3060
tttcatcagc aagtttggaa gaaccccaca tttttcctgc gcgtcatctc tgacacggcc 3120
tccctctgct actccatcct gaaagccaag aacgcaggga tgtcgctggg ggccaagggc 3180
gccgccggcc ctctgccctc cgaggccgtg cagtggctgt gccaccaagc attcctgctc 3240
aagctgactc gacaccgtgt cacctacgtg ccactcctgg ggtcactcag gacagcccag 3300
acgcagctga gtcggaagct cccggggacg acgctgactg ccctggaggc cgcagccaac 3360
ccggcactgc cctcagactt caagaccatc ctggactga 3399

<210> SEQ ID NO 3
<211> LENGTH: 3369
<212> TYPE: DNA
<213> ORGANISM: Artificial
<220> FEATURE:
<223> OTHER INFORMATION: Synthetic

<400> SEQUENCE: 3
atgaccaggg cccctaggtg ccctgccgtg aggagcctgc tgaggagcag gtacagggag 60

-continued

```
gtgtggcctc tggccacctt cgtgaggagg ctgggccctg agggcaggag gctggtgcag    120
cctggcgacc ctaagatcta caggaccctg gtggcccagt gcctggtgtg catgcactgg    180
ggcagccagc ctcctcctgc cgacctgagc ttccaccagg tgagcagcct gaaggagctg    240
gtggccaggg tggtgcagag gctgtgcgag aggaacgaga ggaacgtgct ggccttcggc    300
ttcgagctgc tgaacgaggc caggggcggc cctcctatgg ccttcaccag cagcgtgagg    360
agctacctgc ctaacaccgt gatcgagacc ctgagggtga gcggcgcctg gatgctgctg    420
ctgagcaggg tgggcgacga cctgctggtg tacctgctgg cccactgcgc cctgtacctg    480
ctggtgcctc ctagctgcgc ctaccaggtg tgcggcagcc ctctgtacca gatctgcgcc    540
accaccgaca tctggcctag cgtgagcgcc agctacaggc ctaccaggcc tgtgggcagg    600
aacttcacca acctgaggtt cctgcagcag atcaagagca gcagcaggca ggaggcccct    660
aagcctctgg ccctgcctag caggggcacc aagaggcacc tgagcctgac cagcaccagc    720
gtgcctagcg ccaagaaggc caggtgctac cctgtgccta gggtggagga gggccctcac    780
aggcaggtgc tgcctacccc tagcggcaag agctgggtgc ctagccctgc caggagccct    840
gaggtgccta ccgccgagaa ggacctgagc agcaagggca aggtgagcga cctgagcctg    900
agcggcagcg tgtgctgcaa gcacaagcct agcagcacca gcctgctgag ccctcctagg    960
cagaacgcct tccagctgag gcctttcatc gagaccaggc acttcctgta cagcaggggc   1020
gacggccagg agaggctgaa ccctagcttc ctgctgagca acctgcagcc taacctgacc   1080
ggcgccagga ggctggtgga gatcatcttc ctgggcagca ggcctaggac cagcggccct   1140
ctgtgcagga cccacaggct gagcaggagg tactggcaga tgaggcctct gttccagcag   1200
ctgctggtga accacgccga gtgccagtac gtgaggctgc tgaggagcca ctgcaggttc   1260
aggaccgcca accagcaggt gaccgacgcc ctgaacacca gccctcctca cctgatggac   1320
ctgctgaggc tgcacagcag cccttggcag gtgtacggct tcctgagggc ctgcctgtgc   1380
aaggtggtga gcgccagcct gtggggcacc aggcacaacg agaggaggtt cttcaagaac   1440
ctgaagaagt tcatcagcct gggcaagtac ggcaagctga gcctgcagga gctgatgtgg   1500
aagatgaagg tggaggactg ccactggctg aggagcagcc ctggcaagga cagggtgcct   1560
gccgccgagc acaggctgag ggagaggatc ctggccacct tcctgttctg gctgatggac   1620
acctacgtgg tgcagctgct gaggagcttc ttctacatca ccgagagcac cttccagaag   1680
aacaggctgt tcttctacag gaagagcgtg tggagcaagc tgcagagcat cggcgtgagg   1740
cagcacctgg agagggtgag gctgagggag ctgagccagg aggaggtgag gcaccaccag   1800
gacacctggc tggccatgcc tatctgcagg ctgaggttca tccctaagcc taacggcctg   1860
aggcctatcg tgaacatgag ctacagcatg ggcaccaggg ccctgggcag gaggaagcag   1920
gcccagcact tcacccagag gctgaagacc ctgttcagca tgctgaacta cgagaggacc   1980
aagcaccctc acctgatggg cagcagcgtg ctgggcatga acgacatcta caggacctgg   2040
agggccttcg tgctgagggt gagggccctg gaccagaccc ctaggatgta cttcgtgaag   2100
gccgacgtga ccggcgccta cgacgccatc cctcagggca agctggtgga ggtggtggcc   2160
aacatgatca ggcacagcga gagcacctac tgcatcaggc agtacgccgt ggtgaggagg   2220
gacagccagg gccaggtgca caagagcttc aggaggcagg tgaccaccct gagcgacctg   2280
cagccttaca tgggccagtt cctgaagcac ctgcaggaca gcgacgccag cgccctgagg   2340
aacagcgtgg tgatcgagca gagcatcagc atgaacgaga gcagcagcag cctgttcgac   2400
ttcttcctgc acttcctgag gcacagcgtg gtgaagatcg gcgacaggtg ctacacccag   2460
```

```
tgccagggca tccctcaggg cagcagcctg agcaccctgc tgtgcagcct gtgcttcggc   2520
gacatggaga acaagctgtt cgccgaggtg cagagggacg gcctgctgct gaggttcgtg   2580
gacgacttcc tgctggtgac ccctcacctg gaccaggcca agaccttcct gagcaccctg   2640
gtgcacggcg tgcctgagta cggctgcatg atcaacctgc agaagaccgt ggtgaacttc   2700
cctgtggagc ctggcaccct gggcggcgcc gccccttacc agctgcctgc ccactgcctg   2760
ttcccttggt gcggcctgct gctggacacc cagaccctgg aggtgttctg cgactacagc   2820
ggctacgccc agaccagcat caagaccagc ctgaccttcc agagcgtgtt caaggccggc   2880
aagaccatga ggaacaagct gctgagcgtg ctgaggctga agtgccacgg cctgttcctg   2940
gacctgcagg tgaacagcct gcagaccgtg tgcatcaaca tctacaagat cttcctgctg   3000
caggcctaca ggttccacgc ctgcgtgatc cagctgcctt tcgaccagag ggtgaggaag   3060
aacctgacct tcttcctggg catcatcagc agccaggcca gctgctgcta cgccatcctg   3120
aaggtgaaga accctggcat gaccctgaag gccagcggca gcttccctcc tgaggccgcc   3180
cactggctgt gctaccaggc cttcctgctg aagctggccg cccacagcgt gatctacaag   3240
tgcctgctgg gccctctgag gaccgcccag aagctgctgt gcaggaagct gcctgaggcc   3300
accatgacca tcctgaaggc cgccgccgac cctgccctga gcaccgactt ccagaccatc   3360
ctggactga                                                           3369
```

<210> SEQ ID NO 4
<211> LENGTH: 3369
<212> TYPE: DNA
<213> ORGANISM: Artificial
<220> FEATURE:
<223> OTHER INFORMATION: Synthetic

<400> SEQUENCE: 4

```
atgacccgcg ctcctcgttg ccccgcggtg cgctctctgc tgcgcagccg ataccgggag     60
gtgtggccgc tggcaacctt tgtgcggcgc ctggggcccg agggcaggcg gcttgtgcaa    120
cccggggacc cgaagatcta ccgcactttg gttgcccaat gcctagtgtg catgcactgg    180
ggctcacagc ctccacctgc cgacctttcc ttccaccagg tgtcatccct gaaagagctg    240
gtggccaggg ttgtgcagag actctgcgag cgcaacgaga gaaacgtgct ggcttttggc    300
tttgagctgc ttaacgaggc cagaggcggg cctcccatgg ccttcactag tagcgtgcgt    360
agctacttgc ccaacactgt tattgagacc ctgcgtgtca gtggtgcatg gatgctactg    420
ttgagccgag tgggcgacga cctgctggtc tacctgctgg cacactgtgc tctttatctt    480
ctggtgcccc ccagctgtgc ctaccaggtg tgtgggtctc ccctgtacca aatttgtgcc    540
accacggata tctggccctc tgtgtccgct agttacaggc ccacccgacc cgtgggcagg    600
aatttcacta accttaggtt cttacaacag atcaagagca gtagtcgcca ggaagcaccg    660
aaacccctgg ccttgccatc tcgaggtaca aagaggcatc tgagtctcac cagtacaagt    720
gtgccttcag ctaagaaggc cagatgctat cctgtcccga gagtggagga gggaccccac    780
aggcaggtgc taccaacccc atcaggcaaa tcatgggtgc caagtcctgc tcggtccccc    840
gaggtgccta ctgcagagaa agatttgtct tctaaaggaa aggtgtctga cctgagtctc    900
tctgggtcgg tgtgctgtaa acacaagccc agctccacat ctctgctgtc accaccccgc    960
caaaatgcct ttcagctcag gccatttatt gagaccagac atttccttta ctccagggga   1020
gatggccaag agcgtctaaa cccctcattc ctactcagca acctccagcc taacttgact   1080
```

-continued

```
ggggccagga gactggtgga gatcatcttt ctgggctcaa ggcctaggac atcaggacca   1140
ctctgcagga cacaccgtct atcgcgtcga tactggcaga tgcggcccct gttccaacag   1200
ctgctggtga accatgcaga gtgccaatat gtcagactcc tcaggtcaca ttgcaggttt   1260
cgaacagcaa accaacaggt gacagatgcc ttgaacacca gcccaccgca cctcatggat   1320
ttgctccgcc tgcacagcag tccctggcag gtatatggtt ttcttcgggc ctgtctctgc   1380
aaggtggtgt ctgctagtct ctggggtacc aggcacaatg agcgccgctt ctttaagaac   1440
ttaaagaagt tcatctcgtt ggggaaatac ggcaagctat cactgcagga actgatgtgg   1500
aagatgaaag tagaggattg ccactggctc cgcagcagcc cggggaagga ccgtgtcccc   1560
gctgcagagc accgtctgag ggagaggatc ctggctacgt tcctgttctg gctgatggac   1620
acatacgtgg tacagctgct taggtcattc ttttacatca cagagagcac attccagaag   1680
aacaggctct tcttctaccg taagagtgtg tggagcaagc tgcagagcat tggagtcagg   1740
caacaccttg agagagtgcg gctacgggag ctgtcacaag aggaggtcag gcatcaccag   1800
gacacctggc tagccatgcc catctgcaga ctgcgcttca tccccaagcc caacggcctg   1860
cggcccattg tgaacatgag ttatagcatg ggtaccagag ctttgggcag aaggaagcag   1920
gcccagcatt tcacccagcg tctcaagact ctcttcagca tgctcaacta tgagcggaca   1980
aaacatcctc accttatggg gtcttctgta ctgggtatga atgacatcta caggacctgg   2040
cgggcctttg tgctgcgtgt gcgtgctctg gaccagacac ccaggatgta ctttgttaag   2100
gcagatgtga ccggggcctt tgatgccatc cccccagggta agctggtgga ggttgttgcc   2160
aatatgatca ggcactcgga gagcacgtac tgtatccgcc agtatgcagt ggtccggaga   2220
gatagccaag gccaagtcca caagtccttt aggagacagg tcaccaccct ctctgacctc   2280
cagccataca tgggccagtt ccttaagcat ctgcaggatt cagatgccag tgcactgagg   2340
aactccgttg tcatcgagca gagcatctct atgaatgaga gcagcagcag cctgtttgac   2400
ttcttcctgc acttcctgcg tcacagtgtc gtaaagattg gtgacaggtg ctatacgcag   2460
tgccagggca tcccccaggg ctccagccta tccaccctgc tctgcagtct gtgtttcgga   2520
gacatggaga acaagctgtt tgctgaggtg cagcgggatg ggttgctttt acgttttgtt   2580
gatgactttc tgttggtgac gcctcacttg gaccaagcaa aaaccttcct cagcaccctg   2640
gtccatggcg ttcctgagta tgggtgcatg ataaacttgc agaagacagt ggtgaacttc   2700
cctgtggagc ctggtaccct gggtggtgca gctccatacc agctgcctgc tcactgcctg   2760
tttccctggt gtggcttgct gctggacact cagactttgg aggtgttctg tgactactca   2820
ggttatgccc agacctcaat taagacgagc ctcaccttcc agagtgtctt caaagctggg   2880
aagaccatgc ggaacaagct cctgtcggtc ttgcggttga agtgtcacgg tctatttcta   2940
gacttgcagg tgaacagcct ccagacagtc tgcatcaata tatacaagat cttcctgctt   3000
caggcctaca ggttccatgc atgtgtgatt cagcttccct ttgaccagcg tgttaggaag   3060
aacctcacat tctttctggg catcatctcc agccaagcat cctgctgcta tgctatcctg   3120
aaggtcaaga atccaggaat gacactaaag gcctctggct cctttcctcc tgaagccgca   3180
cattggctct gctaccaggc cttcctgctc aagctggctg ctcattctgt catctacaaa   3240
tgtctcctgg gacctctgag gacagcccaa aaactgctgt gccggaagct cccagaggcg   3300
acaatgacca tccttaaagc tgcagctgac ccagccctaa gcacagactt tcagaccatt   3360
ttggactaa                                                            3369
```

<210> SEQ ID NO 5
<211> LENGTH: 3369
<212> TYPE: DNA
<213> ORGANISM: Artificial
<220> FEATURE:
<223> OTHER INFORMATION: Synthetic

<400> SEQUENCE: 5
atgacccgcg ctcctcgttg ccccgcggtg cgctctctgc tgcgcagccg ataccgggag 60
gtgtggccgc tggcaacctt tgtgcggcgc ctggggcccg agggcaggcg gcttgtgcaa 120
cccggggacc cgaagatcta ccgcactttg gttgcccaat gcctagtgtg catgcactgg 180
ggctcacagc ctccacctgc cgacctttcc ttccaccagg tgtcatccct gaaagagctg 240
gtggccaggg ttgtgcagag actctgcgag cgcaacgaga gaaacgtgct ggcttttggc 300
tttgagctgc ttaacgaggc cagaggcggg cctcccatgg ccttcactag tagcgtgcgt 360
agctacttgc ccaacactgt tattgagacc ctgcgtgtca gtggtgcatg gatgctactg 420
ttgagccgag tgggcgacga cctgctggtc tacctgctgg cacactgtgc tctttatctt 480
ctggtgcccc ccagctgtgc ctaccaggtg tgtgggtctc ccctgtacca aatttgtgcc 540
accacggata tctggccctc tgtgtccgct agttacaggc ccacccgacc cgtgggcagg 600
aatttcacta accttaggtt cttacaacag atcaagagca gtagtcgcca ggaagcaccg 660
aaacccctgg ccttgccatc tcgaggtaca aagaggcatc tgagtctcac cagtacaagt 720
gtgccttcag ctaagaaggc cagatgctat cctgtcccga gagtggagga gggaccccac 780
aggcaggtgc taccaacccc atcaggcaaa tcatgggtgc caagtcctgc tcggtccccc 840
gaggtgccta ctgcagagaa agatttgtct tctaaaggaa aggtgtctga cctgagtctc 900
tctgggtcgg tgtgctgtaa acacaagccc agctccacat ctctgctgtc accaccccgc 960
caaaatgcct ttcagctcag gccatttatt gagaccagac atttccttta ctccagggga 1020
gatggccaag agcgtctaaa cccctcattc ctactcagca acctccagcc taacttgact 1080
ggggccagga gactggtgga gatcatcttt ctgggctcaa ggcctaggac atcaggacca 1140
ctctgcagga cacaccgtct atcgcgtcga tactggcaga tgcggcccct gttccaacag 1200
ctgctggtga accatgcaga gtgccaatat gtcagactcc tcaggtcaca ttgcaggttt 1260
cgaacagcaa accaacaggt gacagatgcc ttgaacacca gcccaccgca cctcatggat 1320
ttgctccgcc tgcacagcag tccctggcag gtatatggtt ttcttcgggc ctgtctctgc 1380
aaggtggtgt ctgctagtct ctggggtacc aggcacaatg agcgccgctt ctttaagaac 1440
ttaaagaagt tcatctcgtt ggggaaatac ggcaagctat cactgcagga actgatgtgg 1500
aagatgaaag tagaggattg ccactggctc cgcagcagcc cggggaagga ccgtgtcccc 1560
gctgcagagc accgtctgag ggagaggatc ctggctacgt tcctgttctg gctgatggac 1620
acatacgtgg tacagctgct taggtcattc ttttacatca cagagagcac attccagaag 1680
aacaggctct tcttctaccg taagagtgtg tggagcaagc tgcagagcat tggagtcagg 1740
caacaccttg agagagtgcg gctacgggag ctgtcacaag aggaggtcag gcatcaccag 1800
gacacctggc tagccatgcc catctgcaga ctgcgcttca tccccaagcc caacggcctg 1860
cggcccattg tgaacatgag ttatagcatg ggtaccagag ctttgggcag aaggaagcag 1920
gcccagcatt tcacccagcg tctcaagact ctcttcagca tgctcaacta tgagcggaca 1980
aaacatcctc accttatggg gtcttctgta ctgggtatga atgacatcta caggacctgg 2040
cgggcctttg tgctgcgtgt gcgtgctctg gaccagacac ccaggatgtt ctttgttaag 2100

```
gcagatgtga ccggggccta tgatgccatc ccccagggta agctggtgga ggttgttgcc   2160

aatatgatca ggcactcgga gagcacgtac tgtatccgcc agtatgcagt ggtccggaga   2220

gatagccaag gccaagtcca caagtccttt aggagacagg tcaccaccct ctctgacctc   2280

cagccataca tgggccagtt ccttaagcat ctgcaggatt cagatgccag tgcactgagg   2340

aactccgttg tcatcgagca gagcatctct atgaatgaga gcagcagcag cctgtttgac   2400

ttcttcctgc acttcctgcg tcacagtgtc gtaaagattg gtgacaggtg ctatacgcag   2460

tgccagggca tcccccaggg ctccagccta tccaccctgc tctgcagtct gtgtttcgga   2520

gacatggaga acaagctgtt tgctgaggtg cagcgggatg ggttgctttt acgttttgtt   2580

gatgactttc tgttggtgac gcctcacttg gaccaagcaa aaaccttcct cagcaccctg   2640

gtccatggcg ttcctgagta tgggtgcatg ataaacttgc agaagacagt ggtgaacttc   2700

cctgtggagc ctggtaccct gggtggtgca gctccatacc agctgcctgc tcactgcctg   2760

tttccctggt gtggcttgct gctggacact cagactttgg aggtgttctg tgactactca   2820

ggttatgccc agacctcaat taagacgagc ctcaccttcc agagtgtctt caaagctggg   2880

aagaccatgc ggaacaagct cctgtcggtc ttgcggttga agtgtcacgg tctatttcta   2940

gacttgcagg tgaacagcct ccagacagtc tgcatcaata tatacaagat cttcctgctt   3000

caggcctaca ggttccatgc atgtgtgatt cagcttccct ttgaccagcg tgttaggaag   3060

aacctcacat tctttctggg catcatctcc agccaagcat cctgctgcta tgctatcctg   3120

aaggtcaaga atccaggaat gacactaaag gcctctggct cctttcctcc tgaagccgca   3180

cattggctct gctaccaggc cttcctgctc aagctggctg ctcattctgt catctacaaa   3240

tgtctcctgg gacctctgag gacagcccaa aaactgctgt gccggaagct cccagaggcg   3300

acaatgacca tccttaaagc tgcagctgac ccagccctaa gcacagactt tcagaccatt   3360

ttggactaa                                                           3369
```

```
<210> SEQ ID NO 6
<211> LENGTH: 1132
<212> TYPE: PRT
<213> ORGANISM: Homo sapiens

<400> SEQUENCE: 6

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140
```

-continued

```
Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
```

-continued

```
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
        915                 920                 925

Pro Trp Cys Gly Leu Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990
```

```
Ser Leu Gln Thr Val Cys Thr Asn  Ile Tyr Lys Ile Leu  Leu Leu Gln
        995                 1000                 1005

Ala Tyr  Arg Phe His Ala Cys  Val Leu Gln Leu Pro  Phe His Gln
    1010                 1015                 1020

Gln Val  Trp Lys Asn Pro Thr  Phe Phe Leu Arg Val  Ile Ser Asp
    1025                 1030                 1035

Thr Ala  Ser Leu Cys Tyr Ser  Ile Leu Lys Ala Lys  Asn Ala Gly
    1040                 1045                 1050

Met Ser  Leu Gly Ala Lys Gly  Ala Ala Gly Pro Leu  Pro Ser Glu
    1055                 1060                 1065

Ala Val  Gln Trp Leu Cys His  Gln Ala Phe Leu Leu  Lys Leu Thr
    1070                 1075                 1080

Arg His  Arg Val Thr Tyr Val  Pro Leu Leu Gly Ser  Leu Arg Thr
    1085                 1090                 1095

Ala Gln  Thr Gln Leu Ser Arg  Lys Leu Pro Gly Thr  Thr Leu Thr
    1100                 1105                 1110

Ala Leu  Glu Ala Ala Ala Asn  Pro Ala Leu Pro Ser  Asp Phe Lys
    1115                 1120                 1125

Thr Ile  Leu Asp
    1130
```

<210> SEQ ID NO 7
<211> LENGTH: 4039
<212> TYPE: DNA
<213> ORGANISM: Homo sapiens

<400> SEQUENCE: 7

```
ctctcctcgc ggcgcgagtt tcaggcagcg ctgcgtcctg ctgcgcacgt gggaagccct     60

ggccccggcc acccccgcga tgccgcgcgc tccccgctgc cgagccgtgc gctccctgct    120

gcgcagccac taccgcgagg tgctgccgct ggccacgttc gtgcggcgcc tggggcccca    180

gggctggcgg ctggtgcagc gcggggaccc ggcggctttc cgcgcgctgg tggcccagtg    240

cctggtgtgc gtgccctggg acgcacggcc gccccccgcc gccccctcct tccgccaggt    300

gtcctgcctg aaggagctgg tggcccgagt gctgcagagg ctgtgcgagc gcggcgcgaa    360

gaacgtgctg gccttcggct tcgcgctgct ggacggggcc cgcgggggcc cccccgaggc    420

cttcaccacc agcgtgcgca gctacctgcc caacacggtg accgacgcac tgcgggggag    480

cggggcgtgg gggctgctgc tgcgccgcgt gggcgacgac gtgctggttc acctgctggc    540

acgctgcgcg ctctttgtgc tggtggctcc cagctgcgcc taccaggtgt gcgggccgcc    600

gctgtaccag ctcggcgctg ccactcaggc ccggcccccg ccacacgcta gtggaccccg    660

aaggcgtctg ggatgcgaac gggcctggaa ccatagcgtc agggaggccg gggtccccct    720

gggcctgcca gccccgggtg cgaggaggcg cgggggcagt gccagccgaa gtctgccgtt    780

gcccaagagg cccaggcgtg gcgctgcccc tgagccggag cggacgcccg ttgggcaggg    840

gtcctgggcc cacccgggca ggacgcgtgg accgagtgac cgtggtttct gtgtggtgtc    900

acctgccaga cccgccgaag aagccacctc tttggagggt gcgctctctg gcacgcgcca    960

ctcccaccca tccgtgggcc gccagcacca cgcgggcccc ccatccacat cgcggccacc   1020

acgtccctgg gacacgcctt gtcccccggt gtacgccgag accaagcact tcctctactc   1080

ctcaggcgac aaggagcagc tgcggccctc cttcctactc agctctctga ggcccagcct   1140

gactggcgct cggaggctcg tggagaccat ctttctgggt tccaggccct ggatgccagg   1200
```

```
gactccccgc aggttgcccc gcctgcccca gcgctactgg caaatgcggc ccctgtttct   1260
ggagctgctt gggaaccacg cgcagtgccc ctacggggtg ctcctcaaga cgcactgccc   1320
gctgcgagct gcggtcaccc cagcagccgg tgtctgtgcc cgggagaagc cccagggctc   1380
tgtggcggcc cccgaggagg aggacacaga cccccgtcgc ctggtgcagc tgctccgcca   1440
gcacagcagc ccctggcagg tgtacggctt cgtgcgggcc tgcctgcgcc ggctggtgcc   1500
cccaggcctc tggggctcca ggcacaacga acgccgcttc ctcaggaaca ccaagaagtt   1560
catctccctg gggaagcatg ccaagctctc gctgcaggag ctgacgtgga agatgagcgt   1620
gcgggactgc gcttggctgc gcaggagccc aggggttggc tgtgttccgg ccgcagagca   1680
ccgtctgcgt gaggagatcc tggccaagtt cctgcactgg ctgatgagtg tgtacgtcgt   1740
cgagctgctc aggtctttct tttatgtcac ggagaccacg tttcaaaaga acaggctctt   1800
tttctaccgg aagagtgtct ggagcaagtt gcaaagcatt ggaatcagac agcacttgaa   1860
gagggtgcag ctgcgggagc tgtcggaagc agaggtcagg cagcatcggg aagccaggcc   1920
cgccctgctg acgtccagac tccgcttcat ccccaagcct gacgggctgc ggccgattgt   1980
gaacatggac tacgtcgtgg gagccagaac gttccgcaga gaaaagaggg ccgagcgtct   2040
cacctcgagg gtgaaggcac tgttcagcgt gctcaactac gagcgggcgc ggcgccccgg   2100
cctcctgggc gcctctgtgc tgggcctgga cgatatccac agggcctggc gcaccttcgt   2160
gctgcgtgtg cgggcccagg acccgccgcc tgagctgtac tttgtcaagg tggatgtgac   2220
gggcgcgtac gacaccatcc cccaggacag gctcacggag gtcatcgcca gcatcatcaa   2280
accccagaac acgtactgcg tgcgtcggta tgccgtggtc cagaaggccg cccatgggca   2340
cgtccgcaag gccttcaaga gccacgtctc taccttgaca gacctccagc cgtacatgcg   2400
acagttcgtg gctcacctgc aggagaccag cccgctgagg gatgccgtcg tcatcgagca   2460
gagctcctcc ctgaatgagg ccagcagtgg cctcttcgac gtcttcctac gcttcatgtg   2520
ccaccacgcc gtgcgcatca ggggcaagtc ctacgtccag tgccagggga tcccgcaggg   2580
ctccatcctc tccacgctgc tctgcagcct gtgctacggc gacatggaga acaagctgtt   2640
tgcggggatt cggcgggacg ggctgctcct gcgtttggtg gatgatttct tgttggtgac   2700
acctcacctc acccacgcga aaaccttcct caggaccctg gtccgaggtg tccctgagta   2760
tggctgcgtg gtgaacttgc ggaagacagt ggtgaacttc cctgtagaag acgaggccct   2820
gggtggcacg gcttttgttc agatgccggc ccacggccta ttcccctggt gcggcctgct   2880
gctggatacc cggaccctgg aggtgcagag cgactactcc agctatgccc ggacctccat   2940
cagagccagt ctcaccttca accgcggctt caaggctggg aggaacatgc gtcgcaaact   3000
ctttggggtc ttgcggctga agtgtcacag cctgtttctg gatttgcagg tgaacagcct   3060
ccagacggtg tgcaccaaca tctacaagat cctcctgctg caggcgtaca ggtttcacgc   3120
atgtgtgctg cagctcccat ttcatcagca agtttggaag aaccccacat tttcctgcg   3180
cgtcatctct gacacggcct ccctctgcta ctccatcctg aaagccaaga acgcagggat   3240
gtcgctgggg gccaagggcg ccgccggccc tctgccctcc gaggccgtgc agtggctgtg   3300
ccaccaagca ttcctgctca agctgactcg acaccgtgtc acctacgtgc cactcctggg   3360
gtcactcagg acagcccaga cgcagctgag tcggaagctc ccggggacga cgctgactgc   3420
cctggaggcc gcagccaacc cggcactgcc ctcagacttc aagaccatcc tggactgatg   3480
gccacccgcc cacagccagg ccgagagcag acaccagcag ccctgtcacg ccgggctcta   3540
cgtcccaggg agggaggggc ggcccacacc caggcccgca ccgctgggag tctgaggcct   3600
```

```
gagtgagtgt ttggccgagg cctgcatgtc cggctgaagg ctgagtgtcc ggctgaggcc   3660

tgagcgagtg tccagccaag ggctgagtgt ccagcacacc tgccgtcttc acttccccac   3720

aggctggcgc tcggctccac cccagggcca gcttttcctc accaggagcc cggcttccac   3780

tccccacata ggaatagtcc atccccagat tcgccattgt tcacccctcg ccctgccctc   3840

ctttgccttc cacccccacc atccaggtgg agaccctgag aaggaccctg ggagctctgg   3900

gaatttggag tgaccaaagg tgtgccctgt acacaggcga ggaccctgca cctggatggg   3960

ggtccctgtg ggtcaaattg gggggaggtg ctgtgggagt aaaatactga atatatgagt   4020

ttttcagttt tgaaaaaaa                                                 4039


<210> SEQ ID NO 8
<211> LENGTH: 1069
<212> TYPE: PRT
<213> ORGANISM: Homo sapiens

<400> SEQUENCE: 8

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285
```

-continued

```
Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
```

```
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Thr Phe Leu Ser Tyr Ala Arg Thr Ser Ile Arg Ala Ser Leu Thr
                885                 890                 895

Phe Asn Arg Gly Phe Lys Ala Gly Arg Asn Met Arg Arg Lys Leu Phe
            900                 905                 910

Gly Val Leu Arg Leu Lys Cys His Ser Leu Phe Leu Asp Leu Gln Val
        915                 920                 925

Asn Ser Leu Gln Thr Val Cys Thr Asn Ile Tyr Lys Ile Leu Leu Leu
    930                 935                 940

Gln Ala Tyr Arg Phe His Ala Cys Val Leu Gln Leu Pro Phe His Gln
945                 950                 955                 960

Gln Val Trp Lys Asn Pro Thr Phe Phe Leu Arg Val Ile Ser Asp Thr
                965                 970                 975

Ala Ser Leu Cys Tyr Ser Ile Leu Lys Ala Lys Asn Ala Gly Met Ser
            980                 985                 990

Leu Gly Ala Lys Gly Ala Ala Gly  Pro Leu Pro Ser Glu  Ala Val Gln
        995                 1000                1005

Trp Leu  Cys His Gln Ala Phe  Leu Leu Lys Leu Thr  Arg His Arg
    1010                1015                1020

Val Thr  Tyr Val Pro Leu Leu  Gly Ser Leu Arg Thr  Ala Gln Thr
    1025                1030                1035

Gln Leu  Ser Arg Lys Leu Pro  Gly Thr Thr Leu Thr  Ala Leu Glu
    1040                1045                1050

Ala Ala  Ala Asn Pro Ala Leu  Pro Ser Asp Phe Lys  Thr Ile Leu
    1055                1060                1065

Asp


<210> SEQ ID NO 9
<211> LENGTH: 3850
<212> TYPE: DNA
<213> ORGANISM: Homo sapiens

<400> SEQUENCE: 9

ctctcctcgc ggcgcgagtt tcaggcagcg ctgcgtcctg ctgcgcacgt gggaagccct     60
```

```
ggccccggcc acccccgcga tgccgcgcgc tccccgctgc cgagccgtgc gctccctgct    120
gcgcagccac taccgcgagg tgctgccgct ggccacgttc gtgcggcgcc tggggcccca    180
gggctggcgg ctggtgcagc gcggggaccc ggcggctttc cgcgcgctgg tggcccagtg    240
cctggtgtgc gtgccctggg acgcacggcc gccccccgcc gccccctcct tccgccaggt    300
gtcctgcctg aaggagctgg tggcccgagt gctgcagagg ctgtgcgagc gcggcgcgaa    360
gaacgtgctg gccttcggct tcgcgctgct ggacggggcc cgcgggggcc cccccgaggc    420
cttcaccacc agcgtgcgca gctacctgcc caacacggtg accgacgcac tgcgggggag    480
cggggcgtgg gggctgctgc tgcgccgcgt gggcgacgac gtgctggttc acctgctggc    540
acgctgcgcg ctctttgtgc tggtggctcc cagctgcgcc taccaggtgt gcgggccgcc    600
gctgtaccag ctcggcgctg ccactcaggc ccggcccccg ccacacgcta gtggaccccg    660
aaggcgtctg ggatgcgaac gggcctggaa ccatagcgtc agggaggccg gggtcccccct   720
gggcctgcca gccccgggtg cgaggaggcg cgggggcagt gccagccgaa gtctgccgtt    780
gcccaagagg cccaggcgtg gcgctgcccc tgagccggag cggacgcccg ttgggcaggg    840
gtcctgggcc cacccgggca ggacgcgtgg accgagtgac cgtggtttct gtgtggtgtc    900
acctgccaga cccgccgaag aagccacctc tttggagggt gcgctctctg gcacgcgcca    960
ctcccaccca tccgtgggcc gccagcacca cgcgggcccc ccatccacat cgcggccacc   1020
acgtccctgg gacacgcctt gtcccccggt gtacgccgag accaagcact tcctctactc   1080
ctcaggcgac aaggagcagc tgcggccctc cttcctactc agctctctga ggcccagcct   1140
gactggcgct cggaggctcg tggagaccat ctttctgggt tccaggccct ggatgccagg   1200
gactccccgc aggttgcccc gcctgcccca gcgctactgg caaatgcggc ccctgtttct   1260
ggagctgctt gggaaccacg cgcagtgccc ctacggggtg ctcctcaaga cgcactgccc   1320
gctgcgagct gcggtcaccc cagcagccgg tgtctgtgcc cgggagaagc cccagggctc   1380
tgtggcggcc cccgaggagg aggacacaga cccccgtcgc ctggtgcagc tgctccgcca   1440
gcacagcagc ccctggcagg tgtacggctt cgtgcgggcc tgcctgcgcc ggctggtgcc   1500
cccaggcctc tggggctcca ggcacaacga acgccgcttc ctcaggaaca ccaagaagtt   1560
catctccctg gggaagcatg ccaagctctc gctgcaggag ctgacgtgga agatgagcgt   1620
gcgggactgc gcttggctgc gcaggagccc aggggttggc tgtgttccgg ccgcagagca   1680
ccgtctgcgt gaggagatcc tggccaagtt cctgcactgg ctgatgagtg tgtacgtcgt   1740
cgagctgctc aggtctttct tttatgtcac ggagaccacg tttcaaaaga acaggctctt   1800
tttctaccgg aagagtgtct ggagcaagtt gcaaagcatt ggaatcagac agcacttgaa   1860
gagggtgcag ctgcgggagc tgtcggaagc agaggtcagg cagcatcggg aagccaggcc   1920
cgccctgctg acgtccagac tccgcttcat ccccaagcct gacgggctgc ggccgattgt   1980
gaacatggac tacgtcgtgg gagccagaac gttccgcaga gaaaagaggg ccgagcgtct   2040
cacctcgagg gtgaaggcac tgttcagcgt gctcaactac gagcgggcgc ggcgccccgg   2100
cctcctgggc gcctctgtgc tgggcctgga cgatatccac agggcctggc gcaccttcgt   2160
gctgcgtgtg cgggcccagg acccgccgcc tgagctgtac tttgtcaagg tggatgtgac   2220
gggcgcgtac gacaccatcc cccaggacag gctcacggag gtcatcgcca gcatcatcaa   2280
accccagaac acgtactgcg tgcgtcggta tgccgtggtc cagaaggccg cccatgggca   2340
cgtccgcaag gccttcaaga gccacgtctc taccttgaca gacctccagc cgtacatgcg   2400
```

-continued acagttcgtg gctcacctgc aggagaccag cccgctgagg gatgccgtcg tcatcgagca 2460
gagctcctcc ctgaatgagg ccagcagtgg cctcttcgac gtcttcctac gcttcatgtg 2520
ccaccacgcc gtgcgcatca ggggcaagtc ctacgtccag tgccagggga tcccgcaggg 2580
ctccatcctc tccacgctgc tctgcagcct gtgctacggc gacatggaga acaagctgtt 2640
tgcggggatt cggcgggacg ggctgctcct gcgtttggtg gatgatttct tgttggtgac 2700
acctcacctc acccacgcga aaaccttcct cagctatgcc cggacctcca tcagagccag 2760
tctcaccttc aaccgcggct tcaaggctgg gaggaacatg cgtcgcaaac tctttggggt 2820
cttgcggctg aagtgtcaca gcctgtttct ggatttgcag gtgaacagcc tccagacggt 2880
gtgcaccaac atctacaaga tcctcctgct gcaggcgtac aggtttcacg catgtgtgct 2940
gcagctccca tttcatcagc aagtttggaa gaaccccaca tttttcctgc gcgtcatctc 3000
tgacacggcc tccctctgct actccatcct gaaagccaag aacgcaggga tgtcgctggg 3060
ggccaagggc gccgccggcc ctctgccctc cgaggccgtg cagtggctgt gccaccaagc 3120
attcctgctc aagctgactc gacaccgtgt cacctacgtg ccactcctgg ggtcactcag 3180
gacagcccag acgcagctga gtcggaagct cccggggacg acgctgactg ccctggaggc 3240
cgcagccaac ccggcactgc cctcagactt caagaccatc ctggactgat ggccacccgc 3300
ccacagccag gccgagagca gacaccagca gccctgtcac gccgggctct acgtcccagg 3360
gagggagggg cggcccacac ccaggcccgc accgctggga gtctgaggcc tgagtgagtg 3420
tttggccgag gcctgcatgt ccggctgaag gctgagtgtc cggctgaggc ctgagcgagt 3480
gtccagccaa gggctgagtg tccagcacac ctgccgtctt cacttcccca caggctggcg 3540
ctcggctcca ccccagggcc agcttttcct caccaggagc ccggcttcca ctccccacat 3600
aggaatagtc catccccaga ttcgccattg ttcacccctc gccctgccct cctttgcctt 3660
ccacccccac catccaggtg gagaccctga gaaggaccct gggagctctg ggaatttgga 3720
gtgaccaaag gtgtgccctg tacacaggcg aggaccctgc acctggatgg gggtccctgt 3780
gggtcaaatt ggggggaggt gctgtgggag taaaatactg aatatatgag tttttcagtt 3840
ttgaaaaaaa 3850

<210> SEQ ID NO 10
<211> LENGTH: 1122
<212> TYPE: PRT
<213> ORGANISM: Mus musculus

<400> SEQUENCE: 10

Met Thr Arg Ala Pro Arg Cys Pro Ala Val Arg Ser Leu Leu Arg Ser
1 5 10 15

Arg Tyr Arg Glu Val Trp Pro Leu Ala Thr Phe Val Arg Arg Leu Gly
20 25 30

Pro Glu Gly Arg Arg Leu Val Gln Pro Gly Asp Pro Lys Ile Tyr Arg
35 40 45

Thr Leu Val Ala Gln Cys Leu Val Cys Met His Trp Gly Ser Gln Pro
50 55 60

Pro Pro Ala Asp Leu Ser Phe His Gln Val Ser Ser Leu Lys Glu Leu
65 70 75 80

Val Ala Arg Val Val Gln Arg Leu Cys Glu Arg Asn Glu Arg Asn Val
85 90 95

Leu Ala Phe Gly Phe Glu Leu Leu Asn Glu Ala Arg Gly Gly Pro Pro
100 105 110

-continued

```
Met Ala Phe Thr Ser Ser Val Arg Ser Tyr Leu Pro Asn Thr Val Ile
        115                 120                 125

Glu Thr Leu Arg Val Ser Gly Ala Trp Met Leu Leu Leu Ser Arg Val
    130                 135                 140

Gly Asp Asp Leu Leu Val Tyr Leu Leu Ala His Cys Ala Leu Tyr Leu
145                 150                 155                 160

Leu Val Pro Pro Ser Cys Ala Tyr Gln Val Cys Gly Ser Pro Leu Tyr
                165                 170                 175

Gln Ile Cys Ala Thr Thr Asp Ile Trp Pro Ser Val Ser Ala Ser Tyr
            180                 185                 190

Arg Pro Thr Arg Pro Val Gly Arg Asn Phe Thr Asn Leu Arg Phe Leu
        195                 200                 205

Gln Gln Ile Lys Ser Ser Ser Arg Gln Glu Ala Pro Lys Pro Leu Ala
    210                 215                 220

Leu Pro Ser Arg Gly Thr Lys Arg His Leu Ser Leu Thr Ser Thr Ser
225                 230                 235                 240

Val Pro Ser Ala Lys Lys Ala Arg Cys Tyr Pro Val Pro Arg Val Glu
                245                 250                 255

Glu Gly Pro His Arg Gln Val Leu Pro Thr Pro Ser Gly Lys Ser Trp
            260                 265                 270

Val Pro Ser Pro Ala Arg Ser Pro Glu Val Pro Thr Ala Glu Lys Asp
        275                 280                 285

Leu Ser Ser Lys Gly Lys Val Ser Asp Leu Ser Leu Ser Gly Ser Val
    290                 295                 300

Cys Cys Lys His Lys Pro Ser Ser Thr Ser Leu Leu Ser Pro Pro Arg
305                 310                 315                 320

Gln Asn Ala Phe Gln Leu Arg Pro Phe Ile Glu Thr Arg His Phe Leu
                325                 330                 335

Tyr Ser Arg Gly Asp Gly Gln Glu Arg Leu Asn Pro Ser Phe Leu Leu
            340                 345                 350

Ser Asn Leu Gln Pro Asn Leu Thr Gly Ala Arg Arg Leu Val Glu Ile
        355                 360                 365

Ile Phe Leu Gly Ser Arg Pro Arg Thr Ser Gly Pro Leu Cys Arg Thr
    370                 375                 380

His Arg Leu Ser Arg Arg Tyr Trp Gln Met Arg Pro Leu Phe Gln Gln
385                 390                 395                 400

Leu Leu Val Asn His Ala Glu Cys Gln Tyr Val Arg Leu Leu Arg Ser
                405                 410                 415

His Cys Arg Phe Arg Thr Ala Asn Gln Gln Val Thr Asp Ala Leu Asn
            420                 425                 430

Thr Ser Pro Pro His Leu Met Asp Leu Leu Arg Leu His Ser Ser Pro
        435                 440                 445

Trp Gln Val Tyr Gly Phe Leu Arg Ala Cys Leu Cys Lys Val Val Ser
    450                 455                 460

Ala Ser Leu Trp Gly Thr Arg His Asn Glu Arg Arg Phe Phe Lys Asn
465                 470                 475                 480

Leu Lys Lys Phe Ile Ser Leu Gly Lys Tyr Gly Lys Leu Ser Leu Gln
                485                 490                 495

Glu Leu Met Trp Lys Met Lys Val Glu Asp Cys His Trp Leu Arg Ser
            500                 505                 510

Ser Pro Gly Lys Asp Arg Val Pro Ala Ala Glu His Arg Leu Arg Glu
        515                 520                 525

Arg Ile Leu Ala Thr Phe Leu Phe Trp Leu Met Asp Thr Tyr Val Val
```

-continued

```
    530                 535                 540

Gln Leu Leu Arg Ser Phe Phe Tyr Ile Thr Glu Ser Thr Phe Gln Lys
545                 550                 555                 560

Asn Arg Leu Phe Phe Tyr Arg Lys Ser Val Trp Ser Lys Leu Gln Ser
                565                 570                 575

Ile Gly Val Arg Gln His Leu Glu Arg Val Arg Leu Arg Glu Leu Ser
            580                 585                 590

Gln Glu Glu Val Arg His His Gln Asp Thr Trp Leu Ala Met Pro Ile
        595                 600                 605

Cys Arg Leu Arg Phe Ile Pro Lys Pro Asn Gly Leu Arg Pro Ile Val
    610                 615                 620

Asn Met Ser Tyr Ser Met Gly Thr Arg Ala Leu Gly Arg Arg Lys Gln
625                 630                 635                 640

Ala Gln His Phe Thr Gln Arg Leu Lys Thr Leu Phe Ser Met Leu Asn
                645                 650                 655

Tyr Glu Arg Thr Lys His Pro His Leu Met Gly Ser Ser Val Leu Gly
            660                 665                 670

Met Asn Asp Ile Tyr Arg Thr Trp Arg Ala Phe Val Leu Arg Val Arg
        675                 680                 685

Ala Leu Asp Gln Thr Pro Arg Met Tyr Phe Val Lys Ala Asp Val Thr
    690                 695                 700

Gly Ala Tyr Asp Ala Ile Pro Gln Gly Lys Leu Val Glu Val Val Ala
705                 710                 715                 720

Asn Met Ile Arg His Ser Glu Ser Thr Tyr Cys Ile Arg Gln Tyr Ala
                725                 730                 735

Val Val Arg Arg Asp Ser Gln Gly Gln Val His Lys Ser Phe Arg Arg
            740                 745                 750

Gln Val Thr Thr Leu Ser Asp Leu Gln Pro Tyr Met Gly Gln Phe Leu
        755                 760                 765

Lys His Leu Gln Asp Ser Asp Ala Ser Ala Leu Arg Asn Ser Val Val
    770                 775                 780

Ile Glu Gln Ser Ile Ser Met Asn Glu Ser Ser Ser Ser Leu Phe Asp
785                 790                 795                 800

Phe Phe Leu His Phe Leu Arg His Ser Val Val Lys Ile Gly Asp Arg
                805                 810                 815

Cys Tyr Thr Gln Cys Gln Gly Ile Pro Gln Gly Ser Ser Leu Ser Thr
            820                 825                 830

Leu Leu Cys Ser Leu Cys Phe Gly Asp Met Glu Asn Lys Leu Phe Ala
        835                 840                 845

Glu Val Gln Arg Asp Gly Leu Leu Leu Arg Phe Val Asp Asp Phe Leu
    850                 855                 860

Leu Val Thr Pro His Leu Asp Gln Ala Lys Thr Phe Leu Ser Thr Leu
865                 870                 875                 880

Val His Gly Val Pro Glu Tyr Gly Cys Met Ile Asn Leu Gln Lys Thr
                885                 890                 895

Val Val Asn Phe Pro Val Glu Pro Gly Thr Leu Gly Gly Ala Ala Pro
            900                 905                 910

Tyr Gln Leu Pro Ala His Cys Leu Phe Pro Trp Cys Gly Leu Leu Leu
        915                 920                 925

Asp Thr Gln Thr Leu Glu Val Phe Cys Asp Tyr Ser Gly Tyr Ala Gln
    930                 935                 940

Thr Ser Ile Lys Thr Ser Leu Thr Phe Gln Ser Val Phe Lys Ala Gly
945                 950                 955                 960
```

```
Lys Thr Met Arg Asn Lys Leu Leu Ser Val Leu Arg Leu Lys Cys His
                965                 970                 975

Gly Leu Phe Leu Asp Leu Gln Val Asn Ser Leu Gln Thr Val Cys Ile
            980                 985                 990

Asn Ile Tyr Lys Ile Phe Leu Leu  Gln Ala Tyr Arg Phe  His Ala Cys
        995                 1000                1005

Val Ile  Gln Leu Pro Phe Asp  Gln Arg Val Arg Lys  Asn Leu Thr
    1010                1015                1020

Phe Phe  Leu Gly Ile Ile Ser  Ser Gln Ala Ser Cys  Cys Tyr Ala
    1025                1030                1035

Ile Leu  Lys Val Lys Asn Pro  Gly Met Thr Leu Lys  Ala Ser Gly
    1040                1045                1050

Ser Phe  Pro Pro Glu Ala Ala  His Trp Leu Cys Tyr  Gln Ala Phe
    1055                1060                1065

Leu Leu  Lys Leu Ala Ala His  Ser Val Ile Tyr Lys  Cys Leu Leu
    1070                1075                1080

Gly Pro  Leu Arg Thr Ala Gln  Lys Leu Leu Cys Arg  Lys Leu Pro
    1085                1090                1095

Glu Ala  Thr Met Thr Ile Leu  Lys Ala Ala Ala Asp  Pro Ala Leu
    1100                1105                1110

Ser Thr  Asp Phe Gln Thr Ile  Leu Asp
    1115                1120


<210> SEQ ID NO 11
<211> LENGTH: 729
<212> TYPE: PRT
<213> ORGANISM: Mus musculus

<400> SEQUENCE: 11

Met Arg Pro Leu Phe Gln Gln Leu Leu Val Asn His Ala Glu Cys Gln
1               5                   10                  15

Tyr Val Arg Leu Leu Arg Ser His Cys Arg Phe Arg Thr Ala Asn Gln
            20                  25                  30

Gln Val Thr Asp Ala Leu Asn Thr Ser Pro Pro His Leu Met Asp Leu
        35                  40                  45

Leu Arg Leu His Ser Ser Pro Trp Gln Val Tyr Gly Phe Leu Arg Ala
    50                  55                  60

Cys Leu Cys Lys Val Val Ser Ala Ser Leu Trp Gly Thr Arg His Asn
65                  70                  75                  80

Glu Arg Arg Phe Phe Lys Asn Leu Lys Lys Phe Ile Ser Leu Gly Lys
                85                  90                  95

Tyr Gly Lys Leu Ser Leu Gln Glu Leu Met Trp Lys Met Lys Val Glu
            100                 105                 110

Asp Cys His Trp Leu Arg Ser Ser Pro Gly Lys Asp Arg Val Pro Ala
        115                 120                 125

Ala Glu His Arg Leu Arg Glu Arg Ile Leu Ala Thr Phe Leu Phe Trp
    130                 135                 140

Leu Met Asp Thr Tyr Val Val Gln Leu Leu Arg Ser Phe Phe Tyr Ile
145                 150                 155                 160

Thr Glu Ser Thr Phe Gln Lys Asn Arg Leu Phe Phe Tyr Arg Lys Ser
                165                 170                 175

Val Trp Ser Lys Leu Gln Ser Ile Gly Val Arg Gln His Leu Glu Arg
            180                 185                 190

Val Arg Leu Arg Glu Leu Ser Gln Glu Glu Val Arg His His Gln Asp
```

-continued

```
        195                 200                 205

Thr Trp Leu Ala Met Pro Ile Cys Arg Leu Arg Phe Ile Pro Lys Pro
    210                 215                 220

Asn Gly Leu Arg Pro Ile Val Asn Met Ser Tyr Ser Met Gly Thr Arg
225                 230                 235                 240

Ala Leu Gly Arg Arg Lys Gln Ala Gln His Phe Thr Gln Arg Leu Lys
                245                 250                 255

Thr Leu Phe Ser Met Leu Asn Tyr Glu Arg Thr Lys His Pro His Leu
            260                 265                 270

Met Gly Ser Ser Val Leu Gly Met Asn Asp Ile Tyr Arg Thr Trp Arg
        275                 280                 285

Ala Phe Val Leu Arg Val Arg Ala Leu Asp Gln Thr Pro Arg Met Tyr
    290                 295                 300

Phe Val Lys Ala Asp Val Thr Gly Ala Tyr Asp Ala Ile Pro Gln Gly
305                 310                 315                 320

Lys Leu Val Glu Val Val Ala Asn Met Ile Arg His Ser Glu Ser Thr
                325                 330                 335

Tyr Cys Ile Arg Gln Tyr Ala Val Val Arg Arg Asp Ser Gln Gly Gln
            340                 345                 350

Val His Lys Ser Phe Arg Arg Gln Val Thr Thr Leu Ser Asp Leu Gln
        355                 360                 365

Pro Tyr Met Gly Gln Phe Leu Lys His Leu Gln Asp Ser Asp Ala Ser
    370                 375                 380

Ala Leu Arg Asn Ser Val Val Ile Glu Gln Ser Ile Ser Met Asn Glu
385                 390                 395                 400

Ser Ser Ser Ser Leu Phe Asp Phe Phe Leu His Phe Leu Arg His Ser
                405                 410                 415

Val Val Lys Ile Gly Asp Arg Cys Tyr Thr Gln Cys Gln Gly Ile Pro
            420                 425                 430

Gln Gly Ser Ser Leu Ser Thr Leu Leu Cys Ser Leu Cys Phe Gly Asp
        435                 440                 445

Met Glu Asn Lys Leu Phe Ala Glu Val Gln Arg Asp Gly Leu Leu Leu
    450                 455                 460

Arg Phe Val Asp Asp Phe Leu Leu Val Thr Pro His Leu Asp Gln Ala
465                 470                 475                 480

Lys Thr Phe Leu Ser Thr Leu Val His Gly Val Pro Glu Tyr Gly Cys
                485                 490                 495

Met Ile Asn Leu Gln Lys Thr Val Val Asn Phe Pro Val Glu Pro Gly
            500                 505                 510

Thr Leu Gly Gly Ala Ala Pro Tyr Gln Leu Pro Ala His Cys Leu Phe
        515                 520                 525

Pro Trp Cys Gly Leu Leu Leu Asp Thr Gln Thr Leu Glu Val Phe Cys
    530                 535                 540

Asp Tyr Ser Gly Tyr Ala Gln Thr Ser Ile Lys Thr Ser Leu Thr Phe
545                 550                 555                 560

Gln Ser Val Phe Lys Ala Gly Lys Thr Met Arg Asn Lys Leu Leu Ser
                565                 570                 575

Val Leu Arg Leu Lys Cys His Gly Leu Phe Leu Asp Leu Gln Val Asn
            580                 585                 590

Ser Leu Gln Thr Val Cys Ile Asn Ile Tyr Lys Ile Phe Leu Leu Gln
        595                 600                 605

Ala Tyr Arg Phe His Ala Cys Val Ile Gln Leu Pro Phe Asp Gln Arg
    610                 615                 620
```

```
Val Arg Lys Asn Leu Thr Phe Phe Leu Gly Ile Ile Ser Ser Gln Ala
625                 630                 635                 640

Ser Cys Cys Tyr Ala Ile Leu Lys Val Lys Asn Pro Gly Met Thr Leu
                645                 650                 655

Lys Ala Ser Gly Ser Phe Pro Pro Glu Ala Ala His Trp Leu Cys Tyr
            660                 665                 670

Gln Ala Phe Leu Leu Lys Leu Ala Ala His Ser Val Ile Tyr Lys Cys
        675                 680                 685

Leu Leu Gly Pro Leu Arg Thr Ala Gln Lys Leu Leu Cys Arg Lys Leu
    690                 695                 700

Pro Glu Ala Thr Met Thr Ile Leu Lys Ala Ala Ala Asp Pro Ala Leu
705                 710                 715                 720

Ser Thr Asp Phe Gln Thr Ile Leu Asp
                725


<210> SEQ ID NO 12
<211> LENGTH: 584
<212> TYPE: PRT
<213> ORGANISM: Mus musculus

<400> SEQUENCE: 12

Met Asp Thr Tyr Val Val Gln Leu Leu Arg Ser Phe Phe Tyr Ile Thr
1               5                   10                  15

Glu Ser Thr Phe Gln Lys Asn Arg Leu Phe Phe Tyr Arg Lys Ser Val
            20                  25                  30

Trp Ser Lys Leu Gln Ser Ile Gly Val Arg Gln His Leu Glu Arg Val
        35                  40                  45

Arg Leu Arg Glu Leu Ser Gln Glu Glu Val Arg His His Gln Asp Thr
    50                  55                  60

Trp Leu Ala Met Pro Ile Cys Arg Leu Arg Phe Ile Pro Lys Pro Asn
65                  70                  75                  80

Gly Leu Arg Pro Ile Val Asn Met Ser Tyr Ser Met Gly Thr Arg Ala
                85                  90                  95

Leu Gly Arg Arg Lys Gln Ala Gln His Phe Thr Gln Arg Leu Lys Thr
            100                 105                 110

Leu Phe Ser Met Leu Asn Tyr Glu Arg Thr Lys His Pro His Leu Met
        115                 120                 125

Gly Ser Ser Val Leu Gly Met Asn Asp Ile Tyr Arg Thr Trp Arg Ala
    130                 135                 140

Phe Val Leu Arg Val Arg Ala Leu Asp Gln Thr Pro Arg Met Tyr Phe
145                 150                 155                 160

Val Lys Ala Asp Val Thr Gly Ala Tyr Asp Ala Ile Pro Gln Gly Lys
                165                 170                 175

Leu Val Glu Val Val Ala Asn Met Ile Arg His Ser Glu Ser Thr Tyr
            180                 185                 190

Cys Ile Arg Gln Tyr Ala Val Val Arg Arg Asp Ser Gln Gly Gln Val
        195                 200                 205

His Lys Ser Phe Arg Arg Gln Val Thr Thr Leu Ser Asp Leu Gln Pro
    210                 215                 220

Tyr Met Gly Gln Phe Leu Lys His Leu Gln Asp Ser Asp Ala Ser Ala
225                 230                 235                 240

Leu Arg Asn Ser Val Val Ile Glu Gln Ser Ile Ser Met Asn Glu Ser
                245                 250                 255

Ser Ser Ser Leu Phe Asp Phe Phe Leu His Phe Leu Arg His Ser Val
```

```
            260                 265                 270

Val Lys Ile Gly Asp Arg Cys Tyr Thr Gln Cys Gln Gly Ile Pro Gln
        275                 280                 285

Gly Ser Ser Leu Ser Thr Leu Leu Cys Ser Leu Cys Phe Gly Asp Met
    290                 295                 300

Glu Asn Lys Leu Phe Ala Glu Val Gln Arg Asp Gly Leu Leu Leu Arg
305                 310                 315                 320

Phe Val Asp Asp Phe Leu Leu Val Thr Pro His Leu Asp Gln Ala Lys
                325                 330                 335

Thr Phe Leu Ser Thr Leu Val His Gly Val Pro Glu Tyr Gly Cys Met
            340                 345                 350

Ile Asn Leu Gln Lys Thr Val Val Asn Phe Pro Val Glu Pro Gly Thr
        355                 360                 365

Leu Gly Gly Ala Ala Pro Tyr Gln Leu Pro Ala His Cys Leu Phe Pro
    370                 375                 380

Trp Cys Gly Leu Leu Leu Asp Thr Gln Thr Leu Glu Val Phe Cys Asp
385                 390                 395                 400

Tyr Ser Gly Tyr Ala Gln Thr Ser Ile Lys Thr Ser Leu Thr Phe Gln
                405                 410                 415

Ser Val Phe Lys Ala Gly Lys Thr Met Arg Asn Lys Leu Leu Ser Val
            420                 425                 430

Leu Arg Leu Lys Cys His Gly Leu Phe Leu Asp Leu Gln Val Asn Ser
        435                 440                 445

Leu Gln Thr Val Cys Ile Asn Ile Tyr Lys Ile Phe Leu Leu Gln Ala
    450                 455                 460

Tyr Arg Phe His Ala Cys Val Ile Gln Leu Pro Phe Asp Gln Arg Val
465                 470                 475                 480

Arg Lys Asn Leu Thr Phe Phe Leu Gly Ile Ile Ser Ser Gln Ala Ser
                485                 490                 495

Cys Cys Tyr Ala Ile Leu Lys Val Lys Asn Pro Gly Met Thr Leu Lys
            500                 505                 510

Ala Ser Gly Ser Phe Pro Pro Glu Ala Ala His Trp Leu Cys Tyr Gln
        515                 520                 525

Ala Phe Leu Leu Lys Leu Ala Ala His Ser Val Ile Tyr Lys Cys Leu
    530                 535                 540

Leu Gly Pro Leu Arg Thr Ala Gln Lys Leu Leu Cys Arg Lys Leu Pro
545                 550                 555                 560

Glu Ala Thr Met Thr Ile Leu Lys Ala Ala Ala Asp Pro Ala Leu Ser
                565                 570                 575

Thr Asp Phe Gln Thr Ile Leu Asp
            580
```

<210> SEQ ID NO 13
<211> LENGTH: 1125
<212> TYPE: PRT
<213> ORGANISM: Rattus norvegicus

<400> SEQUENCE: 13

```
Met Pro Arg Ala Pro Arg Cys Pro Ala Val Arg Ser Leu Leu Arg Ser
1               5                   10                  15

Arg Tyr Arg Glu Val Trp Pro Leu Ala Thr Phe Val Arg Arg Leu Gly
            20                  25                  30

Leu Glu Gly Ser Arg Leu Val Gln Pro Gly Asp Pro Lys Val Phe Arg
        35                  40                  45
```

-continued

```
Thr Leu Val Ala Gln Cys Leu Val Cys Val Pro Trp Gly Ser Gln Pro
    50                  55                  60

Pro Pro Ala Asp Leu Ser Phe His Gln Val Ser Ser Leu Lys Glu Leu
65                  70                  75                  80

Val Ser Arg Val Val Gln Lys Leu Cys Glu Arg Gly Glu Arg Asn Val
                85                  90                  95

Leu Ala Phe Gly Phe Ala Leu Leu Asn Gly Ala Arg Gly Gly Pro Pro
            100                 105                 110

Met Ala Phe Thr Thr Ser Val His Ser Tyr Leu Pro Asn Ser Val Thr
        115                 120                 125

Glu Ser Leu Cys Val Ser Gly Ala Trp Met Leu Leu Leu Ser Arg Val
    130                 135                 140

Gly Asp Asp Leu Leu Val Tyr Leu Leu Ser His Cys Ala Leu Tyr Leu
145                 150                 155                 160

Leu Val Pro Pro Ser Cys Ala Tyr Gln Val Cys Gly Ser Pro Leu Tyr
                165                 170                 175

Gln Ile Cys Ala Thr Thr Asp Thr Trp Ser Ser Val Pro Ala Gly Tyr
            180                 185                 190

Arg Pro Thr Arg Pro Val Gly Gly Asn Phe Thr Asn Leu Gly Ser Ala
        195                 200                 205

His Gln Ile Lys Asn Ser Gly His Gln Glu Ala Pro Lys Pro Gln Ala
    210                 215                 220

Leu Pro Ser Arg Gly Thr Lys Arg Leu Leu Ser Leu Thr Ser Thr Asn
225                 230                 235                 240

Val Pro Ser Ala Lys Lys Ala Arg Phe Glu Pro Ala Leu Arg Val Asp
                245                 250                 255

Lys Gly Pro His Arg Gln Val Val Pro Thr Pro Ser Gly Lys Thr Trp
            260                 265                 270

Ala Pro Ser Pro Ala Ala Ser Pro Lys Val Pro Pro Ala Ala Lys Asn
        275                 280                 285

Leu Ser Leu Lys Gly Lys Ala Ser Asp Pro Ser Leu Ser Gly Ser Val
    290                 295                 300

Cys Cys Lys His Lys Pro Ser Ser Ser Ser Leu Leu Ser Ser Pro Pro
305                 310                 315                 320

Gln Asp Ala Glu Lys Leu Arg Pro Phe Thr Glu Thr Arg His Phe Leu
                325                 330                 335

Tyr Ser Arg Gly Gly Gly Gln Glu Glu Leu Asn Pro Ser Phe Leu Leu
            340                 345                 350

Asn Ser Leu Pro Pro Ser Leu Thr Gly Ala Arg Arg Leu Val Glu Ile
        355                 360                 365

Ile Phe Leu Gly Ser Arg Pro Arg Thr Ser Gly Pro Phe Cys Arg Thr
    370                 375                 380

Arg Arg Leu Pro Arg Arg Tyr Trp Gln Met Arg Pro Leu Phe Gln Gln
385                 390                 395                 400

Leu Leu Met Asn His Ala Lys Cys Gln Tyr Val Arg Phe Leu Arg Ser
                405                 410                 415

His Cys Arg Phe Arg Thr Ala Asn Gln Arg Val Pro Asp Ala Met Asp
            420                 425                 430

Thr Ser Pro Ser His Leu Thr Ser Leu Leu Arg Leu His Ser Ser Pro
        435                 440                 445

Trp Gln Val Tyr Gly Phe Leu Arg Ala Cys Leu Arg Glu Leu Val Pro
    450                 455                 460

Ala Gly Leu Trp Gly Thr Arg His Asn Glu Arg Arg Phe Leu Lys Asn
```

-continued 465 470 475 480

Val Lys Lys Phe Ile Ser Leu Gly Lys Tyr Ala Lys Leu Ser Leu Gln
485 490 495

Glu Leu Met Trp Arg Val Lys Val Glu Asp Cys His Trp Leu Arg Ser
500 505 510

Ser Pro Glu Lys Asp Thr Val Pro Ala Ala Glu His Arg Leu Arg Glu
515 520 525

Arg Ile Leu Ala Met Phe Leu Phe Trp Leu Met Asp Thr Tyr Val Val
530 535 540

Gln Leu Leu Arg Ser Phe Phe Tyr Ile Thr Glu Thr Thr Phe Gln Lys
545 550 555 560

Asn Arg Leu Phe Phe Tyr Arg Lys Ser Val Trp Ser Lys Leu Gln Ser
565 570 575

Ile Gly Ile Arg Gln Gln Leu Glu Arg Val Gln Leu Arg Glu Leu Ser
580 585 590

Gln Glu Glu Val Lys His His Gln Asp Thr Trp Leu Ala Met Pro Ile
595 600 605

Cys Arg Leu Arg Phe Ile Pro Lys Leu Asn Gly Leu Arg Pro Ile Val
610 615 620

Asn Met Ser Tyr Gly Met Asp Thr Arg Ala Phe Gly Lys Lys Lys Gln
625 630 635 640

Thr Gln Cys Phe Thr Gln Ser Leu Lys Thr Leu Phe Ser Val Leu Asn
645 650 655

Tyr Glu Arg Thr Lys His Pro Asn Leu Met Gly Ala Ser Val Leu Gly
660 665 670

Thr Ser Asp Ser Tyr Arg Ile Trp Arg Thr Phe Val Leu Arg Val Arg
675 680 685

Ala Leu Asp Gln Thr Pro Arg Met Tyr Phe Val Lys Ala Asp Val Thr
690 695 700

Gly Ala Tyr Asp Ala Ile Pro Gln Asp Lys Leu Val Glu Ile Val Ala
705 710 715 720

Asn Ile Ile Arg Arg Ser Glu Ser Met Tyr Cys Ile Arg Gln Tyr Ala
725 730 735

Val Val Gln Lys Asp Ser Gln Gly Gln Val His Lys Ser Phe Arg Arg
740 745 750

Gln Val Ser Thr Leu Ser Asp Leu Gln Pro Tyr Met Gly Gln Phe Thr
755 760 765

Lys His Leu Gln Asp Ser Asp Ala Ser Ala Leu Arg Asn Ser Val Val
770 775 780

Ile Glu Gln Ser Ile Ser Met Asn Glu Thr Gly Ser Ser Leu Leu His
785 790 795 800

Phe Phe Leu Arg Phe Val Arg His Ser Val Val Lys Ile Asp Gly Arg
805 810 815

Phe Tyr Val Gln Cys Gln Gly Ile Pro Gln Gly Ser Ser Leu Ser Thr
820 825 830

Leu Leu Cys Ser Leu Cys Phe Gly Asp Met Glu Asn Lys Leu Phe Ala
835 840 845

Glu Val Gln Gln Asp Gly Leu Leu Leu Arg Phe Val Asp Asp Phe Leu
850 855 860

Leu Val Thr Pro His Leu Ala His Ala Lys Ala Phe Leu Ser Thr Leu
865 870 875 880

Val His Gly Val Pro Glu Tyr Gly Cys Met Ile Asn Leu Gln Lys Thr
885 890 895

```
Val Val Asn Phe Pro Val Glu Thr Gly Ala Leu Gly Gly Ala Ala Pro
            900                 905                 910

His Gln Leu Pro Ala His Cys Leu Phe Pro Trp Cys Gly Leu Leu Leu
        915                 920                 925

Asp Thr Arg Thr Leu Glu Val Phe Cys Asp Tyr Ser Gly Tyr Gly Arg
    930                 935                 940

Thr Ser Ile Lys Met Ser Leu Thr Phe Gln Gly Val Ser Arg Ala Gly
945                 950                 955                 960

Lys Thr Met Arg Tyr Lys Leu Leu Ser Val Leu Arg Leu Lys Cys His
                965                 970                 975

Gly Leu Phe Leu Asp Leu Gln Val Asn Ser Leu Gln Thr Val Cys Ile
            980                 985                 990

Asn Ile Tyr Lys Ile Phe Leu Leu  Gln Ala Tyr Arg Phe  His Ala Cys
        995                 1000                1005

Val Ile  Arg Leu Pro Phe Gly  Gln His Val Arg Lys  Asn His Ala
    1010                 1015                1020

Phe Phe  Leu Gly Ile Ile Ser  Asn Leu Ala Ser Cys  Cys Tyr Ala
    1025                 1030                1035

Ile Leu  Lys Val Lys Asn Pro  Gly Val Ser Leu Arg  Ala Lys Gly
    1040                 1045                1050

Ala Pro  Gly Ser Phe Pro Pro  Glu Ala Thr Arg Trp  Leu Cys Tyr
    1055                 1060                1065

Gln Ala  Phe Leu Leu Lys Leu  Ala Ala His Ser Val  Thr Tyr Lys
    1070                 1075                1080

Cys Leu  Leu Gly Pro Leu Arg  Thr Ala Gln Lys Gln  Leu Cys Arg
    1085                 1090                1095

Lys Leu  Pro Glu Ala Thr Met  Thr Leu Leu Lys Thr  Ala Ala Asp
    1100                 1105                1110

Pro Ala  Leu Ser Thr Asp Phe  Gln Thr Ile Leu Asp
    1115                 1120                1125
```

<210> SEQ ID NO 14
<211> LENGTH: 4335
<212> TYPE: DNA
<213> ORGANISM: Mus musculus

<400> SEQUENCE: 14

```
gttcccagcc tcatcttttt cgtcgtggac tctcagtggc ctgggtcctg gctgttttct      60

aagcacaccc ttgcatcttg gttcccgcac gtgggaggcc catcccggcc ttgagcacaa     120

tgacccgcgc tcctcgttgc cccgcggtgc gctctctgct gcgcagccga taccgggagg     180

tgtggccgct ggcaaccttt gtgcggcgcc tggggcccga gggcaggcgg cttgtgcaac     240

ccggggaccc gaagatctac cgcactttgg ttgcccaatg cctagtgtgc atgcactggg     300

gctcacagcc tccacctgcc gacctttcct tccaccaggt gtcatccctg aaagagctgg     360

tggccagggt tgtgcagaga ctctgcgagc gcaacgagag aaacgtgctg gcttttggct     420

ttgagctgct taacgaggcc agaggcgggc ctcccatggc cttcactagt agcgtgcgta     480

gctacttgcc caacactgtt attgagaccc tgcgtgtcag tggtgcatgg atgctactgt     540

tgagccgagt gggcgacgac ctgctggtct acctgctggc acactgtgct ctttatcttc     600

tggtgccccc cagctgtgcc taccaggtgt gtgggtctcc cctgtaccaa atttgtgcca     660

ccacggatat ctggccctct gtgtccgcta gttacaggcc cacccgaccc gtgggcagga     720

atttcactaa ccttaggttc ttacaacaga tcaagagcag tagtcgccag gaagcaccga     780
```

-continued aacccctggc cttgccatct cgaggtacaa agaggcatct gagtctcacc agtacaagtg 840
tgccttcagc taagaaggcc agatgctatc ctgtcccgag agtggaggag ggaccccaca 900
ggcaggtgct accaacccca tcaggcaaat catgggtgcc aagtcctgct cggtcccccg 960
aggtgcctac tgcagagaaa gatttgtctt ctaaaggaaa ggtgtctgac ctgagtctct 1020
ctgggtcggt gtgctgtaaa cacaagccca gctccacatc tctgctgtca ccaccccgcc 1080
aaaatgcctt tcagctcagg ccatttattg agaccagaca tttcctttac tccaggggag 1140
atggccaaga gcgtctaaac ccctcattcc tactcagcaa cctccagcct aacttgactg 1200
gggccaggag actggtggag atcatctttc tgggctcaag gcctaggaca tcaggaccac 1260
tctgcaggac acaccgtcta tcgcgtcgat actggcagat gcggcccctg ttccaacagc 1320
tgctggtgaa ccatgcagag tgccaatatg tcagactcct caggtcacat tgcaggtttc 1380
gaacagcaaa ccaacaggtg acagatgcct tgaacaccag cccaccgcac ctcatggatt 1440
tgctccgcct gcacagcagt ccctggcagg tatatggttt tcttcgggcc tgtctctgca 1500
aggtggtgtc tgctagtctc tggggtacca ggcacaatga gcgccgcttc tttaagaact 1560
taaagaagtt catctcgttg gggaaatacg gcaagctatc actgcaggaa ctgatgtgga 1620
agatgaaagt agaggattgc cactggctcc gcagcagccc ggggaaggac cgtgtccccg 1680
ctgcagagca ccgtctgagg gagaggatcc tggctacgtt cctgttctgg ctgatggaca 1740
catacgtggt acagctgctt aggtcattct tttacatcac agagagcaca ttccagaaga 1800
acaggctctt cttctaccgt aagagtgtgt ggagcaagct gcagagcatt ggagtcaggc 1860
aacaccttga gagagtgcgg ctacgggagc tgtcacaaga ggaggtcagg catcaccagg 1920
acacctggct agccatgccc atctgcagac tgcgcttcat ccccaagccc aacggcctgc 1980
ggcccattgt gaacatgagt tatagcatgg gtaccagagc tttgggcaga aggaagcagg 2040
cccagcattt cacccagcgt ctcaagactc tcttcagcat gctcaactat gagcggacaa 2100
aacatcctca ccttatgggg tcttctgtac tgggtatgaa tgacatctac aggacctggc 2160
gggcctttgt gctgcgtgtg cgtgctctgg accagacacc caggatgtac tttgttaagg 2220
cagatgtgac cggggcctat gatgccatcc cccagggtaa gctggtggag gttgttgcca 2280
atatgatcag gcactcggag agcacgtact gtatccgcca gtatgcagtg gtccggagag 2340
atagccaagg ccaagtccac aagtccttta ggagacaggt caccaccctc tctgacctcc 2400
agccatacat gggccagttc cttaagcatc tgcaggattc agatgccagt gcactgagga 2460
actccgttgt catcgagcag agcatctcta tgaatgagag cagcagcagc ctgtttgact 2520
tcttcctgca cttcctgcgt cacagtgtcg taaagattgg tgacaggtgc tatacgcagt 2580
gccagggcat cccccagggc tccagcctat ccaccctgct ctgcagtctg tgtttcggag 2640
acatggagaa caagctgttt gctgaggtgc agcgggatgg gttgctttta cgttttgttg 2700
atgactttct gttggtgacg cctcacttgg accaagcaaa aaccttcctc agcaccctgg 2760
tccatggcgt tcctgagtat gggtgcatga taaacttgca gaagacagtg gtgaacttcc 2820
ctgtggagcc tggtaccctg ggtggtgcag ctccatacca gctgcctgct cactgcctgt 2880
ttccctggtg tggcttgctg ctggacactc agactttgga ggtgttctgt gactactcag 2940
gttatgccca gacctcaatt aagacgagcc tcaccttcca gagtgtcttc aaagctggga 3000
agaccatgcg gaacaagctc ctgtcggtct tgcggttgaa gtgtcacggt ctatttctag 3060
acttgcaggt gaacagcctc cagacagtct gcatcaatat atacaagatc ttcctgcttc 3120

-continued

```
aggcctacag gttccatgca tgtgtgattc agcttccctt tgaccagcgt gttaggaaga   3180
acctcacatt ctttctgggc atcatctcca gccaagcatc ctgctgctat gctatcctga   3240
aggtcaagaa tccaggaatg acactaaagg cctctggctc ctttcctcct gaagccgcac   3300
attggctctg ctaccaggcc ttcctgctca agctggctgc tcattctgtc atctacaaat   3360
gtctcctggg acctctgagg acagcccaaa aactgctgtg ccggaagctc ccagaggcga   3420
caatgaccat ccttaaagct gcagctgacc cagccctaag cacagacttt cagaccattt   3480
tggactaacc ctgtctcctt ccgctagatg aacatgggca ttgtagcctc agcactcctg   3540
gatccacgtc acaagaggga ctggtcagtt gtgaggctag gtcatcctcc aaacctctgt   3600
gtcatgggtg gtatgggaga ttgtcccagt gccttgtttc ctgtaacagg cttgatttct   3660
ttcctgatgc cctcagggag gcagatccta tccctttttag tggcagggat ccactagcac   3720
cagcacatga ggagtgcacc cagtgcacat gggcactggg acagtggaca ggtgtgagat   3780
tcctgggccc tggagtcttt tcacacctaa ccatggagcc tgtcccagta catcagagtg   3840
cctcggagat gaaaaaggac atcgagccag tgacctaaat tacagcctga atatactctg   3900
aattcatgtg actgccttag ctacttctct actgctgtgt agtaaaacac caagccaact   3960
tataaaagca ggattttcct actggagcag cagctgagag tttacatctt gatccataag   4020
cacaaaagca caagacagag agagagagag agagagagag agagagagag agagagagag   4080
agagagagag agagagtcag tcagtcagtc taacaaataa ctaagaaagg tgaagggtga   4140
tgaagtccac agggatcacg ctagggatgt tccatgcctt ctctgaagct aagattcctt   4200
ggcagcgttt gacagtaacc atagtgggta cctactgaga tcactataaa gataaaatag   4260
ggggaagcgt atttgtactg aactggaaaa acatacaaat aaagagtaaa tcatggaaaa   4320
aaaaaaaaaa aaaaa                                                     4335
```

<210> SEQ ID NO 15
<211> LENGTH: 3826
<212> TYPE: DNA
<213> ORGANISM: Mus musculus

<400> SEQUENCE: 15

```
gttcccagcc tcatcttttt cgtcgtggac tctcagtggc ctgggtcctg gctgttttct     60
aagcacaccc ttgcatcttg gttcccgcac gtgggaggcc catcccggcc ttgagcacaa    120
tgacccgcgc tcctcgttgc cccgcggtgc gctctctgct gcgcagccga taccgggagg    180
tgtggccgct ggcaaccttt gtgcggcgcc tggggcccga gggcaggcgg cttgtgcaac    240
ccggggaccc gaagatctac cgcactttgg ttgcccaatg cctagtgtgc atgcactggg    300
gctcacagcc tccacctgcc gacctttcct tccaccaggt gtcatccctg aaagagctgg    360
tggccagggt tgtgcagaga ctctgcgagc gcaacgagag aaacgtgctg gcttttggct    420
ttgagctgct taacgaggcc agaggcgggc ctcccatggc cttcactagt agcgtgcgta    480
gctacttgcc caacactgtt attgagaccc tgcgtgtcag tggtgcatgg atgctactgt    540
tgagccgagt gggcgacgac ctgctggtct acctgctggc acactgtgct ctttatcttc    600
tggtgccccc cagctgtgcc taccagggga gatggccaag agcgtctaaa cccctcattc    660
ctactcagca acctccagcc taacttgact ggggccagga gactggtgga gatcatcttt    720
ctgggctcaa ggcctaggac atcaggacca ctctgcagga cacaccgtct atcgcgtcga    780
tactggcaga tgcggcccct gttccaacag ctgctggtga accatgcaga gtgccaatat    840
gtcagactcc tcaggtcaca ttgcaggttt cgaacagcaa accaacaggt gacagatgcc    900
```

ttgaacacca gcccaccgca cctcatggat ttgctccgcc tgcacagcag tccctggcag 960
gtatatggtt ttcttcgggc ctgtctctgc aaggtggtgt ctgctagtct ctggggtacc 1020
aggcacaatg agcgccgctt ctttaagaac ttaaagaagt tcatctcgtt ggggaaatac 1080
ggcaagctat cactgcagga actgatgtgg aagatgaaag tagaggattg ccactggctc 1140
cgcagcagcc cggggaagga ccgtgtcccc gctgcagagc accgtctgag ggagaggatc 1200
ctggctacgt tcctgttctg gctgatggac acatacgtgg tacagctgct taggtcattc 1260
ttttacatca cagagagcac attccagaag aacaggctct tcttctaccg taagagtgtg 1320
tggagcaagc tgcagagcat tggagtcagg caacaccttg agagagtgcg gctacgggag 1380
ctgtcacaag aggaggtcag gcatcaccag gacacctggc tagccatgcc catctgcaga 1440
ctgcgcttca tccccaagcc caacggcctg cggcccattg tgaacatgag ttatagcatg 1500
ggtaccagag ctttgggcag aaggaagcag gcccagcatt tcacccagcg tctcaagact 1560
ctcttcagca tgctcaacta tgagcggaca aaacatcctc accttatggg gtcttctgta 1620
ctgggtatga atgacatcta caggacctgg cgggcctttg tgctgcgtgt gcgtgctctg 1680
gaccagacac ccaggatgta ctttgttaag gcagatgtga ccggggccta tgatgccatc 1740
ccccagggta agctggtgga ggttgttgcc aatatgatca ggcactcgga gagcacgtac 1800
tgtatccgcc agtatgcagt ggtccggaga gatagccaag gccaagtcca caagtccttt 1860
aggagacagg tcaccaccct ctctgacctc cagccataca tgggccagtt ccttaagcat 1920
ctgcaggatt cagatgccag tgcactgagg aactccgttg tcatcgagca gagcatctct 1980
atgaatgaga gcagcagcag cctgtttgac ttcttcctgc acttcctgcg tcacagtgtc 2040
gtaaagattg gtgacaggtg ctatacgcag tgccagggca tcccccaggg ctccagccta 2100
tccaccctgc tctgcagtct gtgtttcgga gacatggaga acaagctgtt tgctgaggtg 2160
cagcgggatg ggttgctttt acgttttgtt gatgactttc tgttggtgac gcctcacttg 2220
gaccaagcaa aaaccttcct cagcaccctg gtccatggcg ttcctgagta tgggtgcatg 2280
ataaacttgc agaagacagt ggtgaacttc cctgtggagc ctggtaccct gggtggtgca 2340
gctccatacc agctgcctgc tcactgcctg tttccctggt gtggcttgct gctggacact 2400
cagactttgg aggtgttctg tgactactca ggttatgccc agacctcaat taagacgagc 2460
ctcaccttcc agagtgtctt caaagctggg aagaccatgc ggaacaagct cctgtcggtc 2520
ttgcggttga agtgtcacgg tctatttcta gacttgcagg tgaacagcct ccagacagtc 2580
tgcatcaata tatacaagat cttcctgctt caggcctaca ggttccatgc atgtgtgatt 2640
cagcttccct ttgaccagcg tgttaggaag aacctcacat tctttctggg catcatctcc 2700
agccaagcat cctgctgcta tgctatcctg aaggtcaaga atccaggaat gacactaaag 2760
gcctctggct cctttcctcc tgaagccgca cattggctct gctaccaggc cttcctgctc 2820
aagctggctg ctcattctgt catctacaaa tgtctcctgg gacctctgag gacagcccaa 2880
aaactgctgt gccggaagct cccagaggcg acaatgacca tccttaaagc tgcagctgac 2940
ccagccctaa gcacagactt tcagaccatt ttggactaac cctgtctcct tccgctagat 3000
gaacatgggc attgtagcct cagcactcct ggatccacgt cacaagaggg actggtcagt 3060
tgtgaggcta ggtcatcctc caaacctctg tgtcatgggt ggtatgggag attgtcccag 3120
tgccttgttt cctgtaacag gcttgatttc tttcctgatg ccctcaggga ggcagatcct 3180
atccctttta gtggcaggga tccactagca ccagcacatg aggagtgcac ccagtgcaca 3240

-continued

```
tgggcactgg gacagtggac aggtgtgaga ttcctgggcc ctggagtctt ttcacaccta   3300

accatggagc ctgtcccagt acatcagagt gcctcggaga tgaaaaagga catcgagcca   3360

gtgacctaaa ttacagcctg aatatactct gaattcatgt gactgcctta gctacttctc   3420

tactgctgtg tagtaaaaca ccaagccaac ttataaaagc aggattttcc tactggagca   3480

gcagctgaga gtttacatct tgatccataa gcacaaaagc acaagacaga gagagagaga   3540

gagagagaga gagagagaga gagagagaga gagagagaga gagagagtca gtcagtcagt   3600

ctaacaaata actaagaaag gtgaagggtg atgaagtcca cagggatcac gctagggatg   3660

ttccatgcct tctctgaagc taagattcct tggcagcgtt tgacagtaac catagtgggt   3720

acctactgag atcactataa agataaaata gggggaagcg tatttgtact gaactggaaa   3780

aacatacaaa taaagagtaa atcatggaaa aaaaaaaaaa aaaaaa                 3826
```

<210> SEQ ID NO 16
<211> LENGTH: 3633
<212> TYPE: DNA
<213> ORGANISM: Mus musculus

<400> SEQUENCE: 16

```
gttcccagcc tcatcttttt cgtcgtggac tctcagtggc ctgggtcctg gctgttttct     60

aagcacaccc ttgcatcttg gttcccgcac gtgggaggcc catcccggcc ttgagcacaa    120

tgacccgcgc tcctcgttgc cccgcggtgc gctctctgct gcgcagccga taccgggagg    180

tgtggccgct ggcaaccttt gtgcggcgcc tggggcccga gggcaggcgg cttgtgcaac    240

ccggggaccc gaagatctac cgcactttgg ttgcccaatg cctagtgtgc atgcactggg    300

gctcacagcc tccacctgcc gacctttcct tccaccaggt gtcatccctg aaagagctgg    360

tggccagggt tgtgcagaga ctctgcgagc gcaacgagag aaacgtgctg gcttttggct    420

ttgagctgct taacgaggcc agaggcgggc ctcccatggc cttcactagt agcgtgcgta    480

gctacttgcc caacactgtt attgagaccc tgcgtgtcag tggtgcatgg atgctactgt    540

tgagccgagt gggcgacgac ctgctggtct acctgctggc acactgtgct ctttatcttc    600

tggtgccccc cagctgtgcc taccagggga gatggccaag agcgtctaaa cccctcattc    660

ctactcagca acctccagcc taacttgact ggggccagga gactggtgga gatcatcttt    720

ctgggctcaa ggcctaggac atcaggacca ctctgcagga cacaccgtct atcgcgtcga    780

tactggcaga tgcggcccct gttccaacag ctgctggtga accatgcaga gtgccaatat    840

gtcagactcc tcaggtcaca ttgcaggttt cgaacagcaa accaacaggt gacagatgcc    900

ttgaacacca gcccaccgca cctcatggat ttgctccgcc tgcacagcag tccctggcag    960

ggaaggaccg tgtccccgct gcagagcacc gtctgaggga gaggatcctg gctacgttcc   1020

tgttctggct gatggacaca tacgtggtac agctgcttag gtcattcttt tacatcacag   1080

agagcacatt ccagaagaac aggctcttct tctaccgtaa gagtgtgtgg agcaagctgc   1140

agagcattgg agtcaggcaa caccttgaga gagtgcggct acgggagctg tcacaagagg   1200

aggtcaggca tcaccaggac acctggctag ccatgcccat ctgcagactg cgcttcatcc   1260

ccaagcccaa cggcctgcgg cccattgtga acatgagtta tagcatgggt accagagctt   1320

tgggcagaag gaagcaggcc cagcatttca cccagcgtct caagactctc ttcagcatgc   1380

tcaactatga gcggacaaaa catcctcacc ttatggggtc ttctgtactg ggtatgaatg   1440

acatctacag gacctggcgg gcctttgtgc tgcgtgtgcg tgctctggac cagacaccca   1500

ggatgtactt tgttaaggca gatgtgaccg gggcctatga tgccatcccc cagggtaagc   1560
```

-continued

```
tggtggaggt tgttgccaat atgatcaggc actcggagag cacgtactgt atccgccagt   1620

atgcagtggt ccggagagat agccaaggcc aagtccacaa gtcctttagg agacaggtca   1680

ccaccctctc tgacctccag ccatacatgg gccagttcct taagcatctg caggattcag   1740

atgccagtgc actgaggaac tccgttgtca tcgagcagag catctctatg aatgagagca   1800

gcagcagcct gtttgacttc ttcctgcact tcctgcgtca cagtgtcgta aagattggtg   1860

acaggtgcta tacgcagtgc cagggcatcc cccagggctc cagcctatcc accctgctct   1920

gcagtctgtg tttcggagac atggagaaca agctgtttgc tgaggtgcag cgggatgggt   1980

tgcttttacg ttttgttgat gactttctgt tggtgacgcc tcacttggac caagcaaaaa   2040

ccttcctcag caccctggtc catggcgttc ctgagtatgg gtgcatgata aacttgcaga   2100

agacagtggt gaacttccct gtggagcctg gtaccctggg tggtgcagct ccataccagc   2160

tgcctgctca ctgcctgttt ccctggtgtg gcttgctgct ggacactcag actttggagg   2220

tgttctgtga ctactcaggt tatgcccaga cctcaattaa gacgagcctc accttccaga   2280

gtgtcttcaa agctgggaag accatgcgga acaagctcct gtcggtcttg cggttgaagt   2340

gtcacggtct atttctagac ttgcaggtga acagcctcca gacagtctgc atcaatatat   2400

acaagatctt cctgcttcag gcctacaggt tccatgcatg tgtgattcag cttccctttg   2460

accagcgtgt taggaagaac ctcacattct ttctgggcat catctccagc caagcatcct   2520

gctgctatgc tatcctgaag gtcaagaatc caggaatgac actaaaggcc tctggctcct   2580

ttcctcctga agccgcacat tggctctgct accaggcctt cctgctcaag ctggctgctc   2640

attctgtcat ctacaaatgt ctcctgggac ctctgaggac agcccaaaaa ctgctgtgcc   2700

ggaagctccc agaggcgaca atgaccatcc ttaaagctgc agctgaccca gccctaagca   2760

cagactttca gaccattttg gactaaccct gtctccttcc gctagatgaa catgggcatt   2820

gtagcctcag cactcctgga tccacgtcac aagagggact ggtcagttgt gaggctaggt   2880

catcctccaa acctctgtgt catgggtggt atgggagatt gtcccagtgc cttgtttcct   2940

gtaacaggct tgatttcttt cctgatgccc tcagggaggc agatcctatc ccttttagtg   3000

gcagggatcc actagcacca gcacatgagg agtgcaccca gtgcacatgg gcactgggac   3060

agtggacagg tgtgagattc ctgggccctg gagtcttttc acacctaacc atggagcctg   3120

tcccagtaca tcagagtgcc tcggagatga aaaaggacat cgagccagtg acctaaatta   3180

cagcctgaat atactctgaa ttcatgtgac tgccttagct acttctctac tgctgtgtag   3240

taaaacacca agccaactta taaaagcagg attttcctac tggagcagca gctgagagtt   3300

tacatcttga tccataagca caaaagcaca agacagagag agagagagag agagagagag   3360

agagagagag agagagagag agagagagag agagtcagtc agtcagtcta acaaataact   3420

aagaaaggtg aagggtgatg aagtccacag ggatcacgct agggatgttc catgccttct   3480

ctgaagctaa gattccttgg cagcgtttga cagtaaccat agtgggtacc tactgagatc   3540

actataaaga taaaataggg ggaagcgtat ttgtactgaa ctggaaaaac atacaaataa   3600

agagtaaatc atggaaaaaa aaaaaaaaaa aaa                                3633
```

<210> SEQ ID NO 17
<211> LENGTH: 3378
<212> TYPE: DNA
<213> ORGANISM: Rattus norvegicus

<400> SEQUENCE: 17

-continued

```
atgccccgcg ctcctcgttg ccccgccgtg cgctctctac tgcgcagccg atatcgggag     60
gtgtggccgc tggcgacctt tgtgcggcgc ctggggcttg agggcagtcg gcttgtgcaa    120
cccggggacc cgaaggtctt ccgcacgttg gttgcccagt gcctagtgtg cgtgccctgg    180
ggctcacagc cgccacctgc tgacctttcc ttccaccagg tgtcatccct gaaagagctg    240
gtgtccaggg ttgtgcagaa actttgcgag cgcggtgaga ggaatgtgct ggcttttggc    300
tttgcactgc ttaacggggc cagaggtggg cctcccatgg ccttcacgac cagcgtgcat    360
agctacttgc ccaactcggt tactgagtcc ctgtgtgtca gtggtgcatg gatgctactg    420
ttgagccgag tgggcgacga cctgctggtc tacctgctgt cgcactgtgc gctctacctg    480
ctggtgcccc ccagctgtgc ctaccaggtg tgcgggtcac ccctgtacca aatttgtgcc    540
accacggata cctggtcctc tgtgcccgct ggttacaggc ccactcgacc cgtgggcggg    600
aatttcacta accttgggtc cgcacaccag atcaaaaaca gtggtcacca ggaagcacca    660
aaaccccagg ccttgccatc acgaggtacg aagaggcttc tgagtctcac cagtacaaac    720
gtgccttcag ctaagaaggc caggtttgaa cctgccctga gagtggataa gggaccccac    780
aggcaggtgg taccaacccc atcaggcaaa acatgggcgc caagtcctgc tgcgtccccc    840
aaggtgcctc ctgcagcgaa aaacttgtct ttgaaaggaa aggcatctga cccgagtctc    900
tctgggtcgg tgtgctgtaa acacaagccc agctcctcgt ccctgctgtc atcaccaccc    960
caagatgctg aaaagctcag gccattcact gagaccagac atttccttta ctccagggga   1020
ggtggccaag aggagctaaa tccctcattc ctactcaaca gcctcccgcc tagcttgacc   1080
ggggccagga gactggtgga gatcatcttt ctgggctcaa ggcctaggac atcaggacca   1140
ttctgcagga cccgccgcct gccccgtcga tactggcaga tgcgacccct attccagcag   1200
ctgctcatga accacgcaaa gtgccaatat gtcagattcc tccggtcgca ctgcagattt   1260
cgaacagcaa accagcgggt gccggatgcc atggacacca gcccatccca cctcacgagt   1320
ttgctccggt tacacagcag cccctggcag gtatacggct ttcttcgggc ctgcctccgc   1380
gagctggtgc ctgccggtct ctggggcacc aggcacaatg agcgccgctt cttaaagaac   1440
gtgaagaagt tcatctcgtt ggggaagtac gccaagctat ccctgcagga actgatgtgg   1500
agggtgaaag tggaggactg ccactggctc cgcagcagcc cagagaagga cactgtccct   1560
gccgcagagc accgtctgag ggagaggatc cttgccatgt tcctgttctg gctaatggac   1620
acatatgtgg tacagctgct gaggtcattc ttctacatca cagagaccac gttccagaag   1680
aaccgccttt tcttctaccg taagagtgtg tggagcaagc tgcagagcat tggaatcagg   1740
caacagcttg agagagttca gctacgggaa ctgtcacaag aggaggtcaa gcatcaccag   1800
gacacttggc tggccatgcc tatctgcaga ttgcgcttca tccccaagct caatggtctc   1860
cggcccattg tgaacatgag ttatggcatg gacaccagag cttttggcaa aaagaagcag   1920
acccagtgtt tcactcagag tctcaagact ttgttcagcg tgctcaacta cgagcggacc   1980
aaacatccta accttatggg tgcttcagta ctgggtacga gtgacagcta caggatctgg   2040
cggaccttcg tgctgcgtgt gcgtgctctg gaccagacac ccaggatgta ctttgttaag   2100
gcagatgtga caggggccta tgatgccatc cccaggaca agctcgtgga aattgtcgcc   2160
aatataatca ggcgctcaga gagcatgtac tgtatccgcc agtatgcagt ggttcagaaa   2220
gatagccaag gccaagtcca caagtccttc aggagacagg tctccaccct ctctgacctc   2280
cagccataca tgggccagtt caccaagcat ctgcaggact cagatgccag tgcactgagg   2340
aactctgttg tcatcgagca gagcatctcc atgaatgaga ctggcagtag cctgctccac   2400
```

-continued

```
ttcttcctgc gctttgtccg tcacagtgtc gtgaagatcg atggcaggtt ctatgtgcaa   2460

tgccagggca tcccccaggg ctccagcctg tccaccctgc tctgcagtct gtgtttcgga   2520

gacatggaga acaagctgtt tgccgaggtg cagcaggacg gcttgctttt acgttttgtc   2580

gatgactttc tgttggtgac acctcacctg gcccatgcaa aagcctttct cagcaccctg   2640

gtccatggcg tgcccgagta tggctgcatg ataaacttgc agaagacagt ggtgaacttc   2700

cctgtggaga ccggcgccct gggaggtgca gccccgcacc agctgcctgc tcactgcctg   2760

tttccctggt gtggcttact gctggacact cggactttgg aagtattctg tgactactca   2820

ggttacggac ggacctcaat taagatgagc ctcaccttcc agggtgtctc cagggccggg   2880

aagaccatgc ggtacaagct cttgtcagtc ttgcggttga agtgtcatgg tctgtttcta   2940

gacttgcagg tgaacagcct gcagacagtc tgcatcaata tatacaagat cttcctgctt   3000

caggcctaca ggttccatgc atgtgtgatt cggcttccct ttggccagca tgttaggaag   3060

aaccatgcat tctttctggg catcatctcc aacctagcat cctgctgcta cgccatcctg   3120

aaggtcaaga atccaggagt gtcactaagg gccaagggtg cccctggctc ctttccgccc   3180

gaggccacac gttggctctg ctaccaagcc ttcctgctca agctggctgc tcattctgtc   3240

acctacaagt gtctcctggg acctcttagg acagcccaaa aacagctgtg ccggaagctc   3300

ccagaggcaa caatgaccct ccttaagact gcagctgacc cagccctaag cacagatttt   3360

cagaccattt tggactaa                                                 3378
```

```
<210> SEQ ID NO 18
<211> LENGTH: 1132
<212> TYPE: PRT
<213> ORGANISM: Pan troglodytes

<400> SEQUENCE: 18

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190
```

-continued

```
Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Ser
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Gln Glu Ala Arg Pro Ala Leu Leu Thr Ser Arg Leu Arg Phe Ile
```

-continued

```
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Ile Ile Glu Gln Ser Ser Ser Leu Asn Glu
785                 790                 795                 800

Ala Ser Ser Gly Leu Phe Asp Val Phe Leu Arg Phe Val Cys Arg His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Ala Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

Ala Leu Gly Gly Thr Ala Phe Val Gln Leu Pro Ala His Gly Leu Phe
        915                 920                 925

Pro Trp Cys Gly Leu Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn  Ile Tyr Lys Ile Leu  Leu Leu Gln
        995                 1000                1005

Ala Tyr  Arg Phe His Ala Cys  Val Leu Gln Leu Pro  Phe His Gln
    1010                1015                1020

Gln Val  Trp Lys Asn Pro Thr  Phe Phe Leu Arg Ile  Ile Ser Asp
    1025                1030                1035
```

```
Thr Ala  Ser Leu Cys Tyr Ser  Ile Leu Lys Ala Lys  Asn Ala Gly
    1040                 1045                 1050

Met Ser  Leu Gly Ala Lys Gly  Ala Ala Gly Pro Leu  Pro Ser Glu
    1055                 1060                 1065

Ala Met  Gln Trp Leu Cys His  Gln Ala Phe Leu Leu  Lys Leu Thr
    1070                 1075                 1080

Arg His  Arg Val Thr Tyr Val  Pro Leu Leu Gly Ser  Leu Arg Thr
    1085                 1090                 1095

Ala Gln  Thr Gln Leu Ser Arg  Lys Leu Pro Gly Thr  Thr Leu Ser
    1100                 1105                 1110

Ala Leu  Glu Ala Ala Ala Asn  Pro Ala Leu Pro Ser  Asp Phe Lys
    1115                 1120                 1125

Thr Ile  Leu Asp
    1130


<210> SEQ ID NO 19
<211> LENGTH: 4036
<212> TYPE: DNA
<213> ORGANISM: Pan troglodytes

<400> SEQUENCE: 19

ctcgcggcgc gagtttcagg cagcgctgcg tcctgctgcg cacgtgggaa gccctggccc     60

cggccacccc cgcgatgccg cgcgctcccc gctgccgagc cgtgcgctcc ctgctgcgca    120

gccactaccg cgaggtgctg ccgctggcca cgttcgtgcg gcgcctgggg ccccagggct    180

ggcggctggt gcagcgcggg gacccggcgg ctttccgcgc gctggtggcc cagtgcctgg    240

tgtgcgtgcc ctgggacgca cggccgcccc ccgccgcccc ctccttccgc caggtgtcct    300

gcctgaagga gctggtggcc cgagtgctgc agaggctgtg cgagcgcggc gcgaagaacg    360

tgctggcctt cggcttcgcg ctgctggacg gggcccgcgg gggccccccc gaggccttca    420

ccaccagcgt gcgcagctac ctgcccaaca cggtgaccga cgcactgcgg gggagcgggg    480

cgtgggggct gctgctgcgc cgcgtgggcg acgacgtgct ggttcacctg ctggcacgct    540

gcgcgctctt tgtgctggtg gctcccagct gcgcctacca ggtgtgcggg ccgccgctgt    600

accagctcgg cgctgccact caggcccggc ccccgccaca cgctagtgga ccccgaaggc    660

gtctaggatg cgaacgggcc tggaaccata gcgtcaggga ggccggggtc cccctgggcc    720

tgccagcccc gggtgcgagg aggcgcgggg gcagtgccag ccgaagtctg ccgttgccca    780

agaggcccag gcgtggcgct gcccctgagc cggagcggac gcccgttggg caggggtcct    840

gggcccaccc gggcaggacg cgtggaccga gtgaccgtgg tttctgtgtg gtgtcacctg    900

ccagacccgc cgaagaagcc acctctttgg agggtgcgct ctctggcacg cgccactccc    960

acccatccgt gggccgccag caccacgcgg gccccccatc cacatcgcgg ccaccacgtc   1020

cctgggacac gccttgtccc ccggtgtacg ccgagaccaa gcacttcctc tactcctcag   1080

gcgacaagga gcagctgcgg ccctccttcc tactcagctc tctgaggccc agcctgactg   1140

gcgctcggag gctcgtggag accatctttc tgggttccag gccctggatg ccagggactc   1200

cccgcaggtt gccccgcctg ccccagcgct actggcaaat gcggcccctg tttctggagc   1260

tgcttgggaa ccacgcgcag tgcccctacg gggtgctcct caagacgcac tgcccgctgc   1320

gagctgcggt caccccagca gccggtgtct gtgcccggga gaagccccag ggctctgtgg   1380

cggcccccga ggaggaggac acagaccccc gtcgcctggt gcagctgctc cgccagcaca   1440

gcagcccctg gcaggtgtac ggcttcgtgc gggcctgcct gcgccggctg gtgcccccag   1500
```

-continued

```
gcctctgggg ctccaggcac aacgaacgcc gcttcctcag gaacaccaag aagttcatct   1560
ccctggggaa gcatgccaag ctctcgctgc aggagctgac gtggaagatg agcgtgcggg   1620
actgcgcttg gctgcgcagg agcccagggg ttggctctgt tccggccgca gagcaccgtc   1680
tgcgtgagga gatcctggcc aagttcttgc actggctgat gagtgtgtac gttgtcgagc   1740
tgctcaggtc tttcttttat gtcacggaga ccacgtttca gaagaacagg ctcttttttct   1800
accggaagag tgtctggagc aagttgcaaa gcattggaat cagacagcac ttgaagaggg   1860
tgcagctgcg ggagctgtcg gaagcagagg tcaggcagca tcaggaagcc aggcccgccc   1920
tgctgacgtc cagactccgc ttcatcccca agcctgacgg gctgcggccg attgtgaaca   1980
tggactacgt cgtgggagcc agaacgttcc gcagagaaaa gagggccgag cgtctcacct   2040
cgagggtgaa ggcactgttc agcgtgctca actacgagcg ggcgcggcgc cccggcctcc   2100
tgggcgcctc tgtgctgggc ctggacgata tccacagggc ctggcgcacc ttcgtgctgc   2160
gtgtgcgggc ccaggacccg ccgcctgagc tgtactttgt caaggtggat gtgacgggcg   2220
cgtacgacac catcccccag gacaggctca cggaggtcat cgccagcatc atcaaacccc   2280
agaacacgta ctgcgtgcgt cggtatgctg tggtccagaa ggccgcccat gggcacgtcc   2340
gcaaggcctt caagagccac gtctctacct tgacagacct ccagccgtac atgcgacagt   2400
tcgtggctca cctgcaggag accagcccac tgagggatgc cgtcatcatc gagcagagct   2460
cctccctgaa tgaggccagc agtggcctct tcgacgtctt cctacgcttc gtgtgccgcc   2520
acgccgtgcg catcaggggc aagtcctacg tccagtgcca ggggatcccg cagggctcca   2580
tcctgtccac gctgctctgc agcctgtgct acggcgacat ggagaacaag ctgtttgcgg   2640
ggattcggcg ggacgggctg ctcctgcgtt tggtggatga tttcttgttg gtgacacctc   2700
acctcaccca cgcgaaagcc ttcctcagga ccctggtccg aggtgtccct gagtatggct   2760
gcgtggtgaa cttgcggaag acagtagtga acttccctgt agaagatgag gccctgggtg   2820
gcacggcttt tgttcagctg ccggcccacg gcctattccc ctggtgcggc ctgctgctgg   2880
acacccggac cctggaggtg cagagcgact actccagcta tgcccggacc tccatcagag   2940
ccagtctcac cttcaaccgc ggcttcaagg ctgggaggaa catgcgtcgc aaactctttg   3000
gggtcttgcg gctgaagtgt cacagcctgt ttctggattt gcaggtgaac agcctccaga   3060
cggtgtgcac caacatctac aagatcctcc tgctgcaggc gtacaggttt cacgcatgtg   3120
tgctgcagct cccatttcat cagcaagttt ggaagaaccc cacatttttc ctgcgcatca   3180
tctctgacac ggcctccctc tgctactcca tcctgaaagc caagaacgca gggatgtcgc   3240
tgggggccaa gggtgccgcc ggccctctgc cctccgaggc catgcagtgg ctgtgccacc   3300
aagcattcct gctcaagctg actcgacacc gcgtcaccta cgtgccactc ctggggtcac   3360
tcaggacagc ccagacgcag ctgagtcgga agctcccggg gacgacgctg agtgccctgg   3420
aggccgcagc caacccggca ctgccctcag acttcaagac catcctggac tgatggccac   3480
ccgcccacag ccgggccgag agcagacacc agcagccctg tcacgccggg ctctacgtcc   3540
cagggaggga ggggcggccc acacccagac ccgcaccgct gggagtctga ggcctgagtg   3600
agtgtctggc caaggcctgc atgtccggct gaaggctgag tgtccagctg aggcctgagc   3660
gagtgtccag ccaagggctg agtgtccagc acacctgccg tcttcacttc cccacaggct   3720
ggcgctcggc tccaccccag ggccagcttt tcctcgccag gagcccggct tcccactccc   3780
cacatgggaa tagtccatcc ccagattcgc cattgtccac ccctcgccct gccctccttt   3840
```

-continued

```
gccttccacg cccaccatcc agatggagac cctgagaagg accctgggag ctctgggaat   3900

ttggagtgac caaaggtgtg ccctgtacac aggtgaggac cctgcacctg gatgggggtc   3960

cctgtgggtc aaattggggg gggggtgctg tgggagtaaa atactgaata tatgagtttt   4020

tcagttttga aaaaaa                                                   4036


<210> SEQ ID NO 20
<211> LENGTH: 1132
<212> TYPE: PRT
<213> ORGANISM: Pan troglodytes

<400> SEQUENCE: 20

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335
```

-continued

```
Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Ser
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Gln Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
```

-continued

```
        755                 760                 765

Leu Gln Pro Tyr Met Arg Gln Phe Val Ala His Leu Gln Glu Thr Ser
    770                 775                 780

Pro Leu Arg Asp Ala Val Ile Ile Glu Gln Ser Ser Ser Leu Asn Glu
785                 790                 795                 800

Ala Ser Ser Gly Leu Phe Asp Val Phe Leu Arg Phe Val Cys Arg His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Ala Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

Ala Leu Gly Gly Thr Ala Phe Val Gln Leu Pro Ala His Gly Leu Phe
        915                 920                 925

Pro Trp Cys Gly Leu Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn  Ile Tyr Lys Ile Leu  Leu Leu Gln
        995                 1000                1005

Ala Tyr  Arg Phe His Ala Cys  Val Leu Gln Leu Pro  Phe His Gln
    1010                1015                1020

Gln Val  Trp Lys Asn Pro Thr  Phe Phe Leu Arg Ile  Ile Ser Asp
    1025                1030                1035

Thr Ala  Ser Leu Cys Tyr Ser  Ile Leu Lys Ala Lys  Asn Ala Gly
    1040                1045                1050

Met Ser  Leu Gly Ala Lys Gly  Ala Ala Gly Pro Leu  Pro Ser Glu
    1055                1060                1065

Ala Met  Gln Trp Leu Cys His  Gln Ala Phe Leu Leu  Lys Leu Thr
    1070                1075                1080

Arg His  Arg Val Thr Tyr Val  Pro Leu Leu Gly Ser  Leu Arg Thr
    1085                1090                1095

Ala Gln  Thr Gln Leu Ser Arg  Lys Leu Pro Gly Thr  Thr Leu Ser
    1100                1105                1110

Ala Leu  Glu Ala Ala Ala Asn  Pro Ala Leu Pro Ser  Asp Phe Lys
    1115                1120                1125

Thr Ile  Leu Asp
    1130
```

<210> SEQ ID NO 21
<211> LENGTH: 3396
<212> TYPE: DNA
<213> ORGANISM: Artificial
<220> FEATURE:
<223> OTHER INFORMATION: Synthetic

<400> SEQUENCE: 21
atgccgcgcg cgccgcgctg ccgcgcggtg cgcagcctgc tgcgcagcca ttatcgcgaa 60
gtgctgccgc tggcgacctt tgtgcgccgc ctgggcccgc agggctggcg cctggtgcag 120
cgcggcgatc cggcggcgtt tcgcgcgctg gtggcgcagt gcctggtgtg cgtgccgtgg 180
gatgcgcgcc cgccgccggc ggcgccgagc tttcgccagg tgagctgcct gaaagaactg 240
gtggcgcgcg tgctgcagcg cctgtgcgaa cgcggcgcga aaaacgtgct ggcgtttggc 300
tttgcgctgc tggatggcgc gcgcggcggc ccgccggaag cgtttaccac cagcgtgcgc 360
agctatctgc cgaacaccgt gaccgatgcg ctgcgcggca gcggcgcgtg gggcctgctg 420
ctgcgccgcg tgggcgatga tgtgctggtg catctgctgg cgcgctgcgc gctgtttgtg 480
ctggtggcgc cgagctgcgc gtatcaggtg tgcggcccgc cgctgtatca gctgggcgcg 540
gcgacccagg cgcgcccgcc gccgcatgcg agcggcccgc gccgccgcct gggctgcgaa 600
cgcgcgtgga accatagcgt gcgcgaagcg ggcgtgccgc tgggcctgcc ggcgccgggc 660
gcgcgccgcc gcggcggcag cgcgagccgc agcctgccgc tgccgaaacg cccgcgccgc 720
ggcgcggcgc cggaaccgga acgcaccccg gtgggccagg gcagctgggc gcatccgggc 780
cgcacccgcg gcccgagcga tcgcggcttt tgcgtggtga gcccggcgcg cccggcggaa 840
gaagcgacca gcctggaagg cgcgctgagc ggcacccgcc atagccatcc gagcgtgggc 900
cgccagcatc atgcgggccc gccgagcacc agccgcccgc cgcgcccgtg ggataccccg 960
tgcccgccgg tgtatgcgga aaccaaacat tttctgtata gcagcggcga taaagaacag 1020
ctgcgcccga gctttctgct gagcagcctg cgcccgagcc tgaccggcgc gcgccgcctg 1080
gtggaaacca tttttctggg cagccgcccg tggatgccgg gcaccccgcg ccgcctgccg 1140
cgcctgccgc agcgctattg gcagatgcgc ccgctgtttc tggaactgct gggcaaccat 1200
gcgcagtgcc cgtatggcgt gctgctgaaa acccattgcc cgctgcgcgc ggcggtgacc 1260
ccggcggcgg gcgtgtgcgc gcgcgaaaaa ccgcagggca gcgtggcggc gccggaagaa 1320
gaagataccg atccgcgccg cctggtgcag ctgctgcgcc agcatagcag cccgtggcag 1380
gtgtatggct ttgtgcgcgc gtgcctgcgc cgcctggtgc cgccgggcct gtggggcagc 1440
cgccataacg aacgccgctt tctgcgcaac accaaaaaat ttattagcct gggcaaacat 1500
gcgaaactga gcctgcagga actgacctgg aaaatgagcg tgcgcgattg cgcgtggctg 1560
cgccgcagcc cgggcgtggg cagcgtgccg gcggcggaac atcgcctgcg cgaagaaatt 1620
ctggcgaaat ttctgcattg gctgatgagc gtgtatgtgg tggaactgct gcgcagcttt 1680
ttttatgtga ccgaaaccac ctttcagaaa aaccgcctgt ttttttatcg caaaagcgtg 1740
tggagcaaac tgcagagcat tggcattcgc cagcatctga aacgcgtgca gctgcgcgaa 1800
ctgagcgaag cggaagtgcg ccagcatcag gaagcgcgcc cggcgctgct gaccagccgc 1860
ctgcgcttta ttccgaaacc ggatggcctg cgcccgattg tgaacatgga ttatgtggtg 1920
ggcgcgcgca cctttcgccg cgaaaaacgc gcggaacgcc tgaccagccg cgtgaaagcg 1980
ctgtttagcg tgctgaacta tgaacgcgcg cgccgcccgg gcctgctggg cgcgagcgtg 2040
ctgggcctgg atgatattca tcgcgcgtgg cgcacctttg tgctgcgcgt gcgcgcgcag 2100
gatccgccgc cggaactgta ttttgtgaaa gtggatgtga ccggcgcgta tgataccatt 2160
ccgcaggatc gcctgaccga agtgattgcg agcattatta aaccgcagaa cacctattgc 2220

```
gtgcgccgct atgcggtggt gcagaaagcg gcgcatggcc atgtgcgcaa agcgtttaaa   2280

agccatgtga gcaccctgac cgatctgcag ccgtatatgc gccagtttgt ggcgcatctg   2340

caggaaacca gcccgctgcg cgatgcggtg attattgaac agagcagcag cctgaacgaa   2400

gcgagcagcg gcctgtttga tgtgtttctg cgctttgtgt gccgccatgc ggtgcgcatt   2460

cgcggcaaaa gctatgtgca gtgccagggc attccgcagg gcagcattct gagcaccctg   2520

ctgtgcagcc tgtgctatgg cgatatggaa aacaaactgt ttgcgggcat tcgccgcgat   2580

ggcctgctgc tgcgcctggt ggatgatttt ctgctggtga ccccgcatct gacccatgcg   2640

aaagcgtttc tgcgcaccct ggtgcgcggc gtgccggaat atggctgcgt ggtgaacctg   2700

cgcaaaaccg tggtgaactt tccggtggaa gatgaagcgc tgggcggcac cgcgtttgtg   2760

cagctgccgg cgcatggcct gtttccgtgg tgcggcctgc tgctggatac ccgcaccctg   2820

gaagtgcaga gcgattatag cagctatgcg cgcaccagca ttcgcgcgag cctgaccttt   2880

aaccgcggct ttaaagcggg ccgcaacatg cgccgcaaac tgtttggcgt gctgcgcctg   2940

aaatgccata gcctgtttct ggatctgcag gtgaacagcc tgcagaccgt gtgcaccaac   3000

atttataaaa ttctgctgct gcaggcgtat cgctttcatg cgtgcgtgct gcagctgccg   3060

tttcatcagc aggtgtggaa aaacccgacc ttttttctgc gcattattag cgataccgcg   3120

agcctgtgct atagcattct gaaagcgaaa aacgcgggca tgagcctggg cgcgaaaggc   3180

gcggcgggcc cgctgccgag cgaagcgatg cagtggctgt gccatcaggc gtttctgctg   3240

aaactgaccc gccatcgcgt gacctatgtg ccgctgctgg gcagcctgcg caccgcgcag   3300

acccagctga gccgcaaact gccgggcacc accctgagcg cgctggaagc ggcggcgaac   3360

ccggcgctgc cgagcgattt taaaaccatt ctggat                             3396
```

```
<210> SEQ ID NO 22
<211> LENGTH: 807
<212> TYPE: PRT
<213> ORGANISM: Pan troglodytes

<400> SEQUENCE: 22

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
```

-continued

```
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Ser
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590
```

```
Leu Lys Arg Val Gln Leu Arg Glu Leu Ser Glu Ala Glu Val Arg Gln
        595                 600                 605

His Gln Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Leu Arg Pro Val Pro
        755                 760                 765

Gly Asp Pro Ala Gly Leu His Pro Val His Ala Ala Leu Gln Pro Val
    770                 775                 780

Leu Arg Arg His Gly Glu Gln Ala Val Cys Gly Asp Ser Ala Gly Arg
785                 790                 795                 800

Ala Ala Pro Ala Phe Gly Gly
                805
```

<210> SEQ ID NO 23
<211> LENGTH: 2421
<212> TYPE: DNA
<213> ORGANISM: Artificial
<220> FEATURE:
<223> OTHER INFORMATION: Synthetic

<400> SEQUENCE: 23

```
atgccgcgcg cgccgcgctg ccgcgcggtg cgcagcctgc tgcgcagcca ttatcgcgaa     60

gtgctgccgc tggcgacctt tgtgcgccgc ctgggcccgc agggctggcg cctggtgcag    120

cgcggcgatc cggcggcgtt tcgcgcgctg gtggcgcagt gcctggtgtg cgtgccgtgg    180

gatgcgcgcc cgccgccggc ggcgccgagc tttcgccagg tgagctgcct gaaagaactg    240

gtggcgcgcg tgctgcagcg cctgtgcgaa cgcggcgcga aaaacgtgct ggcgtttggc    300

tttgcgctgc tggatggcgc gcgcggcggc ccgccggaag cgtttaccac cagcgtgcgc    360

agctatctgc cgaacaccgt gaccgatgcg ctgcgcggca gcggcgcgtg gggcctgctg    420

ctgcgccgcg tgggcgatga tgtgctggtg catctgctgg cgcgctgcgc gctgtttgtg    480

ctggtggcgc cgagctgcgc gtatcaggtg tgcggcccgc cgctgtatca gctgggcgcg    540

gcgacccagg cgcgcccgcc gccgcatgcg agcggcccgc gccgccgcct gggctgcgaa    600

cgcgcgtgga accatagcgt gcgcgaagcg ggcgtgccgc tgggcctgcc ggcgccgggc    660

gcgcgccgcc gcggcggcag cgcgagccgc agcctgccgc tgccgaaacg cccgcgccgc    720

ggcgcggcgc cggaaccgga acgcaccccg gtgggccagg gcagctgggc gcatccgggc    780
```

```
cgcacccgcg gcccgagcga tcgcggcttt tgcgtggtga gcccggcgcg cccggcggaa     840
gaagcgacca gcctggaagg cgcgctgagc ggcacccgcc atagccatcc gagcgtgggc     900
cgccagcatc atgcgggccc gccgagcacc agccgcccgc cgcgcccgtg ggataccccg     960
tgcccgccgg tgtatgcgga aaccaaacat tttctgtata gcagcggcga taaagaacag    1020
ctgcgcccga gctttctgct gagcagcctg cgcccgagcc tgaccggcgc gcgccgcctg    1080
gtggaaacca tttttctggg cagccgcccg tggatgccgg gcaccccgcg ccgcctgccg    1140
cgcctgccgc agcgctattg gcagatgcgc ccgctgtttc tggaactgct gggcaaccat    1200
gcgcagtgcc cgtatggcgt gctgctgaaa acccattgcc cgctgcgcgc ggcggtgacc    1260
ccggcggcgg gcgtgtgcgc gcgcgaaaaa ccgcagggca gcgtggcggc gccggaagaa    1320
gaagataccg atccgcgccg cctggtgcag ctgctgcgcc agcatagcag cccgtggcag    1380
gtgtatggct ttgtgcgcgc gtgcctgcgc cgcctggtgc cgccgggcct gtggggcagc    1440
cgccataacg aacgccgctt tctgcgcaac accaaaaaat ttattagcct gggcaaacat    1500
gcgaaactga gcctgcagga actgacctgg aaaatgagcg tgcgcgattg cgcgtggctg    1560
cgccgcagcc cgggcgtggg cagcgtgccg gcggcggaac atcgcctgcg cgaagaaatt    1620
ctggcgaaat ttctgcattg gctgatgagc gtgtatgtgg tggaactgct gcgcagcttt    1680
ttttatgtga ccgaaaccac ctttcagaaa aaccgcctgt ttttttatcg caaaagcgtg    1740
tggagcaaac tgcagagcat tggcattcgc cagcatctga aacgcgtgca gctgcgcgaa    1800
ctgagcgaag cggaagtgcg ccagcatcag gaagcgcgcc cggcgctgct gaccagccgc    1860
ctgcgcttta ttccgaaacc ggatggcctg cgcccgattg tgaacatgga ttatgtggtg    1920
ggcgcgcgca cctttcgccg cgaaaaacgc gcggaacgcc tgaccagccg cgtgaaagcg    1980
ctgtttagcg tgctgaacta tgaacgcgcg cgccgcccgg gcctgctggg cgcgagcgtg    2040
ctgggcctgg atgatattca tcgcgcgtgg cgcacctttg tgctgcgcgt gcgcgcgcag    2100
gatccgccgc cggaactgta ttttgtgaaa gtggatgtga ccggcgcgta tgataccatt    2160
ccgcaggatc gcctgaccga agtgattgcg agcattatta aaccgcagaa cacctattgc    2220
gtgcgccgct atgcggtggt gcagaaagcg gcgcatggcc atgtgcgcaa agcgtttaaa    2280
agccatgtgc tgcgcccggt gccgggcgat ccggcgggcc tgcatccggt gcatgcggcg    2340
ctgcagccgg tgctgcgccg ccatggcgaa caggcggtgt gcggcgatag cgcgggccgc    2400
gcggcgccgg cgtttggcgg c                                              2421
```

<210> SEQ ID NO 24
<211> LENGTH: 1069
<212> TYPE: PRT
<213> ORGANISM: Pan troglodytes

<400> SEQUENCE: 24

```
Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80
```

-continued

```
Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
```

-continued

```
        500                 505                 510

Ser Val Arg Asp Cys Ala Trp Leu Arg Arg Ser Pro Gly Val Gly Ser
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Gln Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Ile Ile Glu Gln Ser Ser Ser Leu Asn Glu
785                 790                 795                 800

Ala Ser Ser Gly Leu Phe Asp Val Phe Leu Arg Phe Val Cys Arg His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Ala Phe Leu Ser Tyr Ala Arg Thr Ser Ile Arg Ala Ser Leu Thr
                885                 890                 895

Phe Asn Arg Gly Phe Lys Ala Gly Arg Asn Met Arg Arg Lys Leu Phe
            900                 905                 910

Gly Val Leu Arg Leu Lys Cys His Ser Leu Phe Leu Asp Leu Gln Val
        915                 920                 925
```

Asn Ser Leu Gln Thr Val Cys Thr Asn Ile Tyr Lys Ile Leu Leu Leu
930 935 940

Gln Ala Tyr Arg Phe His Ala Cys Val Leu Gln Leu Pro Phe His Gln
945 950 955 960

Gln Val Trp Lys Asn Pro Thr Phe Phe Leu Arg Ile Ile Ser Asp Thr
965 970 975

Ala Ser Leu Cys Tyr Ser Ile Leu Lys Ala Lys Asn Ala Gly Met Ser
980 985 990

Leu Gly Ala Lys Gly Ala Ala Gly Pro Leu Pro Ser Glu Ala Met Gln
995 1000 1005

Trp Leu Cys His Gln Ala Phe Leu Leu Lys Leu Thr Arg His Arg
1010 1015 1020

Val Thr Tyr Val Pro Leu Leu Gly Ser Leu Arg Thr Ala Gln Thr
1025 1030 1035

Gln Leu Ser Arg Lys Leu Pro Gly Thr Thr Leu Ser Ala Leu Glu
1040 1045 1050

Ala Ala Ala Asn Pro Ala Leu Pro Ser Asp Phe Lys Thr Ile Leu
1055 1060 1065

Asp

<210> SEQ ID NO 25
<211> LENGTH: 3207
<212> TYPE: DNA
<213> ORGANISM: Artificial
<220> FEATURE:
<223> OTHER INFORMATION: Synthetic

<400> SEQUENCE: 25
atgccgcgcg cgccgcgctg ccgcgcggtg cgcagcctgc tgcgcagcca ttatcgcgaa 60
gtgctgccgc tggcgacctt tgtgcgccgc ctgggcccgc agggctggcg cctggtgcag 120
cgcggcgatc cggcggcgtt tcgcgcgctg gtggcgcagt gcctggtgtg cgtgccgtgg 180
gatgcgcgcc cgccgccggc ggcgccgagc tttcgccagg tgagctgcct gaaagaactg 240
gtggcgcgcg tgctgcagcg cctgtgcgaa cgcggcgcga aaaacgtgct ggcgtttggc 300
tttgcgctgc tggatggcgc gcgcggcggc ccgccggaag cgtttaccac cagcgtgcgc 360
agctatctgc cgaacaccgt gaccgatgcg ctgcgcggca gcggcgcgtg gggcctgctg 420
ctgcgccgcg tgggcgatga tgtgctggtg catctgctgg cgcgctgcgc gctgtttgtg 480
ctggtggcgc cgagctgcgc gtatcaggtg tgcggcccgc cgctgtatca gctgggcgcg 540
gcgacccagg cgcgcccgcc gccgcatgcg agcggcccgc gccgccgcct gggctgcgaa 600
cgcgcgtgga accatagcgt gcgcgaagcg ggcgtgccgc tgggcctgcc ggcgccgggc 660
gcgcgccgcc gcggcggcag cgcgagccgc agcctgccgc tgccgaaacg cccgcgccgc 720
ggcgcggcgc cggaaccgga acgcaccccg gtgggccagg gcagctgggc gcatccgggc 780
cgcacccgcg gcccgagcga tcgcggcttt tgcgtggtga gcccggcgcg cccggcggaa 840
gaagcgacca gcctggaagg cgcgctgagc ggcacccgcc atagccatcc gagcgtgggc 900
cgccagcatc atgcgggccc gccgagcacc agccgcccgc cgcgcccgtg ggataccccg 960
tgcccgccgg tgtatgcgga aaccaaacat tttctgtata gcagcggcga taaagaacag 1020
ctgcgcccga gctttctgct gagcagcctg cgcccgagcc tgaccggcgc gcgccgcctg 1080
gtggaaacca tttttctggg cagccgcccg tggatgccgg gcaccccgcg ccgcctgccg 1140
cgcctgccgc agcgctattg gcagatgcgc ccgctgtttc tggaactgct gggcaaccat 1200
gcgcagtgcc cgtatggcgt gctgctgaaa acccattgcc cgctgcgcgc ggcggtgacc 1260
ccggcggcgg gcgtgtgcgc gcgcgaaaaa ccgcagggca gcgtggcggc gccggaagaa 1320
gaagataccg atccgcgccg cctggtgcag ctgctgcgcc agcatagcag cccgtggcag 1380
gtgtatggct ttgtgcgcgc gtgcctgcgc cgcctggtgc cgccgggcct gtggggcagc 1440
cgccataacg aacgccgctt tctgcgcaac accaaaaaat ttattagcct gggcaaacat 1500
gcgaaactga gcctgcagga actgacctgg aaaatgagcg tgcgcgattg cgcgtggctg 1560
cgccgcagcc cgggcgtggg cagcgtgccg gcggcggaac atcgcctgcg cgaagaaatt 1620
ctggcgaaat ttctgcattg gctgatgagc gtgtatgtgg tggaactgct gcgcagcttt 1680
ttttatgtga ccgaaaccac ctttcagaaa aaccgcctgt ttttttatcg caaaagcgtg 1740
tggagcaaac tgcagagcat tggcattcgc cagcatctga aacgcgtgca gctgcgcgaa 1800
ctgagcgaag cggaagtgcg ccagcatcag gaagcgcgcc cggcgctgct gaccagccgc 1860
ctgcgcttta ttccgaaacc ggatggcctg cgcccgattg tgaacatgga ttatgtggtg 1920
ggcgcgcgca cctttcgccg cgaaaaacgc gcggaacgcc tgaccagccg cgtgaaagcg 1980
ctgtttagcg tgctgaacta tgaacgcgcg cgccgcccgg gcctgctggg cgcgagcgtg 2040
ctgggcctgg atgatattca tcgcgcgtgg cgcacctttg tgctgcgcgt gcgcgcgcag 2100
gatccgccgc cggaactgta ttttgtgaaa gtggatgtga ccggcgcgta tgataccatt 2160
ccgcaggatc gcctgaccga agtgattgcg agcattatta aaccgcagaa cacctattgc 2220
gtgcgccgct atgcggtggt gcagaaagcg gcgcatggcc atgtgcgcaa agcgtttaaa 2280
agccatgtga gcaccctgac cgatctgcag ccgtatatgc gccagtttgt ggcgcatctg 2340
caggaaacca gcccgctgcg cgatgcggtg attattgaac agagcagcag cctgaacgaa 2400
gcgagcagcg gcctgtttga tgtgtttctg cgctttgtgt gccgccatgc ggtgcgcatt 2460
cgcggcaaaa gctatgtgca gtgccagggc attccgcagg gcagcattct gagcaccctg 2520
ctgtgcagcc tgtgctatgg cgatatggaa aacaaactgt ttgcgggcat tcgccgcgat 2580
ggcctgctgc tgcgcctggt ggatgatttt ctgctggtga ccccgcatct gacccatgcg 2640
aaagcgtttc tgagctatgc gcgcaccagc attcgcgcga gcctgacctt taaccgcggc 2700
tttaaagcgg gccgcaacat gcgccgcaaa ctgtttggcg tgctgcgcct gaaatgccat 2760
agcctgtttc tggatctgca ggtgaacagc ctgcagaccg tgtgcaccaa catttataaa 2820
attctgctgc tgcaggcgta tcgctttcat gcgtgcgtgc tgcagctgcc gtttcatcag 2880
caggtgtgga aaaacccgac ctttttttctg cgcattatta gcgataccgc gagcctgtgc 2940
tatagcattc tgaaagcgaa aaacgcgggc atgagcctgg gcgcgaaagg cgcggcgggc 3000
ccgctgccga gcgaagcgat gcagtggctg tgccatcagg cgtttctgct gaaactgacc 3060
cgccatcgcg tgacctatgt gccgctgctg ggcagcctgc gcaccgcgca gacccagctg 3120
agccgcaaac tgccgggcac caccctgagc gcgctggaag cggcggcgaa cccggcgctg 3180
ccgagcgatt ttaaaaccat tctggat 3207

<210> SEQ ID NO 26
<211> LENGTH: 795
<212> TYPE: PRT
<213> ORGANISM: Pan troglodytes

<400> SEQUENCE: 26

Met Pro Arg Ala Pro Arg Cys Arg Ala Val Arg Ser Leu Leu Arg Ser
1 5 10 15

-continued

His Tyr Arg Glu Val Leu Pro Leu Ala Thr Phe Val Arg Arg Leu Gly
20 25 30

Pro Gln Gly Trp Arg Leu Val Gln Arg Gly Asp Pro Ala Ala Phe Arg
35 40 45

Ala Leu Val Ala Gln Cys Leu Val Cys Val Pro Trp Asp Ala Arg Pro
50 55 60

Pro Pro Ala Ala Pro Ser Phe Arg Gln Val Ser Cys Leu Lys Glu Leu
65 70 75 80

Val Ala Arg Val Leu Gln Arg Leu Cys Glu Arg Gly Ala Lys Asn Val
85 90 95

Leu Ala Phe Gly Phe Ala Leu Leu Asp Gly Ala Arg Gly Gly Pro Pro
100 105 110

Glu Ala Phe Thr Thr Ser Val Arg Ser Tyr Leu Pro Asn Thr Val Thr
115 120 125

Asp Ala Leu Arg Gly Ser Gly Ala Trp Gly Leu Leu Leu Arg Arg Val
130 135 140

Gly Asp Asp Val Leu Val His Leu Leu Ala Arg Cys Ala Leu Phe Val
145 150 155 160

Leu Val Ala Pro Ser Cys Ala Tyr Gln Val Cys Gly Pro Pro Leu Tyr
165 170 175

Gln Leu Gly Ala Ala Thr Gln Ala Arg Pro Pro Pro His Ala Ser Gly
180 185 190

Pro Arg Arg Arg Leu Gly Cys Glu Arg Ala Trp Asn His Ser Val Arg
195 200 205

Glu Ala Gly Val Pro Leu Gly Leu Pro Ala Pro Gly Ala Arg Arg Arg
210 215 220

Gly Gly Ser Ala Ser Arg Ser Leu Pro Leu Pro Lys Arg Pro Arg Arg
225 230 235 240

Gly Ala Ala Pro Glu Pro Glu Arg Thr Pro Val Gly Gln Gly Ser Trp
245 250 255

Ala His Pro Gly Arg Thr Arg Gly Pro Ser Asp Arg Gly Phe Cys Val
260 265 270

Val Ser Pro Ala Arg Pro Ala Glu Glu Ala Thr Ser Leu Glu Gly Ala
275 280 285

Leu Ser Gly Thr Arg His Ser His Pro Ser Val Gly Arg Gln His His
290 295 300

Ala Gly Pro Pro Ser Thr Ser Arg Pro Pro Arg Pro Trp Asp Thr Pro
305 310 315 320

Cys Pro Pro Val Tyr Ala Glu Thr Lys His Phe Leu Tyr Ser Ser Gly
325 330 335

Asp Lys Glu Gln Leu Arg Pro Ser Phe Leu Leu Ser Ser Leu Arg Pro
340 345 350

Ser Leu Thr Gly Ala Arg Arg Leu Val Glu Thr Ile Phe Leu Gly Ser
355 360 365

Arg Pro Trp Met Pro Gly Thr Pro Arg Arg Leu Pro Arg Leu Pro Gln
370 375 380

Arg Tyr Trp Gln Met Arg Pro Leu Phe Leu Glu Leu Leu Gly Asn His
385 390 395 400

Ala Gln Cys Pro Tyr Gly Val Leu Leu Lys Thr His Cys Pro Leu Arg
405 410 415

Ala Ala Val Thr Pro Ala Ala Gly Val Cys Ala Arg Glu Lys Pro Gln
420 425 430

-continued

```
Gly Ser Val Ala Ala Pro Glu Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Ser
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Gln Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

Glu Leu Tyr Phe Val Lys Asp Arg Leu Thr Glu Val Ile Ala Ser Ile
705                 710                 715                 720

Ile Lys Pro Gln Asn Thr Tyr Cys Val Arg Arg Tyr Ala Val Val Gln
                725                 730                 735

Lys Ala Ala His Gly His Val Arg Lys Ala Phe Lys Ser His Val Leu
            740                 745                 750

Arg Pro Val Pro Gly Asp Pro Ala Gly Leu His Pro Val His Ala Ala
        755                 760                 765

Leu Gln Pro Val Leu Arg Arg His Gly Glu Gln Ala Val Cys Gly Asp
    770                 775                 780

Ser Ala Gly Arg Ala Ala Pro Ala Phe Gly Gly
785                 790                 795
```

<210> SEQ ID NO 27
<211> LENGTH: 2385
<212> TYPE: DNA
<213> ORGANISM: Artificial
<220> FEATURE:
<223> OTHER INFORMATION: Synthetic

<400> SEQUENCE: 27

-continued

```
atgccgcgcg cgccgcgctg ccgcgcggtg cgcagcctgc tgcgcagcca ttatcgcgaa      60
gtgctgccgc tggcgacctt tgtgcgccgc ctgggcccgc agggctggcg cctggtgcag     120
cgcggcgatc cggcggcgtt tcgcgcgctg gtggcgcagt gcctggtgtg cgtgccgtgg     180
gatgcgcgcc cgccgccggc ggcgccgagc tttcgccagg tgagctgcct gaaagaactg     240
gtggcgcgcg tgctgcagcg cctgtgcgaa cgcggcgcga aaaacgtgct ggcgtttggc     300
tttgcgctgc tggatggcgc gcgcggcggc ccgccggaag cgtttaccac cagcgtgcgc     360
agctatctgc cgaacaccgt gaccgatgcg ctgcgcggca gcggcgcgtg gggcctgctg     420
ctgcgccgcg tgggcgatga tgtgctggtg catctgctgg cgcgctgcgc gctgtttgtg     480
ctggtggcgc cgagctgcgc gtatcaggtg tgcggcccgc cgctgtatca gctgggcgcg     540
gcgacccagg cgcgcccgcc gccgcatgcg agcggcccgc gccgccgcct gggctgcgaa     600
cgcgcgtgga accatagcgt gcgcgaagcg ggcgtgccgc tgggcctgcc ggcgccgggc     660
gcgcgccgcc gcggcggcag cgcgagccgc agcctgccgc tgccgaaacg cccgcgccgc     720
ggcgcggcgc cggaaccgga acgcaccccg gtgggccagg gcagctgggc gcatccgggc     780
cgcacccgcg gcccgagcga tcgcggcttt tgcgtggtga gcccggcgcg cccggcggaa     840
gaagcgacca gcctggaagg cgcgctgagc ggcacccgcc atagccatcc gagcgtgggc     900
cgccagcatc atgcgggccc gccgagcacc agccgcccgc cgcgcccgtg ggataccccg     960
tgcccgccgg tgtatgcgga aaccaaacat tttctgtata gcagcggcga taaagaacag    1020
ctgcgcccga gctttctgct gagcagcctg cgcccgagcc tgaccggcgc gcgccgcctg    1080
gtggaaacca tttttctggg cagccgcccg tggatgccgg gcaccccgcg ccgcctgccg    1140
cgcctgccgc agcgctattg gcagatgcgc ccgctgtttc tggaactgct gggcaaccat    1200
gcgcagtgcc cgtatggcgt gctgctgaaa acccattgcc cgctgcgcgc ggcggtgacc    1260
ccggcggcgg gcgtgtgcgc gcgcgaaaaa ccgcagggca gcgtggcggc gccggaagaa    1320
gaagataccg atccgcgccg cctggtgcag ctgctgcgcc agcatagcag cccgtggcag    1380
gtgtatggct ttgtgcgcgc gtgcctgcgc cgcctggtgc cgccgggcct gtggggcagc    1440
cgccataacg aacgccgctt tctgcgcaac accaaaaaat ttattagcct gggcaaacat    1500
gcgaaactga gcctgcagga actgacctgg aaaatgagcg tgcgcgattg cgcgtggctg    1560
cgccgcagcc cgggcgtggg cagcgtgccg gcggcggaac atcgcctgcg cgaagaaatt    1620
ctggcgaaat ttctgcattg gctgatgagc gtgtatgtgg tggaactgct gcgcagcttt    1680
ttttatgtga ccgaaaccac ctttcagaaa aaccgcctgt ttttttatcg caaaagcgtg    1740
tggagcaaac tgcagagcat tggcattcgc cagcatctga aacgcgtgca gctgcgcgaa    1800
ctgagcgaag cggaagtgcg ccagcatcag gaagcgcgcc cggcgctgct gaccagccgc    1860
ctgcgcttta ttccgaaacc ggatggcctg cgcccgattg tgaacatgga ttatgtggtg    1920
ggcgcgcgca cctttcgccg cgaaaaacgc gcggaacgcc tgaccagccg cgtgaaagcg    1980
ctgtttagcg tgctgaacta tgaacgcgcg cgccgcccgg gcctgctggg cgcgagcgtg    2040
ctgggcctgg atgatattca tcgcgcgtgg cgcacctttg tgctgcgcgt gcgcgcgcag    2100
gatccgccgc cggaactgta ttttgtgaaa gatcgcctga ccgaagtgat tgcgagcatt    2160
attaaaccgc agaacaccta ttgcgtgcgc cgctatgcgg tggtgcagaa agcggcgcat    2220
ggccatgtgc gcaaagcgtt taaaagccat gtgctgcgcc cggtgccggg cgatccggcg    2280
ggcctgcatc cggtgcatgc ggcgctgcag ccggtgctgc gccgccatgg cgaacaggcg    2340
gtgtgcggcg atagcgcggg ccgcgcggcg ccggcgtttg gcggc                    2385
```

<210> SEQ ID NO 28
<211> LENGTH: 1086
<212> TYPE: PRT
<213> ORGANISM: Pan troglodytes

<400> SEQUENCE: 28

```
Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
```

```
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Ser
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Gln Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Ile Ile Glu Gln Ser Ser Ser Leu Asn Glu
785                 790                 795                 800
```

```
Ala Ser Ser Gly Leu Phe Asp Val Phe Leu Arg Phe Val Cys Arg His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Ala Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

Ala Leu Gly Gly Thr Ala Phe Val Gln Leu Pro Ala His Gly Leu Phe
        915                 920                 925

Pro Trp Cys Gly Leu Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn  Ile Tyr Lys Ile Leu  Leu Leu Gln
        995                 1000                1005

Ala Tyr  Arg Phe His Ala Cys  Val Leu Gln Leu Pro  Phe His Gln
    1010                 1015                 1020

Gln Val  Trp Lys Asn Pro Thr  Phe Phe Leu Arg Ile  Ile Ser Asp
    1025                 1030                 1035

Thr Ala  Ser Leu Cys Tyr Ser  Ile Leu Lys Ala Lys  Asn Ala Ala
    1040                 1045                 1050

Gln Thr  Gln Leu Ser Arg Lys  Leu Pro Gly Thr Thr  Leu Ser Ala
    1055                 1060                 1065

Leu Glu  Ala Ala Ala Asn Pro  Ala Leu Pro Ser Asp  Phe Lys Thr
    1070                 1075                 1080

Ile Leu  Asp
    1085
```

<210> SEQ ID NO 29
<211> LENGTH: 3258
<212> TYPE: DNA
<213> ORGANISM: Artificial
<220> FEATURE:
<223> OTHER INFORMATION: Synthetic

<400> SEQUENCE: 29

```
atgccgcgcg cgccgcgctg ccgcgcggtg cgcagcctgc tgcgcagcca ttatcgcgaa     60

gtgctgccgc tggcgacctt tgtgcgccgc ctgggcccgc agggctggcg cctggtgcag    120

cgcggcgatc cggcggcgtt tcgcgcgctg gtggcgcagt gcctggtgtg cgtgccgtgg    180

gatgcgcgcc cgccgccggc ggcgccgagc tttcgccagg tgagctgcct gaaagaactg    240

gtggcgcgcg tgctgcagcg cctgtgcgaa cgcggcgcga aaaacgtgct ggcgtttggc    300

tttgcgctgc tggatggcgc gcgcggcggc ccgccggaag cgtttaccac cagcgtgcgc    360
```

agctatctgc cgaacaccgt gaccgatgcg ctgcgcggca gcggcgcgtg gggcctgctg 420
ctgcgccgcg tgggcgatga tgtgctggtg catctgctgg cgcgctgcgc gctgtttgtg 480
ctggtggcgc cgagctgcgc gtatcaggtg tgcggcccgc cgctgtatca gctgggcgcg 540
gcgacccagg cgcgcccgcc gccgcatgcg agcggcccgc gccgccgcct gggctgcgaa 600
cgcgcgtgga accatagcgt gcgcgaagcg ggcgtgccgc tgggcctgcc ggcgccgggc 660
gcgcgccgcc gcggcggcag cgcgagccgc agcctgccgc tgccgaaacg cccgcgccgc 720
ggcgcggcgc cggaaccgga acgcaccccg gtgggccagg gcagctgggc gcatccgggc 780
cgcacccgcg gcccgagcga tcgcggcttt tgcgtggtga gcccggcgcg cccggcggaa 840
gaagcgacca gcctggaagg cgcgctgagc ggcacccgcc atagccatcc gagcgtgggc 900
cgccagcatc atgcgggccc gccgagcacc agccgcccgc cgcgcccgtg ggataccccg 960
tgcccgccgg tgtatgcgga aaccaaacat tttctgtata gcagcggcga taaagaacag 1020
ctgcgcccga gctttctgct gagcagcctg cgcccgagcc tgaccggcgc gcgccgcctg 1080
gtggaaacca tttttctggg cagccgcccg tggatgccgg gcaccccgcg ccgcctgccg 1140
cgcctgccgc agcgctattg gcagatgcgc ccgctgtttc tggaactgct gggcaaccat 1200
gcgcagtgcc cgtatggcgt gctgctgaaa acccattgcc cgctgcgcgc ggcggtgacc 1260
ccggcggcgg gcgtgtgcgc gcgcgaaaaa ccgcagggca gcgtggcggc gccggaagaa 1320
gaagataccg atccgcgccg cctggtgcag ctgctgcgcc agcatagcag cccgtggcag 1380
gtgtatggct ttgtgcgcgc gtgcctgcgc cgcctggtgc cgccgggcct gtggggcagc 1440
cgccataacg aacgccgctt tctgcgcaac accaaaaaat ttattagcct gggcaaacat 1500
gcgaaactga gcctgcagga actgacctgg aaaatgagcg tgcgcgattg cgcgtggctg 1560
cgccgcagcc cgggcgtggg cagcgtgccg gcggcggaac atcgcctgcg cgaagaaatt 1620
ctggcgaaat ttctgcattg gctgatgagc gtgtatgtgg tggaactgct gcgcagcttt 1680
ttttatgtga ccgaaaccac ctttcagaaa aaccgcctgt ttttttatcg caaaagcgtg 1740
tggagcaaac tgcagagcat tggcattcgc cagcatctga aacgcgtgca gctgcgcgaa 1800
ctgagcgaag cggaagtgcg ccagcatcag gaagcgcgcc cggcgctgct gaccagccgc 1860
ctgcgcttta ttccgaaacc ggatggcctg cgcccgattg tgaacatgga ttatgtggtg 1920
ggcgcgcgca cctttcgccg cgaaaaacgc gcggaacgcc tgaccagccg cgtgaaagcg 1980
ctgtttagcg tgctgaacta tgaacgcgcg cgccgcccgg gcctgctggg cgcgagcgtg 2040
ctgggcctgg atgatattca tcgcgcgtgg cgcacctttg tgctgcgcgt gcgcgcgcag 2100
gatccgccgc cggaactgta ttttgtgaaa gtggatgtga ccggcgcgta tgataccatt 2160
ccgcaggatc gcctgaccga agtgattgcg agcattatta aaccgcagaa cacctattgc 2220
gtgcgccgct atgcggtggt gcagaaagcg gcgcatggcc atgtgcgcaa agcgtttaaa 2280
agccatgtga gcaccctgac cgatctgcag ccgtatatgc gccagtttgt ggcgcatctg 2340
caggaaacca gcccgctgcg cgatgcggtg attattgaac agagcagcag cctgaacgaa 2400
gcgagcagcg gcctgtttga tgtgtttctg cgctttgtgt gccgccatgc ggtgcgcatt 2460
cgcggcaaaa gctatgtgca gtgccagggc attccgcagg gcagcattct gagcaccctg 2520
ctgtgcagcc tgtgctatgg cgatatggaa aacaaactgt ttgcgggcat tcgccgcgat 2580
ggcctgctgc tgcgcctggt ggatgatttt ctgctggtga ccccgcatct gacccatgcg 2640
aaagcgtttc tgcgcaccct ggtgcgcggc gtgccggaat atggctgcgt ggtgaacctg 2700

-continued cgcaaaaccg tggtgaactt tccggtggaa gatgaagcgc tgggcggcac cgcgtttgtg 2760
cagctgccgg cgcatggcct gtttccgtgg tgcggcctgc tgctggatac ccgcaccctg 2820
gaagtgcaga gcgattatag cagctatgcg cgcaccagca ttcgcgcgag cctgaccttt 2880
aaccgcggct ttaaagcggg ccgcaacatg cgccgcaaac tgtttggcgt gctgcgcctg 2940
aaatgccata gcctgtttct ggatctgcag gtgaacagcc tgcagaccgt gtgcaccaac 3000
atttataaaa ttctgctgct gcaggcgtat cgctttcatg cgtgcgtgct gcagctgccg 3060
tttcatcagc aggtgtggaa aaacccgacc tttttctgc gcattattag cgataccgcg 3120
agcctgtgct atagcattct gaaagcgaaa aacgcggcgc agacccagct gagccgcaaa 3180
ctgccgggca ccaccctgag cgcgctggaa gcggcggcga acccggcgct gccgagcgat 3240
tttaaaacca ttctggat 3258

<210> SEQ ID NO 30
<211> LENGTH: 3399
<212> TYPE: DNA
<213> ORGANISM: Homo sapiens

<400> SEQUENCE: 30
atgccgcgcg ctccccgctg ccgagccgtg cgctccctgc tgcgcagcca ctaccgcgag 60
gtgctgccgc tggccacgtt cgtgcggcgc ctggggcccc agggctggcg gctggtgcag 120
cgcggggacc cggcggcttt ccgcgcgctg gtggcccagt gcctggtgtg cgtgccctgg 180
gacgcacggc cgccccccgc cgccccctcc ttccgccagg tgtcctgcct gaaggagctg 240
gtggcccgag tgctgcagag gctgtgcgag cgcggcgcga agaacgtgct ggccttcggc 300
ttcgcgctgc tggacggggc ccgcgggggc ccccccgagg ccttcaccac cagcgtgcgc 360
agctacctgc ccaacacggt gaccgacgca ctgcggggga gcggggcgtg gggctgctg 420 ctgcgccgcg tgggcgacga cgtgctggtt cacctgctgg cacgctgcgc gctctttgtg 480
ctggtggctc ccagctgcgc ctaccaggtg tgcgggccgc cgctgtacca gctcggcgct 540
gccactcagg cccggccccc gccacacgct agtggacccc gaaggcgtct gggatgcgaa 600
cgggcctgga accatagcgt cagggaggcc ggggtccccc tgggcctgcc agccccgggt 660
gcgaggaggc gcgggggcag tgccagccga agtctgccgt tgcccaagag gcccaggcgt 720
ggcgctgccc ctgagccgga gcggacgccc gttgggcagg ggtcctgggc ccacccgggc 780
aggacgcgtg gaccgagtga ccgtggtttc tgtgtggtgt cacctgccag acccgccgaa 840
gaagccacct ctttggaggg tgcgctctct ggcacgcgcc actcccaccc atccgtgggc 900
cgccagcacc acgcgggccc ccatccaca tcgcggccac cacgtccctg ggacacgcct 960
tgtcccccgg tgtacgccga gaccaagcac ttcctctact cctcaggcga caaggagcag 1020
ctgcggccct ccttcctact cagctctctg aggcccagcc tgactggcgc tcggaggctc 1080
gtggagacca tctttctggg ttccaggccc tggatgccag ggactccccg caggttgccc 1140
cgcctgcccc agcgctactg gcaaatgcgg cccctgtttc tggagctgct tgggaaccac 1200
gcgcagtgcc cctacggggt gctcctcaag acgcactgcc cgctgcgagc tgcggtcacc 1260
ccagcagccg gtgtctgtgc ccgggagaag ccccagggct ctgtggcggc ccccgaggag 1320
gaggacacag acccccgtcg cctggtgcag ctgctccgcc agcacagcag cccctggcag 1380
gtgtacggct tcgtgcgggc ctgcctgcgc cggctggtgc ccccaggcct ctggggctcc 1440
aggcacaacg aacgccgctt cctcaggaac accaagaagt tcatctccct ggggaagcat 1500
gccaagctct cgctgcagga gctgacgtgg aagatgagcg tgcgggactg cgcttggctg 1560
cgcaggagcc caggggttgg ctgtgttccg gccgcagagc accgtctgcg tgaggagatc 1620
ctggccaagt tcctgcactg gctgatgagt gtgtacgtcg tcgagctgct caggtctttc 1680
ttttatgtca cggagaccac gtttcaaaag aacaggctct ttttctaccg gaagagtgtc 1740
tggagcaagt tgcaaagcat tggaatcaga cagcacttga agagggtgca gctgcgggag 1800
ctgtcggaag cagaggtcag gcagcatcgg gaagccaggc ccgccctgct gacgtccaga 1860
ctccgcttca tccccaagcc tgacgggctg cggccgattg tgaacatgga ctacgtcgtg 1920
ggagccagaa cgttccgcag agaaaagagg gccgagcgtc tcacctcgag ggtgaaggca 1980
ctgttcagcg tgctcaacta cgagcgggcg cggcgccccg gcctcctggg cgcctctgtg 2040
ctgggcctgg acgatatcca cagggcctgg cgcaccttcg tgctgcgtgt gcgggcccag 2100
gacccgccgc ctgagctgta ctttgtcaag gtggatgtga cgggcgcgta cgacaccatc 2160
ccccaggaca ggctcacgga ggtcatcgcc agcatcatca aaccccagaa cacgtactgc 2220
gtgcgtcggt atgccgtggt ccagaaggcc gcccatgggc acgtccgcaa ggccttcaag 2280
agccacgtct ctaccttgac agacctccag ccgtacatgc gacagttcgt ggctcacctg 2340
caggagacca gcccgctgag ggatgccgtc gtcatcgagc agagctcctc cctgaatgag 2400
gccagcagtg gcctcttcga cgtcttccta cgcttcatgt gccaccacgc cgtgcgcatc 2460
aggggcaagt cctacgtcca gtgccagggg atcccgcagg gctccatcct ctccacgctg 2520
ctctgcagcc tgtgctacgg cgacatggag aacaagctgt ttgcggggat tcggcgggac 2580
gggctgctcc tgcgtttggt ggatgatttc ttgttggtga cacctcacct cacccacgcg 2640
aaaaccttcc tcaggaccct ggtccgaggt gtccctgagt atggctgcgt ggtgaacttg 2700
cggaagacag tggtgaactt ccctgtagaa gacgaggccc tgggtggcac ggcttttgtt 2760
cagatgccgg cccacggcct attcccctgg tgcggcctgc tgctggatac ccggaccctg 2820
gaggtgcaga gcgactactc cagctatgcc cggacctcca tcagagccag tctcaccttc 2880
aaccgcggct tcaaggctgg gaggaacatg cgtcgcaaac tctttggggt cttgcggctg 2940
aagtgtcaca gcctgtttct ggatttgcag gtgaacagcc tccagacggt gtgcaccaac 3000
atctacaaga tcctcctgct gcaggcgtac aggtttcacg catgtgtgct gcagctccca 3060
tttcatcagc aagtttggaa gaaccccaca tttttcctgc gcgtcatctc tgacacggcc 3120
tccctctgct actccatcct gaaagccaag aacgcaggga tgtcgctggg ggccaagggc 3180
gccgccggcc ctctgccctc cgaggccgtg cagtggctgt gccaccaagc attcctgctc 3240
aagctgactc gacaccgtgt cacctacgtg ccactcctgg ggtcactcag gacagcccag 3300
acgcagctga gtcggaagct cccggggacg acgctgactg ccctggaggc cgcagccaac 3360
ccggcactgc cctcagactt caagaccatc ctggactga 3399

<210> SEQ ID NO 31
<211> LENGTH: 3369
<212> TYPE: DNA
<213> ORGANISM: Mus musculus

<400> SEQUENCE: 31
atgacccgcg ctcctcgttg ccccgcggtg cgctctctgc tgcgcagccg ataccgggag 60
gtgtggccgc tggcaacctt tgtgcggcgc ctggggcccg agggcaggcg gcttgtgcaa 120
cccggggacc cgaagatcta ccgcactttg gttgcccaat gcctagtgtg catgcactgg 180
ggctcacagc ctccacctgc cgacctttcc ttccaccagg tgtcatccct gaaagagctg 240

-continued

```
gtggccaggg ttgtgcagag actctgcgag cgcaacgaga gaaacgtgct ggcttttggc    300
tttgagctgc ttaacgaggc cagaggcggg cctcccatgg ccttcactag tagcgtgcgt    360
agctacttgc ccaacactgt tattgagacc ctgcgtgtca gtggtgcatg gatgctactg    420
ttgagccgag tgggcgacga cctgctggtc tacctgctgg cacactgtgc tctttatctt    480
ctggtgcccc ccagctgtgc ctaccaggtg tgtgggtctc ccctgtacca aatttgtgcc    540
accacggata tctggccctc tgtgtccgct agttacaggc ccacccgacc cgtgggcagg    600
aatttcacta accttaggtt cttacaacag atcaagagca gtagtcgcca ggaagcaccg    660
aaacccctgg ccttgccatc tcgaggtaca aagaggcatc tgagtctcac cagtacaagt    720
gtgccttcag ctaagaaggc cagatgctat cctgtcccga gagtggagga gggaccccac    780
aggcaggtgc taccaacccc atcaggcaaa tcatgggtgc caagtcctgc tcggtccccc    840
gaggtgccta ctgcagagaa agatttgtct tctaaaggaa aggtgtctga cctgagtctc    900
tctgggtcgg tgtgctgtaa acacaagccc agctccacat ctctgctgtc accaccccgc    960
caaaatgcct ttcagctcag gccatttatt gagaccagac atttccttta ctccagggga   1020
gatggccaag agcgtctaaa cccctcattc ctactcagca acctccagcc taacttgact   1080
ggggccagga gactggtgga gatcatcttt ctgggctcaa ggcctaggac atcaggacca   1140
ctctgcagga cacaccgtct atcgcgtcga tactggcaga tgcggcccct gttccaacag   1200
ctgctggtga accatgcaga gtgccaatat gtcagactcc tcaggtcaca ttgcaggttt   1260
cgaacagcaa accaacaggt gacagatgcc ttgaacacca gcccaccgca cctcatggat   1320
ttgctccgcc tgcacagcag tccctggcag gtatatggtt ttcttcgggc ctgtctctgc   1380
aaggtggtgt ctgctagtct ctggggtacc aggcacaatg agcgccgctt ctttaagaac   1440
ttaaagaagt tcatctcgtt ggggaaatac ggcaagctat cactgcagga actgatgtgg   1500
aagatgaaag tagaggattg ccactggctc cgcagcagcc cggggaagga ccgtgtcccc   1560
gctgcagagc accgtctgag ggagaggatc ctggctacgt tcctgttctg gctgatggac   1620
acatacgtgg tacagctgct taggtcattc ttttacatca cagagagcac attccagaag   1680
aacaggctct tcttctaccg taagagtgtg tggagcaagc tgcagagcat tggagtcagg   1740
caacaccttg agagagtgcg gctacgggag ctgtcacaag aggaggtcag gcatcaccag   1800
gacacctggc tagccatgcc catctgcaga ctgcgcttca tccccaagcc caacggcctg   1860
cggcccattg tgaacatgag ttatagcatg ggtaccagag ctttgggcag aaggaagcag   1920
gcccagcatt tcacccagcg tctcaagact ctcttcagca tgctcaacta tgagcggaca   1980
aaacatcctc accttatggg gtcttctgta ctgggtatga atgacatcta caggacctgg   2040
cgggcctttg tgctgcgtgt gcgtgctctg gaccagacac ccaggatgta ctttgttaag   2100
gcagatgtga ccggggccta tgatgccatc cccagggta agctggtgga ggttgttgcc   2160
aatatgatca ggcactcgga gagcacgtac tgtatccgcc agtatgcagt ggtccggaga   2220
gatagccaag gccaagtcca caagtccttt aggagacagg tcaccaccct ctctgacctc   2280
cagccataca tgggccagtt ccttaagcat ctgcaggatt cagatgccag tgcactgagg   2340
aactccgttg tcatcgagca gagcatctct atgaatgaga gcagcagcag cctgtttgac   2400
ttcttcctgc acttcctgcg tcacagtgtc gtaaagattg gtgacaggtg ctatacgcag   2460
tgccagggca tcccccaggg ctccagccta tccaccctgc tctgcagtct gtgtttcgga   2520
gacatggaga acaagctgtt tgctgaggtg cagcgggatg ggttgctttt acgttttgtt   2580
gatgactttc tgttggtgac gcctcacttg gaccaagcaa aaaccttcct cagcaccctg   2640
```

gtccatggcg ttcctgagta tgggtgcatg ataaacttgc agaagacagt ggtgaacttc 2700
cctgtggagc ctggtaccct gggtggtgca gctccatacc agctgcctgc tcactgcctg 2760
tttccctggt gtggcttgct gctggacact cagactttgg aggtgttctg tgactactca 2820
ggttatgccc agacctcaat taagacgagc ctcaccttcc agagtgtctt caaagctggg 2880
aagaccatgc ggaacaagct cctgtcggtc ttgcggttga agtgtcacgg tctatttcta 2940
gacttgcagg tgaacagcct ccagacagtc tgcatcaata tatacaagat cttcctgctt 3000
caggcctaca ggttccatgc atgtgtgatt cagcttccct ttgaccagcg tgttaggaag 3060
aacctcacat tctttctggg catcatctcc agccaagcat cctgctgcta tgctatcctg 3120
aaggtcaaga atccaggaat gacactaaag gcctctggct cctttcctcc tgaagccgca 3180
cattggctct gctaccaggc cttcctgctc aagctggctg ctcattctgt catctacaaa 3240
tgtctcctgg gacctctgag gacagcccaa aaactgctgt gccggaagct cccagaggcg 3300
acaatgacca tccttaaagc tgcagctgac ccagccctaa gcacagactt tcagaccatt 3360
ttggactaa 3369

<210> SEQ ID NO 32
<211> LENGTH: 102
<212> TYPE: DNA
<213> ORGANISM: Mus musculus

<400> SEQUENCE: 32
ttaagctgcc ttctgcgggg cttgccttct ggccatgccc ttcttctctc ccttgcacct 60
gtacctcttg gtctttgaat aaagcctgag taggaagtct ag 102

<210> SEQ ID NO 33
<211> LENGTH: 144
<212> TYPE: DNA
<213> ORGANISM: Homo sapiens

<400> SEQUENCE: 33
caattggctc gctttcttgc tgtccaattt ctattaaagg ttcctttgtt ccctaagtcc 60
aactactaaa ctgggggata ttatgaaggg ccttgagcat ctggattctg cctaataaaa 120
aacatttatt ttcattgcga attc 144

<210> SEQ ID NO 34
<211> LENGTH: 145
<212> TYPE: DNA
<213> ORGANISM: Artificial
<220> FEATURE:
<223> OTHER INFORMATION: Synthetic

<400> SEQUENCE: 34
caattggctc gctttcttgc tgtccaattt ctattaaagg ttccttttgt tccctaagtc 60
caactactaa actgggggat attatgaagg gccttgagca tctggattct gcctaataaa 120
aaacatttct tttcattgcg aattc 145

<210> SEQ ID NO 35
<211> LENGTH: 47
<212> TYPE: DNA
<213> ORGANISM: Artificial
<220> FEATURE:
<223> OTHER INFORMATION: Synthetic

<400> SEQUENCE: 35

-continued

```
aggaaataag agagaaaaga agagtaagaa gaaatataag agccacc                 47


<210> SEQ ID NO 36
<211> LENGTH: 57
<212> TYPE: DNA
<213> ORGANISM: Homo sapiens

<400> SEQUENCE: 36

ggacatttgc ttctgacaca actgtgttca ctagcaacct caaacaacta gtacacc      57


<210> SEQ ID NO 37
<211> LENGTH: 3723
<212> TYPE: DNA
<213> ORGANISM: Mus musculus

<400> SEQUENCE: 37

gggacatttg cttctgacac aactgtgttc actagcaacc tcaaacaacc ggtacaccat     60

gacccgcgct cctcgttgcc ccgcggtgcg ctctctgctg cgcagccgat accgggaggt    120

gtggccgctg gcaacctttg tgcggcgcct ggggcccgag ggcaggcggc ttgtgcaacc    180

cggggacccg aagatctacc gcactttggt tgcccaatgc ctagtgtgca tgcactgggg    240

ctcacagcct ccacctgccg acctttcctt ccaccaggtg tcatccctga aagagctggt    300

ggccagggtt gtgcagagac tctgcgagcg caacgagaga aacgtgctgg cttttggctt    360

tgagctgctt aacgaggcca gaggcgggcc tcccatggcc ttcactagta gcgtgcgtag    420

ctacttgccc aacactgtta ttgagaccct gcgtgtcagt ggtgcatgga tgctactgtt    480

gagccgagtg ggcgacgacc tgctggtcta cctgctggca cactgtgctc tttatcttct    540

ggtgcccccc agctgtgcct accaggtgtg tgggtctccc ctgtaccaaa tttgtgccac    600

cacggatatc tggccctctg tgtccgctag ttacaggccc acccgacccg tgggcaggaa    660

tttcactaac cttaggttct tacaacagat caagagcagt agtcgccagg aagcaccgaa    720

acccctggcc ttgccatctc gaggtacaaa gaggcatctg agtctcacca gtacaagtgt    780

gccttcagct aagaaggcca gatgctatcc tgtcccgaga gtggaggagg gaccccacag    840

gcaggtgcta ccaaccccat caggcaaatc atgggtgcca agtcctgctc ggtcccccga    900

ggtgcctact gcagagaaag atttgtcttc taaaggaaag gtgtctgacc tgagtctctc    960

tgggtcggtg tgctgtaaac acaagcccag ctccacatct ctgctgtcac caccccgcca   1020

aaatgccttt cagctcaggc catttattga gaccagacat ttcctttact ccaggggaga   1080

tggccaagag cgtctaaacc cctcattcct actcagcaac ctccagccta acttgactgg   1140

ggccaggaga ctggtggaga tcatctttct gggctcaagg cctaggacat caggaccact   1200

ctgcaggaca caccgtctat cgcgtcgata ctggcagatg cggcccctgt tccaacagct   1260

gctggtgaac catgcagagt gccaatatgt cagactcctc aggtcacatt gcaggtttcg   1320

aacagcaaac caacaggtga cagatgcctt gaacaccagc ccaccgcacc tcatggattt   1380

gctccgcctg cacagcagtc cctggcaggt atatggtttt cttcgggcct gtctctgcaa   1440

ggtggtgtct gctagtctct ggggtaccag gcacaatgag cgccgcttct ttaagaactt   1500

aaagaagttc atctcgttgg ggaaatacgg caagctatca ctgcaggaac tgatgtggaa   1560

gatgaaagta gaggattgcc actggctccg cagcagcccg gggaaggacc gtgtccccgc   1620

tgcagagcac cgtctgaggg agaggatcct ggctacgttc ctgttctggc tgatggacac   1680

atacgtggta cagctgctta ggtcattctt ttacatcaca gagagcacat tccagaagaa   1740

caggctcttc ttctaccgta agagtgtgtg gagcaagctg cagagcattg gagtcaggca   1800
```

```
acaccttgag agagtgcggc tacgggagct gtcacaagag gaggtcaggc atcaccagga   1860
cacctggcta gccatgccca tctgcagact gcgcttcatc cccaagccca acggcctgcg   1920
gcccattgtg aacatgagtt atagcatggg taccagagct ttgggcagaa ggaagcaggc   1980
ccagcatttc acccagcgtc tcaagactct cttcagcatg ctcaactatg agcggacaaa   2040
acatcctcac cttatggggt cttctgtact gggtatgaat gacatctaca ggacctggcg   2100
ggcctttgtg ctgcgtgtgc gtgctctgga ccagacaccc aggatgtact ttgttaaggc   2160
agatgtgacc ggggcctatg atgccatccc ccagggtaag ctggtggagg ttgttgccaa   2220
tatgatcagg cactcggaga gcacgtactg tatccgccag tatgcagtgg tccggagaga   2280
tagccaaggc caagtccaca agtcctttag gagacaggtc accaccctct ctgacctcca   2340
gccatacatg ggccagttcc ttaagcatct gcaggattca gatgccagtg cactgaggaa   2400
ctccgttgtc atcgagcaga gcatctctat gaatgagagc agcagcagcc tgtttgactt   2460
cttcctgcac ttcctgcgtc acagtgtcgt aaagattggt gacaggtgct atacgcagtg   2520
ccagggcatc ccccagggct ccagcctatc caccctgctc tgcagtctgt gtttcggaga   2580
catggagaac aagctgtttg ctgaggtgca gcgggatggg ttgcttttac gttttgttga   2640
tgactttctg ttggtgacgc ctcacttgga ccaagcaaaa accttcctca gcaccctggt   2700
ccatggcgtt cctgagtatg ggtgcatgat aaacttgcag aagacagtgg tgaacttccc   2760
tgtggagcct ggtaccctgg gtggtgcagc tccataccag ctgcctgctc actgcctgtt   2820
tccctggtgt ggcttgctgc tggacactca gactttggag gtgttctgtg actactcagg   2880
ttatgcccag acctcaatta agacgagcct caccttccag agtgtcttca aagctgggaa   2940
gaccatgcgg aacaagctcc tgtcggtctt gcggttgaag tgtcacggtc tatttctaga   3000
cttgcaggtg aacagcctcc agacagtctg catcaatata tacaagatct tcctgcttca   3060
ggcctacagg ttccatgcat gtgtgattca gcttcccttt gaccagcgtg ttaggaagaa   3120
cctcacattc tttctgggca tcatctccag ccaagcatcc tgctgctatg ctatcctgaa   3180
ggtcaagaat ccaggaatga cactaaaggc ctctggctcc tttcctcctg aagccgcaca   3240
ttggctctgc taccaggcct tcctgctcaa gctggctgct cattctgtca tctacaaatg   3300
tctcctggga cctctgagga cagcccaaaa actgctgtgc cggaagctcc cagaggcgac   3360
aatgaccatc cttaaagctg cagctgaccc agccctaagc acagactttc agaccatttt   3420
ggactaacaa ttggctcgct ttcttgctgt ccaatttcta ttaaaggttc cttttgttcc   3480
ctaagtccaa ctactaaact gggggatatt atgaagggcc ttgagcatct ggattctgcc   3540
taataaaaaa catttctttt cattgcgaat tcaaaaaaaa aaaaaaaaaa aaaaaaaaaa   3600
aaaaaaaaaa aaaaaaaaaa aaaaaaaaaa aaaaaaaaaa aaaaaaaaaa aaaaaaaaaa   3660
aaaaaaaaaa aaaaaaaaaa aaaaaaaaaa aaaaaaaaaa aaaaaaaaaa aaaaaaaaaa   3720
aaa                                                                 3723

<210> SEQ ID NO 38
<211> LENGTH: 3601
<212> TYPE: DNA
<213> ORGANISM: Mus musculus

<400> SEQUENCE: 38

aggaaataag agagaaaaga agagtaagaa gaaatataag agccaccatg acccgcgctc     60
ctcgttgccc cgcggtgcgc tctctgctgc gcagccgata ccgggaggtg tggccgctgg    120
```

-continued

```
caacctttgt gcggcgcctg gggcccgagg gcaggcggct tgtgcaaccc ggggacccga    180
agatctaccg cactttggtt gcccaatgcc tagtgtgcat gcactggggc tcacagcctc    240
cacctgccga cctttccttc caccaggtgt catccctgaa agagctggtg gccagggttg    300
tgcagagact ctgcgagcgc aacgagagaa acgtgctggc ttttggcttt gagctgctta    360
acgaggccag aggcgggcct cccatggcct tcactagtag cgtgcgtagc tacttgccca    420
acactgttat tgagaccctg cgtgtcagtg gtgcatggat gctactgttg agccgagtgg    480
gcgacgacct gctggtctac ctgctggcac actgtgctct ttatcttctg gtgcccccca    540
gctgtgccta ccaggtgtgt gggtctcccc tgtaccaaat ttgtgccacc acggatatct    600
ggccctctgt gtccgctagt tacaggccca cccgacccgt gggcaggaat ttcactaacc    660
ttaggttctt acaacagatc aagagcagta gtcgccagga agcaccgaaa cccctggcct    720
tgccatctcg aggtacaaag aggcatctga gtctcaccag tacaagtgtg ccttcagcta    780
agaaggccag atgctatcct gtcccgagag tggaggaggg accccacagg caggtgctac    840
caaccccatc aggcaaatca tgggtgccaa gtcctgctcg gtcccccgag gtgcctactg    900
cagagaaaga tttgtcttct aaaggaaagg tgtctgacct gagtctctct gggtcggtgt    960
gctgtaaaca caagcccagc tccacatctc tgctgtcacc accccgccaa aatgcctttc   1020
agctcaggcc atttattgag accagacatt tcctttactc caggggagat ggccaagagc   1080
gtctaaaccc ctcattccta ctcagcaacc tccagcctaa cttgactggg gccaggagac   1140
tggtggagat catctttctg ggctcaaggc ctaggacatc aggaccactc tgcaggacac   1200
accgtctatc gcgtcgatac tggcagatgc ggcccctgtt ccaacagctg ctggtgaacc   1260
atgcagagtg ccaatatgtc agactcctca ggtcacattg caggtttcga acagcaaacc   1320
aacaggtgac agatgccttg aacaccagcc caccgcacct catggatttg ctccgcctgc   1380
acagcagtcc ctggcaggta tatggttttc ttcgggcctg tctctgcaag gtggtgtctg   1440
ctagtctctg gggtaccagg cacaatgagc gccgcttctt taagaactta aagaagttca   1500
tctcgttggg gaaatacggc aagctatcac tgcaggaact gatgtggaag atgaaagtag   1560
aggattgcca ctggctccgc agcagcccgg ggaaggaccg tgtccccgct gcagagcacc   1620
gtctgaggga gaggatcctg gctacgttcc tgttctggct gatggacaca tacgtggtac   1680
agctgcttag gtcattcttt tacatcacag agagcacatt ccagaagaac aggctcttct   1740
tctaccgtaa gagtgtgtgg agcaagctgc agagcattgg agtcaggcaa caccttgaga   1800
gagtgcggct acgggagctg tcacaagagg aggtcaggca tcaccaggac acctggctag   1860
ccatgcccat ctgcagactg cgcttcatcc ccaagcccaa cggcctgcgg cccattgtga   1920
acatgagtta tagcatgggt accagagctt tgggcagaag gaagcaggcc cagcatttca   1980
cccagcgtct caagactctc ttcagcatgc tcaactatga gcggacaaaa catcctcacc   2040
ttatggggtc ttctgtactg ggtatgaatg acatctacag gacctggcgg gcctttgtgc   2100
tgcgtgtgcg tgctctggac cagacaccca ggatgtactt tgttaaggca gatgtgaccg   2160
gggcctatga tgccatcccc cagggtaagc tggtggaggt tgttgccaat atgatcaggc   2220
actcggagag cacgtactgt atccgccagt atgcagtggt ccggagagat agccaaggcc   2280
aagtccacaa gtcctttagg agacaggtca ccaccctctc tgacctccag ccatacatgg   2340
gccagttcct taagcatctg caggattcag atgccagtgc actgaggaac tccgttgtca   2400
tcgagcagag catctctatg aatgagagca gcagcagcct gtttgacttc ttcctgcact   2460
tcctgcgtca cagtgtcgta aagattggtg acaggtgcta tacgcagtgc cagggcatcc   2520
```

cccagggctc cagcctatcc accctgctct gcagtctgtg tttcggagac atggagaaca 2580
agctgtttgc tgaggtgcag cgggatgggt tgcttttacg ttttgttgat gactttctgt 2640
tggtgacgcc tcacttggac caagcaaaaa ccttcctcag caccctggtc catggcgttc 2700
ctgagtatgg gtgcatgata aacttgcaga agacagtggt gaacttccct gtggagcctg 2760
gtaccctggg tggtgcagct ccataccagc tgcctgctca ctgcctgttt ccctggtgtg 2820
gcttgctgct ggacactcag actttggagg tgttctgtga ctactcaggt tatgcccaga 2880
cctcaattaa gacgagcctc accttccaga gtgtcttcaa agctgggaag accatgcgga 2940
acaagctcct gtcggtcttg cggttgaagt gtcacggtct atttctagac ttgcaggtga 3000
acagcctcca gacagtctgc atcaatatat acaagatctt cctgcttcag gcctacaggt 3060
tccatgcatg tgtgattcag cttccctttg accagcgtgt taggaagaac ctcacattct 3120
ttctgggcat catctccagc caagcatcct gctgctatgc tatcctgaag gtcaagaatc 3180
caggaatgac actaaaggcc tctggctcct ttcctcctga agccgcacat tggctctgct 3240
accaggcctt cctgctcaag ctggctgctc attctgtcat ctacaaatgt ctcctgggac 3300
ctctgaggac agcccaaaaa ctgctgtgcc ggaagctccc agaggcgaca atgaccatcc 3360
ttaaagctgc agctgaccca gccctaagca cagactttca gaccattttg gactaataat 3420
taagctgcct tctgcggggc ttgccttctg gccatgccct tcttctctcc cttgcacctg 3480
tacctcttgg tctttgaata aagcctgagt aggaagtcta gaaaaaaaaa aaaaaaaaaa 3540
aaaaaaaaaa aaaaaaaaaa aaaaaaaaaa aaaaaaaaaa aaaaaaaaaa aaaaaaaaaa 3600
a 3601

<210> SEQ ID NO 39
<211> LENGTH: 3753
<212> TYPE: DNA
<213> ORGANISM: Homo sapiens

<400> SEQUENCE: 39
gggacatttg cttctgacac aactgtgttc actagcaacc tcaaacaact agtacaccat 60
gccgcgcgct ccccgctgcc gagccgtgcg ctccctgctg cgcagccact accgcgaggt 120
gctgccgctg gccacgttcg tgcggcgcct ggggccccag ggctggcggc tggtgcagcg 180
cggggacccg gcggctttcc gcgcgctggt ggcccagtgc ctggtgtgcg tgccctggga 240
cgcacggccg ccccccgccg ccccctcctt ccgccaggtg tcctgcctga aggagctggt 300
ggcccgagtg ctgcagaggc tgtgcgagcg cggcgcgaag aacgtgctgg ccttcggctt 360
cgcgctgctg gacggggccc gcgggggccc ccccgaggcc ttcaccacca gcgtgcgcag 420
ctacctgccc aacacggtga ccgacgcact gcgggggagc ggggcgtggg ggctgctgct 480
gcgccgcgtg ggcgacgacg tgctggttca cctgctggca cgctgcgcgc tctttgtgct 540
ggtggctccc agctgcgcct accaggtgtg cgggccgccg ctgtaccagc tcggcgctgc 600
cactcaggcc cggcccccgc cacacgctag tggaccccga aggcgtctgg gatgcgaacg 660
ggcctggaac catagcgtca gggaggccgg ggtccccctg ggcctgccag ccccgggtgc 720
gaggaggcgc gggggcagtg ccagccgaag tctgccgttg cccaagaggc ccaggcgtgg 780
cgctgcccct gagccggagc ggacgcccgt tgggcagggg tcctgggccc acccgggcag 840
gacgcgtgga ccgagtgacc gtggtttctg tgtggtgtca cctgccagac ccgccgaaga 900
agccacctct ttggagggtg cgctctctgg cacgcgccac tcccacccat ccgtgggccg 960

-continued

```
ccagcaccac gcgggccccc catccacatc gcggccacca cgtccctggg acacgccttg   1020
tcccccggtg tacgccgaga ccaagcactt cctctactcc tcaggcgaca aggagcagct   1080
gcggccctcc ttcctactca gctctctgag gcccagcctg actggcgctc ggaggctcgt   1140
ggagaccatc tttctgggtt ccaggccctg gatgccaggg actccccgca ggttgccccg   1200
cctgccccag cgctactggc aaatgcggcc cctgtttctg gagctgcttg ggaaccacgc   1260
gcagtgcccc tacggggtgc tcctcaagac gcactgcccg ctgcgagctg cggtcacccc   1320
agcagccggt gtctgtgccc gggagaagcc ccagggctct gtggcggccc ccgaggagga   1380
ggacacagac ccccgtcgcc tggtgcagct gctccgccag cacagcagcc cctggcaggt   1440
gtacggcttc gtgcgggcct gcctgcgccg gctggtgccc ccaggcctct ggggctccag   1500
gcacaacgaa cgccgcttcc tcaggaacac caagaagttc atctccctgg ggaagcatgc   1560
caagctctcg ctgcaggagc tgacgtggaa gatgagcgtg cgggactgcg cttggctgcg   1620
caggagccca ggggttggct gtgttccggc cgcagagcac cgtctgcgtg aggagatcct   1680
ggccaagttc ctgcactggc tgatgagtgt gtacgtcgtc gagctgctca ggtctttctt   1740
ttatgtcacg gagaccacgt ttcaaaagaa caggctcttt ttctaccgga agagtgtctg   1800
gagcaagttg caaagcattg gaatcagaca gcacttgaag agggtgcagc tgcgggagct   1860
gtcggaagca gaggtcaggc agcatcggga agccaggccc gccctgctga cgtccagact   1920
ccgcttcatc cccaagcctg acgggctgcg gccgattgtg aacatggact acgtcgtggg   1980
agccagaacg ttccgcagag aaaagagggc cgagcgtctc acctcgaggg tgaaggcact   2040
gttcagcgtg ctcaactacg agcgggcgcg gcgccccggc ctcctgggcg cctctgtgct   2100
gggcctggac gatatccaca gggcctggcg caccttcgtg ctgcgtgtgc gggcccagga   2160
cccgccgcct gagctgtact ttgtcaaggt ggatgtgacg ggcgcgtacg acaccatccc   2220
ccaggacagg ctcacggagg tcatcgccag catcatcaaa ccccagaaca cgtactgcgt   2280
gcgtcggtat gccgtggtcc agaaggccgc ccatgggcac gtccgcaagg ccttcaagag   2340
ccacgtctct accttgacag acctccagcc gtacatgcga cagttcgtgg ctcacctgca   2400
ggagaccagc ccgctgaggg atgccgtcgt catcgagcag agctcctccc tgaatgaggc   2460
cagcagtggc ctcttcgacg tcttcctacg cttcatgtgc caccacgccg tgcgcatcag   2520
gggcaagtcc tacgtccagt gccaggggat cccgcagggc tccatcctct ccacgctgct   2580
ctgcagcctg tgctacggcg acatggagaa caagctgttt gcggggattc ggcgggacgg   2640
gctgctcctg cgtttggtgg atgatttctt gttggtgaca cctcacctca cccacgcgaa   2700
aaccttcctc aggaccctgg tccgaggtgt ccctgagtat ggctgcgtgg tgaacttgcg   2760
gaagacagtg gtgaacttcc ctgtagaaga cgaggccctg ggtggcacgg cttttgttca   2820
gatgccggcc cacggcctat tcccctggtg cggcctgctg ctggataccc ggaccctgga   2880
ggtgcagagc gactactcca gctatgcccg gacctccatc agagccagtc tcaccttcaa   2940
ccgcggcttc aaggctggga ggaacatgcg tcgcaaactc tttggggtct tgcggctgaa   3000
gtgtcacagc ctgtttctgg atttgcaggt gaacagcctc cagacggtgt gcaccaacat   3060
ctacaagatc ctcctgctgc aggcgtacag gtttcacgca tgtgtgctgc agctcccatt   3120
tcatcagcaa gtttggaaga accccacatt tttcctgcgc gtcatctctg acacggcctc   3180
cctctgctac tccatcctga aagccaagaa cgcagggatg tcgctggggg ccaagggcgc   3240
cgccggccct ctgccctccg aggccgtgca gtggctgtgc caccaagcat tcctgctcaa   3300
gctgactcga caccgtgtca cctacgtgcc actcctgggg tcactcagga cagcccagac   3360
```

gcagctgagt cggaagctcc cggggacgac gctgactgcc ctggaggccg cagccaaccc 3420
ggcactgccc tcagacttca agaccatcct ggactgacaa ttggctcgct ttcttgctgt 3480
ccaatttcta ttaaaggttc cttttgttcc ctaagtccaa ctactaaact gggggatatt 3540
atgaagggcc ttgagcatct ggattctgcc taataaaaaa catttctttt cattgcgaat 3600
tcaaaaaaaa aaaaaaaaaa aaaaaaaaaa aaaaaaaaaa aaaaaaaaaa aaaaaaaaaa 3660
aaaaaaaaaa aaaaaaaaaa aaaaaaaaaa aaaaaaaaaa aaaaaaaaaa aaaaaaaaaa 3720
aaaaaaaaaa aaaaaaaaaa aaaaaaaaaa aaa 3753

<210> SEQ ID NO 40
<211> LENGTH: 3665
<212> TYPE: DNA
<213> ORGANISM: Homo sapiens

<400> SEQUENCE: 40
aggaaataag agagaaaaga agagtaagaa gaaatataag agccaccatg ccgcgcgctc 60
cccgctgccg agccgtgcgc tccctgctgc gcagccacta ccgcgaggtg ctgccgctgg 120
ccacgttcgt gcggcgcctg gggccccagg gctggcggct ggtgcagcgc ggggacccgg 180
cggctttccg cgcgctggtg gcccagtgcc tggtgtgcgt gccctgggac gcacggccgc 240
cccccgccgc cccctccttc cgccaggtgt cctgcctgaa ggagctggtg gcccgagtgc 300
tgcagaggct gtgcgagcgc ggcgcgaaga acgtgctggc cttcggcttc gcgctgctgg 360
acggggcccg cgggggcccc cccgaggcct tcaccaccag cgtgcgcagc tacctgccca 420
acacggtgac cgacgcactg cgggggagcg gggcgtgggg gctgctgctg cgccgcgtgg 480
gcgacgacgt gctggttcac ctgctggcac gctgcgcgct ctttgtgctg gtggctccca 540
gctgcgccta ccaggtgtgc gggccgccgc tgtaccagct cggcgctgcc actcaggccc 600
ggcccccgcc acacgctagt ggaccccgaa ggcgtctggg atgcgaacgg gcctggaacc 660
atagcgtcag ggaggccggg gtccccctgg gcctgccagc cccgggtgcg aggaggcgcg 720
ggggcagtgc cagccgaagt ctgccgttgc ccaagaggcc caggcgtggc gctgcccctg 780
agccggagcg gacgcccgtt gggcaggggt cctgggccca cccgggcagg acgcgtggac 840
cgagtgaccg tggtttctgt gtggtgtcac ctgccagacc cgccgaagaa gccacctctt 900
tggagggtgc gctctctggc acgcgccact cccacccatc cgtgggccgc cagcaccacg 960
cgggcccccc atccacatcg cggccaccac gtccctggga cacgccttgt cccccggtgt 1020
acgccgagac caagcacttc ctctactcct caggcgacaa ggagcagctg cggccctcct 1080
tcctactcag ctctctgagg cccagcctga ctggcgctcg gaggctcgtg gagaccatct 1140
ttctgggttc caggccctgg atgccaggga ctccccgcag gttgccccgc ctgccccagc 1200
gctactggca aatgcggccc ctgtttctgg agctgcttgg gaaccacgcg cagtgcccct 1260
acggggtgct cctcaagacg cactgcccgc tgcgagctgc ggtcacccca gcagccggtg 1320
tctgtgcccg ggagaagccc cagggctctg tggcggcccc cgaggaggag gacacagacc 1380
cccgtcgcct ggtgcagctg ctccgccagc acagcagccc ctggcaggtg tacggcttcg 1440
tgcgggcctg cctgcgccgg ctggtgcccc caggcctctg gggctccagg cacaacgaac 1500
gccgcttcct caggaacacc aagaagttca tctccctggg gaagcatgcc aagctctcgc 1560

-continued

```
tgcaggagct gacgtggaag atgagcgtgc gggactgcgc ttggctgcgc aggagcccag   1620
gggttggctg tgttccggcc gcagagcacc gtctgcgtga ggagatcctg gccaagttcc   1680
tgcactggct gatgagtgtg tacgtcgtcg agctgctcag gtctttcttt tatgtcacgg   1740
agaccacgtt tcaaaagaac aggctctttt tctaccggaa gagtgtctgg agcaagttgc   1800
aaagcattgg aatcagacag cacttgaaga gggtgcagct gcgggagctg tcggaagcag   1860
aggtcaggca gcatcgggaa gccaggcccg ccctgctgac gtccagactc cgcttcatcc   1920
ccaagcctga cgggctgcgg ccgattgtga acatggacta cgtcgtggga gccagaacgt   1980
tccgcagaga aaagagggcc gagcgtctca cctcgagggt gaaggcactg ttcagcgtgc   2040
tcaactacga gcgggcgcgg cgccccggcc tcctgggcgc ctctgtgctg ggcctggacg   2100
atatccacag ggcctggcgc accttcgtgc tgcgtgtgcg ggcccaggac ccgccgcctg   2160
agctgtactt tgtcaaggtg gatgtgacgg gcgcgtacga caccatcccc caggacaggc   2220
tcacggaggt catcgccagc atcatcaaac cccagaacac gtactgcgtg cgtcggtatg   2280
ccgtggtcca gaaggccgcc catgggcacg tccgcaaggc cttcaagagc cacgtctcta   2340
ccttgacaga cctccagccg tacatgcgac agttcgtggc tcacctgcag gagaccagcc   2400
cgctgaggga tgccgtcgtc atcgagcaga gctcctccct gaatgaggcc agcagtggcc   2460
tcttcgacgt cttcctacgc ttcatgtgcc accacgccgt gcgcatcagg ggcaagtcct   2520
acgtccagtg ccaggggatc ccgcagggct ccatcctctc cacgctgctc tgcagcctgt   2580
gctacggcga catggagaac aagctgtttg cggggattcg gcgggacggg ctgctcctgc   2640
gtttggtgga tgatttcttg ttggtgacac ctcacctcac ccacgcgaaa accttcctca   2700
ggaccctggt ccgaggtgtc cctgagtatg gctgcgtggt gaacttgcgg aagacagtgg   2760
tgaacttccc tgtagaagac gaggccctgg gtggcacggc ttttgttcag atgccggccc   2820
acggcctatt cccctggtgc ggcctgctgc tggatacccg gaccctggag gtgcagagcg   2880
actactccag ctatgcccgg acctccatca gagccagtct caccttcaac cgcggcttca   2940
aggctgggag gaacatgcgt cgcaaactct ttggggtctt gcggctgaag tgtcacagcc   3000
tgtttctgga tttgcaggtg aacagcctcc agacggtgtg caccaacatc tacaagatcc   3060
tcctgctgca ggcgtacagg tttcacgcat gtgtgctgca gctcccattt catcagcaag   3120
tttggaagaa ccccacattt ttcctgcgcg tcatctctga cacggcctcc ctctgctact   3180
ccatcctgaa agccaagaac gcagggatgt cgctgggggc caagggcgcc gccggccctc   3240
tgccctccga ggccgtgcag tggctgtgcc accaagcatt cctgctcaag ctgactcgac   3300
accgtgtcac ctacgtgcca ctcctggggt cactcaggac agcccagacg cagctgagtc   3360
ggaagctccc ggggacgacg ctgactgccc tggaggccgc agccaacccg gcactgccct   3420
cagacttcaa gaccatcctg gactgataat taagctgcct tctgcggggc ttgccttctg   3480
gccatgccct tcttctctcc cttgcacctg tacctcttgg tctttgaata aagcctgagt   3540
aggaagaaaa aaaaaaaaaa aaaaaaaaaa aaaaaaaaaa aaaaaaaaaa aaaaaaaaaa   3600
aaaaaaaaaa aaaaaaaaaa aaaaaaaaaa aaaaaaaaaa aaaaaaaaaa aaaaaaaaaa   3660
aaaaa                                                               3665
```

COMPOSITIONS AND METHODS FOR DELIVERY OF RNA

CROSS-REFERENCE TO RELATED APPLICATIONS

This application claims priority to and the benefit of U.S. Provisional Patent Application No. 63/169,118, filed on Mar. 31, 2021, the disclosure of which is hereby incorporated by reference in its entirety.

INCORPORATION OF THE SEQUENCE LISTING

The contents of the text file named "REJU_005_01US_SeqList_ST25.txt," which was created on Mar. 30, 2022 and is 205 KB in size, are hereby incorporated by reference in their entirety.

FIELD OF THE DISCLOSURE

The present disclosure relates generally to compositions and methods for delivery of ribonucleic acid (RNA) therapies in the treatment of lung and fibrotic diseases.

BACKGROUND

Numerous lung diseases have been identified for which there is no current treatment. Lung diseases, e.g., pulmonary fibrosis, interstitial lung disease, and lung cancer, often induce fibrosis as part of disease progression, which further limits the extent to which patient recovery can occur. Delivery of polynucleotides to the lung for the treatment of lung disease are one method of treatment in development; however, the compositions and methods for delivery of these treatments are in need of improvement, and no treatment has been developed for treating the resulting fibrosis.

Thus, there remains a need in the art for delivery formulations capable of delivering polynucleotides, e.g., mRNAs, to the lung which treat lung disease and/or lung fibrosis. The following disclosure addresses this need.

SUMMARY

Provided herein are delivery vehicles and compositions thereof for delivery of mRNA to lung cells at high transfection rates. In some embodiments, the mRNA is delivered to lung cells with a low toxicity. In some embodiments, the lung cells include lung alveolar epithelium and vascular endothelium, and the delivery vehicles disclosed herein are useful for delivery of mRNA useful for the treatment or prevention of lung diseases and disorders. In some embodiments, the mRNA delivered to lung cells encodes a protein useful for treatment of a lung disease or disorder. In some embodiments, the mRNA encodes a TERT protein. In some embodiments, the protein is an antigen of a pathogen. In some embodiments, the lung diseases and disorder include, but are not limited to: pulmonary fibrosis, idiopathic pulmonary fibrosis, emphysema, interstitial lung diseases, chronic obstructive pulmonary disease (COPD), a lung infection, pneumonia, tuberculosis, gastric reflux, lung cancer, cystic fibrosis, dyskeratosis congenita, Alpha-1 antitrypsin deficiency, and other acquired or genetic diseases of the lung. The disclosure relates to telomerase reverse transcriptase (TERT) messenger ribonucleic acid (mRNA) therapies for the treatment of fibrotic diseases and conditions, e.g. of the lung, and lung diseases and conditions. Treatment with compositions comprising TERT mRNA may prevent, reverse or treat fibrosis and other pathological features of fibrotic disease and/or lung disease leading to improvements in overall organ function and subject health.

Accordingly, in some embodiments, provided herein are compositions comprising one or more synthetic messenger ribonucleic acids (mRNAs) encoding telomerase reverse transcriptase (TERT).

In some embodiments, the composition comprises: (i) a ribonucleic acid (RNA) encoding telomerase reverse transcriptase (TERT) and (ii) a delivery vehicle, wherein the RNA encoding TERT comprises one or more modified nucleotides and wherein the delivery vehicle of (ii) is operably-linked to the RNA encoding TERT.

In some embodiments of the compositions of the disclosure, the delivery vehicle comprises one or more of a nanoparticle, a liposome, a cationic lipid, an exosome, an extracellular vesicle, a lipid nanoparticle, a natural lipoprotein particle, and an artificial lipoprotein particle.

Provided herein are lipid nanoparticle particle (LNP) capable of transfecting at least 50%, at least 60%, at least 70%, at least 80%, at least 90%, or at least 95% of a population of lung cells.

In some embodiments of the compositions of the disclosure, the delivery vehicle comprises a lipid nanoparticle (LNP). In some embodiments, the delivery vehicle comprises a cationic lipid.

In some embodiments, the delivery vehicle comprises a targeting moiety. In some embodiments, the targeting lipid results in the delivery vehicle specifically or selectively interacting with a lung cell. In some embodiments, the targeting moiety comprises cholesterol. In some embodiments, the targeting moiety is a lipid which specifically or selectively interacts with a lung cell. In some embodiments, the targeting lipid comprises 1,2-dioleoyl-3-trimethylammonium-propane (DOTAP), N,N-distearyl-N,N-dimethylarnmonium bromide (DABB), or 1,2-dimyristoyl-sn-glycero-3-ethylphosphocholine (EPC).

In some embodiments of the compositions of the disclosure, including those in which the delivery vehicle is a lipid nanoparticle (LNP), the delivery vehicle comprises a compound of Formula I:

(1)

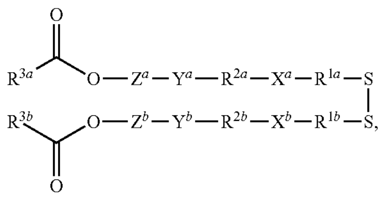

wherein $R^{1a}$ and $R^{1b}$ each independently represents an alkylene group having 1 to 6 carbon atoms, wherein $X^a$ and $X^b$ are each independently an acyclic alkyl tertiary amino group having 1 to 6 carbon atoms and 1 tertiary amino group, or 2 to 5 carbon atoms, and A cyclic alkylene tertiary amino group having 1 to 2 tertiary amino groups, wherein $R^{2a}$ and $R^{2b}$ each independently represent an alkylene group having 8 or less carbon atoms or an oxydialkylene group, wherein $Y^a$ and $Y^b$ each independently represent an ester bond, an amide bond, a carbamate bond, an ether bond or a urea bond; wherein $Z^a$ and $Z^b$ are each independently a divalent group derived from an aromatic compound having 3 to 16 carbon atoms, having at least one aromatic ring, and optionally having a hetero atom, and wherein $R^{3a}$ and $R^{3b}$ each independently represent a residue derived from a reaction product of a fat-soluble vitamin having a hydroxyl group and succinic anhydride or glutaric anhydride, or a sterol derivative having a hydroxyl group and succinic anhydride or a residue derived from a reaction product with glutaric anhydride or an aliphatic hydrocarbon group having 12 to 22 carbon atoms.

In some embodiments of the compositions of the disclosure, including those in which the delivery vehicle is a lipid nanoparticle (LNP), the compound of Formula I is:

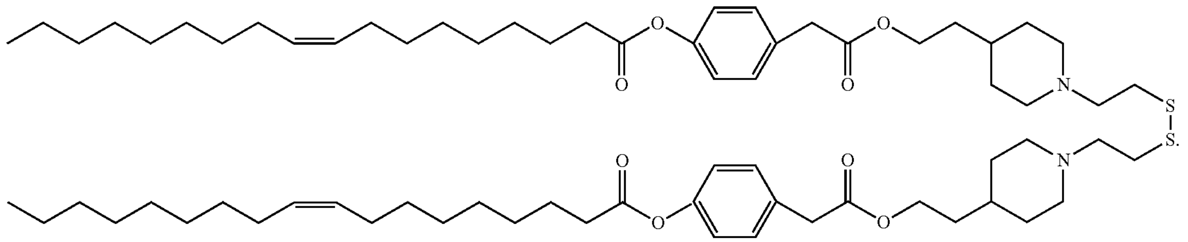

In some embodiments of the compositions of the disclosure, including those in which the delivery vehicle is a lipid nanoparticle (LNP), the compound of Formula I is:

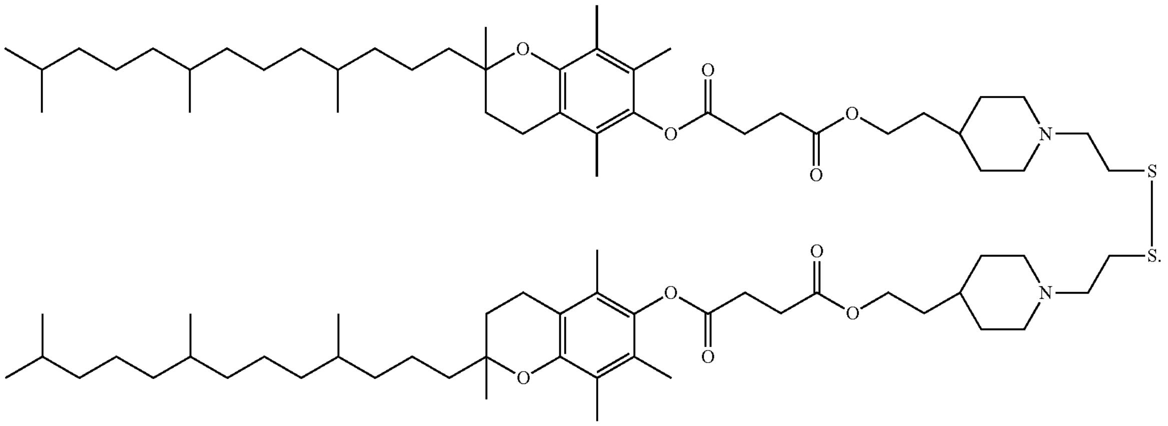 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2]

In some embodiments of the compositions of the disclosure, including those in which the delivery vehicle is a lipid nanoparticle (LNP), the compound of Formula I is:

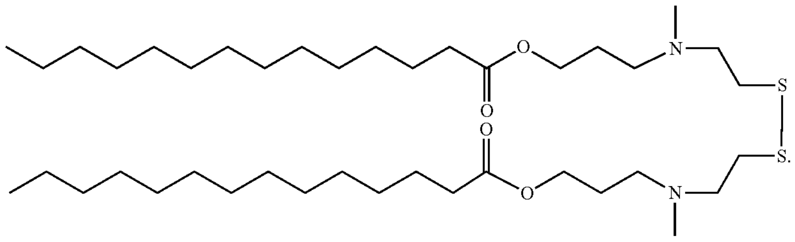 [SMILES: CCCCCCCCCCCCCC(=O)OCCCN(C)CCSSCCN(C)CCCOC(=O)CCCCCCCCCCCCC]

In some embodiments of the compositions of the disclosure, including those in which the delivery vehicle is a lipid nanoparticle (LNP), the compound of Formula I is:

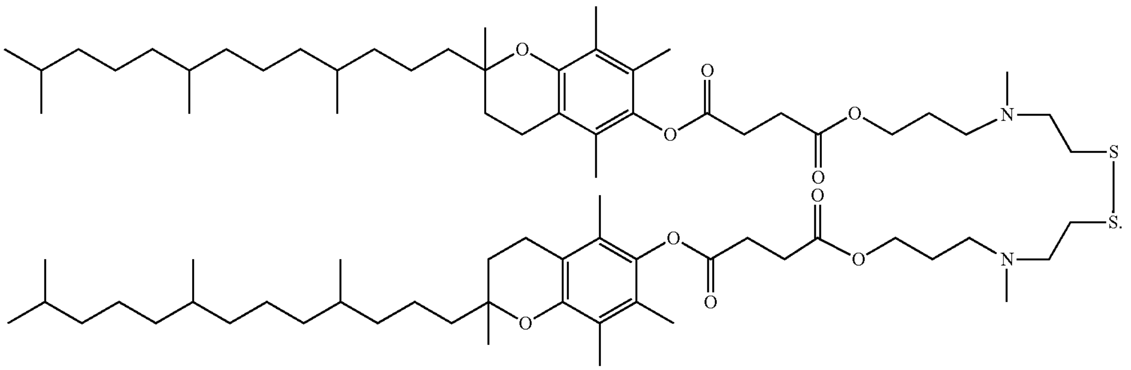 [SMILES: Cc1c(C)c2c(c(C)c1OC(=O)CCC(=O)OCCCN(C)CCSSCCN(C)CCCOC(=O)CCC(=O)Oc1c(C)c(C)c3c(c1C)CCC(C)(CCCC(C)CCCC(C)CCCC(C)C)O3)CCC(C)(CCCC(C)CCCC(C)CCCC(C)C)O2]

In some embodiments of the compositions of the disclosure, including those in which the delivery vehicle is a lipid nanoparticle (LNP), the compound of Formula I is:

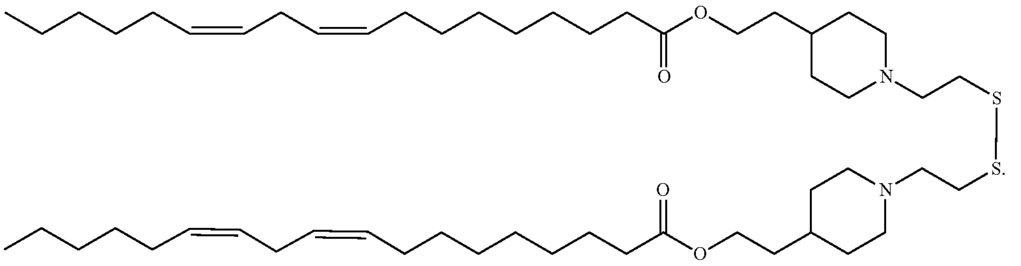 [SMILES: CCCCC/C=C\C/C=C\CCCCCCCC(=O)OCCC1CCN(CCSSCCN2CCC(CCOC(=O)CCCCCCC/C=C\C/C=C\CCCCC)CC2)CC1]

In some embodiments of the compositions of the disclosure, including those in which the delivery vehicle is a lipid nanoparticle (LNP), the compound of Formula I is:

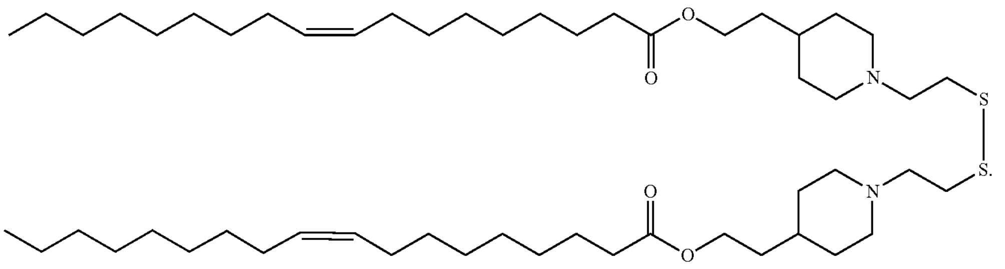 [SMILES: CCCCCCCC/C=C\CCCCCCCC(=O)OCCC1CCN(CCSSCCN2CCC(CCOC(=O)CCCCCCC/C=C\CCCCCCCC)CC2)CC1]

In some embodiments, the RNA comprise a sequence of SEQ ID NOS: 1-5, 30-31, or 37-40, or a nucleic acid sequence at least 70%, at least 75%, at least 80%, at least 85%, at least 90%, at least 95%, at least 96%, at least 97%, at least 98%, or at least 99% identical thereto.

In some embodiments of the compositions of the disclosure, including those in which the delivery vehicle is a lipid nanoparticle (LNP), the RNA comprises a 5' cap. In some embodiments, the 5' cap comprises an anti-reverse cap analog (ARCA). In some embodiments, the ARCA comprises an 3'-O-Me-m7G(5')ppp(5')G structure. In some embodiments, the 5' cap comprises m7G(5')ppp(5')(2'OMeA)pG. In some embodiments, the 5' cap comprises m7(3'OMeG)(5')ppp(5')(2'OMeA)pG.

In some embodiments of the compositions of the disclosure, including those in which the delivery vehicle is a lipid nanoparticle (LNP), the RNA further comprises at least one untranslated region (UTR). The UTR may comprise a sequence of SEQ ID NOs: 32-36, or a nucleic acid sequence at least 70%, at least 75%, at least 80%, at least 85%, at least 90%, at least 95%, at least 96%, at least 97%, at least 98%, or at least 99% identical thereto. In some embodiments, the at least one UTR is positioned 5' to the RNA encoding TERT. In some embodiments, the at least one UTR is positioned 3' to the RNA encoding TERT. In some embodiments, the UTR comprises a human sequence. In some embodiments, the UTR comprises a non-human or synthetic sequence. In some embodiments, the UTR comprises a chimeric sequence. In some embodiments, the UTR increases stability, increases half-life, increases a transcription rate or decreases a time until initiation of transcription of the RNA encoding TERT. In some embodiments, the UTR comprises a sequence having at least 70% identity to a UTR sequence isolated or derived from one or more of α-globin, β-globin, c-fos, and a tobacco etch virus.

In some embodiments of the compositions of the disclosure, including those in which the delivery vehicle is a lipid nanoparticle (LNP), the one or more modified nucleotides of the RNA encoding TERT comprise one or more of a modified adenine or analog thereof, a modified cytidine or analog thereof, a modified guanosine or analog thereof, and a modified uridine or analog thereof. In some embodiments, the one or more modified nucleotides of the RNA encoding TERT comprise one or more of 1-methylpseudouridine also known as N1-Methylpseudouridine, pseudouridine (N1m), 2-thiouridine, and 5-methylcytidine. In some embodiments, the one or more modified nucleotides of the RNA encoding TERT comprise 5-methoxyuridine (5-moU). In some embodiments, the one or more modified nucleotides of the RNA encoding TERT comprise one or more of m1A 1-methyladenosine, m6A N6-methyladenosine, Am 2'-O-methyladenosine, i6A N6-isopentenyladenosine, io6A N6-(cis-hydroxyisopentenyl)adenosine, ms2t6A 2-methylthio-N6-(cis-hydroxyisopentenyl) adenosine, g6A N6-glycinylcarbamoyladenosine, t6A N6-threonylcarbamoyladenosine, ms2t6A 2-methylthio-N6-threonyl carbamoyladenosine, Ar(p) 2'-O-ribosyladenosine (phosphate), m6 2A N6,N6-dimethyladenosine, m6Am N6,2'-O-dimethyladenosine, m6 2Am N6,N6,2'-O-trimethyladenosine, m1Am 1,2'-O-dimethyladenosine, m3C 3-methylcytidine, m5C 5-methylcytidine, Cm 2'-O-methylcytidine, ac4C N4-acetylcytidine, f5C 5-formylcytidine, m4C N4-methylcytidine, hm5C 5-hydroxymethylcytidine, f5Cm 5-formyl-2'-O-methylcytidine, m1G 1-methylguanosine, m2G N2-methylguanosine, m7G 7-methylguanosine, Gm 2'-O-methylguanosine, m2 2G N2,N2-dimethylguanosine, Gr(p) 2'-O-ribosylguanosine (phosphate), yW wybutosine, o2yW peroxywybutosine, OHyW hydroxywybutosine, OHyW* undermodified hydroxywybutosine, imG wyosine, m2,7G N2,7-dimethylguanosine, m2,2,7G N2,N2,7-trimethylguanosine I inosine, m1I 1-methylinosine, Im 2'-O-methylinosine, Q queuosine, galQ galactosyl-queuosine, manQ mannosyl-queuosine, ψ pseudouridine, D dihydrouridine, m5U 5-methyluridine, Um 2'-O-methyluridine, m5Um 5,2'-O-dimethyluridine, m1ψ 1-methylpseudouridine, ψm 2'-O-methylpseudouridine, s2U 2-thiouridine, ho5U 5-hydroxyuridine, chm5U 5-(carboxyhydroxymethyl)uridine, mchm5U 5-(carboxyhydroxymethyl)uridine, methyl ester mcm5U 5-methoxycarbonylmethyluridine, mcm5Um 5-methoxycarbonylmethyl-2'-O-methyluridine, mcm5s2U 5-methoxycarbonylmethyl-2-thiouridine, ncm5U 5-carbamoylmethyluridine, ncm5Um 5-carbamoylmethyl-2'-O-methyluridine, cmnm5U 5-carboxymethylaminomethyluridine, m3U 3-methyluridine, m1acp3ψ 1-methyl-3-(3-amino-3-carboxypropyl) pseudouridine, cm5U 5-carboxymethyluridine, m3Um 3,2'-O-dimethyluridine, m5D 5-methyldihydrouridine, τm5U 5-taurinomethyluridine, τm5s2U 5-taurinomethyl-2-thiouridine, 2-Aminoadenosine, 2-Amino-6-chloropurineriboside, 8-Azaadenosine, 6-Chloropurineriboside, 5-Iodocytidine, 5-Iodouridine, Inosine, 2'-O-Methylinosine, Xanthosine, 4-Thiouridine, 06-Methylguanosine, 5,6-Dihydrouridine, 2-Thiocytidine, 6-Azacytidine, 6-Azauridine, 2'-O-Methyl-2-aminoadenosine, 2'-O-Methylpseudouridine, N1-Methyladenosine, 2'-O-Methyl-5-methyluridine, 7-Deazaguanosine, 8-Azidoadenosine, 5-Bromocytidine, 5-Bromouridine, 7-Deazaadenosine, 5-Aminoallyluridine, 5-Aminoallylcytidine, 8-Oxoguanosine, 2-Aminopurine-riboside, Pseudoisocytidine, N1-Methylpseudouridine, 5,6-Dihydro-5-Methyluridine, N6-Methyl-2-Aminoadenosine, 5-Carboxycytidine, 5-Hydroxymethyluridine, Thienoguanosine, 5-Hydroxy cytidine, 5-Formyluridine, 5-Carboxyuridine, 5-Methoxyuridine, 5-Methoxycytidine, Thienouridine, 5-Carboxymethylesteruridine, Thienocytidine, 8-Oxoadenoosine, Isoguanosine, N1-Ethylpseudouridine, N1-Methyl-2'-O-Methylpseudouridine, N1-Methoxymethylpseudouridine, N1-Propylpseudouridine, 2'-O-Methyl-N6-Methyladenosine, 2-Amino-6-Cl-purine-2'-deoxyriboside, 2-Amino-2'-deoxyadenosine, 2-Aminopurine-2'-deoxyriboside, 5-Bromo-2'-deoxycytidine, 5-Bromo-2'-deoxyuridine, 6-Chloropurine-2'-deoxyriboside, 7-Deaza-2'-deoxyadenosine, 7-Deaza-2'-deoxyguanosine, 2'-Deoxyinosine, 5-Propynyl-2'-deoxycytidine, 5-Propynyl-2'-deoxyuridine, 5-Fluoro-2'-deoxyuridine, 5-Iodo-2'-deoxycytidine, 5-Iodo-2'-deoxyuridine, N6-Methyl-2'-deoxyadenosine, 5-Methyl-2'-deoxycytidine, 06-Methyl-2'-deoxyguanosine, N2-Methyl-2'-deoxyguanosine, 8-Oxo-2'-deoxyadenosine, 8-Oxo-2'-deoxyguanosine, 2-Thiothymidine, 2'-Deoxy-P-nucleoside, 5-Hydroxy-2'-deoxycytidine, 4-Thiothymidine, 2-Thio-2'-deoxycytidine, 6-Aza-2'-deoxyuridine, 6-Thio-2'-deoxyguanosine, 8-Chloro-2'-deoxyadenosine, 5-Aminoallyl-2'-deoxycytidine, 5-Aminoallyl-2'-deoxyuridine, N4-Methyl-2'-deoxycytidine, 2'-Deoxyzebularine, 5-Hydroxymethyl-2'-deoxyuridine, 5-Hydroxymethyl-2'-deoxycytidine, 5-Propargylamino-2'-deoxycytidine, 5-Propargylamino-2'-deoxyuridine, 5-Carboxy-2'-deoxycytidine, 5-Formyl-2'-deoxycytidine, 5-[(3-Indolyl)propionamide-N-allyl]-2'-deoxyuridine, 5-Carboxy-2'-deoxyuridine, 5-Formyl-2'-deoxyuridine, 7-Deaza-7-Propargylamino-2'-deoxyadenosine, 7-Deaza-7-Propargylamino-2'-deoxyguanosine, Biotin-16-Aminoallyl-2'-dUTP, Biotin-16-Aminoallyl-2'-dCTP, Biotin-16-Aminoallylcytidine, N4-Biotin-OBEA-2'-deoxycytidine, Biotin-16-Aminoallyluridine, Dabcyl-5-3-Aminoallyl-2'-dUTP, Desthiobiotin-6-Aminoallyl-2'-deoxycytidine, Desthiobiotin-16-Aminoallyl-Uridine, Biotin-16-7-Deaza-7-Propargylamino-2'-deoxyguanosine, Cyanine 3-5-Propargylamino-2'-deoxycytidine, Cyanine 3-6-Propargylamino-2'-deoxyuridine, Cyanine 5-6-Propargylamino-2'-deoxycytidine, Cyanine 5-6-Propargylamino-2'-deoxyuridine, Cyanine 3-Aminoallylcytidine, Cyanine 3-Aminoallyluridine, Cyanine 5-Aminoallylcytidine, Cyanine 5-Aminoallyluridine, Cyanine 7-Aminoallyluridine, 2'-Fluoro-2'-deoxyadenosine, 2'-Fluoro-2'-deoxycytidine, 2'-Fluoro-2'-deoxyguanosine, 2'-Fluoro-2'-deoxyuridine, 2'-O-Methyladenosine, 2'-O-Methylcytidine, 2'-O-Methylguanosine, 2'-O-Methyluridine, Puromycin, 2'-Amino-2'-deoxycytidine, 2'-Amino-2'-deoxyuridine, 2'-Azido-2'-deoxycytidine, 2'-Azido-2'-deoxyuridine, Aracytidine, Arauridine, 2'-Azido-2'-deoxyadenosine, 2'-Amino-2'-deoxyadenosine, Araadenosine, 2'-Fluoro-thymidine, 3'-O-Methyladenosine, 3'-O-Methylcytidine, 3'-O-Methylguanosine, 3'-O-Methyluridine, 2'-Azido-2'-deoxyguanosine, Araguanosine, 2'-Deoxyuridine, 3'-O-(2-nitrobenzyl)-2'-Deoxyadenosine, 3'-O-(2-nitrobenzyl)-2'-Deoxyinosine, 3'-Deoxyadenosine, 3'-Deoxyguanosine, 3'-Deoxycytidine, 3'-Deoxy-5-Methyluridine, 3'-Deoxyuridine, 2',3'-Dideoxyadenosine, 2',3'-Dideoxyguanosine, 2',3'-Dideoxyuridine, 2',3'-Dideoxythymidine, 2',3'-Dideoxycytidine, 3'-Azido-2',3'-dideoxyadenosine, 3'-Azido-2',3'-dideoxythymidine, 3'-Amino-2',3'-dideoxyadenosine, 3'-Amino-2',3'-dideoxycytidine, 3'-Amino-2',3'-dideoxyguanosine, 3'-Amino-2',3'-dideoxythymidine, 3'-Azido-2',3'-dideoxycytidine, 3'-Azido-2',3'-dideoxyuridine, 5-Bromo-2',3'-dideoxyuridine, 2',3'-Dideoxyinosine, 2'-Deoxyadenosine-5'-O-(1-Thiophosphate), 2'-Deoxycytidine-5'-O-(1-Thiophosphate), 2'-Deoxyguanosine-5'-O-(1-Thiotriphosphate), 2'-Deoxythymidine-5'-O-(1-Thiophosphate), Adenosine-5'-O-(1-Thiophosphate), Cytidine-5'-O-(1-Thiophosphate), Guanosine-5'-O-(1-Thiophosphate), Uridine-5'-O-(1-Thiophosphate), 2',3'-Dideoxyadenosine-5'-O-(1-Thiophosphate), 2',3'-Dideoxycytidine-5'-O-(1-Thiophosphate), 2',3'-Dideoxyguanosine-5'-O-(1-Thiophosphate), 3'-Deoxythymidine-5'-O-(1-Thiophosphate), 3'-Azido-2',3'-dideoxythymidine-5'-O-(1-Thiophosphate), 2',3'-Dideoxyuridine-5'-O-(1-Thiophosphate), 2'-Deoxyadenosine-5'-O-(1-Boranophosphate), 2'-Deoxycytidine-5'-O-(1-Boranophosphate), 2'-Deoxyguanosine-5'-O-(1-Boranophosphate), and 2'-Deoxythymidine-5'-O-(1-Boranophosphate).

In some embodiments of the compositions of the disclosure, including those in which the delivery vehicle is a lipid nanoparticle (LNP), the delivery vehicle comprises the RNA encoding TERT. In some embodiments, one or more of a surface, a layer or a volume of the delivery vehicle comprises the RNA encoding TERT. In some embodiments, the surface comprises an outer surface or an inner surface. In some embodiments, the layer comprises a lipid monolayer or lipid bi-layer. In some embodiments, the volume comprises an internal volume.

In some embodiments, the disclosure provides a composition comprising a (i) a ribonucleic acid (RNA) encoding telomerase reverse transcriptase (TERT) and (ii) a delivery vehicle, wherein the RNA encoding TERT comprises one or more modified nucleotides and wherein the delivery vehicle of (ii) is operably-linked to the RNA encoding TERT.

In some embodiments of the compositions of the disclosure, including those in which the delivery vehicle is a lipid nanoparticle (LNP), the composition further comprises a ribonucleic acid (RNA) encoding TElomerase RNA Component (TERC). In some embodiments, the delivery vehicle is operably-linked to a ribonucleic acid (RNA) encoding TElomerase RNA Component (TERC). In some embodiments, the delivery vehicle comprises the RNA encoding TERC. In some embodiments, one or more of a surface, a layer or a volume of the delivery vehicle comprises the RNA encoding TERC. In some embodiments, the surface comprises an outer surface or an inner surface. In some embodiments, the layer comprises a lipid monolayer or lipid bilayer. In some embodiments, the volume comprises an internal volume.

In some embodiments the RNA encoding TERT comprises a sequence of SEQ ID NOS: 1-5, 7, 9, 14-17, 19, 21, 23, 25, 27, 29-31, 37-40, or a nucleic acid sequence at least 70%, at least 75%, at least 80%, at least 85%, at least 90%, at least 95%, at least 96%, at least 97%, at least 98%, or at least 99% identical thereto. In some embodiments, the RNA encoding TERT comprises a UTR sequence of SEQ ID NOS: 32-34, 35, and 36, or a nucleic acid sequence at least 70%, at least 75%, at least 80%, at least 85%, at least 90%, at least 95%, at least 96%, at least 97%, at least 98%, or at least 99% identical thereto.

In some embodiments, the RNA comprises a self-replicating RNA. In some embodiments, the RNA comprises a circular RNA.

The disclosure provides a method of increasing telomerase activity in a cell, the method comprising contacting the cell and the composition of the disclosure. In some embodiments, the cell is in vivo, ex vivo or in vitro.

The disclosure provides a method of extending telomeres in a cell, the method comprising contacting the cell and the composition of the disclosure. In some embodiments, the cell is in vivo, ex vivo or in vitro.

The disclosure provides a cell comprising the composition of the disclosure.

The disclosure provides a formulation comprising the cell of the disclosure, which comprises a composition of the disclosure. In some embodiments of the formulation, a plurality of cells comprises a cell of the disclosure, which comprises a composition of the disclosure. In some embodiments of the formulation, each cell of the plurality is a cell of the disclosure, which comprises a composition of the disclosure.

The disclosure provides a method of treating a disease or disorder comprising administering to a subject an effective amount of a composition of the disclosure.

The disclosure provides a method of treating a disease or disorder comprising administering to a subject an effective amount of a cell of the disclosure, which comprises a composition of the disclosure.

The disclosure provides a method of treating a disease or disorder comprising administering to a subject an effective amount of a formulation of the disclosure.

The disclosure provides a method of delaying the onset of a disease comprising administering to a subject an effective amount of a composition of the disclosure.

The disclosure provides a method of delaying the onset of a disease comprising administering to a subject an effective amount of a cell of the disclosure, which comprises a composition of the disclosure.

The disclosure provides a method of delaying the onset of a disease comprising administering to a subject an effective amount of a formulation of the disclosure.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The patent or application file contains at least one drawing executed in color. Copies of this patent or patent application publication with color drawings will be provided by the Office upon request and payment of the necessary fee.

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 20A shows the liver mean radiance of the LNP formulations delivering luciferase mRNA according to the percentage of DOTAP. FIG. 20B shows the lung/liver delivery ratio of the LNP formulations according to the percentage of DOTAP.

DETAILED DESCRIPTION

Figure 1:
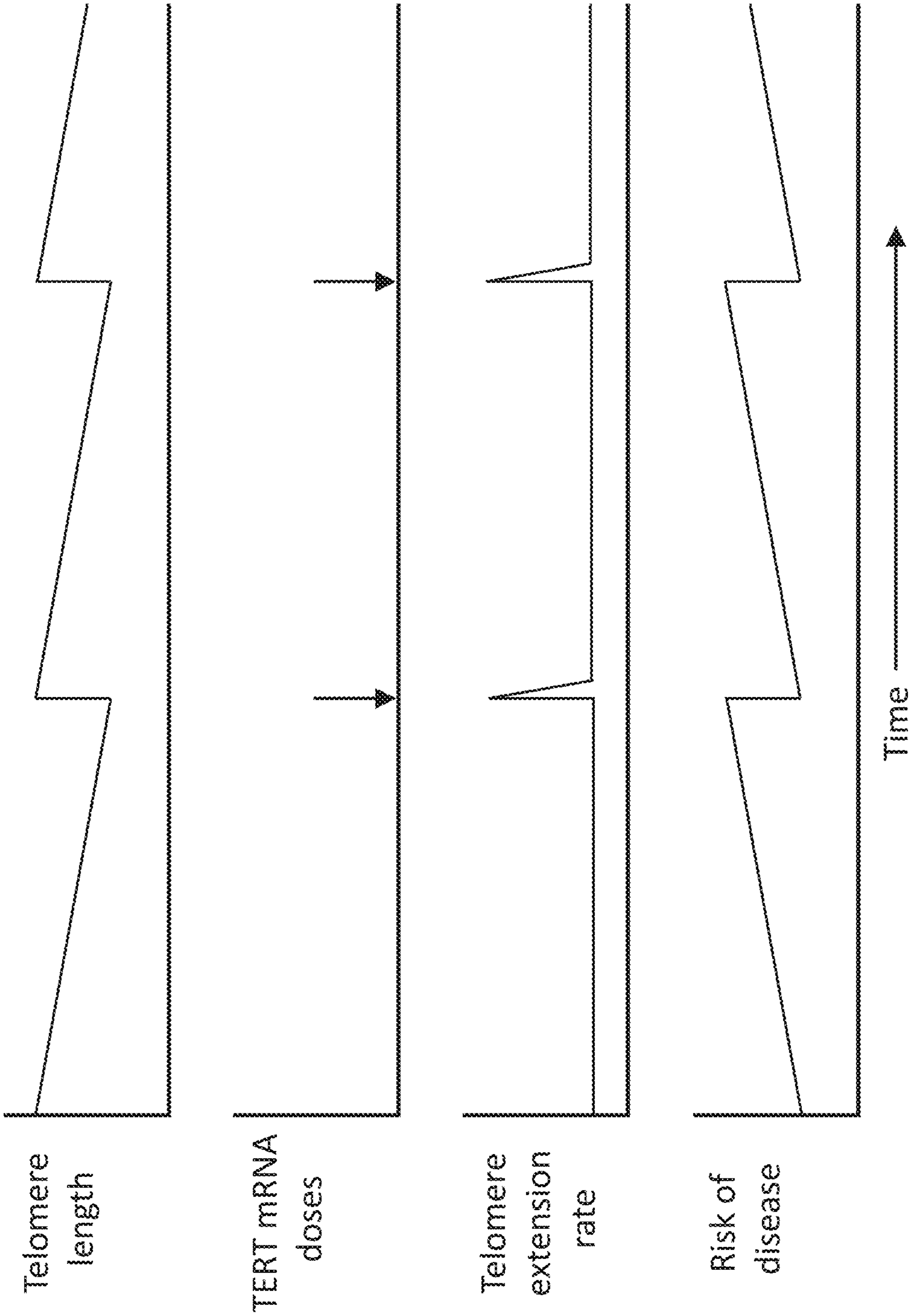
FIG. 1 is a schematic illustrating long-term therapeutic benefit from transient, rapid telomere extension via telomerase reverse transcriptase (TERT) mRNA. In particular, the speed of telomere extension made possible by TERT mRNA treatment enables telomere maintenance by infrequent TERT mRNA dosing. The telomerase activity resulting from TERT mRNA delivery rapidly extends telomeres in a brief period, before the mRNA is turned over, thus allowing the protective anti-cancer mechanism of telomere-shortening to function most of the time. Between treatments, normal telomerase activity and telomere shortening is present, and therefore the anti-cancer safety mechanism of telomere shortening to prevent out-of-control proliferation remains intact, while the risk of short telomere-related disease remains low. In contrast, the best existing small molecule treatment for extending telomeres requires chronic delivery, and thus presents a chronic cancer risk, and even then has a small, inconsistent effect on telomere length, with no detectable effect on telomere length at all in about half of patients.

The compositions and methods of the disclosure provide lipid nanoparticles (LNP) comprising an SS-OP lipid, or analog thereof, such as the compounds of Formula I described herein, and a cationic lipid for intravenous delivery to the lung, e.g., for the treatment of lung disease and/or lung fibrosis. In some variations the SS-OP lipid or analog thereof may be replaced or combined with a cKK lipid or analog thereof. As disclosed herein, the aforementioned LNPs may have improved lung transduction efficiency and/or lung specificity compared to known LNP formulations.

Also provided herein are ribonucleic acids (RNA) encoding telomerase reverse transcriptase (TERT) to be delivered to the lung to treat, for example, lung fibrosis. The RNA encoded TERT may optionally be delivered with the aforementioned SS-OP LNP compositions, or with other LNPs known in the art.

Telomerase reverse transcriptase (TERT) is an enzyme known to maintain and extend chromosomal ends (telomeres). The TERT enzyme is a catalytic subunit of the ribonucleoprotein telomerase. TERT adds simple sequence repeats to telomeres by copying a template sequence 5'-GGTTAG-3' within the RNA component of telomerase. This addition of repetitive deoxyribonucleic acid (DNA) sequences helps slow telomere shortening, which occurs over time, e.g., due to incomplete DNA replication during mitosis.

TERT translocates between the nucleus and cytoplasm and has been shown to be a critical factor in a number of other biological processes, including cell proliferation and cancer metastasis. Thus, the level of TERT in the nucleus may be a critical step in regulating cell and organismal health.

Telomerase reverse transcriptase (TERT) is also known in the art as TRT, cutaneous malignant melanoma 9 (CMM9), dyskeratosis congenita autosomal dominant 2 (DKCA2), autosomal recessive dyskeratosis congenita-4 (DKCB4), human ever shorter telomeres 2 (HEST2), pulmonary fibrosis/bone marrow failure telomere related 1 (PFBMFT1), telomerase catalytic subunit (TCS1), and telomerase associated protein 2 (TP2).

In some embodiments, the treatments described herein may stop, slow, or reverse progression of a fibrotic disease, e.g., a lung disease, or other lung diseases.

TERT mRNA is transient and only requires a few hours to extend telomeres in human cells before being degraded. Therefore, TERT mRNA leaves the protective anti-cancer telomere shortening mechanism intact. The present disclosure provides compositions and methods for delivery of TERT mRNA and treatment of fibrotic diseases and lung diseases.

During normal aging, telomeres shorten by approximately 30-100 base pairs per year due to oxidation and incomplete DNA replication during S phase of the cell cycle (Kurenova E V, et al. Telomere functions. A review. Biochemistry (Mosc) 1997; 62:1242-53). Telomerase, consisting of the TERT protein and a polynucleotide template (TERC), extends telomeres, but in humans, it is inactive in most somatic cell types and is only active at low levels that are insufficient to prevent net telomere shortening in many progenitor cell types. The exception is the spermatogenic lineage, in which telomerase is active enough to maintain telomere length over the human lifespan (Takubo K, Aida J, Izumiyama-Shimomura N, et al. Changes of telomere length with aging. Geriatric Gerontology Int 2010; 10 Suppl 1:S197-206). As the TERC component is present at high levels in all cell types, typically over 10,000 copies per cell, TERT is the limiting component. Because short telomeres limit the proliferative and regenerative capacities of cells, they are associated with aging, early death, and a vast number of diseases and conditions.

Telomeres comprise repetitive DNA sequences at the ends of linear chromosomes that, when sufficiently long, can allow each chromosome end to form a loop that protects the ends from acting as double-stranded or single-stranded DNA breaks. Telomeres can shorten over time, due in part to oxidative damage and incomplete DNA replication, eventually leading to critically short telomeres unable to form the protective loop, exposure of the chromosome ends, chromosome-chromosome fusions, DNA damage responses, and cellular senescence, apoptosis, or malignancy.

Telomere length maintenance can play a role in preventing cellular senescence and apoptosis and resulting cellular and organ dysfunction. In many diseases, the need for cell replication to replace cells damaged or killed by the underlying disease mechanism shortens telomeres more rapidly than normal, exhausting the replicative capacity of cells, and leading to tissue dysfunction, exacerbated or additional symptoms, disability, or death. Further, genetic mutations of telomerase enzyme (TERT) can be linked to fatal inherited diseases of inadequate telomere maintenance, including dyskeratosis congenita and forms of lung fibrosis, lung disease and aplastic anemia. Chromosome-chromosome fusions and cellular senescence due to short telomeres can increase risk of cancer. Short telomeres are also associated with deleterious conditions and diseases of aging and poor outcomes in a large number of diseases. Lung diseases contributing to lung fibrosis include but are not limited to: pulmonary fibrosis, lung cancer, familial pulmonary fibrosis, idiopathic pulmonary fibrosis, pulmonary fibrosis associated with dyskeratosis congenita, an interstitial lung disease, pneumonia, interstitial pneumonia, tuberculosis, bronchitis, emphysema, lung cancer, chronic obstructive pulmonary disease (COPD), aging-associated fibrosis, pulmonary hypertension, asthma, and cystic fibrosis.

The prospect of preventing, delaying, or treating dysfunction, conditions, and diseases by telomere extension motivates a need for safe and effective treatments to extend telomeres in animal cells in vivo and/or in vitro, and safe and effective compositions and methods for delivering therapies to the animal cells to extend telomeres. Further, there is a need to safely and rapidly extend telomeres in cells for use in cell therapy, cell and tissue engineering, and regenerative medicine. At the same time, however, there can be a danger in the constitutive, as opposed to transient, activation of telomerase activity. Indeed, for cell therapy applications, there is a need to avoid cell immortalization. To this end, transient, rather than constitutive, telomerase activity can be advantageous for safety, e.g., if the elevated telomerase activity is not only brief but extends telomeres rapidly enough that the treatment does not need to be repeated continuously.

Thus, there is need for therapies that safely extend telomeres to potentially prevent, delay, ameliorate, or treat these and other conditions and diseases, to do the same for the gradual decline in physical form and function and mental function that accompanies chronological aging, and to enable cell therapies and regenerative medicine. Furthermore, there is need for improved methods of delivering these therapies, e.g., nucleic acid molecules encoding telomerase, to cells.

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well-known and commonly used in the art.

As used herein and in the appended claims, the singular forms "a," "and," and "the" include plural referents unless the context clearly dictates otherwise. Thus, for example, reference to "a drug candidate" refers to one or mixtures of such candidates, and reference to "the method" includes reference to equivalent steps and methods known to those skilled in the art, and so forth.

As used herein, the term "approximately" or "about," as applied to one or more values of interest, refers to a value that is similar in magnitude and/or within a similar range to a stated reference value. In certain embodiments, the term "approximately" or "about" may refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

"G," "C," "A," "T" and "U" generally stand for the bases, guanine, cytosine, adenine, thymidine and uracil, respectively. Nucleobases can form nucleosides by the addition of a five carbon sugar. If the sugar is ribose then the nucleoside is a ribonucleoside. Nucleosides can in turn form nucleotides by the addition of one or more linker groups such as phosphate groups. Nucleotides can in turn form polymers (polynucleotides) which include short polymers (oligonucleotides). However, it will be understood that the terms "base", "nucleobase", "nucleoside", "ribonucleoside", "nucleotide", "ribonucleotide" can also refer to a modified base, nucleobase, nucleoside, ribonucleoside, nucleotide, or ribonucleotide, as further detailed below, or a surrogate replacement moiety (see, e.g., Table 2 and elsewhere herein). The skilled person is well aware that guanine, cytosine, adenine, thymidine, uracil can be replaced by other moieties without substantially impairing one or more of certain properties (such as base pairing properties, translatability, or protein binding properties) of an oligonucleotide or polynucleotide comprising a nucleotide bearing such replacement moiety. Sequences containing such replacement moieties are suitable for the compositions and methods featured in the disclosure. Similarly, the skilled person is well aware that ribose can be replaced with other moieties without impairing certain properties (such as base pairing properties, translatability, or protein binding properties) of an oligonucleotide or polynucleotide comprising a nucleotide bearing such replacement moiety. Sequences containing such replacement moieties are suitable for the compositions and methods featured in the disclosure. Similarly, the skilled person is well aware that phosphate can be replaced with other moieties without impairing certain properties (such as base pairing properties, translatability, or protein binding properties) of an oligonucleotide or polynucleotide comprising a nucleotide bearing such replacement moiety. Sequences containing such replacement moieties are suitable for the compositions and methods featured in the disclosure.

As used herein, the terms "polypeptide," "peptide," and "protein" refer to polymers of amino acids of any length. The terms also encompass an amino acid polymer that has been modified; for example, to include disulfide bond formation, glycosylation, lipidation, phosphorylation, or conjugation with a labeling component.

As used herein, the terms "identity" and "identical" refer, with respect to a polypeptide or polynucleotide sequence-of-interest, to the percentage of exact matching residues in an alignment of that the sequence-of-interest to a reference sequence, such as an alignment generated by the BLAST algorithm. Identity is calculated, unless specified otherwise, across the full length of the reference sequence. Thus a sequence-of-interest "shares at least x % identity to" a reference sequence if, when the reference sequence is aligned (as a query sequence) is aligned to the sequence-of-interest (as subject sequence), at least x % (rounded down) of the residues in the subject sequence are aligned as an exact match to a corresponding residue in the query sequence, the denominator being the full length of the reference sequence plus the lengths of any gaps inserted into the reference sequence by alignment of the reference sequence to the sequence-of-interest. Where the subject sequence has variable positions (e.g., residues denoted X), an alignment to any residue in the query sequence is counted as a match. Sequence alignments may be performed using the NCBI Blast service (BLAST+ version 2.12.0) or another program giving the same results.

The term "native" or "wild-type" as used herein refers to a nucleotide sequence, e.g. gene, or gene product, e.g. RNA or polypeptide, that is present in a wild-type cell, tissue, organ or organism. The term "variant" as used herein refers to a mutant of a reference polynucleotide or polypeptide sequence, for example a native polynucleotide or polypeptide sequence, i.e., having less than 100% sequence identity with the reference polynucleotide or polypeptide sequence. Put another way, a variant comprises at least one nucleotide difference (e.g., nucleotide substitution, nucleotide insertion, nucleotide deletion) or one amino acid difference (e.g., amino acid substitution, amino acid insertion, amino acid deletion) relative to a reference polynucleotide sequence, e.g. a native polynucleotide or polypeptide sequence. For example, a variant may be a polynucleotide having a sequence identity of 50% or more, 60% or more, or 70% or more with a full length native polynucleotide sequence, e.g. an identity of 75% or 80% or more, such as 85%, 90%, or 95% or more, for example, 98% or 99% identity with the full length native polynucleotide sequence. As another example, a variant may be a polypeptide having a sequence identity of 70% or more with a full length native polypeptide sequence, e.g. an identity of 75% or 80% or more, such as 85%, 90%, or 95% or more, for example, 98% or 99% identity with the full length native polypeptide sequence. Variants may also include variant fragments of a reference, e.g. native, sequence sharing a sequence identity of 70% or more with a fragment of the reference, e.g. native, sequence, e.g. an identity of 75% or 80% or more, such as 85%, 90%, or 95% or more, for example, 98% or 99% identity with the native sequence.

As used herein, the term "codon optimized" refers to any process used to improve gene expression and increase the translational efficiency of a gene of interest by accommodating the codon bias of the host organism, and/or to reduce the immunogenicity of the polynucleotide.

The terms "treating" or "treatment" are used herein to generally mean obtaining a desired pharmacologic and/or physiologic effect with a therapeutic agent. The effect may be prophylactic in terms of completely or partially preventing a disease or symptom thereof, e.g. reducing the likelihood that the disease or symptom thereof occurs in the subject, and/or may be therapeutic in terms of completely or partially reducing a symptom, or a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting or slowing the onset or development of the disease; or (c) relieving the disease, e.g., causing regression of the disease or symptoms associated with the disease. The therapeutic agent may be administered before, during or after the onset of disease. The treatment of ongoing disease, where the treatment stabilizes or reduces the undesirable clinical symptoms of the patient, may be of particular interest. In some embodiments, treatment is performed prior to complete loss of function in the affected tissues. In some embodiments, the subject therapy will be administered before the symptomatic stage of the disease; and, in some embodiments, during the symptomatic stage of the disease; and, in some embodiments, after the symptomatic stage of the disease.

In some embodiments, therapies as described herein treat fibrotic diseases or lung diseases, including but not limited to fibrotic lung diseases.

The terms "individual," "subject," and "patient" are used interchangeably herein and refer to any subject for whom treatment or therapy is desired. The subject may be a mammalian subject. Mammalian subjects include, e. g., humans, non-human primates, rodents, (e.g., rats, mice), lagomorphs (e.g., rabbits), ungulates (e.g., cows, sheep, pigs, horses, goats, and the like), etc. In some embodiments, the subject is a human. In some embodiments, the subject is a non-human primate, for example a cynomolgus monkey. In some embodiments, the subject is a companion or service animal (e.g. cats or dogs).

A subject "in need thereof," as used herein, refers to any subject suffering from or identified to be at risk of developing a fibrotic disease or lung disease.

It is to be understood that this disclosure is not limited to the particular methodology, products, apparatus and factors described, as such methods, apparatus and formulations may vary. It is also to be understood that the terminology used herein is for the purpose of describing particular embodiments only, and it is not intended to limit the scope of the present disclosure which will be limited only by appended claims.

I. Synthetic mRNAs

A synthetic ribonucleic acid (RNA) as used herein may refer to any RNA sequence comprising a mutation (point or deletion) or additional nucleotides not found in the wild type sequence. For example, a synthetic TERT messenger RNA (mRNA) may refer to a wild type sequence encoding a human TERT sequence, flanked by the addition of 1, 2, 3, 10, 100 or more nucleotides. Similarly, the nucleotides themselves may encode amino acids distinct from the wild type, or be modified to reduce immunogenicity in the cell or tissue. An mRNA sequence in some embodiments may comprise any of the following modifications, including but not limited to an untranslated region (UTR), a 5' cap, and a poly-adenosine tail. In some embodiments, the RNA may be circular and/or self-replicating.

Illustrative methods of making circular mRNAs are provided in Chen et al. Science. 1995 Apr. 21; 268(5209):415-7; Perriman R. (2002) Circular mRNA Encoding for Monomeric and Polymeric Green Fluorescent Protein. In: Hicks B. W. (eds) Green Fluorescent Protein. Methods in Molecular Biology, vol 183. Humana Press; Wang et al. RNA. 2015 February; 21(2):172-9. doi: 10.1261/rna.048272.114. Epub 2014 Dec. 1; Wesselhoeft et al. *Nat Commun.* 2018 Jul. 6; 9(1):2629; and Wesselhoeft et al. *Mol Cell.* 2019 May 2; 74(3):508-520.e4. Illustrative methods of making self-replicating mRNAs are provided in Tews B. A., Meyers G. (2017) Self-Replicating RNA. In: Kramps T., Elbers K. (eds) RNA Vaccines. *Methods in Molecular Biology*, vol 1499. Humana Press; Leyman et al. *Mol Pharm.* 2018 Feb. 5; 15(2):377-384; and Huysmans et al. *Mol Ther Nucleic Acids.* 2019 Sep. 6; 17:388-395.

TERT mRNAs

In some embodiments, a composition may comprise a reverse transcriptase telomerase (TERT) mRNA sequence to treat one or more phenotypes or symptoms associated with a fibrotic disease or lung disease. In some embodiments, a TERT mRNA refers to an mRNA encoding any full length, functional fragment or portion of a TERT protein, including wild type sequences or variants thereof.

In some embodiments, a TERT mRNA may comprise a codon-optimized sequence. In some embodiments, a TERT mRNA may comprise a uridine depleted human TERT sequence. In some embodiments, the codon-optimized sequence may comprise SEQ ID NO: 1, or a nucleic acid sequence at least 70%, at least 75%, at least 80%, at least 85%, at least 90%, at least 95%, at least 96%, at least 97%, at least 98%, or at least 99% identical thereto.

In some embodiments, a TERT mRNA may comprise a mutant human TERT sequence. In some embodiments, the mutant human TERT mRNA may encode a Y707F mutation in the resulting peptide sequence. In some embodiments a mutation in the TERT mRNA sequence encodes a mutation in the nuclear export signal which may result in nuclear retention of the TERT peptide. In some embodiments, the mutant TERT mRNA sequence may comprise SEQ ID NO: 2, or a nucleic acid sequence at least 70%, at least 75%, at least 80%, at least 85%, at least 90%, at least 95%, at least 96%, at least 97%, at least 98%, or at least 99% identical thereto.

In some embodiments, a mouse TERT mRNA may comprise a codon-optimized sequence. In some embodiments, a TERT mRNA may comprise a uridine depleted mouse TERT sequence. In some embodiments, the codon-optimized sequence may comprise SEQ ID NO: 3, or a nucleic acid sequence at least 70%, at least 75%, at least 80%, at least 85%, at least 90%, at least 95%, at least 96%, at least 97%, at least 98%, or at least 99% identical thereto.

In some embodiments, a mouse TERT mRNA may comprise a mutant mouse TERT sequence. In some embodiments, the mutant mouse TERT mRNA may encode a Y707F mutation in the resulting peptide sequence. In some embodiments a mutation in the TERT mRNA sequence encodes a mutation in the nuclear export signal which may result in nuclear retention of the TERT peptide. In some embodiments, the mutant mouse TERT mRNA sequence may comprise SEQ ID NO: 4, or a nucleic acid sequence at least 70%, at least 75%, at least 80%, at least 85%, at least 90%, at least 95%, at least 96%, at least 97%, at least 98%, or at least 99% identical thereto.

In some embodiments, a mouse TERT mRNA may comprise a mutant mouse TERT sequence. In some embodiments, the mutant mouse TERT mRNA may encode a Y697F mutation in the resulting peptide sequence. In some embodiments a mutation in the TERT mRNA sequence encodes a mutation in the nuclear export signal which may result in nuclear retention of the TERT peptide. In some embodiments, the mutant mouse TERT mRNA sequence may comprise a sequence of SEQ ID NO: 5, or a nucleic acid sequence at least 70%, at least 75%, at least 80%, at least 85%, at least 90%, at least 95%, at least 96%, at least 97%, at least 98%, or at least 99% identical thereto.

The compositions of the disclosure may comprise a ribonucleic acid, e.g., a synthetic ribonucleic acid coding for a telomerase reverse transcriptase (TERT), wherein telomeres are extended within a cell treated with the compound. The ribonucleic acids used in the transient expression of TERT can comprise a ribonucleic acid coding for a TERT protein. The ribonucleic acids can further comprise one or more sequences that affect the expression and/or stability of the ribonucleic acid in a cell. For example, the ribonucleic acids can contain a 5' cap and untranslated region (UTR) to the 5' and/or 3' side of the coding sequence. The ribonucleic acids may further contain a 3' tail, such as a poly-A tail. The poly-A tail can, for example, increase the stability of the ribonucleic acid. In some embodiments, the poly-A tail comprises at least 25 nucleotides, at least 50 nucleotides, at least 75 nucleotides, at least 100 nucleotides, at least 125 nucleotides, at least 150 nucleotides, at least 200 nucleotides, at least 225 nucleotides, at least 250 nucleotides. In some embodiments, the poly-A tail comprises between 1 and 25 nucleotides, between 25 and 50 nucleotides, between 50 and 75 nucleotides, between 75 and 100 nucleotides, between 100 and 125 nucleotides, between 125 and 150 nucleotides, between 150 and 175 nucleotides, between 175 and 200 nucleotides, between 200 and 225 nucleotides, or between 225 and 250 nucleotides, inclusive of the endpoints for each range. In some embodiments, the poly-A tail comprises between 100 and 200 nucleotides, inclusive of the endpoints.

In some embodiments, the 5' cap of the ribonucleic acid is a non-immunogenic cap. In some embodiments, the 5' cap may increase the translation of the ribonucleic acid. In some embodiments, the 5' cap may be treated with phosphatase to modulate the innate immunogenicity of the ribonucleic acid. In some embodiments, the 5' cap is an anti-reverse cap analog ("ARCA"), such as a 3'-O-Me-m7G(5')ppp(5')G RNA cap structure analog. In some embodiments, the 5' cap is m7G(5')ppp(5')(2'OmeA)pG (also known as CleanCap© AG). In some embodiments, the 5' cap is m7(3'OmeG)(5') ppp(5')(2'OmeA)pG (also known as CleanCap® AG (3' OMe)).

The above features, or others, may increase translation of the TERT protein encoded by the ribonucleic acid, may increase or decrease the stability of the ribonucleic acid itself in a cell type-specific or cell type-independent manner, or may do both. In some embodiments, the 5' UTR and/or the 3' UTR are from a gene that has a very stable mRNA and/or an mRNA that is rapidly translated, for example, α-globin or β-globin, c-fos, or tobacco etch virus. In some embodiments, the 5' UTR and 3' UTR are from different genes or are from different species than the species into which the compositions are being delivered. The UTRs may also be assemblies of parts of UTRs from the mRNAs of different genes, where the parts are selected to achieve a certain combination of stability and efficiency of translation. The UTRs may also comprise designed sequences that confer properties to the RNA such as cell type-specific stability or cell type-independent stability.

The ribonucleic acids of the present disclosure may comprise one or more modified nucleosides, and/or comprise primary sequences of nucleosides, that modulate translation, stability, or immunogenicity of the RNA. Most mature RNA molecules in eukaryotic cells contain nucleosides that are modified versions of the canonical unmodified RNA nucleosides, adenine, cytidine, guanosine, and uridine. For example, the 5' cap of mature RNA comprises a modified nucleoside, and other modified nucleosides often occur elsewhere in the RNA. Those modifications may prevent the RNA from being recognized as a foreign RNA. Synthetic RNA molecules made using certain nucleosides are much less immunogenic than unmodified RNA. The immunogenicity can be reduced even further by purifying the synthetic mRNA, for example by using high performance liquid chromatography (HPLC). The modified nucleosides may be, for example, chosen from the nucleosides listed below. The nucleosides are, in some embodiments, pseudouridine, 1-methylpseudouridine, 2-thiouridine, 5-methoxyuridine, or 5-methylcytidine. The primary sequence may be modified in ways that increase or decrease immunogenicity. Under some circumstances, it may be desirable for the modified RNA to retain some immunogenicity.

Accordingly, in some embodiments, the ribonucleic acids of the instant compositions comprise a 1-methylpseudouridine, pseudouridine, a 5-methoxyuridine (5-moU), a 2-thiouridine, a 5-methylcytidine, or another modified nucleoside. Modified nucleosides found in eukaryotic cells include m1A 1-methyladenosine, m6A N6-methyladenosine, Am 2'-O-methyladenosine, i6A N6-isopentenyladenosine, io6A N6-(cis-hydroxyisopentenyl)adenosine, ms2io6A 2-methylthio-N6-(cis-hydroxyisopentenyl) adenosine, g6A N6-glycinylcarbamoyladenosine, t6A N6-threonylcarbamoyladenosine, ms2t6A 2-methylthio-N6-threonyl carbamoyladenosine, Ar(p) 2'-O-ribosyladenosine (phosphate), m6 2A N6,N6-dimethyladenosine, m6Am N6,2'-O-dimethyladenosine, m6 2Am N6,N6,2'-O-trimethyladenosine, m1Am 1,2'-O-dimethyladenosine, m3C 3-methylcytidine, m5C 5-methylcytidine, Cm 2'-O-methylcytidine, ac4C N4-acetylcytidine, f5C 5-formylcytidine, m4C N4-methylcytidine, hm5C 5-hydroxymethylcytidine, f5Cm 5-formyl-2'-O-methylcytidine, m1G 1-methylguanosine, m2G N2-methylguanosine, m7G 7-methylguanosine, Gm 2'-O-methylguanosine, m2 2G N2,N2-dimethylguanosine, Gr(p) 2'-O-ribosylguanosine (phosphate), yW wybutosine, o2yW peroxywybutosine, OhyW hydroxywybutosine, OhyW* undermodified hydroxywybutosine, imG wyosine, m2,7G N2,7-dimethylguanosine, m2,2,7G N2,N2,7-trimethylguanosine I inosine, m1I 1-methylinosine, Im 2'-O-methylinosine, Q queuosine, galQ galactosyl-queuosine, manQ mannosyl-queuosine, ψ pseudouridine, D dihydrouridine, m5U 5-methyluridine, Um 2'-O-methyluridine, m5Um 5,2'-O-dimethyluridine, m1ψ 1-methylpseudouridine, ψm 2'-O-methylpseudouridine, s2U 2-thiouridine, ho5U 5-hydroxyuridine, chm5U 5-(carboxyhydroxymethyl)uridine, mchm5U 5-(carboxyhydroxymethyl)uridine, methyl ester mcm5U 5-methoxycarbonylmethyluridine, mcm5Um 5-methoxycarbonylmethyl-2'-O-methyluridine, mcm5s2U 5-methoxycarbonylmethyl-2-thiouridine, ncm5U 5-carbamoylmethyluridine, ncm5Um 5-carbamoylmethyl-2'-O-methyluridine, cmnm5U 5-carboxymethylaminomethyluridine, m3U 3-methyluridine, m1acp3ψ 1-methyl-3-(3-amino-3-carboxypropyl) pseudouridine, cm5U 5-carboxymethyluridine, m3Um 3,2'-O-dimethyluridine, m5D 5-methyldihydrouridine, τm5U 5-taurinomethyluridine, τm5s2U 5-taurinomethyl-2-thiouridine, 2-Aminoadenosine, 2-Amino-6-chloropurineriboside, 8-Azaadenosine, 6-Chloropurineriboside, 5-Iodocytidine, 5-Iodouridine, Inosine, 2'-O-Methylinosine, Xanthosine, 4-Thiouridine, 06-Methylguanosine, 5,6-Dihydrouridine, 2-Thiocytidine, 6-Azacytidine, 6-Azauridine, 2'-O-Methyl-2-aminoadenosine, 2'-O-Methylpseudouridine, N1-Methyladenosine, 2'-O-Methyl-5-methyluridine, 7-Deazaguanosine, 8-Azidoadenosine, 5-Bromocytidine, 5-Bromouridine, 7-Deazaadenosine, 5-Aminoallyluridine, 5-Aminoallylcytidine, 8-Oxoguanosine, 2-Aminopurine-riboside, Pseudoisocytidine, N1-Methylpseudouridine, 5,6-Dihydro-5-Methyluridine, N6-Methyl-2-Aminoadenosine, 5-Carboxycytidine, 5-Hydroxymethyluridine, Thienoguanosine, 5-Hydroxy cytidine, 5-Formyluridine, 5-Carboxyuridine, 5-Methoxyuridine, 5-Methoxycytidine, Thienouridine, 5-Carboxymethylesteruridine, Thienocytidine, 8-Oxoadenoosine, Isoguanosine, N1-Ethylpseudouridine, N1-Methyl-2'-O-Methylpseudouridine, N1-Methoxymethylpseudouridine, N1-Propylpseudouridine, 2'-O-Methyl-N6-Methyladenosine, 2-Amino-6-Cl-purine-2'-deoxyriboside, 2-Amino-2'-deoxyadenosine, 2-Aminopurine-2'-deoxyriboside, 5-Bromo-2'-deoxycytidine, 5-Bromo-2'-deoxyuridine, 6-Chloropurine-2'-deoxyriboside, 7-Deaza-2'-deoxyadenosine, 7-Deaza-2'-deoxyguanosine, 2'-Deoxyinosine, 5-Propynyl-2'-deoxycytidine, 5-Propynyl-2'-deoxyuridine, 5-Fluoro-2'-deoxyuridine, 5-Iodo-2'-deoxycytidine, 5-Iodo-2'-deoxyuridine, N6-Methyl-2'-deoxyadenosine, 5-Methyl-2'-deoxycytidine, 06-Methyl-2'-deoxyguanosine, N2-Methyl-2'-deoxyguanosine, 8-Oxo-2'-deoxyadenosine, 8-Oxo-2'-deoxyguanosine, 2-Thiothymidine, 2'-Deoxy-P-nucleoside, 5-Hydroxy-2'-deoxycytidine, 4-Thiothymidine, 2-Thio-2'-deoxycytidine, 6-Aza-2'-deoxyuridine, 6-Thio-2'-deoxyguanosine, 8-Chloro-2'-deoxyadenosine, 5-Aminoallyl-2'-deoxycytidine, 5-Aminoallyl-2'-deoxyuridine, N4-Methyl-2'-deoxycytidine, 2'-Deoxyzebularine, 5-Hydroxymethyl-2'-deoxyuridine, 5-Hydroxymethyl-2'-deoxycytidine, 5-Propargylamino-2'-deoxycytidine, 5-Propargylamino-2'-deoxyuridine, 5-Carboxy-2'-deoxycytidine, 5-Formyl-2'-deoxycytidine, 5-[(3-Indolyl)propionamide-N-allyl]-2'-deoxyuridine, 5-Carboxy-2'-deoxyuridine, 5-Formyl-2'-deoxyuridine, 7-Deaza-7-Propargylamino-2'-deoxyadenosine, 7-Deaza-7-Propargylamino-2'-deoxyguanosine, Biotin-16-Aminoallyl-2'-dUTP, Biotin-16-Aminoallyl-2'-dCTP, Biotin-16-Aminoallylcytidine, N4-Biotin-OBEA-2'-deoxycytidine, Biotin-16-Aminoallyluridine, Dabcyl-5-3-Aminoallyl-2'-dUTP, Desthiobiotin-6-Aminoallyl-2'-deoxycytidine, Desthiobiotin-16-Aminoallyl-Uridine, Biotin-16-7-Deaza-7-Propargylamino-2'-deoxyguanosine, Cyanine 3-5-Propargylamino-2'-deoxycytidine, Cyanine 3-6-Propargylamino-2'-deoxyuridine, Cyanine 5-6-Propargylamino-2'-deoxycytidine, Cyanine 5-6-Propargylamino-2'-deoxyuridine, Cyanine 3-Aminoallylcytidine, Cyanine 3-Aminoallyluridine, Cyanine 5-Aminoallylcytidine, Cyanine 5-Aminoallyluridine, Cyanine 7-Aminoallyluridine, 2'-Fluoro-2'-deoxyadenosine, 2'-Fluoro-2'-deoxycytidine, 2'-Fluoro-2'-deoxyguanosine, 2'-Fluoro-2'-deoxyuridine, 2'-O-Methyladenosine, 2'-O-Methylcytidine, 2'-O-Methylguanosine, 2'-O-Methyluridine, Puromycin, 2'-Amino-2'-deoxycytidine, 2'-Amino-2'-deoxyuridine, 2'-Azido-2'-deoxycytidine, 2'-Azido-2'-deoxyuridine, Aracytidine, Arauridine, 2'-Azido-2'-deoxyadenosine, 2'-Amino-2'-deoxyadenosine, Araadenosine, 2'-Fluoro-thymidine, 3'-O-Methyladenosine, 3'-O-Methylcytidine, 3'-O-Methylguanosine, 3'-O-Methyluridine, 2'-Azido-2'-deoxyguanosine, Araguanosine, 2'-Deoxyuridine, 3'-O-(2-nitrobenzyl)-2'-Deoxyadenosine, 3'-O-(2-nitrobenzyl)-2'-Deoxyinosine, 3'-Deoxyadenosine, 3'-Deoxyguanosine, 3'-Deoxycytidine, 3'-Deoxy-5-Methyluridine, 3'-Deoxyuridine, 2',3'-Dideoxyadenosine, 2',3'-Dideoxyguanosine, 2',3'-Dideoxyuridine, 2',3'-Dideoxythymidine, 2',3'-Dideoxycytidine, 3'-Azido-2',3'-dideoxyadenosine, 3'-Azido-2',3'-dideoxythymidine, 3'-Amino-2',3'-dideoxyadenosine, 3'-Amino-2',3'-dideoxycytidine, 3'-Amino-2',3'-dideoxyguanosine, 3'-Amino-2',3'-dideoxythymidine, 3'-Azido-2',3'-dideoxycytidine, 3'-Azido-2',3'-dideoxyuridine, 5-Bromo-2',3'-dideoxyuridine, 2',3'-Dideoxyinosine, 2'-Deoxyadenosine-5'-O-(1-Thiophosphate), 2'-Deoxycytidine-5'-O-(1-Thiophosphate), 2'-Deoxyguanosine-5'-O-(1-Thiophosphate), 2'-Deoxythymidine-5'-O-(1-Thiophosphate), Adenosine-5'-O-(1-Thiophosphate), Cytidine-5'-O-(1-Thiophosphate), Guanosine-5'-O-(1-Thiophosphate), Uridine-5'-O-(1-Thiophosphate), 2',3'-Dideoxyadenosine-5'-O-(1-Thiophosphate), 2',3'-Dideoxycytidine-5'-O-(1-Thiophosphate), 2',3'-Dideoxyguanosine-5'-O-(1-Thiophosphate), 3'-Deoxythymidine-5'-O-(1-Thiophosphate), 3'-Azido-2',3'-dideoxythymidine-5'-O-(1-Thiophosphate), 2',3'-Dideoxyuridine-5'-O-(1-Thiophosphate), 2'-Deoxyadenosine-5'-O-(1-Boranophosphate), 2'-Deoxycytidine-5'-O-(1-Boranophosphate), 2'-Deoxyguanosine-5'-O-(1-Boranophosphate), and 2'-Deoxythymidine-5'-O-(1-Boranophosphate).

Without intending to be bound by theory, the presence of the modified nucleosides, and/or sequences of nucleosides that alter secondary structure of the RNA and/or binding of RNA to RNA binding proteins or microRNA, may enable mRNA to avoid activation of an immune response mediated by various receptors, including the Toll-like receptors and RIG-1. Non-immunogenic mRNA has been used as a therapeutic agent in mice via topical delivery. Kormann et al. (2011) Nature Biotechnology 29:154-157. In some embodiments, the ribonucleic acids comprise more than one of the above nucleosides or combination of the above nucleosides. In some embodiments, the ribonucleic acids comprise 1-methylpseudouridine, 5-methoxyuridine, or pseudouridine and 5-methylcytidine.

In some embodiments, an immune response to the mRNA may be desired, and the RNA may be modified to induce an optimal level of innate immunity. In other embodiments, an immune response to the mRNA may not be desired, and the RNA may be modified in order to minimize such a reaction. The RNA can be modified for either situation.

The ribonucleic acid molecules can be synthetic ribonucleic acids. The term "synthetic", as used herein, can mean that the ribonucleic acids are in some embodiments prepared using the tools of molecular biology under the direction of a human, for example as described below. The synthetic ribonucleic acids may, for example, be prepared by in vitro synthesis using cellular extracts or purified enzymes and nucleic acid templates. The synthetic ribonucleic acids may in some embodiments be prepared by chemical synthesis, either partially or completely. Alternatively, or in addition, the synthetic ribonucleic acids may in some embodiments be prepared by engineered expression in a cell, followed by disruption of the cell and at least partial purification of the ribonucleic acid.

The ribonucleic acids of the present disclosure may be prepared using a variety of techniques, as would be understood by one of ordinary skill in the art. In some embodiments, the ribonucleic acids may be prepared by in vitro synthesis. In some embodiments, the ribonucleic acids may be prepared by chemical synthesis. In some embodiments, the ribonucleic acids may be prepared by a combination of in vitro synthesis and chemical synthesis. As described above, the term "synthetic" should be understood to include ribonucleic acids that are prepared either by chemical synthesis, by in vitro synthesis, by expression in vivo and at least partial purification, or by a combination of such, or other, chemical or molecular biological methods.

The ribonucleic acids may, in some embodiments, be purified. As noted above, purification may reduce immunogenicity of the ribonucleic acids and may be advantageous in some circumstances. In some embodiments, the ribonucleic acids are purified by one or more of HPLC, DNAse treatment, protease treatment, or by affinity capture and elution.

The protein structure of TERT can include at least three distinct domains: a long extension at the amino-terminus (the N-terminal extension, NTE) that contains conserved domains and an unstructured linker region; a catalytic reverse-transcriptase domain in the middle of the primary sequence that includes seven conserved reverse transcriptase (RT) motifs; and a short extension at the carboxyl-terminus. In some embodiments, the ribonucleic acid codes for a full-length TERT. In some embodiments, the ribonucleic acid codes for a catalytic reverse transcriptase domain of TERT. In some embodiments, the ribonucleic acid codes for a polypeptide having TERT activity. TERT activity may be measured using known methods including the telomerase repeat amplification protocol (TRAP).

The TERT encoded by the ribonucleic acids of the instant disclosure may be a mammalian, avian, reptilian, or fish TERT. In some embodiments, the TERT is a mammalian TERT, such as human TERT. Meyerson et al. (1997) Cell 90:785-795; Nakamura et al. (1997) Science 277:955-959; Wick et al. (1999) Gene 232:97-106.

The amino acid sequence of two human TERT isoforms are available as NCBI Reference Sequences: NP_937983.2 and NP_001180305.1.

The amino acid sequence of human TERT isoform 1 may comprise or consist of the sequence of SEQ ID NO: 6 (also described at GenBank Accession No. NP_937983.2).

The nucleic acid sequence of human TERT isoform 1 may comprise or consist of the sequence of SEQ ID NO: 7 (also described at GenBank Accession No. NM_198253.3).

The amino acid sequence of human TERT isoform 2 may comprise or consist of the sequence of SEQ ID NO: 8 (also described at GenBank Accession No. NP_001180305.1).

The amino acid sequence of human TERT isoform 2 may comprise or consist of the sequence of SEQ ID NO: 9 (also described at GenBank Accession No. NM_001193376.3).

In some embodiments, a human TERT mRNA may comprise a wild type TERT sequence. In some embodiments, the wild type TERT sequence may comprise a sequence of SEQ ID NO: 30, or a nucleic acid sequence at least 70%, at least 75%, at least 80%, at least 85%, at least 90%, at least 95%, at least 96%, at least 97%, at least 98%, or at least 99% identical thereto.

In some embodiments, a mouse TERT mRNA may comprise a wild type TERT sequence. In some embodiments, the wild type TERT sequence may comprise SEQ ID NO: 31, or a nucleic acid sequence at least 70%, at least 75%, at least 80%, at least 85%, at least 90%, at least 95%, at least 96%, at least 97%, at least 98%, or at least 99% identical thereto.

In some embodiments, a TERT mRNA may comprise a nucleic acid sequence at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NOS: 1-5, 7, 9 or 30.

In some embodiments, a TERT mRNA may encode a modified TERT protein containing one or more amino acid substitutions, deletions, and/or insertions as compared to SEQ ID NOS: 6 or 8, while retaining substantial TERT activity. In some embodiments, a TERT mRNA may encode an amino acid sequence at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% to SEQ ID NO: 6 or SEQ ID NO: 8.

In other embodiments, a TERT mRNA may encode an amino acid sequence with a mutation of L55Q, P65A, V70M, A202T, A279T, V299M, H412Y, a deletion of residue 441, R522K, K570N, R631Q, G682D, V694M, Y697F, P704S, Y707F, A716T, P721R, T726M, Y772C, P785L, V7911, R811C, L841F, R865H, V867M, R901W, K902N, P923L, S948R, R979W, V1025F, A1062T, V1090M, T1110M, and/or F1127L relative to the amino acid sequences of SEQ ID NO: 6. In some embodiments, the TERT mRNA may encode a TERT isoform in which the translated protein lacks amino acid residues 711-722, 764-807, 808-1132, or 885-947 relative to the amino acid sequences of SEQ ID NO: 6. In some embodiments about 1, about 5, about 10, about 20, or about 100 amino acids preceding or following the domain are also deleted from the amino acid sequence of SEQ ID NO: 6.

In some embodiments, the TERT mRNA may encode an amino acid sequence in which one or more of the protein regions are deleted or repeated relative to the amino acid sequences of SEQ ID NO: 6: residues 1-230 corresponding to the RNA-interacting domain 1, residues 58-197 corresponding to a "GQ" residue motif, residues 137-141 associated with the specificity of telomeric DNA and primer elongation, residues 210-320 corresponding to a disordered region, residues 231-324 associated with a linker sequence, residues 301-538 associated with oligomerization, residues 325-550 or 460-594 corresponding to an RNA-interacting domain, residues 376-521 corresponding to a "QFP" residue motif, residues 397-417 corresponding to a "CP" residue motif, residues 825-884 corresponding to a DNA repeat template, residues 618-729 corresponding to a reverse transcriptase like element, residues 914-928 associated with oligomerization, residues 930-934 associated with a primer grip sequence, and/or residues 936-1132 corresponding to the C-terminus. In some embodiments about 1, about 5, about 10, about 20, or about 100 amino acids preceding or following the domain are also deleted or repeated.

In some embodiments, a TERT mRNA may comprise or consist of a nucleotide sequence at least at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more identical to any subsequence of a disclosed nucleic acid sequence, e.g., any 100 base pair (bp), 200 bp, 300 bp, 400 bp, 500 bp, or more of a disclosed nucleic acid sequence. In some embodiments, a TERT mRNA may encode an amino acid sequence at least at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more identical to any of one of the disclosed polypeptide sequences, or to any subsequence of a disclosed polypeptide sequence, e.g., any 50 amino acid (aa), 100 aa, 200 aa, 300 aa, 400 aa, 500 aa, or more of a disclosed polypeptide sequence.

Non-limiting TERT sequences of the disclosure, include TERT nucleic acid and amino acid sequences listed in Table 1.

TABLE 1

Non-human TERT sequences

| TERT Species | Amino Acid SEQ ID NO: | Amino Acid Sequence | Example Nucleic Acid SEQ ID NO: | Example Nucleic Acid Sequence |
|---|---|---|---|---|
| Cat | | ASO67359.1 | | KX620456.1 |
| Dog | | NP_001026800.1 | | NM_001031630.1 |
| Mouse | | AAI27069.1 | | BC127068.1 |
| Mouse, isoform 1 | 10 | NP_033380.1 | 14 | NM_009354.2 |
| Mouse, isoform 2 | 11 | NP_001349316.1 | 15 | NM_001362387.1 |
| Mouse, isoform 3 | 12 | NP_001349317.1 | 16 | NM_001362388.1 |
| Mouse | | EDL37055.1 | | Machine reverse translation of EDL37055.1 |
| Cow | | NP_001039707.1 | | NM_001046242.1 |
| Sheep, isoform 1 | | XP_027835754.1 | | XM_027979953.1 |
| Sheep, isoform 2 | | XP_027835755.1 | | XM_027979954.1 |
| Pig | | NP_001231229.1 | | NM_001244300.1 |
| African Elephant | | XP_023401395.1 | | XM_023545627.1 |
| Chicken | | NP_001026178.1 | | NM_001031007.1 |
| Rat | 13 | NP_445875.1 | 17 | NM_053423.1 |
| Zebrafish | | NP_001077335.1 | | NM_001083866.1 |
| Japanese medaka | | NP_001098286.1 | | NM_001104816.1 |
| Horse, isoform 1 | | XP_023481649.1 | | XM_023625881.1 |

TABLE 1-continued

| Non-human TERT sequences | | | | |
|---|---|---|---|---|
| TERT Species | Amino Acid SEQ ID NO: | Amino Acid Sequence | Example Nucleic Acid SEQ ID NO: | Example Nucleic Acid Sequence |
| Horse, isoform 2 | | XP_023481650.1 | | XM_023625882.1 |
| Horse, isoform 3 | | XP_023481651.1 | | XM_023625883.1 |

In some embodiments of the compositions and methods of the disclosure, an amino acid sequence of TERT may comprise or consist of a sequence of SEQ ID NOS: 6-8 or 10-13, or an amino acid sequence at least 70%, at least 75%, at least 80%, at least 85%, at least 90%, at least 95%, at least 96%, at least 97%, at least 98%, or at least 99% identical thereto. In some embodiments of the compositions and methods of the disclosure, an amino acid sequence of a portion of TERT, functional or non-functional, may comprise or consist of a sequence having at least 70%, 75%, 80%, 85%, 90%, 95%, 97%, 99% identity to a subsequence of one or more of SEQ ID NOS: 6-8 or 10-13.

In some embodiments of the compositions and methods of the disclosure, a nucleic acid sequence of TERT may comprise or consist of a sequence of SEQ ID Nos: 1-5, 7, 9, 14-17, 30 or 31, or a nucleic acid sequence at least 70%, at least 75%, at least 80%, at least 85%, at least 90%, at least 95%, at least 96%, at least 97%, at least 98%, or at least 99% identical thereto.

The amino acid sequence of non-human primate TERT isoform 1 may comprise or consist of the sequence of SEQ ID NO: 18 (also described at GenBank Accession No. XP_016808391.2).

The nucleic acid sequence of non-human primate TERT isoform 1 may comprise or consist of the sequence of SEQ ID NO: 19 (also described at GenBank Accession No. XM_016952902.2).

The amino acid sequence of non-human primate TERT isoform 2 may comprise or consist of the sequence of SEQ ID NO: 20, GenBank Accession No. PNI27662.1.

The nucleic acid sequence of non-human primate TERT isoform 2 may comprise or consist of the sequence of SEQ ID NO: 21 (reverse machine translation of GenBank Accession No. PNI27662.1).

The amino acid sequence of non-human primate TERT isoform 3 may comprise or consist of the sequence of SEQ ID NO: 22 (also described at GenBank Accession No. PNI27663.1).

The nucleic acid sequence of non-human primate TERT isoform 3 may comprise or consist of the sequence of SEQ ID NO: 23 (reverse machine translation of GenBank Accession No. PNI27663.1).

The amino acid sequence of non-human primate TERT isoform 4 may comprise or consist of the sequence of SEQ ID NO: 24 (also described at GenBank Accession No. PNI27664.1).

The nucleic acid sequence of non-human primate TERT isoform 4 may comprise or consist of the sequence of SEQ ID NO: 25 (reverse machine translation of GenBank Accession No. PNI27664.1).

The amino acid sequence of non-human primate TERT isoform 5 may comprise or consist of the sequence of SEQ ID NO: 26 (also described at GenBank Accession No. PNI27665.1).

The nucleic acid sequence of non-human primate TERT isoform 5 may comprise or consist of the sequence of SEQ ID NO: 27 (reverse machine translation of GenBank Accession No. PNI27665.1).

The amino acid sequence of non-human primate TERT isoform 6 may comprise or consist of the sequence of SEQ ID NO: 28 (also described at GenBank Accession No. PNI27666.1).

The nucleic acid sequence of non-human primate TERT isoform 6 may comprise or consist of the sequence of SEQ ID NO: 29 (reverse machine translation of GenBank Accession No. PNI27666.1).

In some embodiments of the compositions and methods of the disclosure, an amino acid sequence of TERT may comprise or consist of a sequence of SEQ ID NOS: 6, 8, 10-13, 18, 20, 22, 24, 26, or 28, or an amino acid sequence at least 70%, at least 75%, at least 80%, at least 85%, at least 90%, at least 95%, at least 96%, at least 97%, at least 98%, or at least 99% identical thereto.

In some embodiments of the compositions and methods of the disclosure, a nucleic acid sequence of TERT may comprise or consist of a sequence of SEQ ID Nos: 1-5, 7, 9, 14-17, 19, 21, 23, 25, 27, 29, 30, or 31, sequence at least 70%, at least 75%, at least 80%, at least 85%, at least 90%, at least 95%, at least 96%, at least 97%, at least 98%, or at least 99% identical thereto. In some embodiments, the instant ribonucleic acids may correspond to the native gene sequences coding for the above-listed TERT proteins or may correspond to variants that are made possible due to the redundancy of the genetic code, as would be understood by one of ordinary skill in the art. In some embodiments, the codon selection may be optimized to optimize protein expression and/or reduced or increased immunogenicity using algorithms and methods known by those of ordinary skill in the art.

In some embodiments, an mRNA sequence may be synthesized as an unmodified or modified mRNA. An mRNA may be modified to enhance stability and/or evade immune detection and degradation. A modified mRNA may include, for example, one or more of a nucleotide modification, a nucleoside modification, a backbone modification, a sugar modification, and/or a base modification. In some embodiments, the modified nucleoside is pseudouridine or a pseudouridine analog. In some embodiments, the pseudouridine analog is N-1-methylpseudouridine. In some embodiments, the modified nucleoside is 5-methoxyuridine. In some embodiments a modified nucleoside as used herein may comprise any of the moieties listed in Table 2.

TABLE 2

| Common name |
|---|
| pseudouridine |
| N-1-methylpseudouridine |
| 5-methoxyuridine |
| 1,2'-O-dimethyladenosine |
| 1-methyl-3-(3-amino-3-carboxypropyl) pseudouridine |
| 1-methyladenosine |
| 1-methylguanosine |
| 1-methylinosine |
| 1-methylpseudouridine |
| 2,2-dimethyl-guanosine |
| 2',3'-dideoxyadenosine |
| 2',3'-Dideoxycytidine |
| 2',3'-Dideoxyguanosine |
| 2',3'-Dideoxyinosine |
| 2',3'-dideoxynucleosides |
| 2',3'-Dideoxythymidine |
| 2',3'-dideoxythymine |

TABLE 2-continued

| Common name |
|---|
| 2',3'-Dideoxyuridine |
| 2,6-diaminopurine |
| 2'-O-ribosyladenosine (phosphate) |
| 2'-Amino-2'-deoxyadenosine |
| 2-Amino-2'-deoxyadenosine |
| 2'-Amino-2'-deoxyuridine |
| 2-Amino-6-chloropurineriboside |
| 2-Amino-6-Cl-purine-2'-deoxyriboside |
| 2-aminoadenosine |
| 2-Aminoadenosine |
| 2-Aminopurine-2'-deoxyriboside |
| 2-Aminopurine-riboside |
| 2'-Azido-2'-deoxyadenosine |
| 2'-Azido-2'-deoxycytidine |
| 2'-Azido-2'-deoxyguanosine |
| 2'-Azido-2'-deoxyuridine |
| 2'-Deoxyinosine |
| 2'-Deoxy-P-nucleoside |
| 2'-Deoxyuridine |
| 2'-Deoxyzebularine |
| 2'-Fluoro-2'-deoxyadenosine |
| 2'-Fluoro-2'-deoxycytidine |
| 2'-Fluoro-2'-deoxyguanosine |
| 2'-Fluoro-2'-deoxyuridine |
| 2'-Fluoro-thymidine |
| 2-methyl-adenosine |
| 2-methyl-guanosine |
| 2-methylthio-$N^6$-(cis-hydroxyisopentenyl) adenosine |
| 2-methylthio-N-6-isopentenyl-adenosine |
| 2-methylthio-$N^6$-threonylcarbamoyladenosine |
| 2'-O-Methyl-2-aminoadenosine |
| 2'-O-Methyl-5-methyluridine |
| 2'-O-methyladenosine |
| 2'-O-methylcytidine |
| 2'-O-methylguanosine |
| 2'-O-methylinosine |
| 2'-O-Methyl-N6-Methyladenosine |
| 2'-O-methylpseudouridine |
| 2'-O-methyluridine |
| 2'-O-ribosylguanosine (phosphate) |
| 2-Thio-2'-deoxycytidine |
| 2-Thiocytidine |
| 2-Thiothymidine |
| 2-thiouridine |
| 3,2'-O-dimethyluridine |
| 3'-Amino-2',3'-dideoxyadenosine |
| 3'-Amino-2',3'-dideoxycytidine |
| 3'-Amino-2',3'-dideoxyguanosine |
| 3'-Amino-2',3'-dideoxythymidine |
| 3'-Azido-2',3'-dideoxyadenosine |
| 3'-Azido-2',3'-dideoxycytidine |
| 3'-Azido-2',3'-dideoxythymidine |
| 3'-Azido-2',3'-dideoxyuridine |
| 3'-Deoxy-5-Methyluridine |
| 3'-Deoxyadenosine |
| 3'-deoxyadenosine (cordycepin) |
| 3'-Deoxycytidine |
| 3'-Deoxyguanosine |
| 3'-deoxythymine |
| 3'-Deoxyuridine |
| 3-methylcytidine |
| 3-methyluridine |
| 3'-O-(2-nitrobenzyl)-2'-Deoxyadenosine |
| 3'-O-(2-nitrobenzyl)-2'-Deoxyinosine |
| 3'-O-Methyladenosine |
| 3'-O-Methylcytidine |
| 3'-O-Methylguanosine |
| 3'-O-Methyluridine |
| 4-acetyl-cytidine |
| 4-Thiothymidine |
| 4-Thiouridine |
| 5-(carboxyhydroxymethyl) uridine methyl ester |
| 5-(carboxyhydroxymethyl)uridine |
| 5,2'-O-dimethyluridine |
| 5,6-Dihydro-5-Methyluridine |
| 5,6-Dihydrouridine |
| 5-[(3-Indoly)propionamide-N-allyl]-2'-deoxyuridine |
| 5-Aminoallyl-2'-deoxycytidine |

TABLE 2-continued

| Common name |
|---|
| 5-Aminoallyl-2'-deoxyuridine |
| 5-Aminoallylcytidine |
| 5-Aminoallyluridine |
| 5-Bromo-2',3'-dideoxyuridine |
| 5-Bromo-2'-deoxycytidine |
| 5-Bromo-2'-deoxyuridine |
| 5-Bromocytidine |
| 5-Bromouridine |
| 5-carbamoylmethyl-2'-O-methyluridine |
| 5-carbamoylmethyluridine |
| 5-Carboxy-2'-deoxycytidine |
| 5-Carboxycytidine |
| 5-carboxymethylaminomethyl-2-thio-uridine |
| 5-carboxymethylaminomethyluridine |
| 5-Carboxymethylesteruridine |
| 5-carboxymethyluridine |
| 5-Carboxyuridine |
| 5-Fluoro-2'-deoxyuridine |
| 5-fluoro-uridine |
| 5-Formyl-2'-deoxycytidine |
| 5-Formyl-2'-deoxyuridine |
| 5-formyl-2'-O-methylcytidine |
| 5-formylcytidine |
| 5-Formyluridine |
| 5-Hydroxy-2'-deoxycytidine |
| 5-Hydroxycytidine |
| 5-Hydroxymethyl-2'-deoxycytidine |
| 5-Hydroxymethyl-2'-deoxyuridine |
| 5-hydroxymethylcytidine |
| 5-Hydroxymethyluridine |
| 5-hydroxyuridine |
| 5-Iodo-2'-deoxycytidine |
| 5-Iodo-2'-deoxyuridine |
| 5-Iodocytidine |
| 5-Iodouridine |
| 5-methoxyaminomethyl-2-thio-uridine |
| 5-methoxycarbonylmethyl-2'-O-methyluridine |
| 5-methoxycarbonylmethyl-2-thiouridine |
| 5'-methoxycarbonylmethyl-uridine |
| 5-methoxycarbonylmethyluridine |
| 5-Methoxycytidine |
| 5-Methoxyuridine |
| 5-methoxy-uridine |
| 5-Methyl-2'-deoxycytidine |
| 5-methyl-2-thio-uridine |
| 5-methylaminomethyl-uridine |
| 5-methylcytidine |
| 5-methyldihydrouridine |
| 5-methyluridine |
| 5-Propargylamino-2'-deoxycytidine |
| 5-Propargylamino-2'-deoxyuridine |
| 5-Propynyl-2'-deoxycytidine |
| 5-taurinomethyl-2-thiouridine |
| 5-taurinomethyluridine |
| 6-Aza-2'-deoxyuridine |
| 6-Azacytidine |
| 6-Azauridine |
| 6-chloropurine riboside |
| 6-Chloropurine-2'-deoxyriboside |
| 6-O-methylguanosine |
| 6-Thio-2'-deoxyguanosine |
| 7-Deaza-2'-deoxyadenosine |
| 7-Deaza-2'-deoxyguanosine |
| 7-Deaza-7-Propargylamino-2'-deoxyadenosine |
| 7-Deaza-7-Propargylamino-2'-deoxyguanosine |
| 7-Deazaadenosine |
| 7-Deazaguanosine |
| 7-methylguanosine |
| 7-methyl-guanosine |
| 8-Azaadenosine |
| 8-Azidoadenosine |
| 8-Chloro-2'-deoxyadenosine |
| 8-Oxo-2'-deoxyadenosine |
| 8-Oxo-2'-deoxyguanosine |
| 8-Oxoadenoosine |
| 8-Oxoguanosine |
| a 2'-deoxynucleoside |
| ac4C N4-acetylcytidine |

TABLE 2-continued

| Common name |
|---|
| Am 2'-O-methyladenosine |
| an -O-methylnucleoside |
| Ar(p) 2'-O-ribosyladenosine (phosphate) |
| Araadenosine |
| Aracytidine |
| Araguanosine |
| Arauridin |
| benzimidazole riboside |
| beta-D-mannosyl-queosine |
| Biotin-16-7-Deaza-7-Propargylamino-2'-deoxyguanosine |
| Biotin-16-Aminoallyl-2'-dCTP |
| Biotin-16-Aminoallyl-2'-dUTP |
| Biotin-16-Aminoallylcytidine |
| Biotin-16-Aminoallyluridine |
| chm5U 5-(carboxyhydroxymethyl)uridine |
| 2'-O-methylcytidine |
| 5-carboxymethyluridine |
| 5-carboxymethylaminomethyluridine |
| Cyanine 3-5-Propargylamino-2'-deoxycytidine |
| Cyanine 3-6-Propargylamino-2'-deoxyuridine |
| Cyanine 3-Aminoallylcytidine |
| Cyanine 3-Aminoallyluridine |
| Cyanine 5-6-Propargylamino-2'-deoxycytidine |
| Cyanine 5-6-Propargylamino-2'-deoxyuridine |
| Cyanine 5-Aminoallylcytidine |
| Cyanine 5-Aminoallyluridine |
| Cyanine 7-Aminoallyluridine |
| dihydrouridine |
| Dabcyl-5-3-Aminoallyl-2'-dUTP |
| Desthiobiotin-16-Aminoallyl-Uridine |
| Desthiobiotin-6-Aminoallyl-2'-deoxycytidine |
| dihydrouridine |
| 5-formylcytidine |
| 5-formyl-2'-O-methylcytidine |
| N6-glycinylcarbamoyladenosine |
| galactosyl-queuosine |
| 2'-O-methylguanosine |
| 2'-O-ribosylguanosine (phosphate) |
| 5-hydroxymethylcytidine |
| 5-hydroxyuridine |
| hydroxywybutosine |
| N6-isopentenyladenosine |
| 2'-O-methylinosine |
| wyosine |
| inosine |
| N6-(cis-hydroxyisopentenyl)adenosine |
| Isoguanosine |
| 1-methylguanosine |
| 1-methyladenosine |
| 1-methyl-3-(3-amino-3-carboxypropyl) pseudouridine |
| 1,2'-O-dimethyladenosine |
| 1-methylguanosine |
| 1-methylinosine |
| 1-methylpseudouridine |
| N2,N2-dimethylguanosine |
| N2,N2,7-trimethylguanosine I inosine |
| N2,7-dimethylguanosine |
| N2-methylguanosine |
| 3-methylcytidine |
| 3-methyluridine |
| 3,2'-O-dimethyluridine |
| N4-methylcytidine |
| 5-methylcytidine |
| 5-methyldihydrouridine |
| 5-methyluridine |
| 5,2'-O-dimethyluridine |
| N6,N6-dimethyladenosine |
| N6,N6,2'-O-trimethyladenosine |
| N6-methyladenosine |
| N6,2'-O-dimethyladenosine |
| 7-methylguanosine |
| mannosyl-queuosine |
| 5-(carboxyhydroxymethyl)uridine |
| 5-methoxycarbonylmethyl-2-thiouridine |
| 5-methoxycarbonylmethyl-2'-O-methyluridine |
| 5-methoxycarbonylmethyluridine |

TABLE 2-continued

| Common name |
|---|
| 2-methylthio-N6-(cis-hydroxyisopentenyl) adenosine |
| 2-methylthio-N6-threonyl carbamoyladenosine |
| N1-Ethylpseudouridine |
| N1-Methoxymethylpseudouridine |
| N1-Methyl-2'-O-Methylpseudouridine |
| N1-Methyladenosine |
| N1-Propylpseudouridine |
| $N^2$,7-dimethylguanosine |
| $N^2$,$N^2$,7-trimethylguanosine |
| $N^2$,$N^2$-dimethylguanosine |
| $N^2$-Methyl-2'-deoxyguanosine |
| $N^2$-methylguanosine |
| $N^4$-acetylcytidine |
| N4-Biotin-OBEA-2'-deoxycytidine |
| N4-Methyl-2'-deoxycytidine |
| $N^4$-methylcytidine |
| $N^6$-(cis-hydroxyisopentenyl)-adenosine |
| $N^6$,2'-O-dimethyladenosine |
| $N^6$,$N^6$,2'-O-trimethyladenosine |
| $N^6$,$N^6$-dimethyladenosine |
| $N^6$-glycinylcarbamoyladenosine |
| $N^6$-isopentenyladenosine |
| N6-isopentenyl-adenosine |
| N6-Methyl-2-Aminoadenosine |
| N6-Methyl-2'-deoxyadenosine |
| $N^6$-methyladenosine |
| N6-methyl-adenosine |
| $N^6$-threonylcarbamoyladenosine |
| ncm5U 5-carbamoylmethyluridine |
| ncm5Um 5-carbamoylmethyl-2'-O-methyluridine |
| Nl-methyladenosine |
| N-uridine-5-oxyaceticacidmethylester |
| peroxywybutosine |
| O6-Methyl-2'-deoxyguanosine |
| O6-Methylguanosine |
| hydroxywybutosine |
| undermodified hydroxywybutosine |
| O-Methylpseudouridine |
| peroxywybutosine |
| Pseudoisocytidine |
| Puromycin |
| queosine |
| 2-thiouridine |
| N6-threonylcarbamoyladenosine |
| Thienocytidine |
| Thienoguanosine |
| Thienouridine |
| 2'-O-methyluridine |
| undermodified hydroxywybutosine |
| uridine-5-oxyaceticacid(v) |
| uridine-5-oxyaceticacidmethylester |
| wybutosine |
| wybutoxosine |
| wyosine |
| Xanthosine |
| 5-taurinomethyl-2-thiouridine |
| 5-taurinomethyluridine |
| 2'-O-methylpseudouridine |

In some embodiments, an RNA, e.g. an mRNA, may be synthesized from naturally occurring bases and/or base analogs (modified bases) including, but not limited to, purines (adenine (A), guanine (G)) or pyrimidines (thymine (T), cytosine (C), uracil (U)), and analogues and derivatives thereof, e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), pseudouridine, N-1-methyl-pseudouridine, dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, beta-D-mannosyl-queosine, wybutoxosine, and phosphoramidates, phosphorothioates, peptide nucleotides, methylphosphonates, 7-deazaguanosine, 5-methylcytosine and inosine.

In some embodiments, an RNA, e.g., an mRNA, may be synthesized from naturally occurring nucleosides and/or nucleoside analogs (modified nucleosides) including, but not limited to, nucleosides comprising adenosine (A), guanosine (G)) or pyrimidines (thymine (T), cytidine (C), uridine (U)), and nucleoside comprising analogues and derivatives thereof, e.g., 3'-deoxyadenosine (cordycepin), 3'-deoxyuridine, 3'-deoxycytosine, 3'-deoxyguanosine, 3'-deoxythymine, 2',3'-dideoxynucleosides, 2',3'-dideoxyadenosine, 2',3'-dideoxyuridine, 2',3'-dideoxycytosine, 2',3'-dideoxyguanosine, 2',3'-dideoxythymine, a 2'-deoxynucleoside, —O-methylnucleoside, 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouridine, N-1-methyl-pseudouridine, dihydro-uracil, 2-thio-uracil, 4-thio-uridine, 5-carboxymethylaminomethyl-2-thio-uridine, 5-(carboxyhydroxymethyl)-uridine, 5-fluoro-uridine, 5-bromo-uridine, 5-carboxymethylaminomethyl-uridine, 5-methyl-2-thio-uridine, 5-methyl-uridine, N-uridine-5-oxyacetic acid methyl ester, 5-methylaminomethyl-uridine, 5-methoxyaminomethyl-2-thio-uridine, 5'-methoxycarbonylmethyl-uracil, 5-methoxy-uracil, uracil-5-oxyacetic acid methyl ester, uracil-5-oxyacetic acid (v), 1-methyl-pseudouridine, queosine, beta-D-mannosyl-queosine, wybutoxosine, 7-deazaguanosine, 5-methylcytosine, and inosine.

The preparation of such base, nucleoside, nucleotide, and backbone analogues, modifications, and derivatives is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, all of which are incorporated by reference in their entirety.

In some embodiments, uracil nucleosides of the mRNA are about 80%, about 90%, 95%, 99%, or 100% depleted and replaced with a uracil nucleoside analog, e.g., pseudouridine, 5-methoxyuridine, or N-1-methyl-pseudouridine.

In some embodiments, an RNA may contain an RNA backbone modification. Typically, a backbone modification is a modification in which the phosphates of the backbone of the nucleotides contained in the RNA are chemically modified. Exemplary backbone modifications may include, but are not limited to, modifications in which the phosphodiester linkage is replaced with a member from the group consisting of peptides, methylphosphonates, methylphosphoramidates, phosphoramidates, phosphorothioates (e.g., cytidine 5'-O-(1-thiophosphate)), boranophosphates, and/or positively charged guanidimum groups, or other means of replacing the phosphodiester linkage.

In some embodiments, an RNA may contain sugar modifications. A sugar modification may include but is not limited to, 2' O-methyl sugar modifications, 2' fluoro sugar modifications (e.g. 2'-fluororibose), 3' amino sugar modifications, 2' thio sugar modifications, 2'-O-alkyl sugar modifications, 5-methylthioribose, and sugar modifications of 2'-deoxy-2'-fluoro-ribonucleotide (2'-fluoro-2'-deoxycytidine, 2'-fluoro-2'-deoxyuridine), 2'-deoxy-2'-deamine-ribonucleotide (2'-amino-2'-deoxycytidine, 2-amino-2'-deoxyuridine), 2'-O-alkylribonucleotide, 2'-deoxy-2'-C-alkylribonucleotide (2'-O-methylcytidine, 2'-methyluridine), 2'-C-alkylribonucleotide, and isomers thereof (2'-aracytidine, 2'-arauridine), or azidophosphates (2'-azido-2'-deoxycytidine, 2'-azido-2'-deoxyuridine).

In some embodiments, an RNA may be synthesized from one or more of the nucleotide triphosphates comprising any of the nucleosides and nucleotides disclosed herein, or any of the following nucleoside triphosphates: 2'-Deoxyadenosine-5'-O-(1-Thiotriphosphate), 2'-Deoxycytidine-5'-O-(1-Thiotriphosphate), 2'-Deoxyguanosine-5'-O-(1-Thiotriphosphate), 2'-Deoxythymidine-5'-O-(1-Thiotriphosphate), Adenosine-5'-O-(1-Thiotriphosphate), Cytidine-5'-O-(1-Thiotriphosphate), Guanosine-5'-O-(1-Thiotriphosphate), Uridine-5'-O-(1-Thiotriphosphate), 2',3'-Dideoxyadenosine-5'-O-(1-Thiotriphosphate), 2',3'-Dideoxycytidine-5'-O-(1-Thiotriphosphate), 2',3'-Dideoxyguanosine-5'-O-(1-Thiotriphosphate), 3'-Deoxythymidine-5'-O-(1-Thiotriphosphate), 3'-Azido-2',3'-dideoxythymidine-5'-O-(1-Thiotriphosphate), 2',3'-Dideoxyuridine-5'-O-(1-Thiotriphosphate), 2'-Deoxyadenosine-5'-O-(1-Boranotriphosphate), 2'-Deoxycytidine-5'-O-(1-Boranotriphosphate), 2'-Deoxyguanosine-5'-O-(1-Boranotriphosphate), and 2'-Deoxythymidine-5'-O-(1-Boranotriphosphate).

In some embodiments, an mRNA may include the addition of a "cap" on the N-terminal (5') end, and a "tail" on the C-terminal (3') end. The presence of the cap may provide resistance to nucleases found in eukaryotic cells. The presence of a "tail" may protect the mRNA from exonuclease degradation.

Cap Structure

In some embodiments, an mRNA may include a 5' cap structure. A 5' cap may comprise for example, a triphosphate linkage and a guanine nucleotide in which the 7-nitrogen is methylated. Examples of cap structures include, but are not limited to, m7G(5')ppp (5')A, G(5')ppp(5')A, and G(5')ppp (5')G. Naturally occurring cap structures comprise a 7-methyl guanosine that is linked via a triphosphate bridge to the 5'-end of the first transcribed nucleotide, resulting in a dinucleotide cap of m7G(5')ppp(5')N, where N is any nucleoside. In vivo, the cap is added in the nucleus by the enzyme guanylyl transferase immediately after initiation of transcription.

In some embodiments, a 5' cap may comprise an m7(3'OmeG)(5')ppp(5')(2'OmeA)pG or (CleanCap™ 3' OMe) structure. In some embodiments, a 5' cap may comprise a m7G(5')ppp(5')G. In some embodiments, the Anti-Reverse Cap Analog ("ARCA") or modified ARCA, is a 5' cap in which the 2' or 3' OH group is replaced with —OCH3. In some embodiments, the ARCA comprises an 3'-O-Me-m7G(5')ppp(5')G structure. In some embodiments, the 5' cap comprises m7G(5')ppp(5')(2'OmeA)pG. Additional mRNA caps may include, but are not limited to, a chemical structures selected from the group consisting of m7GpppG, m7GpppA, m7GpppC; unmethylated caps (e.g., GpppG); a 44 emethylated cap (e.g., m2'7GpppG), a trimethylated cap analog, or anti reverse cap analogs (e.g., ARCA; m7,2'Ome-GpppG, m72'dGpppG, m7'3'OmeGpppG, m7,3 dGpppG and their tetraphosphate derivatives) (see, e.g., Jemielity, J. et al, 'Wove anti-reverse cap analogs with superior translational properties", RNA, 9: 1108-1122 (2003)).

In some embodiments, a suitable cap is a 7-methyl guanylate ("m7G") linked via a triphosphate bridge to the 5'-end of the first transcribed nucleotide, resulting in m7G (5')ppp(5')N, where N is any nucleoside. A embodiment of a m7G cap utilized in embodiments of the disclosure is m7G(5')ppp(5')G. In some embodiments, the cap is a Cap0 structure. Cap0 structures lack a 2'-O-methyl residue of the ribose attached to bases 1 and 2. In some embodiments, the cap is a Cap1 structure. Cap1 structures have a 2'-O-methyl residue at base 2. In some embodiments, the cap is a Cap2 structure. Cap2 structures have a 2'-O-methyl residue attached to both bases 2 and 3.

A variety of m7G cap analogs are known in the art, many of which are commercially available. These include the m7 GpppG described above, as well as the ARCA 3'-OCH3 and 2'-OCH3 cap analogs (Jemielity, J. et al., RNA, 9: 1108-1122 (2003)). Additional cap analogs for use in embodiments of the disclosure include N7-benzylated dinucleoside tetraphosphate analogs (described in Grudzien, E. et at, RNA, 10: 1479-1487 (2004)), phosphorothioate cap analogs (described in Grudzien-Nogalska, E., et al, RNA, 13: 1745-1755 (2007)), and cap analogs (including biotinylated cap analogs) described in U.S. Pat. Nos. 8,093,367 and 8,304,529, incorporated by reference herein.

In some embodiments, the 5' cap is inosine, N1-methyl-guanosine, 2' fluoro-guanosine, 7-deaza-guanosine, m7(3'OmeG)(5')ppp(5')(2'OmeA)pG, CleanCap™, m7(3'OmeG)(5')ppp(5')(2'OmeA)pG, 8-oxo-guanosine, 2-amino-guanosine, LNA-guanosine, 2-azido-guanosine, Cap2, Cap4, CAP-003, or CAP-225.

In some embodiments, the 5' cap comprises or consists of an internal ribosome entry site (IRES). In some embodiments the IRES is within the 5' UTR. In some embodiments, the 5' cap comprises or consists of a 2A self-cleavage peptide, e.g, one or more of P2A, T2A, E2A and F2A.

Tail Structure

The presence of a "tail" may serve to protect an mRNA from exonuclease degradation. The poly-A tail is thought to stabilize natural messengers and synthetic sense RNA. Therefore, in certain embodiments a long poly-A tail can be added to an mRNA molecule thus rendering the RNA more stable. Poly-A tails can be added using a variety of art-recognized techniques. For example, long poly-A tails can be added to synthetic or in vitro transcribed RNA using poly-A polymerase (Yokoe, et al. Nature Biotechnology. 1996; 14: 1252-1256). A transcription vector can also encode long poly-A tails. In addition, poly-A tails can be added by transcription directly from PCR products. Poly-A may also be ligated to the 3' end of a sense RNA with RNA ligase (see, e.g., Molecular Cloning A Laboratory Manual, $2^{nd}$ Ed., ed. By Sambrook, Fritsch and Maniatis (Cold Spring Harbor Laboratory Press: 1991 edition)).

In some embodiments, an mRNA may include a 3' poly (A) tail structure. The length of the poly-A tail may be at least about 10, 50, 100, 200, 300, 400 or at least about 500 nucleotides. In some embodiments, a poly-A tail on the 3' terminus of an mRNA may include about 10 to 300 adenosine nucleotides (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, the poly A tail is 120 adenosine nucleotides.

In some embodiments, an mRNA may include a 3' poly-C tail structure. A poly-C tail on the 3' terminus of mRNA may include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail. In some embodiments, the length of the poly-A or poly C tail is associated with the stability of a modified sense mRNA and, therefore, the transcription of the protein. For example, because the length of the poly-A tail may influence the half-life of a sense mRNA molecule, the length of the poly-A tail may be adjusted to modify the level of resistance of the mRNA to nucleases, thereby providing more control over the time course of polynucleotide expression and/or polypeptide production.

5' an' 3' Untranslated Regions (UTRs)

In some embodiments, an mRNA may include 5' untranslated region (UTR) and/or a 3' UTR. In some embodiments, a 5' UTR may include one or more elements that affect the stability or translation of an mRNA. In some embodiments, the 5'UTR for example, may include an iron responsive element. In some embodiments, 5' UTR may be between about 50 to about 100, or from about 50 to about 500 nucleotides in length. In some embodiments, 3' UTR includes one or more of a poly-A signal, a binding site for proteins that may affect mRNA stability or localization, or one or more binding sites for miRNAs. In some embodiments, 3' UTR may be between about 0 and about 50 nucleotides, or about 50 to about 100 nucleotides in length.

Example 3' an' 5' UTR sequences may be derived from mRNAs with relatively long half-lives (e.g., globin, actin, GAPDH, tubulin, histone, or citric acid cycle enzymes) to increase the stability of the sense mRNA molecule. For example, 5' UTR sequence may include a partial sequence of a cytomegalovirus (CMV) immediate-early 1 (IE1) gene, or a fragment thereof to improve the nuclease resistance and/or improve the half-life of the polynucleotide. Generally, these modifications improve the stability and/or pharmacokinetic properties (e.g., half-life) of the polynucleotide relative to their unmodified counterparts, and include, for example modifications made to improve such polynucleotides resistance to in vivo nuclease digestion.

In some embodiments, a UTR may improve tissue specific expression, e.g., in the lung. In some embodiments, the 3' UTR is a mouse alpha-globin 3' UTR. In some embodiments, the 3' UTR comprises a sequence of SEQ ID NO: 32, or a nucleic acid sequence at least 70%, at least 70%, at least 75%, at least 80%, at least 85%, at least 90%, at least 95%, at least 96%, at least 97%, at least 98%, or at least 99% identical thereto.

In some embodiments, the 3' UTR is a wild type human beta-globin 3' UTR. In some embodiments, the 3' UTR comprises a sequence of SEQ ID NO: 33, or a nucleic acid at least 70%, at least 75%, at least 80%, at least 85%, at least 90%, at least 95%, at least 96%, at least 97%, at least 98%, or at least 99% identical thereto.

In some embodiments, the 3' UTR is a variant human beta-globin 3' UTR. In some embodiments, the 3' UTR comprises a sequence of SEQ ID NO: 34, or a nucleic acid sequence at least 70%, at least 75%, at least 80%, at least 85%, at least 90%, at least 95%, at least 96%, at least 97%, at least 98%, or at least 99% identical thereto.

In some embodiments, the 5' UTR is a synthetic 5' UTR. In some embodiments, the 5' UTR comprises a sequence of SEQ ID NO: 35, or a nucleic acid at least 70%, at least 75%, at least 80%, at least 85%, at least 90%, at least 95%, at least 96%, at least 97%, at least 98%, or at least 99% identical thereto.

In some embodiments, the 5' UTR is a human beta-globin 5' UTR. In some embodiments, the 5' UTR comprises a sequence of SEQ ID NO: 36, or a nucleic acid at least 70%, at least 75%, at least 80%, at least 85%, at least 90%, at least 95%, at least 96%, at least 97%, at least 98%, or at least 99% identical thereto.

In some embodiments, the UTR may be any of, or functional variants of, those described in any of PCT Application No. WO2017053297A1 and Patent No. U.S. Ser. No. 10/519,189B2, both of which are incorporated herein in their entirety.

Exemplary Therapeutic TERT mRNA Sequences

In some embodiments, a TERT mRNA may refer to the full length mRNA sequence, ie. coding and non-coding, delivered to the tissue, e.g. the lung. Example sequences include the sequences comprising mouse TERT of SEQ ID NOS: 37 and 38, and the sequences comprising human TERT of SEQ ID NOS: 39 and 40.

In some embodiments, the mouse TERT mRNA comprises a sequence of SEQ ID NO: 37, or a nucleic acid sequence at least 70%, at least 75%, at least 80%, at least 85%, at least 90%, at least 95%, at least 96%, at least 97%, at least 98%, or at least 99% identical thereto.

In some embodiments, the mouse TERT mRNA comprises a sequence of SEQ ID NO: 38, or a nucleic acid sequence at least 70%, at least 75%, at least 80%, at least 85%, at least 90%, at least 95%, at least 96%, at least 97%, at least 98%, or at least 99% identical thereto.

In some embodiments, the human TERT mRNA comprises a sequence of SEQ ID NO: 39, or a nucleic acid at least 70%, at least 75%, at least 80%, at least 85%, at least 90%, at least 95%, at least 96%, at least 97%, at least 98%, or at least 99% identical thereto.

In some embodiments, the human TERT mRNA comprises a sequence of SEQ ID NO: 40, or a nucleic acid sequence at least 70%, at least 75%, at least 80%, at least 85%, at least 90%, at least 95%, at least 96%, at least 97%, at least 98%, or at least 99% identical thereto.

In some embodiments, a TERT mRNA may comprise a nucleic acid sequence at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NOS: 38-40.

The disclosure provides compositions for the extension of telomeres in a cell, the compositions comprising a compound of the present disclosure, as described above, and a further component. In some embodiments, the further component comprises a telomerase RNA component (TERC). In some embodiments, the compositions further comprise a telomerase RNA component (TERC). In some embodiments, the compositions further comprise one or more additional components that may facilitate delivery of the RNA to cells in vitro and/or in vivo. In some embodiments, the one or more additional components comprise a nanoparticle. In some embodiments, the nanoparticle comprises a lipid. In some embodiments, the nanoparticle or the lipid comprise a coatsome-like lipid or a compound of the disclosure. In some embodiments, the nanoparticle or the lipid comprise a compound of the disclosure according to Formula I.

II. Delivery Vehicles

In some embodiments, one or more mRNAs may be delivered to a cell or tissue via delivery vehicles. In some embodiments a delivery vehicle may be a nanoparticle. In some embodiments, the delivery vehicle is a lipid nanoparticle (LNP) including but not limited to a nanoparticle comprising lipids and/or polymers, a liposome, a liposomal nanoparticle, a cationic lipid, or an exosome. As used herein, liposomal nanoparticles may be characterized as microscopic vesicles having an interior aqueous space sequestered from an outer medium by a membrane of one or more bilayers.

In some embodiments, the nanoparticle is a polymeric nanoparticle. In some embodiments, the nanoparticle is a metal nanoparticle. In other embodiments, the delivery vehicle comprises or consists of a recombinant virus or virus-like particle, e.g., an adenovirus, adeno-associated virus (AAV), herpesvirus, or retrovirus, e.g., lentivirus. In some embodiments, the delivery vehicle comprises or consists of a modified viral vector, e.g., an adenovirus dodecahedron or recombinant adenovirus conglomerate. In other embodiments, the delivery vehicle may comprise or consist of calcium phosphate nucleotides, aptamers, cell-penetrating peptides or other vectorial tags.

In some embodiments, a suitable delivery vehicle is a lipid nanoparticle (LNP), Exemplary LNPs may comprise one or more different lipids and/or polymers. In some embodiments, an LNP comprises one or more of ionizable lipids, cationic lipids, structural lipids, cholesterols, and/or insulator lipids (e.g., PEGylated lipids).

Compositions of the disclosure may comprise one or more components that may facilitate delivery of the RNA to cells. Collectively or in part, components of the composition may comprise a delivery vehicle. In some embodiments, the delivery vehicle facilitates targeting and uptake of the ribonucleic acid of a composition of the disclosure to a target cell. Exemplary delivery vehicles include, but are not limited to, nanoparticles, lipid nanoparticles (LNPs), liposomes, micelles, exosomes, cationic lipids and a natural or artificial lipoprotein particle.

Ionizable Lipids

In some embodiments of the disclosure, an LNP may comprise an ionizable lipid, e.g. SS-OP or analogs thereof. The charge of the lipid may depend on pH of the surrounding solution, making it an ionizable lipid. The ionizable lipid may also be cleavable. The ionizable lipid may be cationic at ranges of pH found in endosomes or lysosomes in mammalian cells.

An ionizable lipid may refer to any of a number of lipid species that have a net positive charge at a selected pH, such as a physiological pH. In some embodiments, an LNP may comprise an ionizable lipid as disclosed in either of WO 2010/053572 or WO 2012/170930, or variations thereof, both of which are incorporated herein by reference in their entirety.

In some embodiments, an LNP for lung delivery of a TERT mRNA may comprise one or more of MC3 (((6Z,9Z,28Z,31Z)-heptatriaconta-6,9,28,31-tetraen-19-yl 4-(dimethylamino)butanoate), 1,2-dilineoyl-3-dimethylammonium-propane (DLinDAP), DLin-MC3-DMA 4-(dimethylamino)-butanoic acid, (10Z,13Z)-1-(9Z,12Z)-9,12-octadecadien-1-yl-10,13-nonadecadien-1-yl ester and/or cKK-E12 3,6-Bis(4-(bis(2-hydroxydodecyl)amino)butyl)piperazine-2,5-dione. In some embodiments the LNP comprises 2,2-dilinoleyl-4-dimethylaminoethyl-[1,3]-dioxolane (Dlin-KC2-DMA, 1) and/or (6Z,9Z,28Z,31Z)-Heptatriaconta-6,9,28,31-tetraen-19-yl 4-(dimethylamino)butanoate.

In some embodiments, the ionizable lipid may comprise SS-OP or analogs thereof. In some embodiments, the ionizable lipid is a compound of Formula (1):

(1)

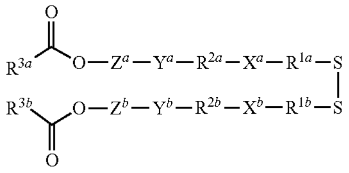

In the formula (1): $R^{1a}$ and $R^{1b}$ each independently represents an alkylene group having 1 to 6 carbon atoms, and may be linear or branched. The alkylene group may have 1 to 4 carbon atoms, or may have 1 to 2. Specific examples of the alkylene group having 1 to 6 carbon atoms include a methylene group, an ethylene group, a trimethylene group, an isopropylene group, a tetramethylene group, an isobutylene group, a pentamethylene group, and a neopentylene group. $R^{1a}$ and $R^{1b}$ may be each independently a methylene group, an ethylene group, a trimethylene group, an isopropylene group, or a tetramethylene group, and may be an ethylene group.

$R^{1a}$ may be different or be the same as $R^{1b}$.

$X^a$ and $X^b$ are each independently an acyclic alkyl tertiary amino group having 1 to 6 carbon atoms and 1 tertiary amino group, or 2 to 5 carbon atoms, and a cyclic alkylene tertiary amino group having 1 to 2 tertiary amino groups, and/or each independently a cyclic alkylene having 2 to 5 carbon atoms and 1 to 2 tertiary amino groups and an alkylene tertiary amino group.

The alkyl group having 1 to 6 carbon atoms in the acyclic alkyl tertiary amino group having 1 to 6 carbon atoms and 1 tertiary amino group is branched even if it is linear. The alkyl group may be annular. The alkyl group may have 1 to 3 carbon atoms. Specific examples of the alkyl group having 1 to 6 carbon atoms include methyl group, ethyl group, propyl group, isopropyl group, n-butyl group, sec-butyl group, isobutyl group, tert-butyl group, pentyl group, and isopentyl group. Neopentyl group, t-pentyl group, 1,2-dimethylpropyl group, 2-methylbutyl group, 2-methylpentyl group, 3-methylpentyl group, 2,2-dimethylbutyl group, 2,3-dimethylbutyl group, A cyclohexyl group etc. can be mentioned.

A specific structure of an acyclic alkyl tertiary amino group having 1 to 6 carbon atoms and 1 tertiary amino group is represented by $X^1$.

$X^1 =$ 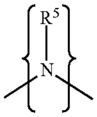

$R^5$ of $X^1$ represents an alkyl group having 1 to 6 carbon atoms and may be linear, branched or cyclic. The alkyl group may have 1 to 3 carbon atoms. Specific examples of the alkyl group having 1 to 6 carbon atoms include methyl group, ethyl group, propyl group, isopropyl group, n-butyl group, sec-butyl group, isobutyl group, tert-butyl group, pentyl group, and isopentyl group. Neopentyl group, t-pentyl group, 1,2-dimethylpropyl group, 2-methylbutyl group, 2-methylpentyl group, 3-methylpentyl group, 2,2-dimethylbutyl group, 2,3-dimethylbutyl group, A cyclohexyl group etc. can be mentioned.

The number of carbon atoms in the cyclic alkylene tertiary amino group having 2 to 5 carbon atoms and 1 to 2 tertiary amino groups may be 4 to 5. Specific examples of the cyclic alkylene tertiary amino group having 2 to 5 carbon atoms and 1 to 2 tertiary amino groups include aziridylene group, azetidylene group, pyrrolidylene group, piperidylene group, imidazolidylene group, a piperazylene group, optionally a pyrrolidylene group, a piperidylene group or a piperazylene group.

Number is 2 to 5 carbon atoms, and specific structure of alkylene tertiary amino groups containing 1 annular tertiary amino group represented by $X^2$.

$X^2 =$ 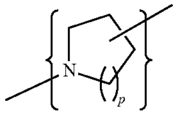

P of $X^2$ is 1 or 2. When p is 1, $X^2$ is a pyrrolidylene group, and when p is 2, $X^2$ is a piperidylene group.

A specific structure of a cyclic alkylene tertiary amino group having 2 to 5 carbon atoms and 2 tertiary amino groups is represented by $X^3$.

$X^3 =$ 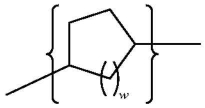

W of $X^3$ is 1 or 2. When w is 1, $X^3$ is an imidazolidylene group, and when w is 2, $X^3$ is a piperazylene group.

$X^a$ may be different be identical to $X^b$.

$R^{2a}$ and $R^{2b}$ each independently represent an alkylene group or an oxydialkylene group having 8 or less carbon atoms, optionally each independently an alkylene group having 8 or less carbon atoms.

The alkylene group having 8 or less carbon atoms may be linear or branched but is optionally linear. The number of carbon atoms contained in the alkylene group is optionally 6 or less, and optionally 4 or less. Specific examples of the alkylene group having 8 or less carbon atoms include methylene group, ethylene group, propylene group, isopropylene group, tetramethylene group, isobutylene group, pentamethylene group, hexamethylene group, heptamethylene group, octamethylene group, and the like. In some embodiments included are a methylene group, an ethylene group, a propylene group, and a tetramethylene group.

The oxydialkylene group having 8 or less carbon atoms refers to an alkylene group (alkylene-O-alkylene) via an ether bond, and the total number of carbon atoms of two alkylene groups is 8 or less. Here, the two alkylenes may be the same or different, but are optionally the same. Specific examples of the oxydialkylene group having 8 or less carbon atoms include an oxydimethylene group, an oxydiethylene group, an oxydipropylene group, and an oxydibutylene group.

$R^{2a}$ may be same or different and $R^{2b}$.

$Y^a$ and $Y^b$ are each independently an ester bond, an amide bond, a carbamate bond, an ether bond or a urea bond, optionally each independently an ester bond, an amide bond or a carbamate bond. While Y binding orientation of $Y^a$ and $Y^b$ are not limited, if $Y^a$ and $Y^b$ is an ester bond, optionally, $—Z^a—CO—R^{2a}—$ and $—Z^b—CO—O—R^{2b}$-Structure.

$Y^a$ may be different or identical to $Y^b$.

$Z^a$ and $Z^b$ are each independently a divalent group derived from an aromatic compound having 3 to 16 carbon atoms, having at least one aromatic ring, and optionally having a hetero atom. Represents. The number of carbon atoms contained in the aromatic compound is optionally 6 to 12, or 6 to 7. Moreover, the number of aromatic rings contained in the aromatic compound is optionally one.

As the types of aromatic rings contained in the aromatic compound having 3 to 16 carbon atoms, as for aromatic hydrocarbon rings, benzene ring, naphthalene ring, anthracene ring, and aromatic heterocycles as imidazole ring, pyrazole ring, oxazole ring, Isoxazole ring, thiazole ring, isothiazole ring, triazine ring, pyrrole ring, furanthiophene ring, pyrimidine ring, pyridazine ring, pyrazine ring, pyridine ring, purine ring, pteridine ring, benzimidazole ring, indole ring, benzofuran ring, quinazoline ring, phthalazine ring, quinoline ring, isoquinoline ring, coumarin ring, chromone ring, benzodiazepine ring, phenoxazine ring, phenothiazine ring, acridine ring, etc., optionally benzene ring, naphthalene ring, anthracene ring. The aromatic ring may have a substituent. Examples of the substituent include an acyl group having 2 to 4 carbon atoms, an alkoxycarbonyl group having 2 to 4 carbon atoms, a carbamoyl group having 2 to 4 carbon atoms, and 2 to 2 carbon atoms. 4 acyloxy groups, acylamino groups having 2 to 4 carbon atoms, alkoxy carbonylamino groups having 2 to 4 carbon atoms, fluorine atoms, chlorine atoms, bromine atoms, iodine atoms, alkylsulfanyl groups having 1 to 4 carbon atoms, 1 carbon atom Alkylsulfonyl group having 4 to 4, arylsulfonyl group having 6 to 10 carbon atoms, nitro group, trifluoromethyl group, cyano group, alkyl group having 1 to 4 carbon atoms, ureido group having 1 to 4 carbon atoms, 1 to carbon atoms 4 alkoxy groups, aryl groups having 6 to 10 carbon atoms, aryloxy groups having 6 to 10 carbon atoms, and the like. Some examples include acetyl groups, methoxycarbonyl groups, methyl carbonate groups, and the like, moyl group, acetoxy group, acetamide group, methoxycarbonylamino group, fluorine atom, chlorine atom, bromine atom, iodine atom, methylsulfanyl group, phenylsulfonyl group, nitro group, trifluoromethyl group, cyano group, methyl group, ethyl group Propyl group, isopropyl group, t-butyl group, ureido group, methoxy group, ethoxy group, propoxy group, isopropoxy group, t-butoxy group, phenyl group and phenoxy group.

A specific structure of $Z^a$ and $Z^b$ includes $Z^1$.

$Z^1$ =
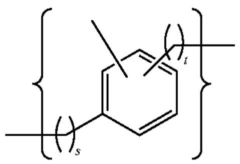

Wherein, s represents an integer of 0 to 3, t represents an integer of 0 to 3, u represents an integer of 0 to 4, represents a u-number of R4 is independently a substituent.

S in $Z^1$ is optionally an integer of 0 to 1.

T in $Z^1$ is optionally an integer of 0 to 2.

U in $Z^1$ is optionally an integer of 0 to 2.

R4 in $Z^1$ is a substituent of an aromatic ring (benzene ring) contained in an aromatic compound having 3 to 16 carbon atoms that does not inhibit the reaction in the process of synthesizing the ionizable lipid. Examples of the substituent include an acyl group having 2 to 4 carbon atoms, an alkoxycarbonyl group having 2 to 4 carbon atoms, a carbamoyl group having 2 to 4 carbon atoms, an acyloxy group having 2 to 4 carbon atoms, and an acylamino group having 2 to 4 carbon atoms, an alkoxycarbonylamino group having 2 to 4 carbon atoms, fluorine atom, chlorine atom, bromine atom, iodine atom, alkylsulfanyl group having 1 to 4 carbon atoms, alkylsulfonyl group having 1 to 4 carbon atoms, 6 to 10 carbon atoms Arylsulfonyl group, nitro group, trifluoromethyl group, cyano group, alkyl group having 1 to 4 carbon atoms, ureido group having 1 to 4 carbon atoms, alkoxy group having 1 to 4 carbon atoms, aryl group having 6 to 10 carbon atoms And aryloxy groups having 6 to 10 carbon atoms, and examples include acetyl, methoxycarbonyl, methylcarbamoyl, acetoxy, Mido group, methoxycarbonylamino group, fluorine atom, chlorine atom, bromine atom, iodine atom, methylsulfanyl group, phenylsulfonyl group, nitro group, trifluoromethyl group, cyano group, methyl group, ethyl group, propyl group, isopropyl group, T-butyl group, ureido group, methoxy group, ethoxy group, propoxy group, isopropoxy group, t-butoxy group, phenyl group and phenoxy group. When a plurality of $R^4$ are present, each $R^4$ may be the same or different.

$Z^a$ may be different even identical to the $Z^b$.

$R^{3a}$ and $R^{3b}$ are each independently a residue derived from a reaction product of a fat-soluble vitamin having a hydroxyl group and succinic anhydride or glutaric anhydride, or a sterol derivative having a hydroxyl group and succinic anhydride or glutaric acid. Represents a residue derived from a reaction product with an anhydride, or an aliphatic hydrocarbon group having 12 to 22 carbon atoms, and optionally each independently a fat-soluble vitamin having a hydroxyl group and succinic anhydride or glutaric anhydride. Or a C12-22 aliphatic hydrocarbon group, and optionally each independently an aliphatic hydrocarbon group having 12-22 carbon atoms.

Examples of the fat-soluble vitamin having a hydroxyl group include retinol, ergosterol, 7-dehydrocholesterol, calciferol, corcalciferol, dihydroergocalciferol, dihydrotaxolol, tocopherol, and tocotrienol. The fat-soluble vitamin having a hydroxyl group is optionally tocopherol.

Examples of the sterol derivative having a hydroxyl group include cholesterol, cholestanol, stigmasterol, β-sitosterol, lanosterol, ergosterol and the like, optionally cholesterol or cholestanol.

The aliphatic hydrocarbon group having 12 to 22 carbon atoms may be linear or branched. The aliphatic hydrocarbon group may be saturated or unsaturated. In the case of an unsaturated aliphatic hydrocarbon group, the number of unsaturated bonds contained in the aliphatic hydrocarbon group is usually 1 to 6, optionally 1 to 3, or 1 to 2. Unsaturated bonds include carbon-carbon double bonds and carbon-carbon triple bonds. The number of carbon atoms contained in the aliphatic hydrocarbon group is optionally 13 to 19, or 13 to 17. The aliphatic hydrocarbon group includes an alkyl group, an alkenyl group, an alkynyl group and the like, and optionally includes an alkyl group or an alkenyl group. Specific examples of the aliphatic hydrocarbon group having 12 to 22 carbon atoms include dodecyl, tridecyl, tetradecyl, pentadecyl, hexadecyl, heptadecyl, octadecyl, nonadecyl, icosyl, heicosyl, docosyl, Dodecenyl group, tridecenyl group, tetradecenyl group, pentadecenyl group, hexadecenyl group, heptadecenyl group, octadecenyl group, nonadecenyl group, icocenyl group, henicocenyl group, dococenyl group, dodecadienyl group, tridecadienyl group, tetradecadienyl group, pentadecadienyl group Group, hexadecadienyl group, heptadecadienyl group, octadecadienyl group, nonadecadienyl group, icosadenyl group, henicosadienyl group, docosadienyl group, octadecatrienyl group, icosatrienyl group, Cosatetraenyl group, icosapentaenyl group, docosahexaenyl group, isostearyl group, 1-hexylheptyl group, 1-hexylnonyl group, 1-octylnonyl group, 1-octylundecyl group, 1-decylundecyl group, etc. be able to. The aliphatic hydrocarbon group having 12 to 22 carbon atoms is optionally a tridecyl group, a pentadecyl group, a heptadecyl group, a nonadecyl group, a heptadecenyl group, a heptadecadienyl group, or a 1-hexylnonyl group, or a tridecyl group, A heptadecyl group, a heptadecenyl group, and a heptadecadienyl group.

In one embodiment of the present disclosure, the aliphatic hydrocarbon group having 12 to 22 carbon atoms represented by $R^{3a}$ and $R^{3b}$ is derived from a fatty acid. In this case, the carbonyl carbon derived from the fatty acid is contained in —CO—O— in the formula (1). Specific examples of the aliphatic hydrocarbon group include a heptadecenyl group when linoleic acid is used as the fatty acid, and a heptadecenyl group when oleic acid is used as the fatty acid.

$R^{3a}$ may be different be the same as $R^{3b}$.

In one embodiment of the present disclosure, $R^{1a}$ is the same as $R^{1b}$, $X^a$ is the same as $X^b$, $R^{2a}$ is the same as $R^{2b}$, $Y^a$ is the same as $Y^b$, and $Z^a$ is identical to the $Z^b$, $R^{3a}$ is the same as $R^{3b}$.

Preferable examples of the ionizable lipid represented by the formula (1) include the following ionizable lipids: Ionizable lipid (1-1); R1a and R1b are each independently an alkylene group having 1 to 6 carbon atoms (eg, methylene group, ethylene group); X a and X b are each independently an acyclic alkyl tertiary amino group having 1 to 6 carbon atoms and 1 tertiary amino group (eg, —N(CH3)-), Or a cyclic alkylene tertiary amino group having 2 to 5 carbon atoms and 1 to 2 tertiary amino groups (eg, piperidylene group); $R^{2a}$ and $R^{2b}$ are each independently an alkylene group having 8 or less carbon atoms (eg, methylene group, ethylene group, propylene group); $Y^a$ and $Y^b$ are each independently an ester bond or an amide bond; $Z^a$ and $Z^b$ are each independently a divalent group derived from an aromatic compound having 3 to 16 carbon atoms, having at least one aromatic ring, and optionally having a hetero atom. (Eg, —C6H4-CH2-, —CH2-C6H4-CH2-); $R^{3a}$ and $R^{3b}$ are each independently a residue derived from a reaction product of a fat-soluble vitamin having a hydroxyl group (eg, tocopherol) and succinic anhydride or glutaric anhydride, or an aliphatic group having 12 to 22 carbon atoms A hydrocarbon group (eg, heptadecenyl group, heptadecadienyl group, 1-hexylnonyl group);

Ionizable lipid (1-2); $R^{1a}$ and $R^{1b}$ are each independently an alkylene group having 1 to 4 carbon atoms (eg, methylene group, ethylene group); X a and X b are each independently an acyclic alkyl tertiary amino group having 1 to 3 carbon atoms and 1 tertiary amino group (eg, —N(CH3)-), Or a cyclic alkylene tertiary amino group having 2 to 5 carbon atoms and 1 tertiary amino group (eg, piperidylene group); $R^{2a}$ and $R^{2b}$ are each independently an alkylene group having 6 or less carbon atoms (eg, methylene group, ethylene group, propylene group); $Y^a$ and $Y^b$ are each independently an ester bond or an amide bond; Z a and Z b are each independently a divalent group derived from an aromatic compound having 6 to 12 carbon atoms, one aromatic ring, and optionally having a hetero atom (Eg, —C6H4-CH2-, —CH2-C6H4-CH2-); $R^{3a}$ and $R^{3b}$ are each independently a residue derived from a reaction product of a fat-soluble vitamin having a hydroxyl group (eg, tocopherol) and succinic anhydride, or an aliphatic hydrocarbon group having 13 to 19 carbon atoms (eg, Heptadecenyl group, heptadecadienyl group, 1-hexylnonyl group).

Ionizable lipid (1-3); $R^{1a}$ and $R^{1b}$ are each independently an alkylene group having 1 to 2 carbon atoms (eg, methylene group, ethylene group); $X^a$ and $X^b$ are each independently $X^1$:

$X^1$ =
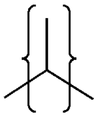

wherein $R^5$ is an alkyl group having 1 to 3 carbon atoms (eg, a methyl group)), or $X^2$;

$X^2$ =
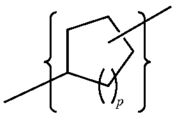

wherein p is 1 or 2), $R^{2a}$ and $R^{2b}$ are each independently an alkylene group having 4 or less carbon atoms (eg, methylene group, ethylene group, propylene group); $Y^a$ and $Y^b$ are each independently an ester bond or an amide bond; $Z^a$ and $Z^b$ are each independently $Z^1$:

$Z^1$ =
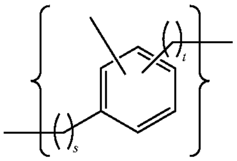

wherein s is an integer from 0 to 1, t is an integer from 0 to 2, u is an integer from 0 to 2 (optionally 0), and $(R^4)$u are each independently represents a substituent. $R^{3a}$ and $R^{3b}$ are each independently a residue derived from a reaction product of a fat-soluble vitamin having a hydroxyl group (eg, tocopherol) and succinic anhydride, or an aliphatic hydrocarbon group having 13 to 17 carbon atoms (eg, Heptadecenyl group, heptadecadienyl group, 1-hexylnonyl group);

Specific examples of the ionizable lipid according to Formula 1 of the present disclosure include the following O-Ph-P3C1, O-Ph-P4C1, O-Ph-P4C2, O-Bn-P4C2, E-Ph-P4C2, L-Ph-P4C2, HD-Ph-P4C2, O-Ph-amide-P4C2, and O-Ph-C3M as seen in Tables 3, 4, and 5.

TABLE 3
Ionizable lipids
O-Ph-P3C1
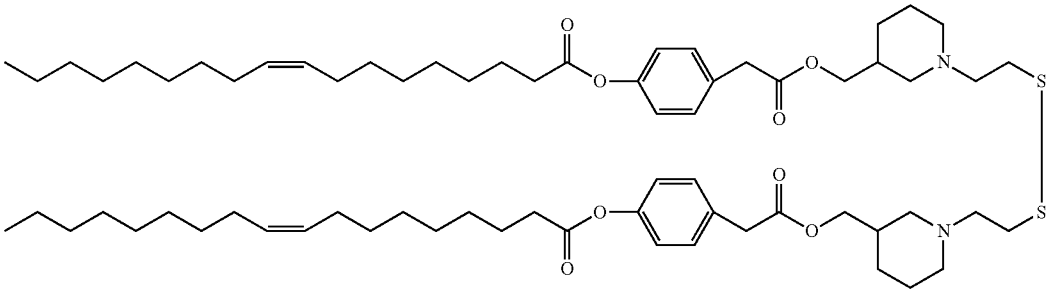 [SMILES: CCCCCCCC/C=C\CCCCCCCC(=O)Oc1ccc(CC(=O)OCC2CCCN(CCSSCCN3CCCC(COC(=O)Cc4ccc(OC(=O)CCCCCCC/C=C\CCCCCCCC)cc4)C3)C2)cc1]
O-Ph-P4C1
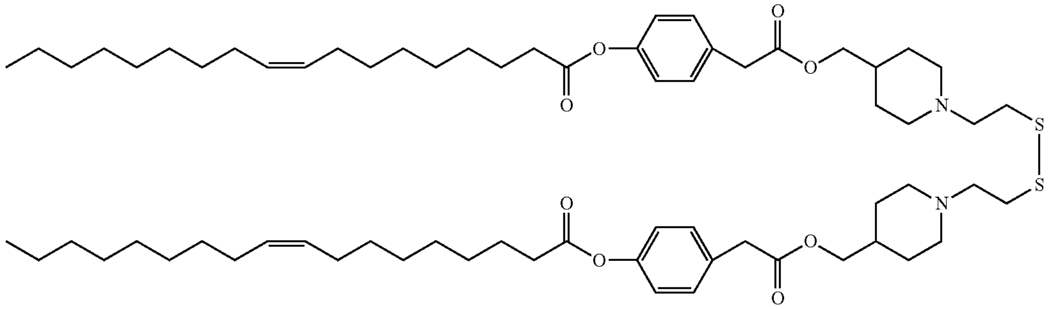 [SMILES: CCCCCCCC/C=C\CCCCCCCC(=O)Oc1ccc(CC(=O)OCC2CCN(CCSSCCN3CCC(COC(=O)Cc4ccc(OC(=O)CCCCCCC/C=C\CCCCCCCC)cc4)CC3)CC2)cc1]
O-Ph-P4C2
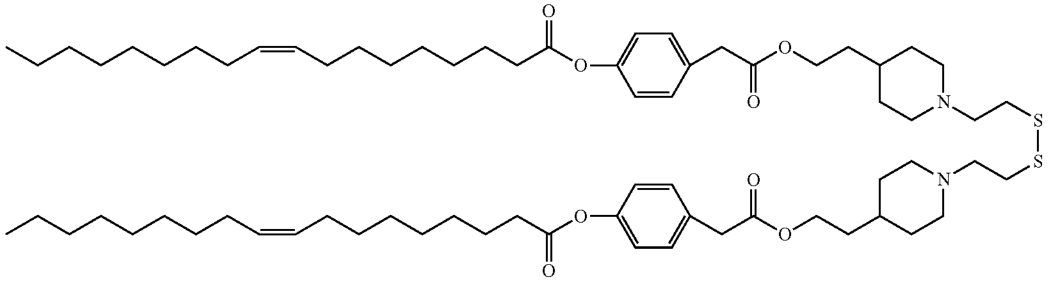 [SMILES: CCCCCCCC/C=C\CCCCCCCC(=O)Oc1ccc(CC(=O)OCCC2CCN(CCSSCCN3CCC(CCOC(=O)Cc4ccc(OC(=O)CCCCCCC/C=C\CCCCCCCC)cc4)CC3)CC2)cc1]
O-Bn-P4C2
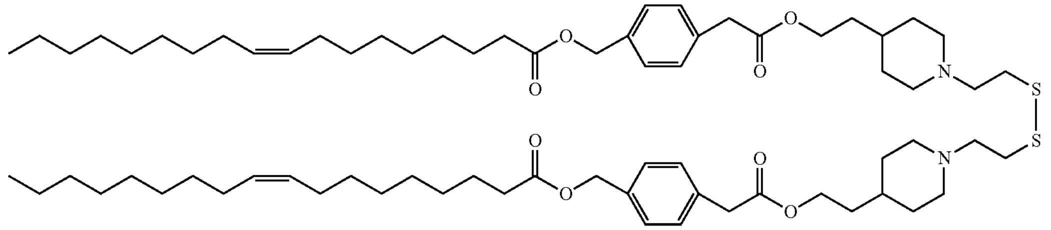 [SMILES: CCCCCCCC/C=C\CCCCCCCC(=O)OCc1ccc(CC(=O)OCCC2CCN(CCSSCCN3CCC(CCOC(=O)Cc4ccc(COC(=O)CCCCCCC/C=C\CCCCCCCC)cc4)CC3)CC2)cc1]
E-Ph-P4C2
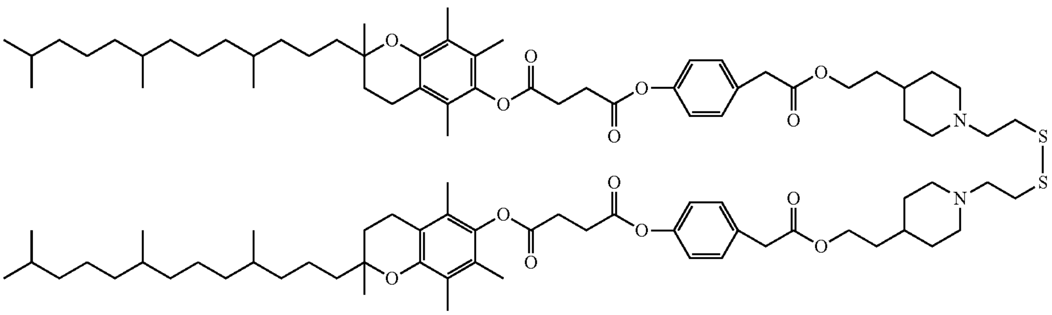 [SMILES: Cc1c(C)c2c(c(C)c1OC(=O)CCC(=O)Oc1ccc(CC(=O)OCCC3CCN(CCSSCCN4CCC(CCOC(=O)Cc5ccc(OC(=O)CCC(=O)Oc6c(C)c(C)c7c(c6C)CCC(C)(CCCC(C)CCCC(C)CCCC(C)C)O7)cc5)CC4)CC3)cc1)CCC(C)(CCCC(C)CCCC(C)CCCC(C)C)O2]

TABLE 3-continued
| Ionizable lipids | |
|---|---|
| L-Ph-P4C2 | 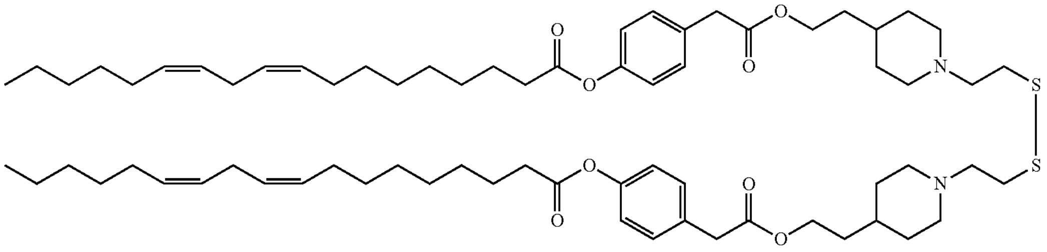 [SMILES: CCCCC/C=C\C/C=C\CCCCCCCC(=O)Oc1ccc(CC(=O)OCCC2CCN(CCSSCCN3CCC(CCOC(=O)Cc4ccc(OC(=O)CCCCCCC/C=C\C/C=C\CCCCC)cc4)CC3)CC2)cc1] |
| HD-Ph-P4C2 | 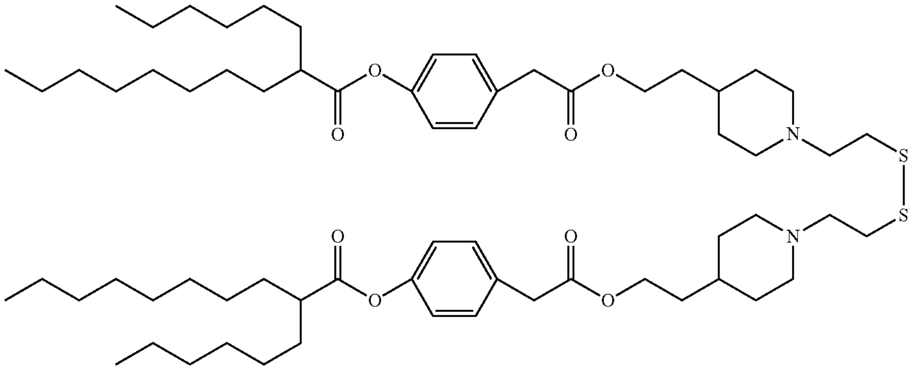 [SMILES: CCCCCCCCC(CCCCCC)C(=O)Oc1ccc(CC(=O)OCCC2CCN(CCSSCCN3CCC(CCOC(=O)Cc4ccc(OC(=O)C(CCCCCC)CCCCCCCC)cc4)CC3)CC2)cc1] |
| O-Ph-amide-P4C2 | 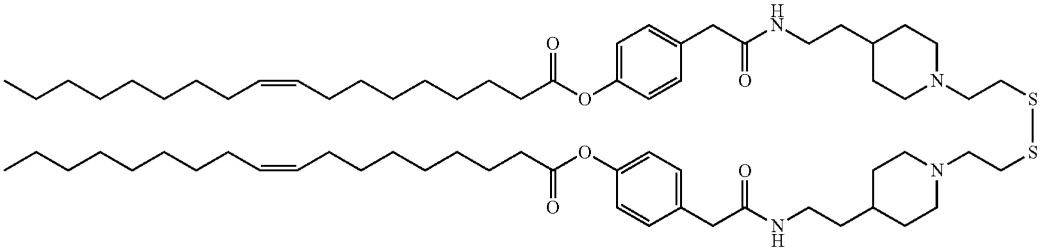 [SMILES: CCCCCCCC/C=C\CCCCCCCC(=O)Oc1ccc(CC(=O)NCCC2CCN(CCSSCCN3CCC(CCNC(=O)Cc4ccc(OC(=O)CCCCCCC/C=C\CCCCCCCC)cc4)CC3)CC2)cc1] |
| O-Ph-C3M | 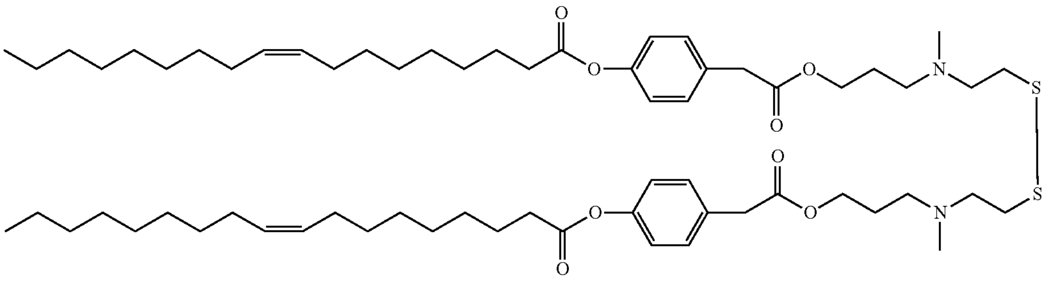 [SMILES: CCCCCCCC/C=C\CCCCCCCC(=O)Oc1ccc(CC(=O)OCCCN(C)CCSSCCN(C)CCCOC(=O)Cc2ccc(OC(=O)CCCCCCC/C=C\CCCCCCCC)cc2)cc1] |

TABLE 4

| Ionizable lipids | |
|---|---|
| α-D-Tocopherolsuccinoyl | 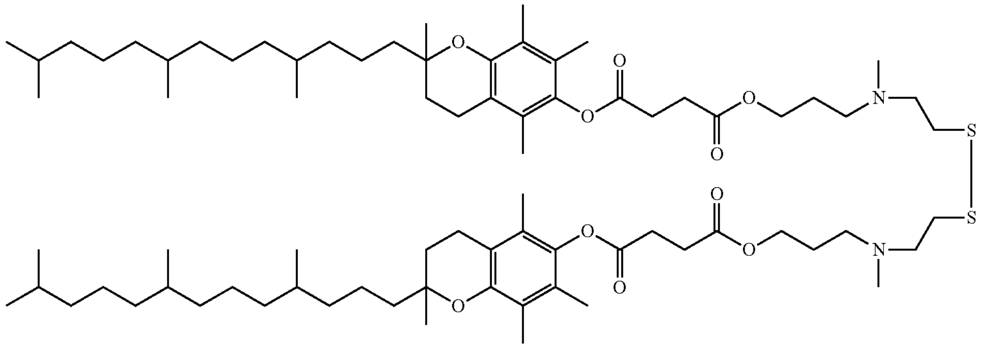 [SMILES: Cc1c(C)c2c(c(C)c1OC(=O)CCC(=O)OCCCN(C)CCSSCCN(C)CCCOC(=O)CCC(=O)Oc1c(C)c(C)c3c(c1C)CCC(C)(CCCC(C)CCCC(C)CCCC(C)C)O3)CCC(C)(CCCC(C)CCCC(C)CCCC(C)C)O2] |
| Linoleoyl | 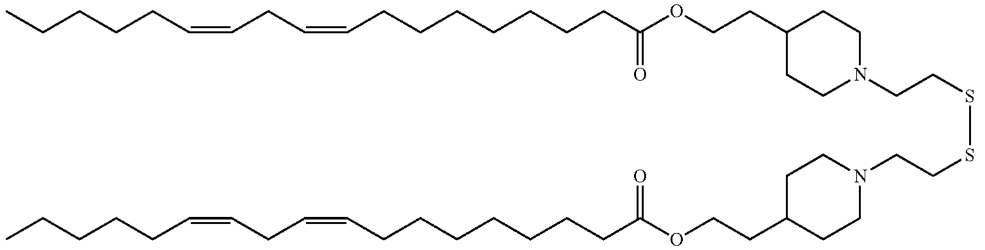 [SMILES: CCCCC/C=C\C/C=C\CCCCCCCC(=O)OCCC1CCN(CCSSCCN2CCC(CCOC(=O)CCCCCCC/C=C\C/C=C\CCCCC)CC2)CC1] |
| Oleoyl | 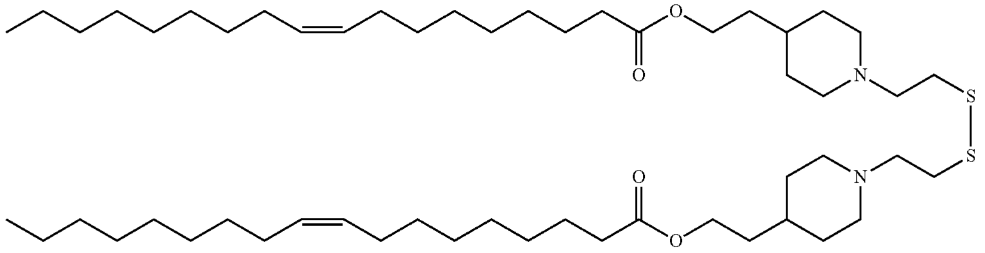 [SMILES: CCCCCCCC/C=C\CCCCCCCC(=O)OCCC1CCN(CCSSCCN2CCC(CCOC(=O)CCCCCCC/C=C\CCCCCCCC)CC2)CC1] |

In some embodiments, the delivery vehicle is an LNP capable of transfecting at least 50%, at least 60%, at least 70%, at least 80%, at least 90%, or at least 95% of a population of lung cells wherein the ionizable lipid is at least 1000, at least 20%, at least 30%, at least 40%, at least 50%, at least 60%, at least 70%, or at least 80% of the molar percentage of the LNP.

In some embodiments, the ionizable lipid is no more than 20%, no more than 30%, no more than 40%, no more than 50%, no more than 60%, no more than 70%, or no more than 90% of the molar percentage of the LNP. Example ionizable lipids include, but are not limited to: (15Z,18Z)—N,N-dimethyl-6-(9Z,12Z)-octadeca-9,12-dien-1-yl)tetracosa-15,18-dien-1-amine (HGT5000), (15Z,18Z)—N,N-dimethyl-6-((9Z,12Z)-octadeca-9,12-dien-1-yl)tetracosa-4,15,18-trien-1-amine (HGT5001), and (15Z,18Z)—N,N-dimethyl-6-((9Z,12Z)-octadeca-9,12-dien-1-yl)tetracosa-5,15,18-trien-1-amine (HGT5002).

Lipids having the structure of Formula I are shown in Table 5 below. For example, SS-OP is also named O-Ph-P4C2. The term "SS-OP analog" as used herein refers to a compound of Formula I.

TABLE 5

| Nomenclature of Lipids | |
|---|---|
| Name | Structure |
| SS-M | 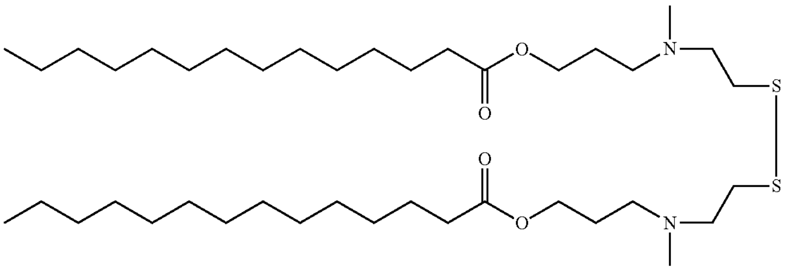 [SMILES: CCCCCCCCCCCCCC(=O)OCCCN(C)CCSSCCN(C)CCCOC(=O)CCCCCCCCCCCCC] |

TABLE 5-continued
| Nomenclature of Lipids | |
|---|---|
| Name | Structure |
| SS-E | 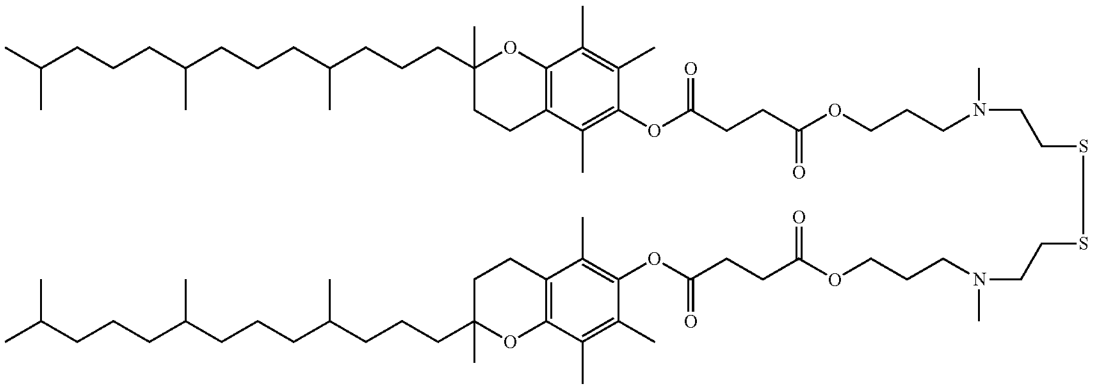 [SMILES: Cc1c(C)c2c(c(C)c1OC(=O)CCC(=O)OCCCN(C)CCSSCCN(C)CCCOC(=O)CCC(=O)Oc1c(C)c(C)c3c(c1C)CCC(C)(CCCC(C)CCCC(C)CCCC(C)C)O3)CCC(C)(CCCC(C)CCCC(C)CCCC(C)C)O2] |
| SS-EC | 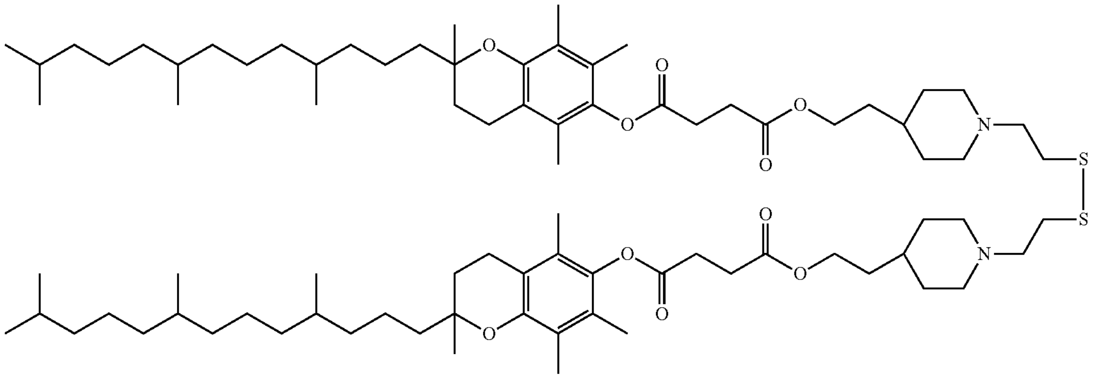 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2] |
| SS-LC | 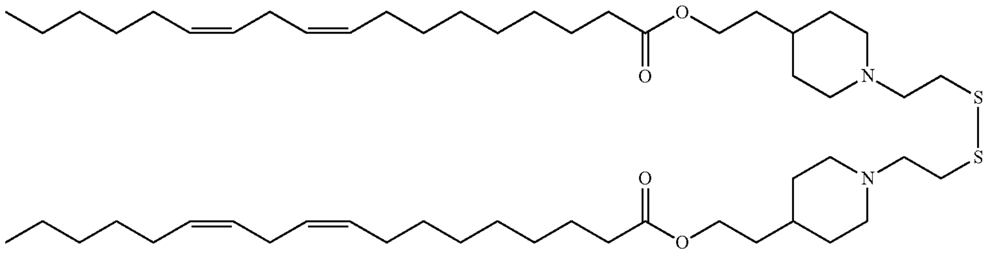 [SMILES: CCCCC/C=C\C/C=C\CCCCCCCC(=O)OCCC1CCN(CCSSCCN2CCC(CCOC(=O)CCCCCCC/C=C\C/C=C\CCCCC)CC2)CC1] |
| SS-OC | 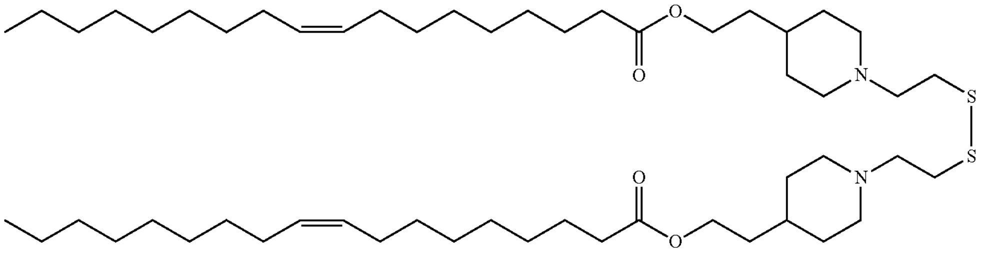 [SMILES: CCCCCCCC/C=C\CCCCCCCC(=O)OCCC1CCN(CCSSCCN2CCC(CCOC(=O)CCCCCCC/C=C\CCCCCCCC)CC2)CC1] |
| SS-OP | 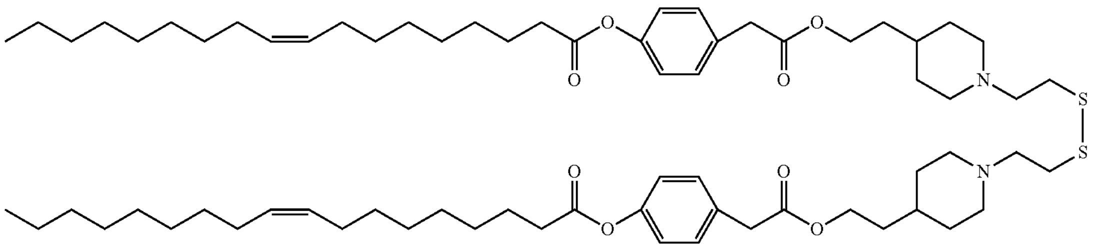 [SMILES: CCCCCCCC/C=C\CCCCCCCC(=O)Oc1ccc(CC(=O)OCCC2CCN(CCSSCCN3CCC(CCOC(=O)Cc4ccc(OC(=O)CCCCCCC/C=C\CCCCCCCC)cc4)CC3)CC2)cc1] |

Cationic Lipids

In some embodiments, a lipid nanoparticle (LNP) of the disclosure comprises a cationic lipid, e.g. DOTAP or variations thereof. The cationic lipid may be a "permanent cationic lipid." The term cationic lipid may be cationic in pH ranges found in mammalian physiological environments such as blood or interstitial fluids. Cationic lipids may be composed of a cationic amine moiety and a lipid moiety, and the cationic amine moiety and a polyanion nucleic acid may interact to form a positively charged liposome or lipid membrane structure. Thus, uptake into cells may be promoted and nucleic acids delivered into cells.

In some embodiments, the cationic lipid may selected from one or more of 1,2-dioleoyl-3-trimethylammonium-propane (DOTAP), N,N-distearyl-N,N-dimethylamnmonium bromide (DABB), or 1,2-dimyristoyl-sn-glycero-3-ethylphosphocholine (EPC). In some embodiments, an LNP comprises a ionizable lipid wherein the ionizable lipid is one or more of N-[1-(2,3-dioleyloxy)propyl]-N,N,N-trimethylammonium chloride (DOTMA), 5-carboxyspermylglycinedioctadecylamide (DOGS), 2,3-dioleyloxy-N-[2(spermine-carboxamido)ethyl]-N,N-dimethyl-1-propanaminium (DOSPA), 1,2-Dioleoyl-3-Dimethylammonium-Propane (DODAP), 11,2-distearyloxy-N,N-dimethyl-3-aminopropane (DSDMA), 1,2-dioleyloxy-N,N-dimethyl-3-aminopropane (DODMA), 1,2-dilinoleyloxy-N,N-dimethyl-3-aminopropane (DLinDMA), dimethyldioctadecylammonium (DDA), 1,2-dilinolenyloxy-N,N-dimethyl-3-aminopropane (DLenDMA), N-dioleyl-N,N-dimethylammonium chloride (DODAC), N,N-distearyl-N,N-dimethylammonium bromide (DDAB), N-(1,2-dimyristyloxyprop-3-yl)-N,N-dimethyl-N-hydroxyethyl ammonium bromide (DMRIE), 3-dimethylamino-2-(cholest-5-en-3-beta-oxybutan-4-oxy)-1-(cis,cis-9,12-oc-tadecadienoxy)propane (CLinDMA), 2-[5'-(cholest-5-en-3-beta-oxy)-3'-oxapentoxy)-3-dimethy 1-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 2,3-Dilinoleoyloxy-N,N-dimethylpropylamine (DLinDAP), 1,2-N,N'-Dilinoleylcarbamyl-3-dimethylaminopropane (DLincarbDAP), 1,2-Dilinoleoylcarbamyl-3-dimethylaminopropane or (DLinCDAP), 2,2-dilinoleyl-4-dimethylaminomethyl-[1,3]-dioxolane (DLin-K-DMA), 2,2-dilinoleyl-4-dimethylaminoethyl-[1,3]-dioxolane (DLin-K-XTC2-DMA), and mixtures thereof.

In some embodiments, a cationic lipid refers to a cationic cholesterol lipid. In some embodiments of the disclosure an LNP comprises imidazole cholesterol ester (ICE). In some embodiments, an ICE structure is substantially similar to:

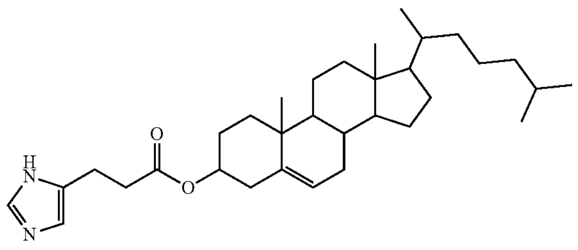 [SMILES: CC(C)CCCC(C)C1CCC2C3CC=C4CC(OC(=O)CCc5cnc[nH]5)CCC4(C)C3CCC12C]

In some embodiments of the disclosure an LNP comprises 25-Hydroxycholesterol (25 OH Chol). In some embodiments, 25 OH Chol structure is substantially similar to:

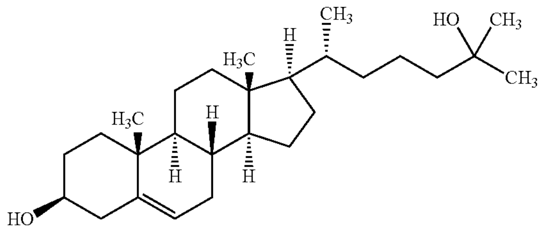

In some embodiments of the disclosure an LNP comprises 20α-hydroxycholesterol 5-cholestene-3α.

In some embodiments, the 20α-hydroxycholesterol 5-cholestene-3α (also known as 20α-diol or 20α chol structure) is substantially similar to:

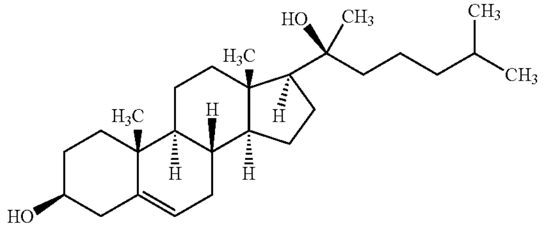

In some embodiments, a cationic lipid refers to dimethyldioctadecylammonium bromide (DDAB). In some embodiments of the disclosure an LNP comprises dimethyldioctadecylammonium bromide (DDAB). In some embodiments, a dimethyldioctadecylammonium bromide (DDAB) structure is substantially similar to:

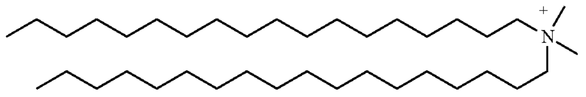

Structural Lipids

In some embodiments, the LNP comprises a structural lipid. As used herein, structural lipids are lipids that contribute a physical or chemical property to the LNP that is in addition to, or independent of, electrical charge. As an example, structural lipids may tend to have a shape, size, rigidity, hydrophobicity, or other property that increases the therapeutic utility of the LNP, such as, for example, by increasing its stability, half-life, deformability, transfection efficiency, tropism, thermostability, resistance to aggregation, membrane fluidity, or other parameter. In some embodiments, structural lipids are neutral in charge, either due to lacking charged moieties, or due to being zwitterionic with balanced charges summing to zero net charge.

In some embodiments, an LNP may comprise a structural lipid selected from one more of: 1,2-di-(9Z-octadecenoyl)-sn-glycero-3-phosphoethanolamine (DOPE), glycerol-monooleate (GMO), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), or variants thereof.

In some embodiments, an LNP may include one or more phosphatidyl lipids, for example, the phosphatidyl compounds (e.g., phosphatidylglycerol, phosphatidylcholine, phosphatidylserine and phosphatidylethanolamine). In some embodiments, an LNP may comprise sphingolipids, for example but not limited to, sphingosine, ceramide, sphingomyelin, cerebroside and ganglioside. In some embodiments, the aforementioned "structural" lipids contribute to the stability and/or specificity of the LNP composition.

Cholesterol-Based Lipids

In some embodiments, an LNP may comprise one or more cholesterol-based lipids. A cholesterol-based lipid may include but is not limited to: PEGylated cholesterol, DC-Choi (N,N-dimethyl-N-ethylcarboxamidocholesterol), 1,4-bis(3-N-oleylamino-propyl)piperazine.

PEGylated Lipids

In some embodiments of the disclosure, an LNP may comprise one or more PEGylated lipids. For example, the use of polyethylene glycol (PEG)-modified phospholipids and derivatized lipids such as derivatized ceramides (PEG-CER), including N-Octanoyl-Sphingosine-1-[Succinyl (Methoxy Polyethylene Glycol)-2000] (C8 PEG-2000 ceramide) is contemplated by the present disclosure in combination with one or more of the ionizable and/or other lipids. In some embodiments, PEGylated lipids comprise PEG-ceramides having shorter acyl chains (e.g., C14 or C18). In some embodiments, the PEGylated lipid DSPE-PEG-Maleimide-Lectin may be used. Other contemplated PEG-modified lipids include, but are not limited to, a polyethylene glycol chain of up to 5 kDa in length covalently attached to a lipid with alkyl chain(s) of C6-C2o length. Without wishing to be bound by a particular theory, it is contemplated that the addition of PEGylated lipids may prevent complex aggregation and increase circulation lifetime to facilitate the delivery of the liposome encapsulated mRNA to the target cell.

In some embodiments, a lipid nanoparticle formulation may comprise, consist essentially of or consist of any of those described in U.S. Pat. Nos. 11,185,595; 9,868,693; 10,195,156; 9,877,919; 9,738,593; 10,399,937; 10,106,490; 9,738,593; 10,821,186; or 8,058,069, each of which is incorporated by reference herein in its entirety; or described in U.S. Patent Application Publication Nos. US20180085474A1, US20210259980A1, US20200206362A1, US20210267895A1, US20200283372A1, or US20200163878A1, each of which is incorporated by reference herein in its entirety.

Lipid Nanoparticle (LNP) Compositions

The following example LNP formulations are not intended to be limiting.

In some embodiments of the disclosure, an LNP may comprise an ionizable lipid, e.g. an SS-OP or SS-OP analog in a molar percentage of about 20, about 25, about 30, about 35, about 40, about 45, about 55, or about 60 relative to the total lipid; and a cationic lipid, e.g. DOTAP, ICE, DDAB or a cationic cholesterol lipid, in a molar percentage of about 15, about 20, about 25, about 30, about 35, about 40, about 45, or about 50 relative to the total lipid.

In some embodiments of the disclosure, the LNP comprises the cationic lipid at a molar percentage of between about 25% and about 35%. In some embodiments, the LNP comprises the cationic lipid at a molar percentage of about 30%.

In some embodiments of the disclosure, the LNP comprises a structural lipid. In some embodiments, the structural lipid is DOPC. In some embodiments, the LNP comprises DOPC in a molar ration of about 1%, about 2%, about 3%, about 4%, or about 5% of the total lipid.

In some embodiments of the disclosure, the LNP is substantially free of structural lipids and/or comprises at most 1% structural lipids.

In some embodiments of the disclosure, the LNP comprises cholesterol. In some embodiments, the LNP comprises a molar percentage of about 20% to about 40% cholesterol relative to the total lipid. In some embodiments, the LNP is substantially free of cholesterol.

In some embodiments of the disclosure, the LNP comprises an insulator lipid. In some embodiments, the LNP comprises an insulator lipid in a molar ratio of about 0.10% to about 2%. In some embodiments, the LNP comprises an insulator lipid in a molar ratio of about 0.5% to about 1.5%. In some embodiments, the LNP is substantially free of insulator lipids.

Polymer Nanoparticles

In some embodiments, a suitable delivery vehicle is formulated using a polymer as a carrier, alone or in combination with other carriers including various lipids described herein. Thus, in some embodiments, liposomal delivery vehicles, as used herein, also encompass polymer containing nanoparticles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, polyethylene glycol (PEG)-modified (PEGylated) protamine, poly-D-lysine (PLL), PEGylated PLL and polyethylenimine (PEI). When PEI is present, it may be linear or branched PEI of a molecular weight ranging from 10 to 40 kDA, e.g., 25 kDa branched PEI (Sigma #408727). In some embodiments the PEGylated lipid is 14:0 PEG2000 PE and/or DMG-PEG2000.

Lung Targeting

The delivery vehicles disclosed herein preferentially target the lung. In various embodiments, the delivery vehicles may deliver and/or transfect a polynucleotide, e.g. an mRNA to lung cells 10, $10^2$, $10^3$, $10^4$, $10^5$, $10^6$, $10^7$, $10^8$, $10^9$, or $10^{10}$-fold more effectively compared to the liver. LNP compositions as provided herein preferentially deliver to and/or transfects a polynucleotide, e.g. an RNA, to the lung compared to liver.

However, it will be understood that some level of delivery to non-target cells/organs may be tolerated without decreasing the effectiveness in the target organ/cell. In some embodiments, the lipid composition of a delivery vehicle enhances delivery to the lung relative to other lipid compositions known in the art. In other embodiments, the lipid composition of a delivery vehicle enhances delivery to the lung relative to other lipid compositions. In some embodiments, the presence or level of cholesterol enhances delivery of a delivery vehicle, e.g. an LNP or extracellular vesicle to the lung. In some embodiments, a delivery vehicle comprises an organ-specific targeting ligand to enhance delivery to a particular organ, e.g. the lung III. Formulation of mRNA and Nanoparticle Delivery Vehicle Compositions The methods of synthesis of mRNA and lipid nanoparticles (LNPs) are well established. Synthetic mRNAs, e.g., comprising a 5' cap, 5' and 3' UTRs coding sequence, and a poly-A tail, may be synthesized from modified and unmodified nucleotides by in vitro transcription of a DNA template using an RNA polymerase, for example T7 RNA polymerase. The DNA template may be generated, for example, by PCR or plasmid amplification and restriction digest, followed by purification.

Lipid nanoparticles (LNPs), liposomes, or polymer nanoparticle delivery vehicles carrying mRNA may be produced, for example, by mixing the lipids or polymers in an organic solvent, e.g, ethanol, with one or more mRNAs in an aqueous buffer, and then subject to buffer exchange and concentration. In some embodiments, the LNP, liposome, or polymer nanoparticle delivery vehicle may be produced using a microfluidic device to rapidly mix reagents and form monodisperse particles of controlled size. For example, the microfluidic mixer could be a staggered herringbone mixer (SHM). For example, the microfluidic mixer could be produce by the NanoAsssemblr made by Precision Nanosystems (PNI). In other embodiments, the LNP, liposome, or polymer nanoparticle delivery vehicle may be produced by a T-mixer. In some embodiments, the LNP, liposome, or polymer nanoparticle may encapsulate an mRNA and/or associate with one or more mRNAs through electrostatic interactions. The buffer exchange and concentration of the LNP, liposome, or polymer nanoparticle may be performed by tangential flow filtration. In other embodiments, the buffer exchange and concentration of the LNP, liposome, or polymer nanoparticle may be performed by centrifugal ultrafiltration using a membrane with a nominal molecule weight cutoff of <=500,000 Da, for example 100,000 Da.

In some embodiments, the lipid nanoparticle particles (LNP) formulations provided herein are capable of transfecting at least 50% at least 60%, at least 70%, at least 80%, at least 90% or at least 95% of a population of lung cells.

The form of the lipid membrane structure of the present disclosure is not particularly limited. For example, as a form in which the lipid of the present disclosure is dispersed in an aqueous solvent, liposomes (for example, monolayer liposomes, multilamellar liposomes, etc.), spherical micelles, string micelles, lipid nanoparticles (LNPs) or unspecified layered structures.

The lipid membrane structure of the present disclosure may further contain other component. Examples of the other components include lipids (phospholipids (such as phosphatidylinositol, phosphatidylethanolamine, phosphatidylserine, phosphatidic acid, phosphatidylglycerol, phosphatidylcholine), glycolipids, peptide lipids, cholesterol, ionizable lipids, cationic lipids. PEGylated lipids, etc.), surfactants (eg 3-[(3-cholamidopropyl) dimethylammonio] propane sulfonate, cholic acid sodium salt, octyl glycoside, ND-gluco-N-methylalkanamides), polyethylene glycol, proteins and the like. The content of the other constituents in the lipid membrane structure of the present disclosure is usually 5 to 95 mol %, optionally 10 to 90 mol %, or 30 to 80 mol %.

The lipid membrane structure of the present disclosure is prepared by dispersing the lipids of the present disclosure and other components (lipids, etc.) in a suitable solvent or dispersion medium, for example, an aqueous solvent or an alcoholic solvent, and if necessary, tissue It can be prepared by performing an operation that induces crystallization.

Examples of the "operation for inducing organization" include an ethanol dilution method using a microchannel or a vortex, a simple hydration method, an ultrasonic treatment, a heating, a vortex, an ether injection method, a French press method, and a cholic acid method. Examples thereof include, but are not limited to, methods known per se such as Ca 2+ fusion method, freeze-thaw method, and reverse phase evaporation method.

The nucleic acid can be introduced into the cell in vivo and/or in vitro by encapsulating the nucleic acid in the lipid membrane structure containing the ionizable lipid of the present disclosure and bringing it into contact with the cell. Therefore, the present disclosure provides a nucleic acid introduction agent comprising the ionizable lipid or lipid membrane structure of the present disclosure.

The nucleic acid introduction agent of the present disclosure can introduce any nucleic acid into cells. Examples of the nucleic acid include, but are not limited to, DNA, RNA, RNA chimeric nucleic acid, DNA/RNA hybrid, and the like. The nucleic acid can be any one of 1 to 3 strands, but is optionally single strand or double strand. Nucleic acids may be other types of nucleotides that are N-glycosides of purine or pyrimidine bases, or other oligomers having a non-nucleotide backbone (e.g., commercially available peptide nucleic acids (PNA), etc.) or other oligomers with special linkages. The oligomer may contain nucleotides having a configuration that allows base pairing or base attachment as found in DNA or RNA. In addition, the nucleic acid may be substituted with, for example, a known modified nucleic acid, a labeled nucleic acid, a capped nucleic acid, a methylated nucleic acid, or one or more natural nucleotides known in the art, intramolecular nucleotide modified nucleic acids, nucleic acids with uncharged bonds (e.g., methyl sulfonate, phosphotriester, phosphoramidate, carbamate, etc.), charged bonds or sulfur containing bonds (eg phosphorothioate), side chain groups such as proteins (e.g., nucleases, nuclease inhibitors, toxins, antibodies, signal peptides, poly-L-lysine, etc.) and sugars (eg, monosaccharides), nucleic acids and nucleic acids with intercurrent compounds (eg, acridine, psoralen, etc.), nucleic acids containing chelate compounds (eg, metals, radioactive metals, boron, oxidizing metals, etc.), nucleic acids containing alkylating agents, and nucleic acids with modified bonds (eg, alpha anomeric nucleic acids, etc.)

The type of DNA that can be used in the present disclosure is not particularly limited, and can be appropriately selected depending on the purpose of use. Examples include plasmid DNA, cDNA, antisense DNA, chromosomal DNA, PAC. BAC, and CpG oligo, optionally plasmid DNA, cDNA, and antisense DNA, or plasmid DNA. Circular DNA such as plasmid DNA can be appropriately digested with a restriction enzyme or the like and used as linear DNA.

The type of RNA that can be used in the present disclosure is not particularly limited, and can be appropriately selected depending on the purpose of use. For example, siRNA, miRNA, shRNA, antisense RNA, messenger RNA (mRNA), single-stranded RNA genome, double-stranded RNA genome, RNA replicon, transfer RNA, ribosomal RNA, etc., optionally siRNA, miRNA, shRNA, mRNA, antisense RNA. RNA replicon.

The nucleic acid used in the present disclosure is optionally purified by a method commonly used by those skilled in the art.

The nucleic acid-introducing agent of the present disclosure encapsulating nucleic acid can be administered in vivo for the purpose of, for example, prevention and/or treatment of diseases. Accordingly, the nucleic acid used in the present disclosure is optionally a nucleic acid having preventive and/or therapeutic activity against a given disease (prophylactic/therapeutic nucleic acid). Examples of such nucleic acids include nucleic acids used for so-called gene therapy.

In order to introduce a nucleic acid into a cell using the nucleic acid introduction agent of the present disclosure, the nucleic acid was encapsulated by coexisting the target nucleic acid when forming the lipid membrane structure of the present disclosure. The lipid membrane structure of the present disclosure is formed. For example, when liposomes are formed by the ethanol dilution method, the aqueous solution of nucleic acid and the ethanol solution of the components of the lipid membrane structure of the present disclosure (lipids, etc.) are vigorously mixed by vortex or microchannel, etc. Is diluted with an appropriate buffer. When liposomes are formed by the simple hydration method, the components (lipids, etc.) of the lipid membrane structure of the present disclosure are dissolved in an appropriate organic solvent, the solution is placed in a glass container, and the solvent is retained by drying under reduced pressure and left to obtain a lipid film. Here, an aqueous solution of nucleic acid is added and hydrated, followed by sonication with a sonicator. The present disclosure also provides the above lipid membrane structure in which such a nucleic acid is encapsulated.

An example of a lipid membrane structure in which a nucleic acid is encapsulated is LNP encapsulated in a nucleic acid by forming an electrostatic complex between the nucleic acid and a ionizable lipid. This LNP can be used as a drug delivery system for selectively delivering a nucleic acid or the like into a specific cell. For example, a DNA vaccine by introducing an antigen gene into a dendritic cell, a gene therapy drug for a tumor, RNA It is useful for nucleic acid drugs that suppress the expression of target genes using interference.

The particle diameter of the lipid membrane structure of the present disclosure encapsulating nucleic acid is not particularly limited, but is optionally 10 nm to 500 nm, or 20 nm to 200 nm. The particle diameter can be measured using a particle size distribution measuring apparatus such as Zetasizer Nano (Malvern). The particle diameter of the lipid membrane structure can be appropriately adjusted according to the method for preparing the lipid membrane structure.

The surface potential (zeta potential) of the lipid membrane structure of the present disclosure encapsulating nucleic acid is not particularly limited, but may be −60 to +60 mV, −45 to 45 mV, −30 to +30 mV, −15 to +15 mV, or −10 to +10 mV. The zeta potential of the lipid membrane structure may be positive (>0 mV), +5 mV to +60 mV, +30 mM to +45 mV, or +10 mV to +45 mV In conventional gene transfer, particles having a positive surface potential have been mainly used. While this is useful as a method to promote electrostatic interaction with negatively charged cell surface heparin sulfate and promote cellular uptake, positive surface charge is delivered intracellularly. There is a possibility that the nucleic acid release from the carrier due to the interaction with the nucleic acid is suppressed, and the protein synthesis due to the interaction between the mRNA and the delivery nucleic acid is suppressed. By adjusting the surface charge within the above range, this problem can be solved. The surface charge can be measured by using a zeta potential measuring device such as Zetasizer Nano. The surface charge of the lipid membrane structure can be adjusted by the composition of the components of the lipid membrane structure.

The lipid membrane surface pKa (hereinafter referred to as Liposomal pKa) of the lipid membrane structure of the present disclosure is not particularly limited, but may have a pKa of 5.5 to 7.2, or a pKa of 6.0, to 6.8 Liposomal pKa is used as an index indicating that the lipid membrane structure taken up by endocytosis is susceptible to protonation of the lipid membrane structure in a weakly acidic environment within the endosome. Liposomal pKa can be adjusted by the composition of the components of the lipid membrane structure.

The hemolysis activity (membrane fusion ability) of a lipid membrane structure of the present disclosure is not particularly limited, but may have no hemolysis activity (less than 5%) at physiological pH (pH 7.4), and may be endosomal. The higher the hemolysis activity, the more efficiently the nucleic acid can be delivered into the cytoplasm. However, if the hemolysis activity is present at physiological pH, the nucleic acid will be delivered to unintended cells during residence in the blood, resulting in decreased target-directedness and toxicity. Therefore, it is preferable to have hemolysis activity only in the endosomal environment as described above. The hemolysis activity can be adjusted by the composition of the components of the lipid membrane structure.

By bringing the lipid membrane structure of the present disclosure in which nucleic acid is encapsulated into contact with the cell, the encapsulated nucleic acid can be introduced into the cell. The cell may be a cultured cell line containing cancer cells, a cell isolated from an individual or tissue, or a tissue or tissue piece of cell. Further, the cells may be adherent cells or non-adherent cells.

The step of bringing the lipid membrane structure of the present disclosure encapsulating nucleic acid into contact with cells in vitro will be specifically described below.

Cells are suspended in an appropriate medium several days before contact with the lipid membrane structure and cultured under appropriate conditions. Upon contact with the lipid membrane structure, the cell may or may not be in the growth phase.

The culture medium at the time of the contact may be a serum-containing medium or a serum-free medium, but the serum concentration in the medium may be 30% by weight or less, more may be 20% by weight or less. If the medium contains excessive protein such as serum, the contact between the lipid membrane structure and the cell may be inhibited.

The cell density at the time of the contact is not particularly limited and can be appropriately set in consideration of the cell type, but is usually in the range of $1\times10^4$ to $1\times10^7$ cells/mL.

For example, a suspension of the lipid membrane structure of the present disclosure in which the above-described nucleic acid is encapsulated is added to the cells thus prepared. The addition amount of the suspension is not particularly limited, and can be appropriately set in consideration of the number of cells and the like. The concentration of the lipid membrane structure at the time of contacting the cell is not particularly limited as long as the introduction of the target nucleic acid into the cell can be achieved, but the lipid concentration is usually 1 to 100 nmol/mL, and may be 0.1 to 10 μg/mL.

After adding the above suspension to the cells, the cells are cultured. The culture temperature, humidity, $CO_2$ concentration, etc. are appropriately set in consideration of the cell type. When the cells are mammalian cells, the temperature is usually about 37° C., the humidity is about 95%, and the $CO_2$ concentration is about 5%. In addition, the culture time can be appropriately set in consideration of conditions such as the type of cells used, but may be in the range of 0.1 to 76 hours, or in the range of 0.2 to 24 hours, and may be 0.5-12 hours. If the culture time is too short, the nucleic acid is not sufficiently introduced into the cells, and if the culture time is too long, the cells may be weakened.

The nucleic acid is introduced into the cells by the above-described culture. The medium may be replaced with a fresh medium, or the fresh medium is added to the medium and the cultivation is further continued. If the cells are mammalian cells, the fresh medium may contain serum or nutrient factors.

The lipid membrane structure of the present disclosure may further contain other components in addition to the ionizable lipid of the present disclosure. Examples of the other components include lipids (phospholipids (such as phosphatidylinositol, phosphatidylethanolamine, phosphatidylserine, phosphatidic acid, phosphatidylglycerol, phosphatidylcholine), glycolipids, peptide lipids, cholesterol, ionizable lipids other than cationic lipids. PEG lipids, etc.), surfactants (eg 3-[(3-cholamidopropyl) dimethylammonio] propane sulfonate, cholic acid sodium salt, octyl glycoside, ND-gluco-N-methylalkanamides), polyethylene glycol, proteins and the like.

The lipid membrane structure of the present disclosure is prepared by dispersing the ionizable lipid of the present disclosure and other components (lipids, etc.) in a suitable solvent or dispersion medium, for example, an aqueous solvent or an alcoholic solvent, and if necessary, tissue. It can be prepared by performing an operation that induces crystallization.

Examples of the "operation for inducing organization" include an ethanol dilution method using a microchannel or a vortex, a simple hydration method, an ultrasonic treatment, a heating, a vortex, an ether injection method, a French press method, and a cholic acid method. Examples thereof include, but are not limited to, methods known per se such as Ca 2+ fusion method, freeze-thaw method, and reverse phase evaporation method.

The nucleic acid can be introduced into the cell in vivo and/or in vitro by encapsulating the nucleic acid in the lipid membrane structure containing the ionizable lipid of the present disclosure and bringing it into contact with the cell. Therefore, the present disclosure provides a nucleic acid introduction agent comprising the ionizable lipid or lipid membrane structure of the present disclosure.

The nucleic acid introduction agent of the present disclosure can introduce any nucleic acid into cells. Examples of the nucleic acid include, but are not limited to, DNA, RNA, RNA chimeric nucleic acid, DNA/RNA hybrid, and the like. The nucleic acid can be any one of 1 to 3 strands, but may be single strand or double strand. Nucleic acids may be other types of nucleotides that are N-glycosides of purine or pyrimidine bases, or other oligomers having a non-nucleotide backbone (eg, commercially available peptide nucleic acids (PNA), etc.) or other oligomers with special linkages. The oligomer may contain nucleotides having a configuration that allows base pairing or base attachment as found in DNA or RNA.

The type of RNA that can be used in the present disclosure is not particularly limited, and can be appropriately selected depending on the purpose of use. For example, siRNA, miRNA, shRNA, antisense RNA, messenger RNA (mRNA), single-stranded RNA genome, double-stranded RNA genome. RNA replicon, transfer RNA, ribosomal RNA, etc., or siRNA, miRNA, shRNA, mRNA, antisense RNA, or an RNA replicon.

The nucleic acid used in the present disclosure may be purified by a method commonly used by those skilled in the art.

The nucleic acid-introducing agent of the present disclosure encapsulating nucleic acid can be administered in vivo for the purpose of, for example, prevention and/or treatment of diseases. Accordingly, the nucleic acid used in the present disclosure may be a nucleic acid having preventive and at/or therapeutic activity against a given disease (prophylactic/therapeutic nucleic acid). Examples of such nucleic acids include nucleic acids used for so-called gene therapy.

IV. Methods of Treatment

Methods of treatment as described herein refer to the treatment of fibrotic disease and/or lung disease and/or lung fibrosis in a subject in need thereof by administration of a composition comprising one or more TERT mRNA sequences. Compositions and methods of the disclosure may be used for the treatment of fibrotic conditions, including fibrosis. In some embodiments, compositions and/or methods of use of compositions of the disclosure intended for treatment of fibrotic conditions, including fibrosis, induce TERT expression or increase TERT activity in a lung cell. In some embodiments, compositions and/or methods of use of compositions of the disclosure intended for treatment of fibrotic conditions, including fibrosis, do not induce cellular, tissue or systemic toxicity. Compositions may be administered systemically, e.g., intravenously.

Dosage and Timing of Telomerase Reverse Transcriptase (TERT) mRNA

In the compositions and methods described herein, in some embodiments, a TERT mRNA is administered in a dose of about 0.001 mg/kg per the subject's body weight to about 2.0 mg/kg per the subject's body weight to a subject in need thereof. In some embodiments, a TERT mRNA is administered to a subject in need thereof in a dose of about 0.01 mg/kg; in some embodiments in a dose of about 0.025 mg/kg; in some embodiments in a dose of about 0.05 mg/kg; in some embodiments in a dose of about 0.075 mg/kg; in some embodiments in a dose of about 0.1 mg/kg; in some embodiments in a dose of about 0.125 mg/kg; in some embodiments in a dose of about 0.150 mg/kg; in some embodiments in a dose of about 0.175 mg/kg; in some embodiments in a dose of about 0.2 mg/kg; in some embodiments in a dose of about 0.5 mg/kg; in some embodiments in a dose of about 0.75 mg/kg; in some embodiments in a dose of about 1.0 mg/kg; in some embodiments, in a dose of about 1.25 mg/kg; in some embodiment in a dose of about 1.5 mg/kg; or in some embodiment in a dose of about 2.0 mg/kg. In some embodiments the TERT mRNA is administered to a subject in need thereof in a dose of 0.1 mg/kg. In some embodiments the TERT mRNA is administered to a subject in need thereof in a dose of 0.125 mg/kg.

In some embodiments the TERT mRNA is administered to a subject in need thereof in a single dose. In some embodiments the TERT mRNA is administered to a subject in need thereof two, three, four, or five or more times. In some embodiments, the TERT mRNA is administered twice a week, every week, every two weeks, every four weeks, every six weeks, every twelve weeks, or every fifteen weeks. In some embodiments, the TERT mRNA is administered every month, every two months, every three months, every six months, once a year, on an ongoing basis, or as determined by their physician.

TERT mRNA Co-Therapies

In some embodiments, co-administration of a TERT mRNA may be combined with other anti-fibrotic drugs used in the treatment of fibrotic diseases and/or lung diseases. Drugs that may be used include, but are not limited to nintedanib, pirfenidone, prednisone, azathioprine, cyclophosphamide, mycophenolate mofetil, Pamrevlumab, and N-acetylcysteine.

Routes of Administration

In some embodiments, a TERT mRNA may be delivered orally, subcutaneously, intravenously, intranasally, intradermally, transdermally, intraperitoneally, intramuscularly, intrapulmonarily, vaginally, rectally, or intraocularly. In example embodiments a TERT mRNA may be administered intravenously or through inhalation.

Subjects and Treatment

The methods of treatment described herein are useful for the treatment of lung disease and/or lung fibrosis in a subject in need thereof. Lung and lung fibrotic diseases may include, but are not limited to pulmonary fibrosis, lung cancer, familial pulmonary fibrosis, idiopathic pulmonary fibrosis, pulmonary fibrosis associated with dyskeratosis congenita, an interstitial lung disease (ILD), pneumonia, interstitial pneumonia, tuberculosis, bronchitis, emphysema, lung cancer, chronic obstructive pulmonary disease (COPD), aging-associated fibrosis, pulmonary hypertension, asthma, and cystic fibrosis.

In some embodiments, a subject in need of the combination treatments described herein is a subject with a genetic disorder or mutation in telomerase reverse transcriptase (TERT). In some embodiments the subject has no symptoms of fibrosis. In other embodiments, the subject has symptoms and the treatment completely or partially ameliorates the symptoms. In other embodiments, the treatment slows progression of the symptoms.

In some embodiments, a subject in need of treatments described herein is a subject with a genetic disorder or mutation in telomerase reverse transcriptase (TERT). In some embodiments the subject has no symptoms of lung disease and/or lung fibrosis. In other embodiments, the subject has symptoms and the treatment completely or partially ameliorates the symptoms. In other embodiments, the treatment slows progression of the symptoms.

In some embodiments, the subject is human.

In some embodiments, efficacy of the treatment may be measured by lung or pulmonary function may be performed by methods including not limited to: spirometry, body plethysmography, methacholine inhalation challenge, six-minute walk test, exhaled nitric oxide test, arterial blood gas test, lung volume test, lung diffusion capacity, cardiopulmonary exercise test, oximetry with ambulation, respiratory muscle strength test, altitude simulation tests, exercise challenge (with spirometry before and after), shunt study (100% 02), forced expiratory volume (FEV1), forced vital capacity (FVC), and maximal voluntary volume (MVV).

In some embodiments, administration of a TERT mRNA reduces fibrotic tissue in a subject by at least 5%, at least 10%, at least 20%, at least 30%, at least 40%, at least 50%, at least 60%, at least 70%, at least 80%, at least 90%, at least 95%, at least 99%, or at least 100% over the treatment period and/or after the treatment period.

In some embodiments, administration of a TERT mRNA stops or slows the increase in fibrotic tissue over time relative to a subject without treatment. In some embodiments, the administration of a TERT mRNA slows the increase in amount of fibrotic tissue in a subject by at least 5%, at least 10%, at least 20%, at least 30%, at least 40%, at least 50%, at least 60%, at least 70%, at least 80%, at least 90%, at least 95%, at least 99%, or at least 100% over the treatment period and/or after the treatment period.

In some embodiments, administration of a TERT mRNA increases lung function relative to a subject without treatment. In some embodiments, the administration of a TERT mRNA increases lung function in a subject by at least 5%, at least 10%, at least 20%, at least 30%, at least 40%, or at least 50% over the treatment period and/or after the treatment period.

In some embodiments, administration of a TERT mRNA extends survival relative to a subject without treatment. In some embodiments, administration of a TERT mRNA extends lung transplant-free survival relative to a subject without treatment. In some embodiments, the administration of a TERT mRNA extends survival of a subject by at least 5%, at least 10%, at least 20%, at least 30%, at least 40%, at least 50%, at least 60%, at least 70%, at least 80%, at least 90%, at least 95%, at least 99%, at least 100%, at least 200%, at least 300%, at least 400%, at least 500%, at least 1000%, over the treatment period and/or after the treatment period. In some embodiments, administration of a TERT mRNA reduces hospitalization time and/or number of hospitalization visits to treat the lung disease and/or lung fibrosis. In some embodiments, administration of a TERT mRNA delays time to lung transplant.

V. Pharmaceutical Combinations

In some embodiments, a composition comprising a TERT mRNA includes an excipient, or carrier, e.g., an aqueous carrier. A variety of aqueous carriers can be used, e.g., buffered saline. The compositions may contain pharmaceutically acceptable auxiliary substances as those required to approximate physiological conditions such as pH and buffering agents, toxicity countering agents, e.g., sodium acetate, sodium chloride, sodium citrate, potassium chloride, calcium chloride, and sodium lactate. In some embodiments, the pharmaceutical composition comprises 10 mM sodium citrate buffered to pH 6.4. The composition may contain a cryoprotectant, e.g., glycerol, ethylene glycol, sucrose, propylene glycol, or dimethylsulfoxide (DMSO). The concentration of active agent in these formulations can vary and are selected based on fluid volumes, viscosities, and body weight in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

VI. Methods of Extending Telomeres

In another aspect, the instant disclosure provides methods of extending telomeres, comprising the step of administering any of the above-described compounds or compositions to a cell with shortened telomeres, wherein telomeres are extended within the cell. The instant disclosure also provides methods of treatment, comprising the step of administering any of the above-described compounds or compositions to an animal subject in need of, or that may benefit from, telomere extension.

In some embodiments, the compounds or compositions are administered to a cell, wherein the cell is an isolated cell or is part of a cell culture, an isolated tissue culture, an isolated organ, or the like (i.e., the administration is in vitro).

In other embodiments, the compounds or compositions are administered without isolating the cell or cells, the tissue, or the organ from the subject (i.e., the administration is in vivo). In some of these embodiments, the compound or composition is delivered to all, or almost all, cells in the subject's body. In some embodiments, the compound or composition is delivered to a specific cell, cell type, tissue, or organ in the subject's body.

Administration of the compounds or compositions of the instant disclosure may result in the transient expression of a telomerase activity in the cell. The increased activity may be measured by various assays, such as, for example, the telomerase repeat amplification protocol (TRAP) assay.

Commercial versions of the TRAP assay are available, for example the Trapeze® telomerase detection kit (Millipore), which provides a sensitive detection and quantitation of telomerase activity, although other measurement techniques are also possible.

As previously noted, one of the advantages of the instant techniques is that the expression of telomerase activity is transient in the treated cells. In particular, such transient expression is in contrast to previous techniques where a telomerase reverse transcriptase gene persists in an episomal DNA moiety, or is inserted into the genomic sequence of the cell or otherwise permanently modifies the genetic make-up of the targeted cell and results in constitutive activity of the nucleic acid sequence.

FIG. 1 graphically illustrates some of the advantages of the compounds, compositions, and methods disclosed herein. In particular, the speed of telomere extension made possible with these compounds, compositions, and methods enables telomere maintenance by very infrequent delivery of TERT mRNA. The expressed telomerase activity rapidly extends telomeres in a brief period, before being turned over, thus allowing the protective anti-cancer mechanism of telomere-shortening to function most of the time. Between treatments, normal telomerase activity and telomere shortening is present, and therefore the anti-cancer safety mechanism of telomere shortening to prevent out-of-control proliferation remains intact, while the risk of short telomere-related disease remains low. In contrast, small molecule treatments for extending telomeres may require chronic delivery, and thus present a chronic cancer risk, with minimal therapeutic benefit.

In some embodiments of the instant methods, the transient expression is independent of cell cycle.

As noted above, the transient expression of telomerase reverse transcriptase results in the extension of shortened telomeres in treated cells. Telomere length can be measured using techniques such as terminal restriction fragment (TRF) length analysis, qPCR, MMqPCR, TeSLA, flow FISH, and Q-FISH, as would be understood by one of ordinary skill in the art. In some embodiments, the instant methods increase average telomere length in treated cells by at least 0.1 kb, at least 0.2 kb, at least 0.3 kb, at least 0.4 kb, at least 0.5 kb, at least 1 kb, at least 2 kb, at least 3 kb, at least 4 kb, at least 5 kb, or even more. In some embodiments, the instant methods reduce the percentage of telomeres with lengths below a certain length, for example 1 kb, 2 kb, 3 kb, 4 kb, 5 kb, or more.

One of the advantages of the instant compounds, compositions, and methods, is the rapidity of extension of telomeres achieved by these techniques. The techniques allow treatments to be brief, and thus the interval between treatments can be long, and thus the treatments can be safe because the normal protective telomere shortening mechanism remains intact for most of the time i.e. between treatments.

The transient expression of telomerase reverse transcriptase also results in an increased replicative capacity in treated cells. Increased replicative capacity is readily monitored in cells that are approaching replicative senescence by measuring additional population doublings in such cells. Senescent cells do not divide in response to many conditions that cause normal cells to divide, for example passage in culture or treatment with serum. Senescent cells are further often characterized by the expression of pH-dependent 0-galactosidase activity, expression of cell cycle inhibitors p53 and p19, and other altered patterns of gene expression, and an enlarged cell size. It is known in the art that, absent treatment with TERT mRNA, certain types of cells (e.g., human lung fibroblast cells) typically double 50-60 times after birth before senescing; with TERT mRNA treatments, however, these cells achieve an additional 16-28 population doublings. If treated again several weeks later, additional proliferative capacity is conferred again. This process of intermittent treatments to periodically re-extend telomeres may be applied additional times, with the interval between treatments depending on factors such as the rate of telomere shortening, the rate of cell divisions, and the amount of telomere extension provided by the treatment. Likewise, human microvascular dermal endothelial cells from an aged individual, absent treatment with the instant compositions, may achieve only 1-2 population doublings, whereas treated cells may achieve 3, 4, or even more population doublings.

Accordingly, in some embodiments, the instant treatment methods increase the number of population doublings of treated cells.

Compositions of the disclosure may treat genetic diseases resulting from mutations in genes not involved directly in telomere maintenance, but resulting in shortened telomeres. Such diseases include, for example, dyskeratosis congenita (DC) and forms of pulmonary fibrosis, lung disease, bone marrow failure, and aplastic anemia.

In addition, various types of cancer may be prevented or delayed by treatment with compounds of the present disclosure, and indeed chromosome-chromosome fusions caused by critically short telomeres are believed to be a cause of cancer.

VII. Therapeutic Kits

Therapeutic kits comprising a pharmaceutical composition of a TERT mRNA, or sequences thereof (including complementary sequences), and instructions for use are also contemplated herein. In some embodiments, the therapeutic kit comprises devices for administration, including but not limited to syringes, inhalers, nebulizers, and vials or containers.

In another aspect, the instant disclosure provides ready-to-use kits for use in extending telomeres in a mammalian cell. The kits comprise any of the above-described compounds or compositions, together with instructions for their use. In some embodiments, the kits further comprise packaging materials. In some embodiments, the packaging materials are air-tight. In these embodiments, the packaging materials may optionally be filled with an inert gas, such as, for example, nitrogen, argon, or the like. In some embodiments, the packaging materials comprise a metal foil container, such as, for example, a sealed aluminum pouch or the like. Such packaging materials are well known by those of ordinary skill in the art. The kit may also comprise a delivery vehicle, such as a lipid as described herein. In some embodiments, one or more components of the formulation are provided frozen with a cryoprotectant, or lyophilized.

In some embodiments, the kit may further comprise a desiccant, a culture medium, an RNase inhibitor, or other such components. In some embodiments, the kit may further comprise a combination of more than one of these additional components. In some kit embodiments, the composition of the kit is sterile.

ENUMERATED EMBODIMENTS

The disclosure may be defined by reference to the following enumerated, illustrative embodiments.

Embodiments I

Embodiment I-1. A composition comprising a (i) a ribonucleic acid (RNA) encoding telomerase reverse transcriptase (TERT) and (ii) a delivery vehicle, wherein the RNA of (i) comprises one or more modified nucleotides and wherein the delivery vehicle of (ii) is operably-linked to the RNA of (i).

Embodiment I-2. The composition of embodiment I-1, wherein the delivery vehicle comprises one or more of a nanoparticle, a liposome, a cationic lipid, an ionizable lipid, an exosome, a lipid nanoparticle, a natural lipoprotein particle and an artificial lipoprotein particle.

Embodiment I-3. The composition of embodiment I-1, wherein the delivery vehicle comprises a lipid nanoparticle.

Embodiment I-4. The composition of embodiment I-1, wherein the delivery vehicle comprises a ionizable lipid nanoparticle.

Embodiment I-5. The composition of any one of embodiments I-1 to I-4, wherein the delivery vehicle comprises a targeting lipid.

Embodiment I-6. The composition of embodiment I-5, wherein the targeting lipid specifically or selectively interacts with a liver cell.

Embodiment I-7. The composition of embodiment I-6, wherein the targeting lipid comprises cholesterol.

Embodiment I-8. The composition of embodiment I-5, wherein the targeting lipid specifically or selectively interacts with a lung cell.

Embodiment I-9. The composition of embodiment I-8, wherein the targeting lipid comprises 1,2-dioleoyl-3-trimethylammonium-propane (DOTAP), N,N-distearyl-N,N-dimethylammonium bromide (DABB), or 1,2-dimyristoyl-sn-glycero-3-ethylphosphocholine (EPC).

Embodiment I-10. The composition of any one of embodiments I-1 to I-9, wherein the delivery vehicle comprises a compound of Formula I:

(1)

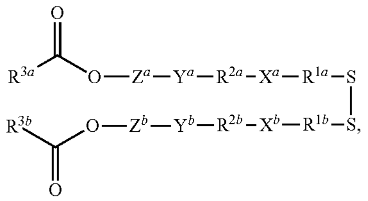

wherein $R^{1a}$ and $R^{1b}$ each independently represents an alkylene group having 1 to 6 carbon atoms, wherein $X^a$ and $X^b$ are each independently an acyclic alkyl tertiary amino group having 1 to 6 carbon atoms and 1 tertiary amino group, or 2 to 5 carbon atoms, and A cyclic alkylene tertiary amino group having 1 to 2 tertiary amino groups, wherein $R^{2a}$ and $R^{2b}$ each independently represent an alkylene group having 8 or less carbon atoms or an oxydialkylene group, wherein $Y^a$ and $Y^b$ each independently represent an ester bond, an amide bond, a carbamate bond, an ether bond or a urea bond;

wherein $Z^a$ and $Z^b$ are each independently a divalent group derived from an aromatic compound having 3 to 16 carbon atoms, having at least one aromatic ring, and optionally having a hetero atom, and wherein $R^{3a}$ and $R^{3b}$ each independently represent a residue derived from a reaction product of a fat-soluble vitamin having a hydroxyl group and succinic anhydride or glutaric anhydride, or a sterol derivative having a hydroxyl group and succinic anhydride or a residue derived from a reaction product with glutaric anhydride or an aliphatic hydrocarbon group having 12 to 22 carbon atoms.

Embodiment I-11. The composition of embodiment I-10, wherein the compound of Formula I is:

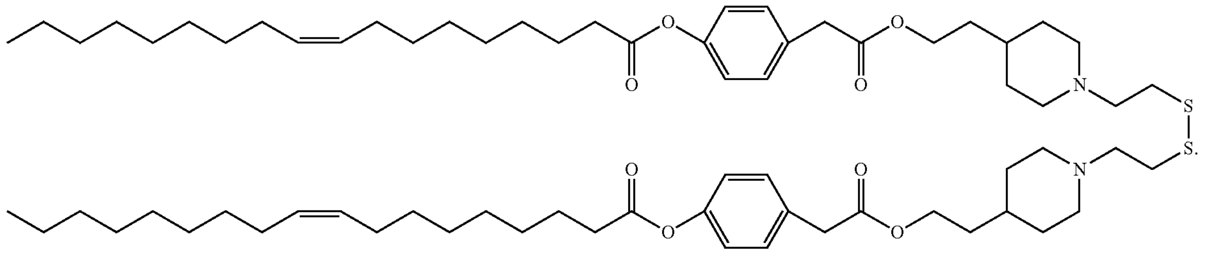 [SMILES: CCCCCCCC/C=C\CCCCCCCC(=O)Oc1ccc(CC(=O)OCCC2CCN(CCSSCCN3CCC(CCOC(=O)Cc4ccc(OC(=O)CCCCCCC/C=C\CCCCCCCC)cc4)CC3)CC2)cc1]

Embodiment I-12. The composition of embodiment I-10, wherein the compound of Formula I is:
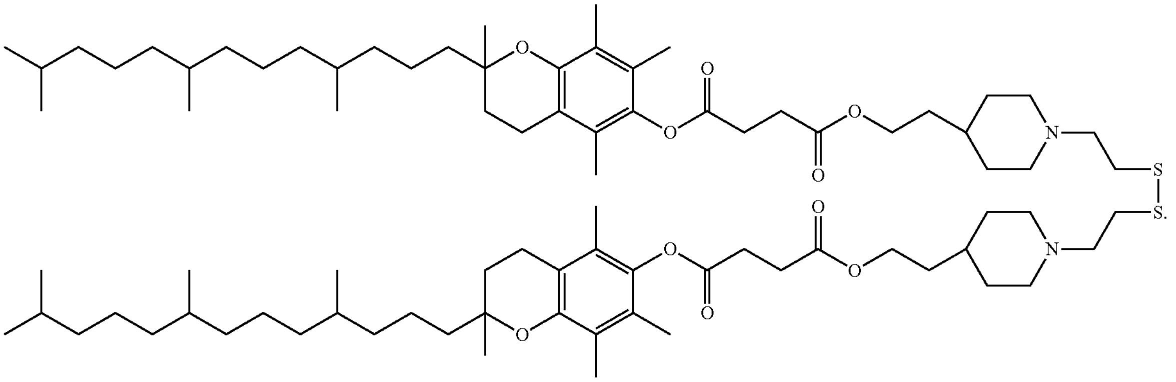 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2]
Embodiment I-13. The composition of embodiment I-10, wherein the compound of Formula I is:
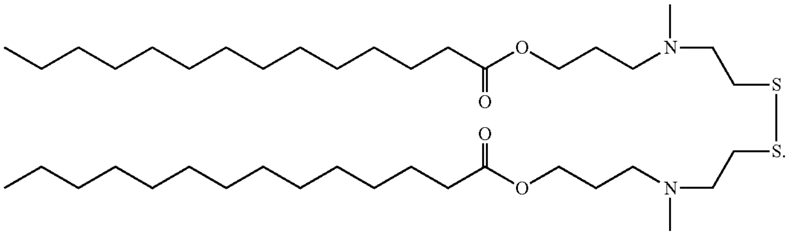 [SMILES: CCCCCCCCCCCCCC(=O)OCCCN(C)CCSSCCN(C)CCCOC(=O)CCCCCCCCCCCCC]
Embodiment I-14. The composition of embodiment I-10, wherein the compound of Formula I is:
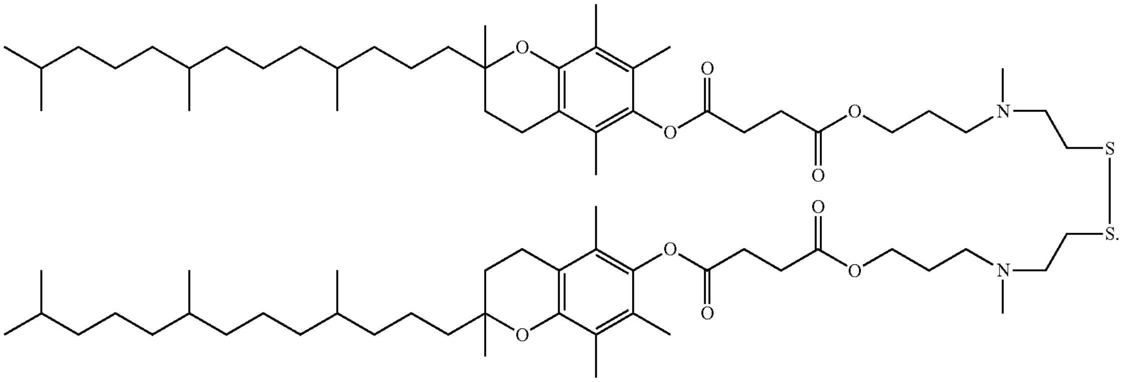 [SMILES: Cc1c(C)c2c(c(C)c1OC(=O)CCC(=O)OCCCN(C)CCSCSCCN(C)CCCOC(=O)CCC(=O)Oc1c(C)c(C)c3c(c1C)CCC(C)(CCCC(C)CCCC(C)CCCC(C)C)O3)CCC(C)(CCCC(C)CCCC(C)CCCC(C)C)O2]
Embodiment I-15. The composition of embodiment I-10 wherein the compound of Formula I is:
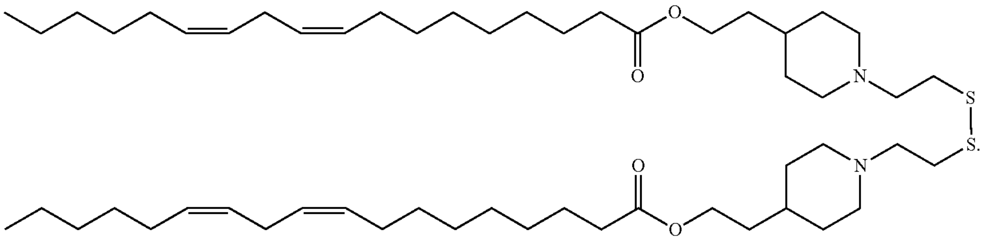 [SMILES: CCCCC/C=C\C/C=C\CCCCCCCC(=O)OCCC1CCN(CCSSCCN2CCC(CCOC(=O)CCCCCCC/C=C\C/C=C\CCCCC)CC2)CC1]

Embodiment I-16. The composition of embodiment I-10, wherein the compound of Formula I is:

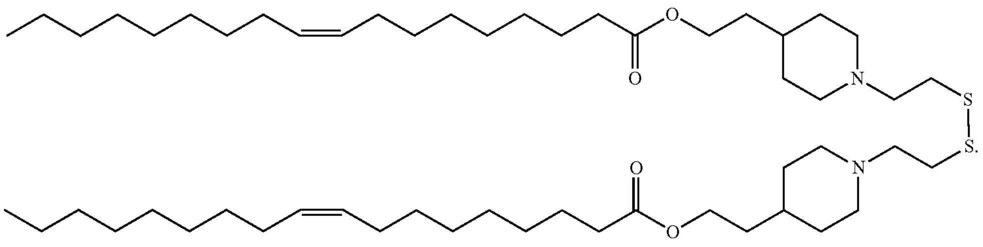 [SMILES: CCCCCCCC/C=C\CCCCCCCC(=O)OCCC1CCN(CCSSCCN2CCC(CCOC(=O)CCCCCCC/C=C\CCCCCCCC)CC2)CC1]

Embodiment I-17. The composition of any one of embodiments I-1 to I-16, wherein the RNA comprises a human sequence of SEQ ID NO: 3 or 4 or a sequence at least 70% identical to the sequence of SEQ ID NO: 3 or 4.

Embodiment I-18. The composition of embodiment I-17, wherein the RNA comprises a 5' cap.

Embodiment I-19. The composition of embodiment I-18, wherein the 5'-cap comprises an anti-reverse cap analog (ARCA).

Embodiment I-20. The composition of embodiment I-19, wherein the ARCA comprises an 3'-O-Me-m7G(5')ppp(5')G structure.

Embodiment I-21. The composition of embodiment I-18, wherein the 5' cap comprises m7G(5')ppp(5')(2'OMeA)pG.

Embodiment I-22. The composition of any one of embodiments I-1 to I-21, wherein the RNA further comprises at least one untranslated region (UTR).

Embodiment I-23. The composition of embodiment I-22, wherein the at least one UTR is positioned 5' to the RNA of (i).

Embodiment I-24. The composition of embodiment I-22, wherein the at least one UTR is positioned 3' to the RNA of (i).

Embodiment I-25. The composition of any one of embodiments I-22 to I-24, wherein the UTR comprises a human sequence.

Embodiment I-26. The composition of any one of embodiments I-22 to I-24, wherein the UTR comprises a non-human sequence.

Embodiment I-27. The composition of any one of embodiments I-22 to I-26, wherein the UTR comprises a chimeric sequence.

Embodiment I-28. The composition of embodiment I-27, wherein the chimeric sequence increases stability, increases a transcription rate or decreases a time until initiation of transcription of the RNA of (i).

Embodiment I-29. The composition of any one of embodiments I-22 to I-28, wherein the UTR comprises a sequence having at least 70% identity to a UTR sequence isolated or derived from one or more of α-globin, β-globin, c-fos, and a tobacco etch virus.

Embodiment I-30. The composition of any one of embodiments I-1 to I-29, wherein the one or more modified nucleotides of the RNA of (i) comprise one or more of a modified adenine or analog thereof, a modified cytidine or analog thereof, a modified guanosine or analog thereof, and a modified uridine or analog thereof.

Embodiment I-31. The composition of any one of embodiments I-1 to I-30, wherein the one or more modified nucleotides of the RNA of (i) comprise one or more of 1-methylpseudouridine, pseudouridine, 2-thiouridine, and 5-methylcytidine.

Embodiment I-32. The composition of any one of embodiments I-1 to I-31, wherein the one or more modified nucleotides of the RNA of (i) comprise 5-methoxyuridine (5-moU).

Embodiment I-33. The composition of any one of embodiments I-1 to I-32, wherein the one or more modified nucleotides of the RNA of (i) comprise one or more of m1A 1-methyladenosine, m6A N6-methyladenosine, Am 2'-O-methyladenosine, i6A N6-isopentenyladenosine, io6A N6-(cis-hydroxyisopentenyl)adenosine, ms2io6A 2-methylthio-N6-(cis-hydroxyisopentenyl) adenosine, g6A N6-glycinylcarbamoyladenosine, t6A N6-threonylcarbamoyladenosine, ms2t6A 2-methylthio-N6-threonyl carbamoyladenosine, Ar(p) 2'-O-ribosyladenosine (phosphate), m6 2A N6,N6-dimethyladenosine, m6Am N6,2'-O-dimethyladenosine, m6 2Am N6,N6,2'-O-trimethyladenosine, m1Am 1,2'-O-dimethyladenosine, m3C 3-methylcytidine, m5C 5-methylcytidine, Cm 2'-O-methylcytidine, ac4C N4-acetylcytidine, f5C 5-formylcytidine, m4C N4-methylcytidine, hm5C 5-hydroxymethylcytidine, f5Cm 5-formyl-2'-O-methylcytidine, m1G 1-methylguanosine, m2G N2-methylguanosine, m7G 7-methylguanosine, Gm 2'-O-methylguanosine, m2 2G N2,N2-dimethylguanosine, Gr(p) 2'-O-ribosylguanosine (phosphate), yW wybutosine, o2yW peroxywybutosine, OHyW hydroxywybutosine, OHyW* undermodified hydroxywybutosine, imG wyosine, m2,7G N2,7-dimethylguanosine, m2,2,7G N2,N2,7-trimethylguanosine I inosine, m1I 1-methylinosine, Im 2'-O-methylinosine, Q queuosine, galQ galactosyl-queuosine, manQ mannosyl-queuosine, ψ pseudouridine, D dihydrouridine, m5U 5-methyluridine, Um 2'-O-methyluridine, m5Um 5,2'-O-dimethyluridine, m1ψ 1-methylpseudouridine, ψm 2'-O-methylpseudouridine, s2U 2-thiouridine, ho5U 5-hydroxyuridine, chm5U 5-(carboxyhydroxymethyl)uridine, mchm5U 5-(carboxyhydroxymethyl)uridine, methyl ester mcm5U 5-methoxycarbonylmethyluridine, mcm5Um 5-methoxycarbonylmethyl-2'-O-methyluridine, mcm5s2U 5-methoxycarbonylmethyl-2-thiouridine, ncm5U 5-carbamoylmethyluridine, ncm5Um 5-carbamoylmethyl-2'-O-methyluridine, cmnm5U 5-carboxymethylaminomethyluridine, m3U 3-methyluridine, m1acp3ψ 1-methyl-3-(3-amino-3-carboxypropyl) pseudouridine, cm5U 5-carboxymethyluridine, m3Um 3,2'-O-dimethyluridine, m5D 5-methyldihydrouridine, τm5U 5-taurinomethyluridine, τm5s2U 5-taurinomethyl-2-thiouridine, 2-Aminoadenosine, 2-Amino-6-chloropurineriboside, 8-Azaadenosine, 6-Chloropurineriboside, 5-Iodocytidine, 5-Iodouridine, Inosine, 2'-O-Methylinosine, Xanthosine, 4-Thiouridine, 06-Methylguanosine, 5,6-Dihydrouridine, 2-Thiocytidine, 6-Azacytidine, 6-Azauridine, 2'-O-Methyl-2-aminoadenosine, 2'-O-Methylpseudouridine, N1-Methyladenosine, 2'-O-Methyl-5-methyluridine, 7-Deazaguanosine, 8-Azidoadenosine, 5-Bromocytidine, 5-Bromouridine, 7-Deazaadenosine, 5-Aminoallyluridine, 5-Aminoallylcytidine, 8-Oxoguanosine, 2-Aminopurine-riboside, Pseudoisocytidine, N1-Methylpseudouridine, 5,6-Dihydro-5-Methyluridine, N6-Methyl-2-Aminoadenosine, 5-Carboxycytidine, 5-Hydroxymethyluridine, Thienoguanosine, 5-Hydroxy cytidine, 5-Formyluridine, 5-Carboxyuridine, 5-Methoxyuridine, 5-Methoxycytidine, Thienouridine, 5-Carboxymethylesteruridine, Thienocytidine, 8-Oxoadenoosine, Isoguanosine, N1-Ethylpseudouridine, N1-Methyl-2'-O-Methylpseudouridine, N1-Methoxymethylpseudouridine, N1-Propylpseudouridine, 2'-O-Methyl-N6-Methyladenosine, 2-Amino-6-Cl-purine-2'-deoxyriboside, 2-Amino-2'-deoxyadenosine, 2-Aminopurine-2'-deoxyriboside, 5-Bromo-2'-deoxycytidine, 5-Bromo-2'-deoxyuridine, 6-Chloropurine-2'-deoxyriboside, 7-Deaza-2'-deoxyadenosine, 7-Deaza-2'-deoxyguanosine, 2'-Deoxyinosine, 5-Propynyl-2'-deoxycytidine, 5-Propynyl-2'-deoxyuridine, 5-Fluoro-2'-deoxyuridine, 5-Iodo-2'-deoxycytidine, 5-Iodo-2'-deoxyuridine, N6-Methyl-2'-deoxyadenosine, 5-Methyl-2'-deoxycytidine, 06-Methyl-2'-deoxyguanosine, N2-Methyl-2'-deoxyguanosine, 8-Oxo-2'-deoxyadenosine, 8-Oxo-2'-deoxyguanosine, 2-Thiothymidine, 2'-Deoxy-P-nucleoside, 5-Hydroxy-2'-deoxycytidine, 4-Thiothymidine, 2-Thio-2'-deoxycytidine, 6-Aza-2'-deoxyuridine, 6-Thio-2'-deoxyguanosine, 8-Chloro-2'-deoxyadenosine, 5-Aminoallyl-2'-deoxycytidine, 5-Aminoallyl-2'-deoxyuridine, N4-Methyl-2'-deoxycytidine, 2'-Deoxyzebularine, 5-Hydroxymethyl-2'-deoxyuridine, 5-Hydroxymethyl-2'-deoxycytidine, 5-Propargylamino-2'-deoxycytidine, 5-Propargylamino-2'-deoxyuridine, 5-Carboxy-2'-deoxycytidine, 5-Formyl-2'-deoxycytidine, 5-[(3-Indolyl)propionamide-N-allyl]-2'-deoxyuridine, 5-Carboxy-2'-deoxyuridine, 5-Formyl-2'-deoxyuridine, 7-Deaza-7-Propargylamino-2'-deoxyadenosine, 7-Deaza-7-Propargylamino-2'-deoxyguanosine, Biotin-16-Aminoallyl-2'-dUTP, Biotin-16-Aminoallyl-2'-dCTP, Biotin-16-Aminoallylcytidine, N4-Biotin-OBEA-2'-deoxycytidine, Biotin-16-Aminoallyluridine, Dabcyl-5-3-Aminoallyl-2'-dUTP, Desthiobiotin-6-Aminoallyl-2'-deoxycytidine, Desthiobiotin-16-Aminoallyl-Uridine, Biotin-16-7-Deaza-7-Propargylamino-2'-deoxyguanosine, Cyanine 3-5-Propargylamino-2'-deoxycytidine, Cyanine 3-6-Propargylamino-2'-deoxyuridine, Cyanine 5-6-Propargylamino-2'-deoxycytidine, Cyanine 5-6-Propargylamino-2'-deoxyuridine, Cyanine 3-Aminoallylcytidine, Cyanine 3-Aminoallyluridine, Cyanine 5-Aminoallylcytidine, Cyanine 5-Aminoallyluridine, Cyanine 7-Aminoallyluridine, 2'-Fluoro-2'-deoxyadenosine, 2'-Fluoro-2'-deoxycytidine, 2'-Fluoro-2'-deoxyguanosine, 2'-Fluoro-2'-deoxyuridine, 2'-O-Methyladenosine, 2'-O-Methylcytidine, 2'-O-Methylguanosine, 2'-O-Methyluridine, Puromycin, 2'-Amino-2'-deoxycytidine, 2'-Amino-2'-deoxyuridine, 2'-Azido-2'-deoxycytidine, 2'-Azido-2'-deoxyuridine, Aracytidine, Arauridine, 2'-Azido-2'-deoxyadenosine, 2'-Amino-2'-deoxyadenosine, Araadenosine, 2'-Fluoro-thymidine, 3'-O-Methyladenosine, 3'-O-Methylcytidine, 3'-O-Methylguanosine, 3'-O-Methyluridine, 2'-Azido-2'-deoxyguanosine, Araguanosine, 2'-Deoxyuridine, 3'-O-(2-nitrobenzyl)-2'-Deoxyadenosine, 3'-O-(2-nitrobenzyl)-2'-Deoxyinosine, 3'-Deoxyadenosine, 3'-Deoxyguanosine, 3'-Deoxycytidine, 3'-Deoxy-5-Methyluridine, 3'-Deoxyuridine, 2',3'-Dideoxyadenosine, 2',3'-Dideoxyguanosine, 2',3'-Dideoxyuridine, 2',3'-Dideoxythymidine, 2',3'-Dideoxycytidine, 3'-Azido-2',3'-dideoxyadenosine, 3'-Azido-2',3'-dideoxythymidine, 3'-Amino-2',3'-dideoxyadenosine, 3'-Amino-2',3'-dideoxycytidine, 3'-Amino-2',3'-dideoxyguanosine, 3'-Amino-2',3'-dideoxythymidine, 3'-Azido-2',3'-dideoxycytidine, 3'-Azido-2',3'-dideoxyuridine, 5-Bromo-2',3'-dideoxyuridine, 2',3'-Dideoxyinosine, 2'-Deoxyadenosine-5'-O-(1-Thiotriphosphate), 2'-Deoxycytidine-5'-O-(1-Thiotriphosphate), 2'-Deoxyguanosine-5'-O-(1-Thiotriphosphate), 2'-Deoxythymidine-5'-O-(1-Thiotriphosphate), Adenosine-5'-O-(1-Thiotriphosphate), Cytidine-5'-O-(1-Thiotriphosphate), Guanosine-5'-O-(1-Thiotriphosphate), Uridine-5'-O-(1-Thiotriphosphate), 2',3'-Dideoxyadenosine-5'-O-(1-Thiotriphosphate), 2',3'-Dideoxycytidine-5'-O-(1-Thiotriphosphate), 2',3'-Dideoxyguanosine-5'-O-(1-Thiotriphosphate), 3'-Deoxythymidine-5'-O-(1-Thiotriphosphate), 3'-Azido-2',3'-dideoxythymidine-5'-O-(1-Thiotriphosphate), 2',3'-Dideoxyuridine-5'-O-(1-Thiotriphosphate), 2'-Deoxyadenosine-5'-O-(1-Boranotriphosphate), 2'-Deoxycytidine-5'-O-(1-Boranotriphosphate), 2'-Deoxyguanosine-5'-O-(1-Boranotriphosphate), and 2'-Deoxythymidine-5'-O-(1-Boranotriphosphate).

Embodiment I-34. The composition of any one of embodiments I-1 to I-33, wherein the composition further comprises a ribonucleic acid (RNA) encoding TElomerase RNA Component (TERC).

Embodiment I-35. The composition of any one of embodiments I-1 to I-34, wherein the delivery vehicle comprises the RNA encoding TERT.

Embodiment I-36. The composition of embodiment I-35, wherein one or more of a surface, a layer or a volume of the delivery vehicle comprises the RNA encoding TERT.

Embodiment I-37. The composition of embodiment I-36, wherein the surface comprises an outer surface or an inner surface.

Embodiment I-38. The composition of embodiment I-36, wherein the layer comprises a lipid monolayer or lipid bi-layer.

Embodiment I-39. The composition of embodiment I-36, wherein the volume comprises an internal volume.

Embodiment I-40. The composition of any one of embodiments I-1 to I-39, wherein the delivery vehicle is operably-linked to a ribonucleic acid (RNA) encoding TElomerase RNA Component (TERC).

Embodiment I-41. The composition of embodiment I-40, wherein the delivery vehicle comprises the RNA encoding TERC.

Embodiment I-42. The composition of embodiment I-35, wherein one or more of a surface, a layer or a volume of the delivery vehicle comprises the RNA encoding TERC.

Embodiment I-43. The composition of embodiment I-42, wherein the surface comprises an outer surface or an inner surface.

Embodiment I-44. The composition of embodiment I-42, wherein the layer comprises a lipid monolayer or lipid bi-layer.

Embodiment I-45. The composition of embodiment I-42, wherein the volume comprises an internal volume.

Embodiment I-46. A method of increasing telomerase activity in a cell, the method comprising contacting the cell and the composition of any one of embodiments I-1 to I-45.

Embodiment I-47. A method of extending telomeres in a cell, the method comprising contacting the cell and the composition of any one of embodiments I-1 to I-45.

Embodiment I-48. The method of embodiment I-46 or 1-47, wherein the cell is in vivo, ex vivo or in vitro.

Embodiment I-49. A cell comprising the composition of any one of embodiments I-1 to I-45.

Embodiment I-50. A formulation comprising the cell of embodiment I-49.

Embodiment I-51. The formulation of embodiment I-50, wherein a plurality of cells comprises the cell of embodiment I-49.

Embodiment I-52. The formulation of embodiment I-51, wherein each cell of the plurality is a cell according to embodiment I-49.

Embodiment I-53. A method of treating a disease or disorder comprising administering to a subject an effective amount of a composition according to any one of embodiments I-1 to 1-45.

Embodiment I-54. A method of treating a disease or disorder comprising administering to a subject an effective amount of a cell according to embodiment I-49.

Embodiment I-55. A method of treating a disease or disorder comprising administering to a subject an effective amount of a formulation according to any one of embodiments I-50 to 1-52.

Embodiment I-56. A method of delaying the onset of a disease comprising administering to a subject an effective amount of a composition according to any one of embodiments I-1 to I-45.

Embodiment I-57. A method of delaying the onset of a disease comprising administering to a subject an effective amount of a cell according to embodiment I-49.

Embodiment I-58. A method of delaying the onset of a disease comprising administering to a subject an effective amount of a formulation according to any one of embodiments I-50 to I-52.

Embodiment I-59. The composition of any one of embodiments I-1 to I-45, wherein the composition is capable of transfecting at least 50%, at least 60%, at least 70%, at least 80%, at least 90%, or at least 95% of a population of lung cells.

Embodiment I-60. A composition comprising a lipid nanoparticle particle (LNP) capable of transfecting at least 50%, at least 60%, at least 70%, at least 80%, at least 90%, or at least 95% of a population of lung cells.

Embodiment I-61. The composition of embodiment I-60, comprising a polynucleotide.

Embodiment I-62. The composition of embodiment I-61, wherein the polynucleotide is an RNA.

Embodiment I-63. The composition of embodiment I-62, wherein the RNA is an mRNA.

Embodiment I-64. The composition of any one of embodiments I-60 to I-63, wherein the LNP is capable of transfecting about 50%-99%, about 60%-99%, about 70%-99%, about 80%-99%, or about 90%-99% of the population of lung cells.

Embodiment I-65. The composition of any one of embodiments I-60 to I-63, wherein the LNP is capable of transfecting 50%-95%, about 60%-95%, about 70%-95%, about 80%-95%, or about 90%-95% of the population of lung cells.

Embodiment I-66. The composition of any one of embodiments I-60 to I-65, wherein the population of lung cells comprises lung endothelial cells.

Embodiment I-67. The composition of embodiment I-66, wherein the lung endothelial cells comprise vascular endothelial cells.

Embodiment I-68. The composition of embodiment I-66, wherein the lung endothelial cells comprise alveolar endothelial cells.

Embodiment I-69. The composition of any one of embodiments I-60 to I-68, wherein the population of lung cells comprises lung epithelial cells.

Embodiment I-70. The composition of embodiment I-69, wherein the lung epithelial cells comprise lung alveolar epithelial cells.

Embodiment I-71. The composition of embodiment I-70, wherein the lung alveolar epithelial cells comprise alveolar type 1 (AT1) cells.

Embodiment I-72. The composition of embodiment I-70, wherein the lung alveolar epithelial cells comprise alveolar type 2 (AT2) cells.

Embodiment I-73. The composition of any one of embodiments I-60 to I-72, wherein the lung cells comprise any one or more of macrophages, mast cells, club cells, brush cells, neuroepithelial cells, and goblet cells.

Embodiment I-74. The composition of any one of embodiments I-60 to I-73, wherein the lung cells comprise one or more of fibroblasts, myofibroblasts, lipofibroblasts, and fibromyocytes.

Embodiment I-75. The composition of any one of embodiments I-60 to I-74, wherein the population of lung cells comprise bronchial cells.

Embodiment I-76. The composition of any one of embodiments I-60 to I-75, wherein the population of lung cells comprises bronchioalveolar stem cells.

Embodiment I-77. The composition of any one of embodiments I-60 to I-76, wherein the population of lung cells comprises lung immune cells.

Embodiment I-78. The composition of any one of embodiments I-60 to I-77, wherein the population of lung cells comprises lung fibroblasts.

Embodiment I-79. The composition of any one of embodiments I-60 to I-78, wherein the population of lung cells comprises one or more of lung precancerous and cancer cells.

Embodiment I-80. The composition of any one of embodiments I-60 to I-79, wherein the population of lung cells comprise lung alveolar endothelial cells and lung alveolar epithelial cells, and at least 60%, at least 70%, at least 80%, or at least 90% of the lung endothelial cells are transfected, and at least 60%, at least 70%, at least 80%, or at least 90% of the lung epithelial cells are transfected.

Embodiment I-81. The composition of any one of any one of embodiments I-60 to I-80, wherein the lung cells are transfected when administered to a subject by intravenous injection.

Embodiment I-82. The composition of any one of embodiments I-60 to I-80, the lung cells are transfected when administered to a subject by one or more of aerosol injection, aerosolization, inhalation, nebulization or instillation.

Embodiment I-83. The composition of any one of embodiments I-60 to I-82, wherein the composition comprises an ionizable lipid.

Embodiment I-84. The composition of embodiment I-83, wherein the ionizable lipid is about 40-60% of the molar percentage of the LNP.

Embodiment I-85. The composition of any one of embodiments I-60 to I-84, wherein the composition comprises a compound of Formula I.

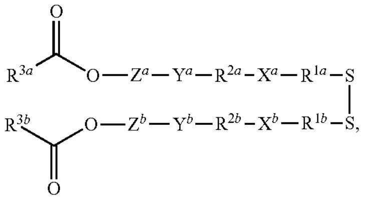

(1)

wherein $R^{1a}$ and $R^{1b}$ each independently represents an alkylene group having 1 to 6 carbon atoms, wherein $X^a$ and $X^b$ are each independently an acyclic alkyl tertiary amino group having 1 to 6 carbon atoms and 1 tertiary amino group, or 2 to 5 carbon atoms, and A cyclic alkylene tertiary amino group having 1 to 2 tertiary amino groups, wherein $R^{2a}$ and $R^{2b}$ each independently represent an alkylene group having 8 or less carbon atoms or an oxydialkylene group, wherein $Y^a$ and $Y^b$ each independently represent an ester bond, an amide bond, a carbamate bond, an ether bond or a urea bond;

wherein $Z^a$ and $Z^b$ are each independently a divalent group derived from an aromatic compound having 3 to 16 carbon atoms, having at least one aromatic ring, and optionally having a hetero atom, and wherein $R^{3a}$ and $R^{3b}$ each independently represent a residue derived from a reaction product of a fat-soluble vitamin having a hydroxyl group and succinic anhydride or glutaric anhydride, or a sterol derivative having a hydroxyl group and succinic anhydride or a residue derived from a reaction product with glutaric anhydride or an aliphatic hydrocarbon group having 12 to 22 carbon atoms.

Embodiment I-86. The composition of embodiment I-84, wherein the compound of Formula I is:

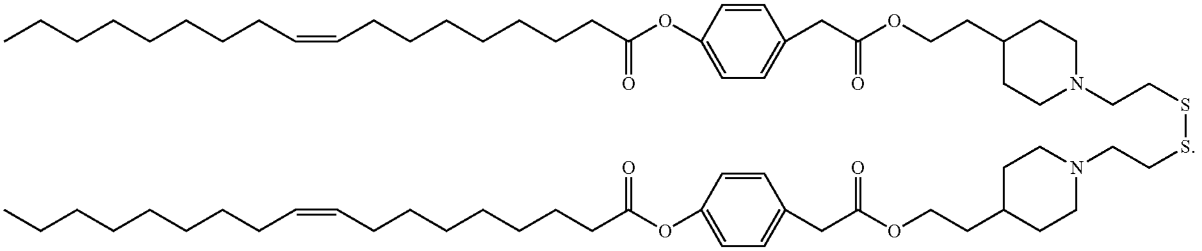 [SMILES: CCCCCCCC/C=C\CCCCCCCC(=O)Oc1ccc(CC(=O)OCCC2CCN(CCSSCCN3CCC(CCOC(=O)Cc4ccc(OC(=O)CCCCCCC/C=C\CCCCCCCC)cc4)CC3)CC2)cc1]

Embodiment I-87. The composition of embodiment I-84, wherein the compound of Formula I is:

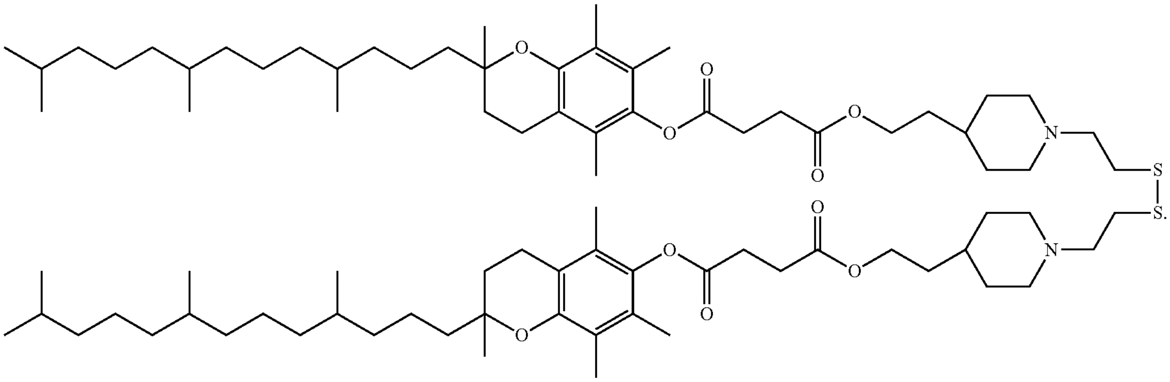 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2]

Embodiment I-88. The composition of embodiment I-84, wherein the compound of Formula I is:

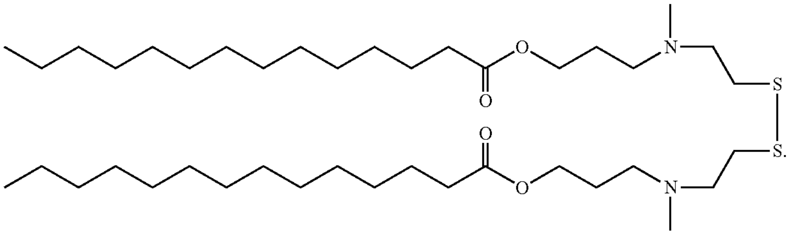 [SMILES: CCCCCCCCCCCCCC(=O)OCCCN(C)CCSSCCN(C)CCCOC(=O)CCCCCCCCCCCCC]

Embodiment I-89. The composition of embodiment I-84, wherein the compound of Formula I is:

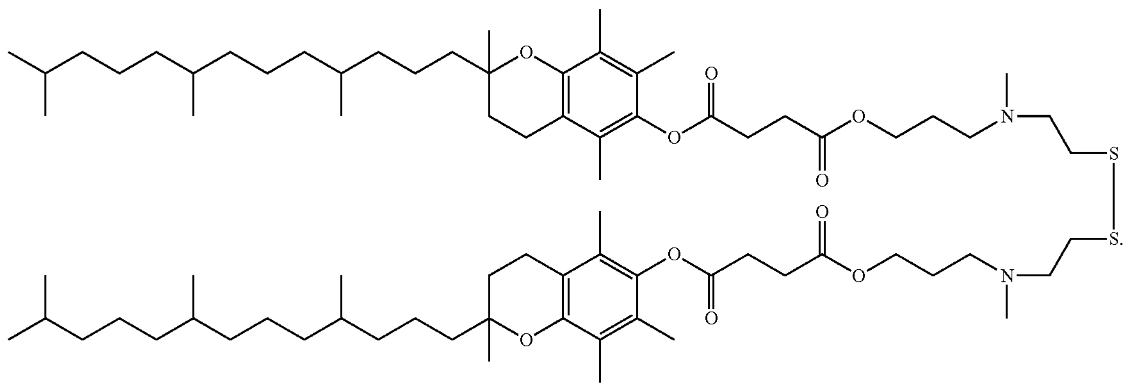 [SMILES: Cc1c(C)c2c(c(C)c1OC(=O)CCC(=O)OCCCN(C)CCSCSCCN(C)CCCOC(=O)CCC(=O)Oc1c(C)c(C)c3c(c1C)CCC(C)(CCCC(C)CCCC(C)CCCC(C)C)O3)CCC(C)(CCCC(C)CCCC(C)CCCC(C)C)O2]

Embodiment I-90. The composition of embodiment I-84, wherein the compound of Formula I is:

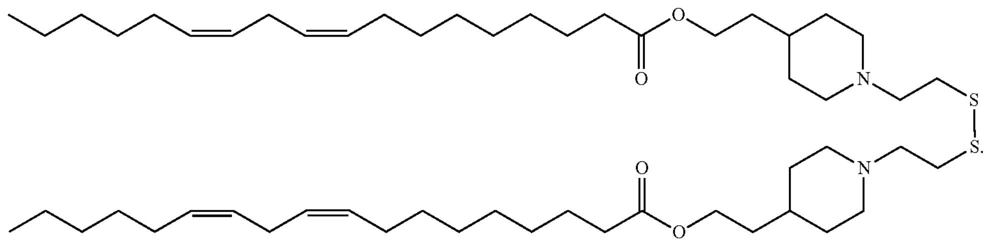 [SMILES: CCCCC/C=C\C/C=C\CCCCCCCC(=O)OCCC1CCN(CCSSCCN2CCC(CCOC(=O)CCCCCCC/C=C\C/C=C\CCCCC)CC2)CC1]

Embodiment I-91. The composition of embodiment I-84, wherein the compound of Formula I is:

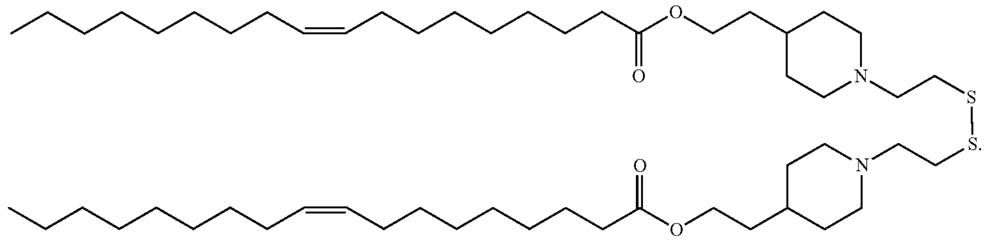 [SMILES: CCCCCCCC/C=C\CCCCCCCC(=O)OCCC1CCN(CCSSCCN2CCC(CCOC(=O)CCCCCCC/C=C\CCCCCCCC)CC2)CC1]

Embodiment I-92. The composition of any one of embodiments I-60 to I-91, wherein the compound of Formula I comprises a carbon chain having between 8 and 24 carbon atoms.

Embodiment I-93. The composition of any one of embodiments I-60 to I-92, wherein the LNP comprises a mixture of two or more ionizable lipids.

Embodiment I-94. The composition of any one of embodiments I-82 to I-92, wherein the cationic lipid is an ionizable lipid and a targeting lipid.

Embodiment I-95. The composition of any one of embodiments I-60 to I-93, wherein the LNP comprises a sterol.

Embodiment I-96. The composition of embodiment I-94, wherein the sterol is a cholesterol.

Embodiment I-97. The composition of any one of embodiments I-94 to I-96, wherein the sterol is about 10-30% of the molar percentage of the LNP.

Embodiment I-98. The composition of any one of embodiments I-1 to I-97, wherein the LNP comprises an insulator lipid.

Embodiment I-99. The composition of embodiment I-98, wherein the insulator lipid is a PEGylated lipid.

Embodiment I-100. The composition of any one of embodiments I-98 to I-99, wherein the PEGylated lipid is linear.

Embodiment I-101. The composition of any one of embodiments I-98 to I-99, wherein the PEGylated lipid is branched.

Embodiment I-102. The composition of any one of embodiments I-98 to I-101, wherein the PEGylated lipid comprises a carbon chain having between 8 and 24 carbon atoms.

Embodiment I-103. The composition of any one of embodiments I-98 to I-102, wherein the insulator lipid is conjugated to a blood protein or a peptide sequence of a blood protein, wherein the blood protein is albumin or a globulin.

Embodiment I-104. The composition of any one of embodiments I-98 to I-101, wherein the insulator lipid is at least 0.25-5% of the molar percentage of the LNP.

Embodiment I-105. The composition of any one of embodiments I-1 to I-104, wherein the LNP comprises a cationic lipid.

Embodiment I-106. The composition of embodiment I-105, wherein the cationic lipid is any one or more of 1,2-dioleoyl-3-trimethylammonium-propane (DOTAP), and a DOTAP analog.

Embodiment I-107. The composition of embodiment I-105, wherein the cationic lipid is any one or more of N-[1-(2,3-dioleyloxy)propyl]-N,N,N-trimethylammonium chloride (DOTMA), 5-carboxyspermylglycinedioctadecylamide (DOGS), 2,3-dioleyloxy-N-[2(spermine-carboxamido)ethyl]-N,N-dimethyl-1-propanaminium (DOSPA), 1,2-Dioleoyl-3-Dimethylammonium-Propane (DODAP), 1,2-Dioleoyl-3-Trimethylammonium-Propane (DOTAP), 1,2-distearyloxy-N,N-dimethyl-3-aminopropane (DSDMA), 1,2-dioleyloxy-N,N-dimethyl-3-aminopropane (DODMA), 1,2-dilinoleyloxy-N,N-dimethyl-3-aminopropane (DLinDMA), dimethyldioctadecylammonium (DDA), 1,2-dilinolenyloxy-N,N-dimethyl-3-aminopropane (DLenDMA), N-dioleyl-N,N-dimethylammonium chloride (DODAC), N,N-distearyl-N,N-dimethylammonium bromide (DDAB), N-(1,2-dimyristyloxyprop-3-yl)-N,N-dimethyl-N-hy droxyethyl ammonium bromide (DMRIE), 3-dimethylamino-2-(cholest-5-en-3-beta-oxybutan-4-oxy)-1-(cis,cis-9,12-oc-tadecadienoxy)propane (CLinDMA), 2-[5'-(cholest-5-en-3-beta-oxy)-3'-oxapentoxy)-3-dimethy 1-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 2,3-Dilinoleoyloxy-N,N-dimethylpropylamine (DLinDAP), 1,2-N,N'-Dilinoleylcarbamyl-3-dimethylaminopropane (DLincarbDAP), 1,2-Dilinoleoylcarbamyl-3-dimethylaminopropane or (DLinCDAP), 2,2-dilinoleyl-4-dimethylaminomethyl-[1,3]-dioxolane (DLin-K-DMA), 2,2-dilinoleyl-4-dimethylaminoethyl-[1,3]-dioxolane (DLin-K-XTC2-DMA), and mixtures thereof.

Embodiment I-108. The composition of any one of embodiments I-1 to I-107, wherein the LNP comprises a structural lipid.

Embodiment I-109. The composition of embodiment I-108, wherein the structural lipid is any one or more of 1,2-di-(9Z-octadecenoyl)-sn-glycero-3-phosphoethanolamine (DOPE), glycerol-monooleate (GMO), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanolamine (SOPE), cholesterol or another sterol, and mixtures thereof.

Embodiment I-110. The composition of any one of embodiments I-1 to I-109, wherein the LNP comprises at least a first component, a second component, and a third component, wherein:

the first component is an ionizable lipid;
the second component is a cationic lipid; and
the third component is a structural lipid.

Embodiment I-111. The composition of embodiment I-110, further comprising a sterol.

Embodiment I-112. The composition of any one of embodiments I-110 to I-111, comprising an insulator lipid selected from: 14:0 PEG2000 PE and a DMG-PEGylated lipid, and a lipid conjugated to a blood protein or a peptide sequence of a blood protein, wherein the blood protein is albumin or a globulin.

Embodiment I-113. The composition of any one of embodiments I-1 to I-112, wherein the LNP comprises SS-OP or an SS-OP analog, DOPC, a cholesterol, DMG-PEG2000, and DOTAP.

Embodiment I-114. The composition of embodiment I-113, wherein the LNP comprises 45-55% cationic lipid and SS-OP or an analog thereof at between 20-40%.

Embodiment I-115. The composition of embodiment I-114, wherein the LNP comprise 45-55% DOTAP.

Embodiment I-116. The LNP of embodiment I-113, wherein the LNP comprises SS-OP, DOPC, a cholesterol, DMG-PEG2000, and DOTAP.

Embodiment I-117. The composition of embodiment I-114, wherein the LNP comprises 25-29% of SS-OP; 1-3% DOPC; 15-35% cholesterol; 0.8-1.6% DMG-PEG2000; and 45-55% DOTAP.

Embodiment I-118. The composition of embodiment I-114, wherein the LNP comprises 27% of SS-OP; 2.5% DOPC; 20% cholesterol; 1.2% DMG-PEG2000; and 50% DOTAP.

Embodiment I-119. The composition of any one of embodiments I-60 to I-118, wherein the LNP comprises cKK-E12 or a cKK-E12 analog, DOPE, a cholesterol, PEG2000 PE, and DOTAP.

Embodiment I-120. A method of delivering a cargo to a population of lung cells in a subject in a subject in need thereof, comprising administering the composition of any one of embodiments I-1 to I-45 or embodiments I-1 to I-119 to the subject.

Embodiment I-121. A method of treating a lung disease or disorder in a subject in need thereof, comprising administering the composition of any one of embodiments I-1 to I-45 or embodiments I-60 to I-119 to the subject.

Embodiment I-122. The method of any one of embodiments I-120 to I-121, the method comprising administering the composition by intravenous injection.

Embodiment I-123. The method of any one of embodiments I-120 to I-121, the method comprising administering the LNP by one or more of aerosol injection, aerosolization, inhalation, nebulization or instillation.

Embodiment I-124. The method of any one of embodiments I-120 to I-123, wherein the cargo comprises a polynucleotide.

Embodiment I-125. The method of embodiment I-124, wherein the polynucleotide is an RNA.

Embodiment I-126. The method of embodiment I-125, wherein the RNA is an mRNA.

Embodiment I-127. The method of embodiment I-126, wherein the mRNA encodes one or more of TERT, a Cystic Fibrosis Transmembrane Conductance Regulator (CFTR) protein, a growth factor, a transcription factor, and a gene-editing protein.

Embodiment I-128. The method of any one of embodiments I-120 to I-127, wherein at least 50%, at least 60%, at least 70%, at least 80%, or at least 90% of a population of lung cells of the subject are transfected.

Embodiment I-129. The method of any one of embodiments I-120 to I-128, wherein about 50%-99%, about 60%-99%, about 70%-99%, about 80%-99%, or about 90%-99% of a population of lung cells of the subject are transfected.

Embodiment I-130. The method of any one of embodiments I-120 to I-129, wherein about 50%-95%, about 60%-95%, about 70%-95%, about 80%-95%, or about 90%-95% of a population of lung cells of the subject are transfected.

Embodiment I-131. The method of any one of embodiments I-120 to I-130, wherein the lung disease or disorder is selected from: pulmonary fibrosis, idiopathic pulmonary fibrosis, emphysema, interstitial lung diseases, chronic obstructive pulmonary disease (COPD), a lung infection, pneumonia, tuberculosis, gastric reflux, lung cancer, cystic fibrosis, dyskeratosis congenita, Alpha-1 antitrypsin deficiency, and other genetic diseases of the lung.

Embodiment I-132. The method of any one of embodiments I-120 to I-131, wherein the LNP is administered to the subject as a single dose.

Embodiment I-133. The method of any one of embodiments I-120 to I-131, wherein the LNP is administered to the subject as multiple doses, wherein the multiple doses comprise at least two doses.

Embodiment I-134. The method of any one of embodiments I-120 to I-133, wherein a dose of the LNP is administered to the subject is at least 0.01, 0.1, 1, 2, 5, 10, 20, 30, 40, 50, 60, 70, or 80 mg/kg by weight of the subject.

Embodiment I-135. The method of any one of embodiments I-120 to I-134, wherein the cargo is an mRNA, and the mRNA is administered to the subject at a dose of about 0.1, about 0.2, about 0.3, about 0.4, about 0.5, about 0.6, about 0.7, about 0.8, about 0.9, about 1, about 1.5, about 2, or about 2.5 mg/kg by weight of the subject.

Embodiment I-136. The method of any one of embodiments I-120 to I-135, wherein the subject is human.

Embodiments II

Embodiment II-1. A method of delivering a polynucleotide to the lung of a subject, comprising administering, by intravenous injection, a polynucleotide encapsulated in a lipid nanoparticle (LNP) comprising:

(i) a cationic lipid in a molar percentage of between about 20% and about 50%, (ii) a SS-OP or an SS-OP analog at a molar percentage of between about 20% and about 60%.

Embodiment II-2. The method of embodiment II-1, wherein the SS-OP analog is any one or more of SS-M, SS-E, SS-EC, SS-LC, and SS-OC.

Embodiment II-3. The method of embodiment II-1 or II-2, wherein the cationic lipid is is any one or more of 2-Dioleoyl-3-Trimethylammonium-Propane (DOTAP), Dimethyldioctadecylammonium bromide (DDAB), Imidazole Cholesterol Ester (ICE), 25-Hydroxycholesterol (25 OH Chol), 20α-hydroxycholesterol 5-cholestene-3α, 20α-diol (20α Chol), N-[1-(2,3-dioleyloxy)propyl]-N,N,N-trimethylammonium chloride (DOTMA), 5-carboxyspermylglycinedioctadecylamide (DOGS), 2,3-dioleyloxy-N-[2(spermine-carboxamido)ethyl]-N,N-dimethyl-1-propanaminium (DOSPA), 1,2-Dioleoyl-3-Dimethylammonium-Propane (DODAP), 11,2-distearyloxy-N,N-dimethyl-3-aminopropane (DSDMA), 1,2-dioleyloxy-N,N-dimethyl-3-aminopropane (DODMA), 1,2-dilinoleyloxy-N,N-dimethyl-3-aminopropane (DLinDMA), dimethyldioctadecylammonium (DDA), 1,2-dilinolenyloxy-N,N-dimethyl-3-aminopropane (DLenDMA), N-dioleyl-N,N-dimethylammonium chloride (DODAC), N,N-distearyl-N,N-dimethylammonium bromide (DDAB), N-(1,2-dimyristyloxyprop-3-yl)-N,N-dimethyl-N-hydroxyethyl ammonium bromide (DMRIE), 3-dimethylamino-2-(cholest-5-en-3-beta-oxybutan-4-oxy)-1-(cis,cis-9,12-oc-tadecadienoxy)propane (CLinDMA), 2-[5'-(cholest-5-en-3-beta-oxy)-3'-oxapentoxy)-3-dimethy 1-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 2,3-Dilinoleoyloxy-N,N-dimethylpropylamine (DLinDAP), 1,2-N,N'-Dilinoleylcarbamyl-3-dimethylaminopropane (DLincarbDAP), 1,2-Dilinoleoylcarbamyl-3-dimethylaminopropane or (DLinCDAP), 2,2-dilinoleyl-4-dimethylaminomethyl-[1,3]-dioxolane (DLin-K-DMA), 2,2-dilinoleyl-4-dimethylaminoethyl-[1,3]-dioxolane (DLin-K-XTC2-DMA), and mixtures thereof.

Embodiment II-4. The method of embodiment II-4, wherein the cationic lipid is DOTAP.

Embodiment II-5. The method of any one of embodiments II-1 to II-4, wherein the LNP comprises the cationic lipid at a molar percentage of between about 25% and about 35%.

Embodiment II-6. The method of any one of embodiments II-1 to II-4, wherein the LNP comprises the cationic lipid at a molar percentage of about 30%.

Embodiment II-7. The method of any one of embodiments II-1 to II-6, wherein the LNP comprises a structural lipid.

Embodiment II-8. The method of embodiment II-7, wherein the structural lipid is any one or more of 1,2-di-(9Z-octadecenoyl)-sn-glycero-3-phosphoethanolamine (DOPE), glycerol-monooleate (GMO), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanolamine (SOPE), cholesterol or another sterol, and mixtures thereof.

Embodiment II-9. The method of embodiment II-7, wherein the structural lipid is DOPC.

Embodiment II-10. The method of embodiment II-9, wherein the LNP comprises between about 1% and about 5% DOPC.

Embodiment II-11. The method of any one of embodiments II-1 to II-6, wherein the LNP is substantially free of structural lipids and/or comprises at most 1% structural lipids.

Embodiment II-12. The method of any one of embodiments II-1 to II-11, wherein the LNP comprises between about 20% and about 40% cholesterol.

Embodiment II-13. The method of any one of embodiments II-1 to II-11, wherein the LNP is substantially free of cholesterol.

Embodiment II-14. The method of any one of embodiments II-1 to II-13, wherein the LNP comprises an insulator lipid.

Embodiment II-15. The method of any one of embodiments II-1 to II-13, wherein the LNP is substantially free of insulator lipids.

Embodiment II-16. The method of any one of embodiments II-1 to II-15, wherein the LNP preferentially delivers to and/or transfects the lung compared to liver.

Embodiment II-17. The method of any one of embodiments II-1 to II-16, wherein the polynucleotide is a synthetic ribonucleic acid (RNA).

Embodiment II-18. The method of embodiment II-17, wherein the synthetic ribonucleic acid (RNA) encodes telomerase reverse transcriptase (TERT).

Embodiment II-19. A method of treating a lung fibrosis in a subject in need thereof, comprising administering an effective amount of a composition comprising a delivery vehicle comprising a synthetic ribonucleic acid (RNA) encoding telomerase reverse transcriptase (TERT).

Embodiment II-20. The method of embodiment II-19, wherein the delivery vehicle is a lipid nanoparticle (LNP).

Embodiment II-21. The method of embodiment II-20, wherein the LNP comprises a cationic lipid at a molar percentage of between about 20% and about 50%, a SS-OP or an SS-OP analog at a molar percentage of between about 20% and 60%, and optionally one or more of a structural lipid, an insulator lipid, and a cholesterol.

Embodiment II-22. The method of any one of embodiments II-19 to II-21, wherein the TERT synthetic mRNA comprises at least one modified nucleoside from the list in Table 2.

Embodiment II-23. The method of embodiment II-22, wherein the modified nucleoside is pseudouridine or a pseudouridine analog.

Embodiment II-24. The method of embodiment II-22, wherein the pseudouridine analog is N-1-methylpseudouridine.

Embodiment II-25. The method of any one of embodiments II-19 to II-24, wherein the TERT synthetic mRNA comprises an untranslated region (UTR).

Embodiment II-26. The method of any one of embodiments II-19 to II-25, wherein the TERT synthetic mRNA comprises a 5' cap structure, wherein the 5' cap structure is m7(3'OMeG)(5')ppp(5')(2'OMeA)pG, IRES, Cap0, Cap1, ARCA, inosine, N1-methyl-guanosine, 2' fluoro-guanosine, 7-deaza-guanosine, CleanCap™, 8-oxo-guanosine, 2-amino-guanosine, LNA-guanosine, 2-azido-guanosine, Cap2, Cap4, CAP-003, or CAP-225.

Embodiment II-27. The method of any one of embodiments II-19 to II-26, wherein the TERT synthetic mRNA comprises a poly-adenosine (poly-A) nucleotide sequence 3' to the encoding region.

Embodiment II-28. The method of any one of embodiments II-19 to II-27, wherein the TERT synthetic mRNA comprises a chain terminating nucleotide, wherein the nucleotide is 3'-deoxyadenosine (cordycepin), 3'-deoxyuridine, 3'-deoxycytosine, 3'-deoxyguanosine, 3'-deoxythymine, 2',3'-dideoxynucleosides, 2',3'-dideoxyadenosine, 2',3'-dideoxyuridine, 2',3'-dideoxycytosine, 2',3'-dideoxyguanosine, 2',3'-dideoxythymine, a 2'-deoxynucleoside, or —O-methylnucleoside.

Embodiment II-29. The method of any one of embodiments II-19 to II-28, wherein the TERT synthetic mRNA is codon optimized.

Embodiment II-30. The method of any one of embodiments II-19 to II-28, wherein the lung fibrosis is associated with a lung disease.

Embodiment II-31. The method of embodiment II-30, wherein the lung disease is pulmonary fibrosis, familial pulmonary fibrosis, idiopathic pulmonary fibrosis, pulmonary fibrosis associated with dyskeratosis congenita, an interstitial lung disease, pneumonia, interstitial pneumonia, emphysema, or lung cancer.

Embodiment II-32. The method of any one of embodiments II-19 to II-31, wherein the lung fibrosis is associated with a TERT mutation.

Embodiment II-33. The method of any one of embodiments II-19 to II-32, wherein the subject is human.

Embodiment II-34. The method of any one of embodiments II-19 to II-33, wherein the composition is administered to the subject via intravenous injection.

Embodiment II-35. The method of any one of embodiments II-19 to II-33, wherein the composition is administered to the subject via inhalation.

Embodiment II-36. A composition, comprising a polynucleotide encapsulated in a lipid nanoparticle (LNP) comprising:

(i) a cationic lipid in a molar percentage of between about 20% and about 50%, (ii) a SS-OP or an SS-OP analog at a molar percentage of between about 20% and about 60%.

Embodiment II-37. The composition of embodiment II-36, wherein the SS-OP analog is any one or more of SS-M, SS-E, SS-EC, SS-LC, and SS-OC.

Embodiment II-38. The composition of embodiment II-36, wherein the cationic lipid is any one or more of 2-Dioleoyl-3-Trimethylammonium-Propane (DOTAP), Dimethyldioctadecylammonium bromide (DDAB), Imidazole Cholesterol Ester (ICE), 25-Hydroxycholesterol (25 OH Chol), 20α-hydroxycholesterol 5-cholestene-3α, 20α-diol (20α Chol), N-[1-(2,3-dioleyloxy)propyl]-N,N,N-trimethylammonium chloride (DOTMA), 5-carboxyspermylglycinedioctadecylamide (DOGS), 2,3-dioleyloxy-N-[2 (spermine-carboxamido)ethyl]-N,N-dimethyl-1-propanaminium (DOSPA), 1,2-Dioleoyl-3-Dimethylammonium-Propane (DODAP), 11,2-distearyloxy-N,N-dimethyl-3-aminopropane (DSDMA), 1,2-dioleyloxy-N,N-dimethyl-3-aminopropane (DODMA), 1,2-dilinoleyloxy-N,N-dimethyl-3-aminopropane (DLinDMA), dimethyldioctadecylammonium (DDA), 1,2-dilinolenyloxy-N,N-dimethyl-3-aminopropane (DLenDMA), N-dioleyl-N,N-dimethylammonium chloride (DODAC), N,N-distearyl-N,N-dimethylammonium bromide (DDAB), N-(1,2-dimyristyloxyprop-3-yl)-N,N-dimethyl-N-hydroxyethyl ammonium bromide (DMRIE), 3-dimethylamino-2-(cholest-5-en-3-beta-oxybutan-4-oxy)-1-(cis,cis-9,12-oc-tadecadienoxy)propane (CLinDMA), 2-[5'-(cholest-5-en-3-beta-oxy)-3'-oxapentoxy)-3-dimethy 1-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 2,3-Dilinoleoyloxy-N,N-dimethylpropylamine (DLinDAP), 1,2-N,N'-Dilinoleylcarbamyl-3-dimethylaminopropane (DLincarbDAP), 1,2-Dilinoleoylcarbamyl-3-dimethylaminopropane or (DLinCDAP), 2,2-dilinoleyl-4-dimethylaminomethyl-[1,3]-dioxolane (DLin-K-DMA), 2,2-dilinoleyl-4-dimethylaminoethyl-[1,3]-dioxolane (DLin-K-XTC2-DMA), and mixtures thereof.

Embodiment II-39. The composition of embodiment II-38, wherein the cationic lipid is DOTAP.

Embodiment II-40. The composition of any one of embodiments II-36 to II-39, wherein the LNP comprises the cationic lipid at a molar percentage of between about 25% and about 35%.

Embodiment II-41. The composition of any one of embodiments II-36 to II-39, wherein the LNP comprises the cationic lipid at a molar percentage of about 30%.

Embodiment II-42. The composition of any one of embodiments II-36 to II-41, wherein the LNP comprises a structural lipid.

Embodiment II-43. The composition of embodiment II-42, wherein the structural lipid is any one or more of 1,2-di-(9Z-octadecenoyl)-sn-glycero-3-phosphoethanolamine (DOPE), glycerol-monooleate (GMO), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanolamine (SOPE), cholesterol or another sterol, and mixtures thereof.

Embodiment II-44. The composition of embodiment II-43, wherein the structural lipid is DOPC.

Embodiment II-45. The composition of embodiment II-44, wherein the LNP comprises between about 1% and about 5% DOPC.

Embodiment II-46. The compositon of any one of embodiments II-36 to II-45, wherein the LNP is substantially free of structural lipids and/or comprises at most 1% structural lipids.

Embodiment II-47. The composition of any one of embodiments II-36 to II-46, wherein the LNP comprises between about 20% and about 40% cholesterol.

Embodiment II-48. The composition of any one of embodiments II-36 to II-46, wherein the LNP is substantially free of cholesterol.

Embodiment II-49. The composition of any one of embodiments II-36 to II-48, wherein the LNP comprises an insulator lipid.

Embodiment II-50. The composition of any one of embodiments II-36 to II-48, wherein the LNP is substantially free of insulator lipids.

Embodiment II-51. The composition of any one of embodiments II-36 to II-50, wherein the LNP preferentially delivers to and/or transfects the lung compared to liver.

Embodiment II-52. The composition of any one of embodiments II-36 to II-51, wherein the polynucleotide is a synthetic ribonucleic acid (RNA).

Embodiment II-53. The composition of embodiment II-52, wherein the synthetic ribonucleic acid (RNA) encodes telomerase reverse transcriptase (TERT).

Embodiment II-54. The composition of embodiment II-53, wherein the TERT synthetic RNA comprises at least one modified nucleoside from the list in Table 2.

Embodiment II-55. The composition of embodiment II-54, wherein the modified nucleoside is pseudouridine or a pseudouridine analog.

Embodiment II-56. The composition of embodiment II-54, wherein the pseudouridine analog is N-1-methylpseudouridine.

Embodiment II-57. The composition of embodiments II-53 to II-56, wherein the TERT synthetic RNA comprises an untranslated region (UTR).

Embodiment II-58. The composition of any one of embodiments II-53 to II-57, wherein the wherein the TERT synthetic RNA comprises a 5' cap structure, wherein the 5' cap structure ism7(3'OMeG)(5')ppp(5')(2'OMeA)pG, IRES, Cap0, Cap1, ARCA, inosine, N1-methyl-guanosine, 2' fluoro-guanosine, 7-deaza-guanosine, CleanCap™, 8-oxo-guanosine, 2-amino-guanosine, LNA-guanosine, 2-azido-guanosine, Cap2, Cap4, CAP-003, or CAP-225.

Embodiment II-59. The composition of any one of embodiments II-53 to II-58, wherein the TERT synthetic RNA comprises a poly-adenosine (poly-A) nucleotide sequence 3' to the encoding region.

Embodiment II-60. The composition of any one of embodiments II-53 to II-59, wherein the TERT synthetic RNA comprises a chain terminating nucleotide, wherein the nucleotide is 3'-deoxyadenosine (cordycepin), 3'-deoxyuridine, 3'-deoxycytosine, 3'-deoxyguanosine, 3'-deoxythymine, 2',3'-dideoxynucleosides, 2',3'-dideoxyadenosine, 2',3'-dideoxyuridine, 2',3'-dideoxycytosine, 2',3'-dideoxyguanosine, 2',3'-dideoxythymine, a 2'-deoxynucleoside, or —O-methylnucleoside.

Embodiment II-61. The composition of any one of embodiments II-53 to II-60, wherein the TERT synthetic RNA is codon optimized.

Embodiment II-62. Use of the composition of any one of embodiments II-36 to II-61, for the treatment of lung fibrosis in a subject in need thereof.

Embodiment II-63. Use of the composition according to embodiment II-62, wherein the lung fibrosis is associated with a lung disease, and wherein the lung disease is pulmonary fibrosis, familial pulmonary fibrosis, idiopathic pulmonary fibrosis, pulmonary fibrosis associated with dyskeratosis congenita, an interstitial lung disease, pneumonia, interstitial pneumonia, emphysema, or lung cancer.

Embodiment II-64. Use of the composition according to embodiment II-62 or II-63, wherein the lung fibrosis is associated with a TERT mutation in the subject.

Embodiment II-65. Use of the composition according to any of embodiments II-62 to 11-64, wherein the composition is administered to the subject via intravenous injection.

Embodiment II-66. A pharmaceutical composition comprising:

(i) a delivery vehicle comprising a ribonucleic acid (RNA) encoding telomerase reverse transcriptase (TERT); and (ii) and a pharmaceutically acceptable solvent or excipient;

wherein the delivery vehicle is capable of preferentially delivering to and/or transfecting lung cells.

Embodiment II-67. The pharmaceutical composition of embodiment II-66, wherein the delivery vehicle is an LNP.

Embodiment II-68. The pharmaceutical composition of embodiment II-67, wherein the LNP comprises:

(i) a cationic lipid in a molar percentage of between about 20% and about 50%; and (ii) a SS-OP or an SS-OP analog at a molar percentage of between about 20% and about 60%.

Embodiment II-69. The pharmaceutical composition of embodiment II-68, wherein the SS-OP analog is any one or more of SS-M, SS-E, SS-EC, SS-LC, and SS-OC.

Embodiment II-70. The pharmaceutical composition of embodiment II-68 or II-69, wherein the cationic lipid is any one or more of 2-Dioleoyl-3-Trimethylammonium-Propane (DOTAP), Dimethyldioctadecylammonium bromide (DDAB), Imidazole Cholesterol Ester (ICE), 25-Hydroxycholesterol (25 OH Chol), 20α-hydroxycholesterol 5-cholestene-3α, 20α-diol (20α Chol), N-[1-(2,3-dioleyloxy)propyl]-N,N,N-trimethylammonium chloride (DOTMA), 5-carboxyspermylglycinedioctadecylamide (DOGS), 2,3-dioleyloxy-N-[2(spermine-carboxamido)ethyl]-N,N-dimethyl-1-propanaminium (DOSPA), 1,2-Dioleoyl-3-Dimethylammonium-Propane (DODAP), 11,2-distearyloxy-N,N-dimethyl-3-aminopropane (DSDMA), 1,2-dioleyloxy-N,N-dimethyl-3-aminopropane (DODMA), 1,2-dilinoleyloxy-N,N-dimethyl-3-aminopropane (DLinDMA), dimethyldioctadecylammonium (DDA), 1,2-dilinolenyloxy-N,N-dimethyl-3-aminopropane (DLenDMA), N-dioleyl-N,N-dimethylammonium chloride (DODAC), N,N-distearyl-N,N-dimethylammonium bromide (DDAB), N-(1,2-dimyristyloxyprop-3-yl)-N,N-dimethyl-N-hydroxyethyl ammonium bromide (DMRIE), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethy 1-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 2,3-Dilinoleoyloxy-N,N-dimethylpropylamine (DLinDAP), 1,2-N,N'-Dilinoleylcarbamyl-3-dimethylaminopropane (DLincarbDAP), 1,2-Dilinoleoylcarbamyl-3-dimethylaminopropane or (DLinCDAP), 2,2-dilinoleyl-4-dimethylaminomethyl-[1,3]-dioxolane (DLin-K-DMA), 2,2-dilinoleyl-4-dimethylaminoethyl-[1,3]-dioxolane (DLin-K-XTC2-DMA), and mixtures thereof.

Embodiment II-71. The pharmaceutical composition of embodiment II-70, wherein the cationic lipid is DOTAP.

Embodiment II-72. The pharmaceutical composition of any one of embodiments II-68 to II-71, wherein the LNP comprises the cationic lipid at a molar percentage of between about 25% and about 35%.

Embodiment II-73. The pharmaceutical composition of any one of embodiments II-68 to II-71, wherein the LNP comprises the cationic lipid at a molar percentage of about 30%.

Embodiment II-74. The pharmaceutical composition of any one of embodiments II-68 to II-73, wherein the LNP comprises a structural lipid.

Embodiment II-75. The pharmaceutical composition of embodiment II-74, wherein the structural lipid is any one or more of 1,2-di-(9Z-octadecenoyl)-sn-glycero-3-phosphoethanolamine (DOPE), glycerol-monooleate (GMO), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanolamine (SOPE), cholesterol or another sterol, and mixtures thereof.

Embodiment II-76. The pharmaceutical composition of embodiment II-75, wherein the structural lipid is DOPC.

Embodiment II-77. The pharmaceutical composition of embodiment II-76, wherein the LNP comprises between about 1% and about 5% DOPC.

Embodiment II-78. The pharmaceutical composition of any one of embodiments II-68 to II-77, wherein the LNP is substantially free of structural lipids and/or comprises at most 1% structural lipids.

Embodiment II-79. The pharmaceutical composition of any one of embodiments II-68 to II-78, wherein the LNP comprises between about 20% and about 40% cholesterol.

Embodiment II-80. The pharmaceutical composition of any one of embodiments II-68 to II-78, wherein the LNP is substantially free of cholesterol.

Embodiment II-81. The pharmaceutical composition of any one of embodiments II-68 to II-80, wherein the LNP comprises an insulator lipid.

Embodiment II-82. The pharmaceutical composition of any one of embodiments II-68 to II-80, wherein the LNP is substantially free of insulator lipids.

Embodiment II-83. The pharmaceutical composition of any one of embodiments II-68 to II-82, wherein the LNP preferentially delivers to and/or transfects the lung compared to liver.

Embodiment II-84. The pharmaceutical composition of any one of embodiments II-66 to II-83, wherein the TERT synthetic RNA comprises at least one modified nucleoside from the list in Table 2.

Embodiment II-85. The pharmaceutical composition of embodiment II-84, wherein the modified nucleoside is pseudouridine or a pseudouridine analog.

Embodiment II-86. The pharmaceutical composition of embodiment II-85, wherein the pseudouridine analog is N-1-methylpseudouridine.

Embodiment II-87. The pharmaceutical composition of embodiments II-66 to II-86, wherein the TERT synthetic RNA comprises an untranslated region (UTR).

Embodiment II-88. The pharmaceutical composition of any one of embodiments II-66 to II-87, wherein the wherein the TERT synthetic RNA comprises a 5' cap structure, wherein the 5' cap structure is m7(3'OMeG)(5')ppp(5')(2'OMeA)pG, IRES, Cap0, Cap1, ARCA, inosine, N1-methyl-guanosine, 2' fluoro-guanosine, 7-deaza-guanosine, CleanCap™, 8-oxo-guanosine, 2-amino-guanosine, LNA-guanosine, 2-azido-guanosine, Cap2, Cap4, CAP-003, or CAP-225.

Embodiment II-89. The pharmaceutical composition of any one of embodiments II-66 to II-88, wherein the TERT synthetic RNA comprises a poly-adenosine (poly-A) nucleotide sequence 3' to the encoding region.

Embodiment II-90. The pharmaceutical composition of any one of embodiments II-66 to II-89, wherein the TERT synthetic RNA comprises a chain terminating nucleotide, wherein the nucleotide is 3'-deoxyadenosine (cordycepin), 3'-deoxyuridine, 3'-deoxycytosine, 3'-deoxyguanosine, 3'-deoxythymine, 2',3'-dideoxynucleosides, 2',3'-dideoxyadenosine, 2',3'-dideoxyuridine, 2',3'-dideoxycytosine, 2',3'-dideoxyguanosine, 2',3'-dideoxythymine, a 2'-deoxynucleoside, or —O-methylnucleoside.

Embodiment II-91. The pharmaceutical composition of any one of embodiments II-66 to II-90, wherein the TERT synthetic RNA is codon optimized.

Embodiment II-92. Use of the pharmaceutical composition of any one of embodiments II-66 to II-91, for the treatment of lung fibrosis in a subject in need thereof.

Embodiment II-93. Use of the pharmaceutical composition according to embodiment II-92, wherein the lung fibrosis is associated with a lung disease, and wherein the lung disease is pulmonary fibrosis, familial pulmonary fibrosis, idiopathic pulmonary fibrosis, pulmonary fibrosis associated with dyskeratosis congenita, an interstitial lung disease, pneumonia, interstitial pneumonia, emphysema, or lung cancer.

Embodiment II-94. Use of the pharmaceutical composition according to embodiment II-92 or II-93, wherein the lung fibrosis is associated with a TERT mutation in the subject.

Embodiment II-95. Use of the pharmaceutical composition according to any of embodiments II-92 to II-94, wherein the composition is administered to the subject via intravenous injection.

EXAMPLES

The following examples are included for illustrative purposes and are not intended to limit the scope of the disclosure.

Example 1: Lipid Nanoparticle Formulations

Compositions and methods of the disclosure may be used for delivery of cargo, such as a polynucleotide, by a delivery vehicle to lung cells. In some embodiments, the delivery vehicle is a lipid nanoparticle (LNP) as disclosed herein. In some embodiments, the LNPs disclosed herein are used for delivery of an mRNA to a population of lung cells.

Tables 6A-6B below show exemplary formulations for an LNP that can be used as a delivery vehicle, and Table 6C below shows example ranges of molar percentages for an LNP with classes of lipids that can be used as a delivery vehicle.

Figure 2:
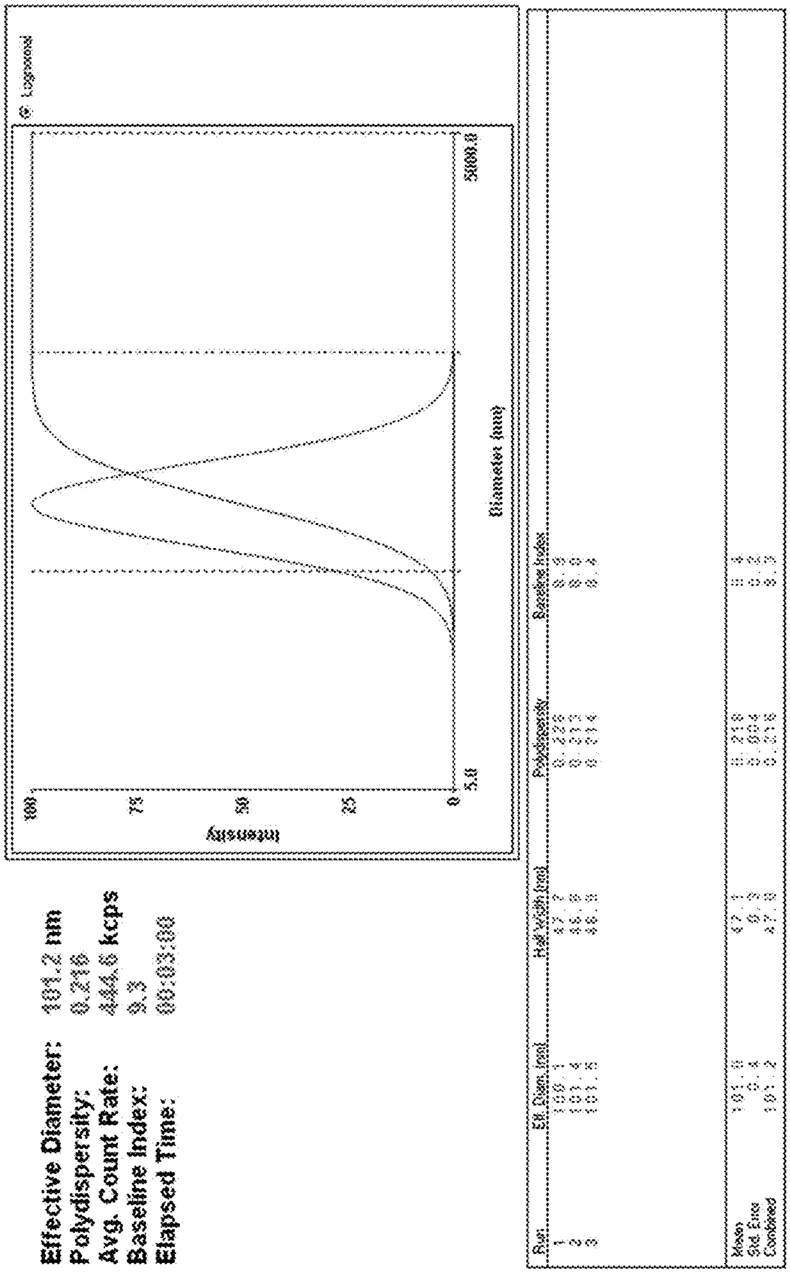
FIG. 2 depicts a representative dynamic light scattering (DLS) plot of the mRNA-LNPs made using exemplary lipid components disclosed here.

FIG. 2 depicts a representative dynamic light scattering (DLS) plot of the mRNA-LNPs made using the exemplary lipid components shown in Table 6A.

TABLE 6A

| Compound | | pK | Molar Ratio | Molar Percentage |
|---|---|---|---|---|
| SS-OP | Ionizable lipid | ~6.4 | 55 | 27.2% |
| DOPC | | | 5 | 2.5% |
| Cholesterol | | | 40 | 19.8% |
| DMG-PEG2000 | | | 2.5 | 1.2% |
| DOTAP | Cationic lipid | | 100 | 49.4% |

TABLE 6B

| Compound | Molar Ratio | Molar Percentage |
|---|---|---|
| cKK-E12 | 35 | 17.5% |
| DOPE | 16 | 8.0% |
| Cholesterol | 46.5 | 23.3% |
| 14:0 PEG2000 PE | 2.5 | 1.3% |
| DOTAP | 100 | 50.0% |

TABLE 6C

| Compound | Molar Percentage |
|---|---|
| Ionizable lipid | 10-50% |
| Structural lipid | 0-15% |
| Chole sterol | 0-40% |
| Insulator lipid | 0.2-6% |
| Cationic lipid | 20-80% |

Example 2: Intravenous Injection of mRNA-LNPs in Mice

Figure 3:
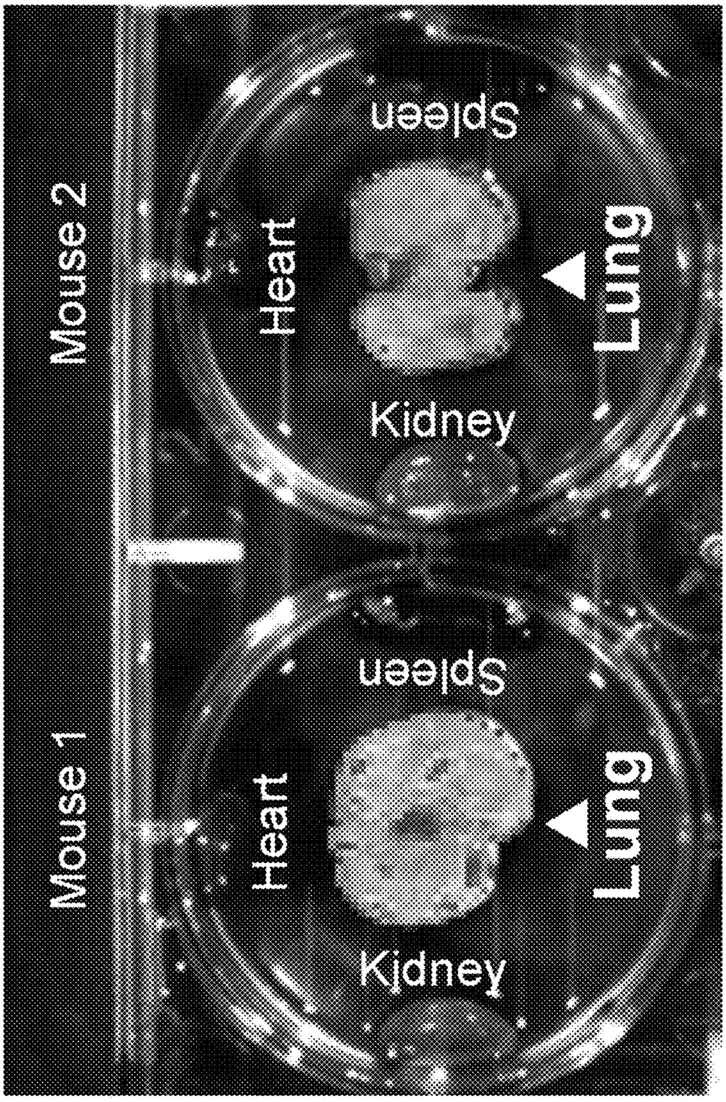
FIG. 3 depicts bioluminescent imaging of whole organs in mice that were injected with mRNA-LNPs.

FIG. 3 depicts bioluminescent imaging of whole organs in mice that were injected with mRNA-LNPs. mRNA-LNPs were prepared by formulated using microfluidic mixing, and were next processed by concentration and buffer exchange prior to injection. The organs were harvested and imaged 26 hours after the mice were dosed intravenously with Luciferase mRNA-LNPs at 0.6 mg/kg of total mRNA to body weight. The bioluminescent imaging demonstrates that the LNP delivery vehicles were capable of delivering mRNA cargo to the lung.

Example 3: mRNA Translation from Intravenous Injection in Mice

Figure 4A:
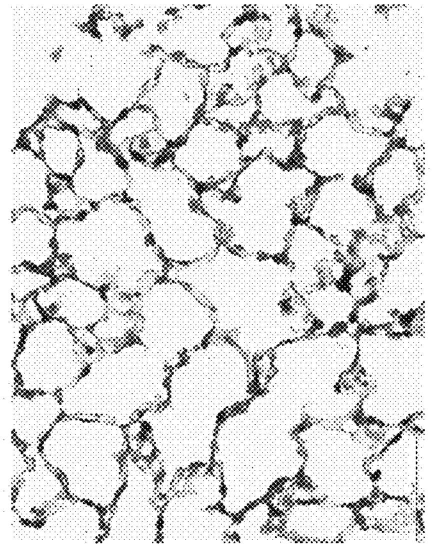
FIGS. 4A-4B depict immunohistochemistry staining for tdTomato in lung cells from a mouse treated with an mRNA reporter (FIG. 4A) and an untreated control mouse (FIG. 4B).
Figure 4B:
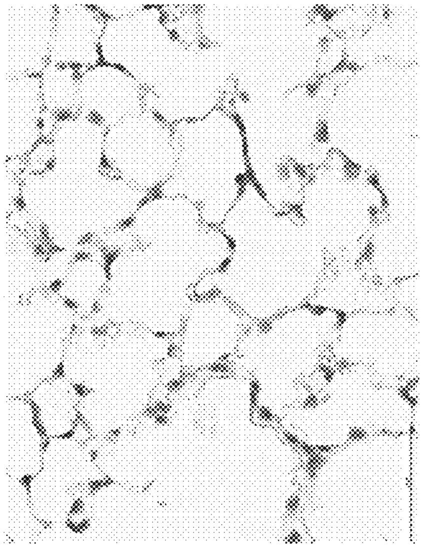

FIGS. 4A-4B depict immunohistochemistry staining for tdTomato in lung cells from a mouse treated with an mRNA reporter, and an untreated control mouse, respectively. tdTomato fl/fl mice were dosed intravenously with Cre mRNA LNPs at 0.6 mg/kg or saline. Lungs were harvested 4 days later. These figures demonstrate that in cells successfully targeted by Cre mRNA-LNP, Cre mRNA was translated and Cre recombinase excised the STOP codon allowing for tdTomato expression under the CAG promoter in the Rosa26 locus. In FIGS. 4A-4B, the scale bar is 50 μM.

Figures 5A, 5B:
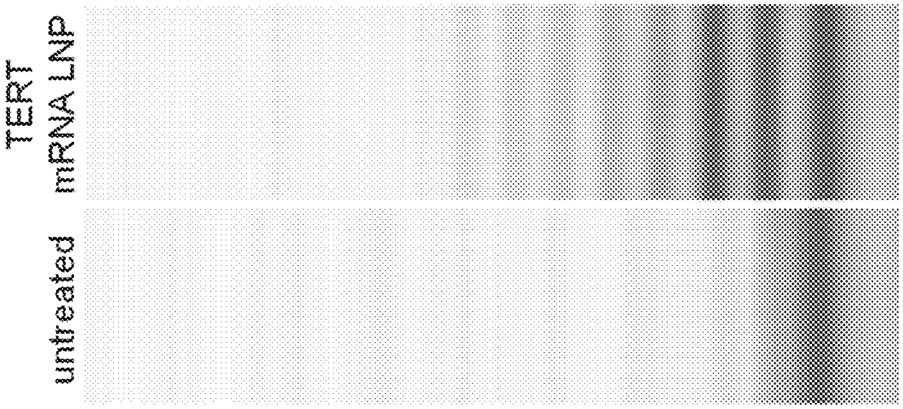
FIGS. 5A-5B depict measurements of telomerase activity in mouse lung after delivery of TERT mRNA-LNP (FIG. 5B) and in mouse lung of an untreated control (FIG. 5A).

Example 4: Telomerase Activity Measurements in Mouse Lung after TERT mRNA-LNA Delivery FIGS. 5A-5B depict measurements of telomerase activity in mouse lung after delivery of TERT mRNA-LNP, and in mouse lung of an untreated control, respectively. TERT knockout (KO) mice were dosed intravenously with TERT mRNA LNPs at 2.0 mg/kg and lungs were harvested 19 hours later. As a control, lungs were also harvested from an untreated TERT KO mouse. The telomere repeat amplification protocol (TRAP) was run on lung lysates. The banding pattern observed in the lung lysate of the TERT mRNA LNP treated mouse demonstrates that telomerase activity was present.

The TRAP assay was performed as follows. Protein lysate from cells or tissues was incubated with an artificial telomere (DNA oligonucleotide). If active telomerase is present, it extends the artificial telomere 6 bp at a time, producing a ladder pattern. This extension reaction is then amplified by PCR and run on a gel (Agilent bioanalyzer, using a microfluidic agarose gel). The presence of a ladder in 6 bp increments indicates telomerase activity.

Example 5: Transfection Efficiency of Lung Delivery Vehicle Formulation

Figure 6A:
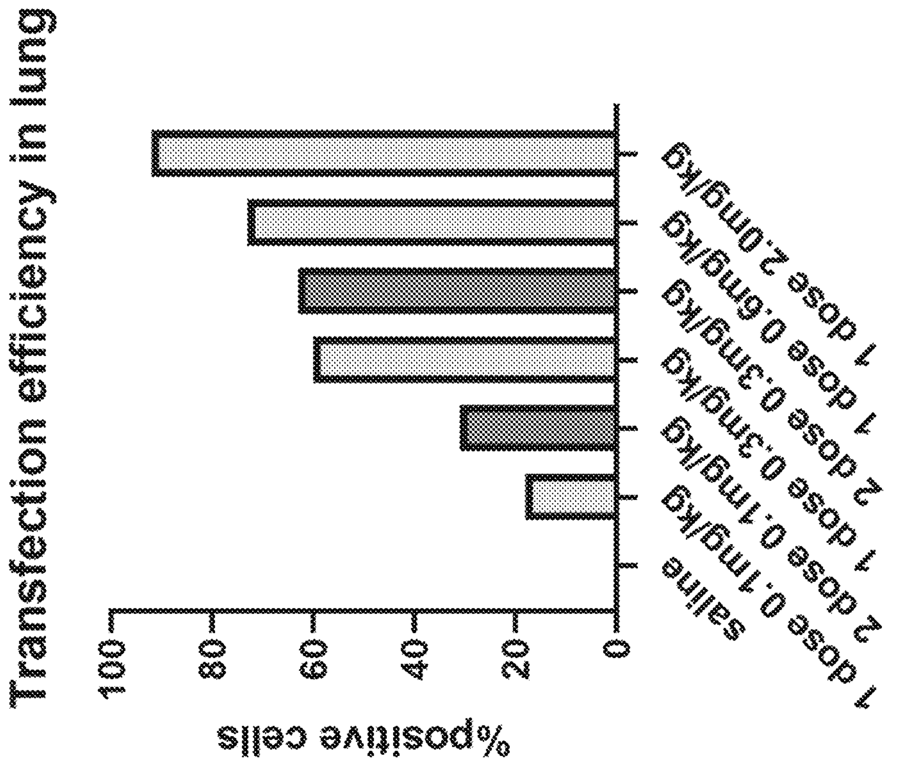
FIG. 6A is a bar graph depicting the transfection efficiency of an exemplary lung delivery vehicle formulation.
Figure 6B:
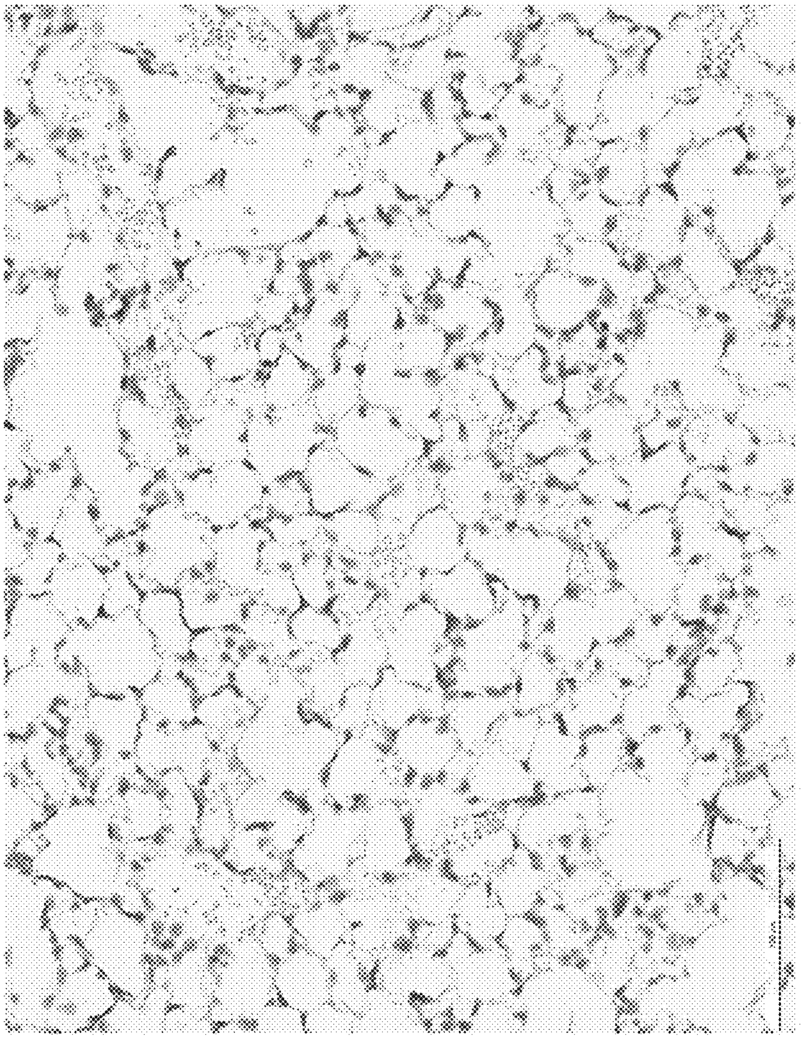
FIGS. 6B-6F depict representative images of lung sections harvested from the mice as described above, with the reporter protein shown as a darkened stain.
Figure 6C:
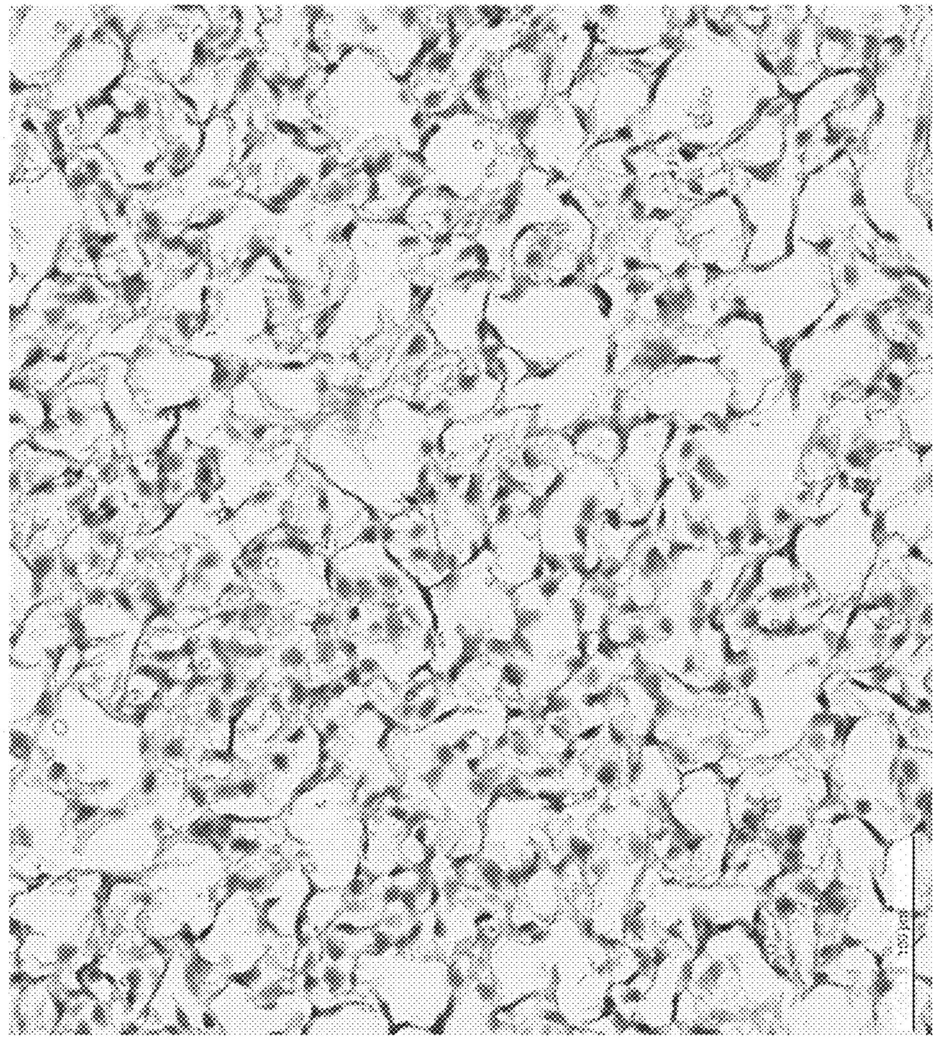
Figure 6D:
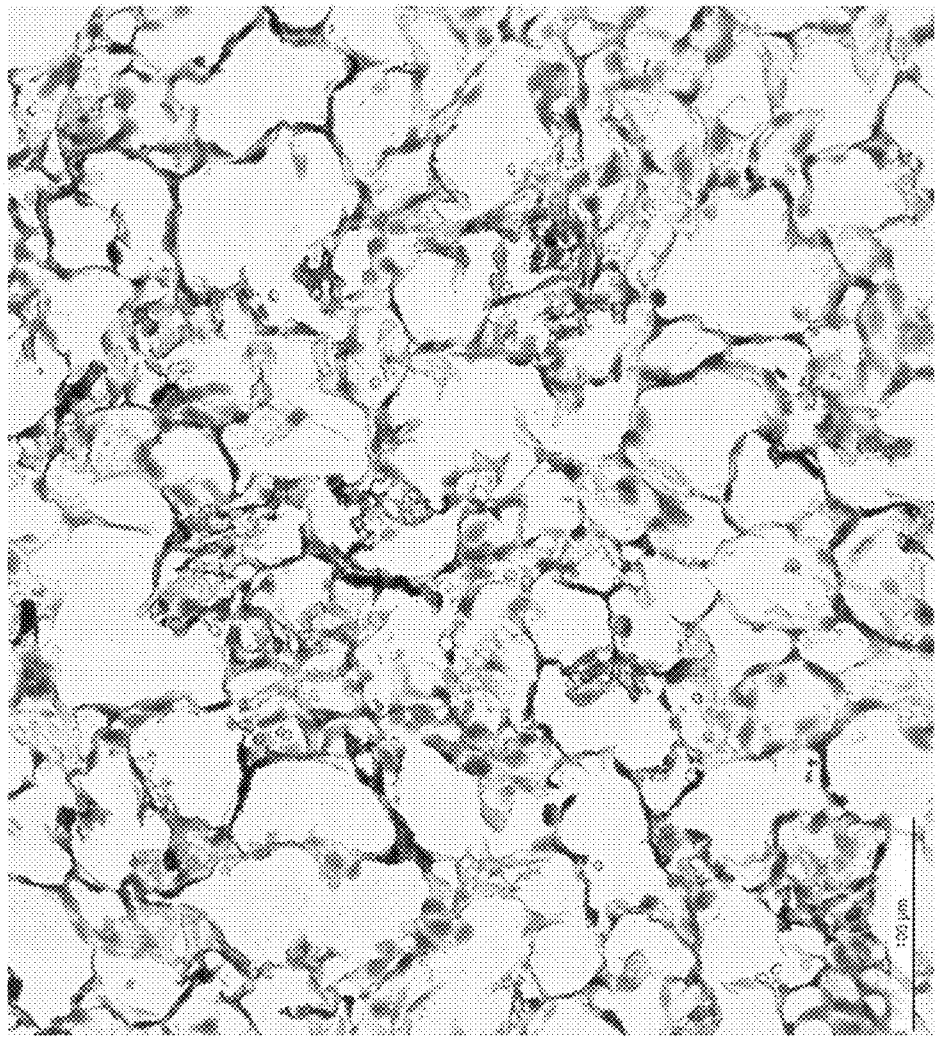
Figure 6E:
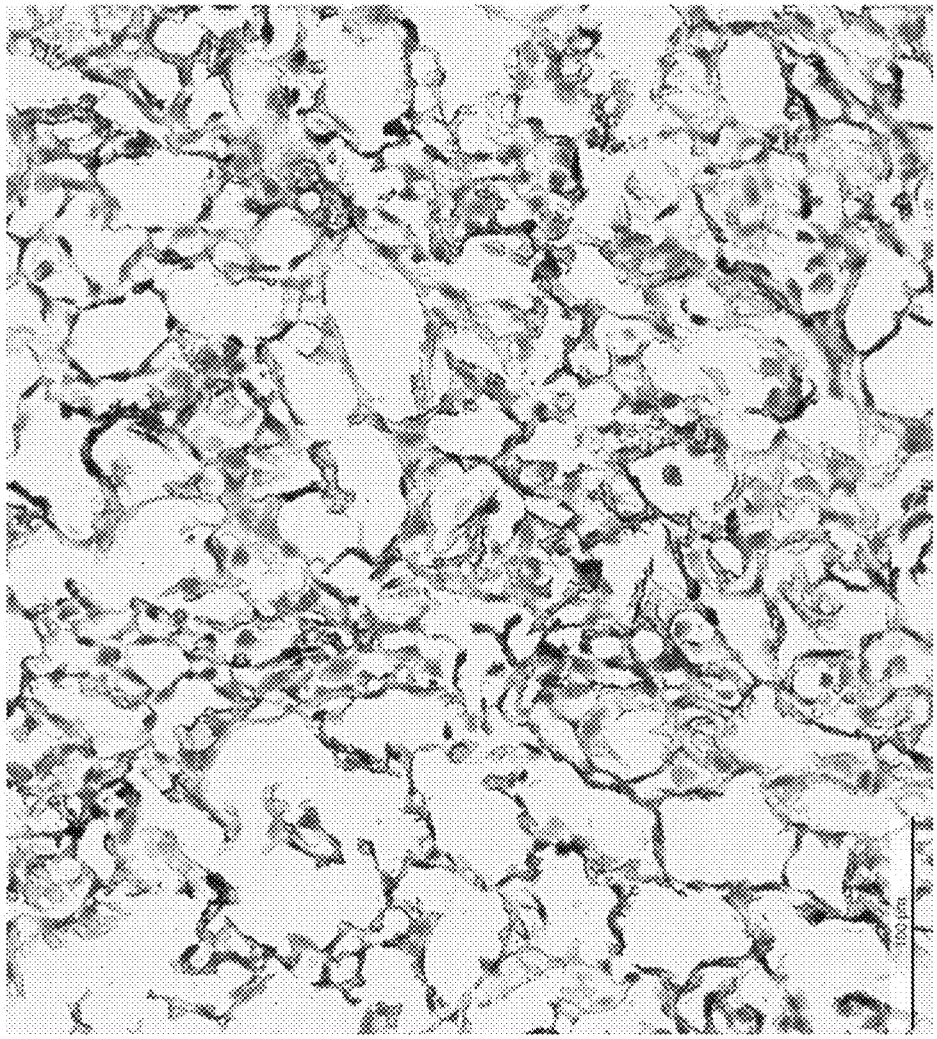
Figure 6F:
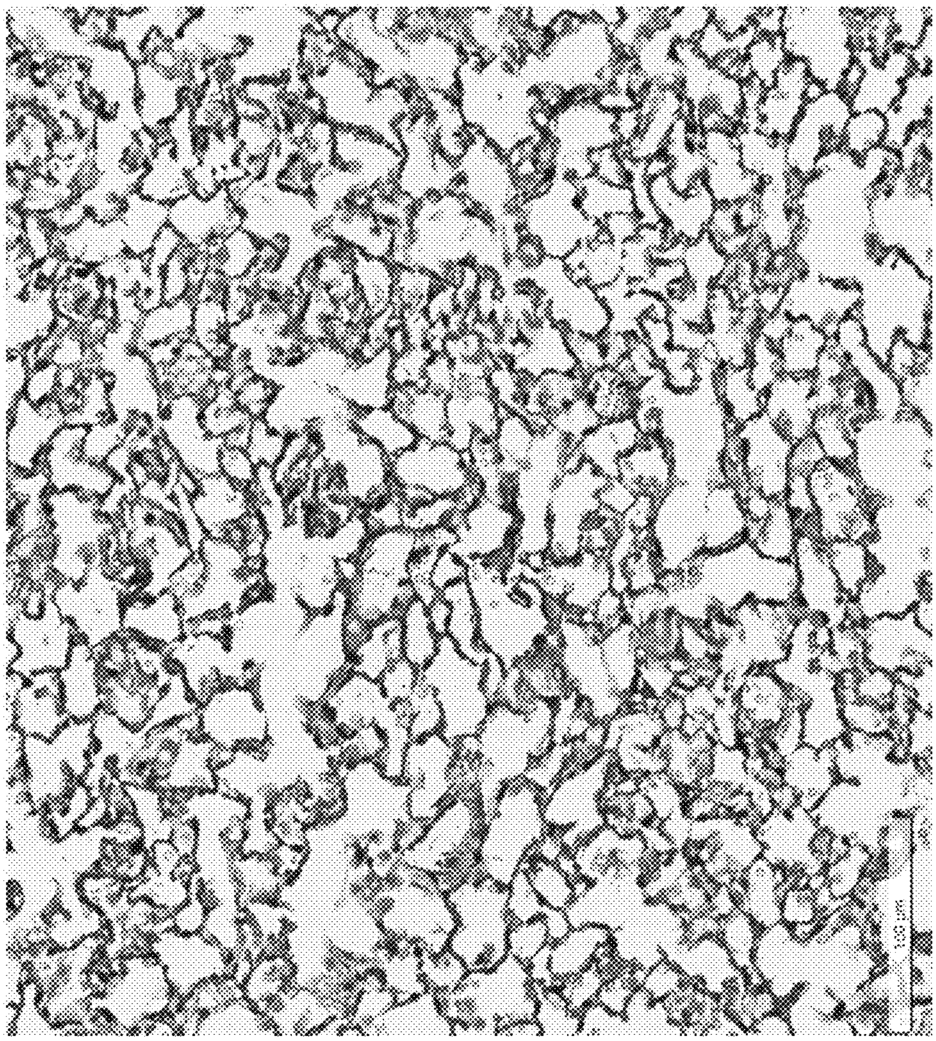

FIG. 6A is a bar graph depicting the transfection efficiency of an exemplary lung delivery vehicle formulation, as a function of Cre dose, number of doses, and genotype in mice. Cre mRNA complexed with the LNP lung vehicle of the Table 6A was delivered at the indicated doses via tail vein injection to mice carrying a tdTomato reporter gene that requires Cre to turn on. Lungs were harvested for histological analysis by immunostaining of the reporter gene. FIG. 6A demonstrates that the Cre mRNA LNPs formulation transfected the cells of the lung and turned on the reporter gene in a dose-dependent manner.

FIGS. 6B-6F depict representative images of lung sections harvested from the mice as described above, with the reporter protein shown as a darkened stain. Lung cells were harvested after treatment with saline control (FIG. 6B), 0.1 mg/kg (FIG. 6C), 0.3 mg/kg (FIG. 6D), 0.6 mg/kg (FIG. 6E), or 2.0 mg/kg (FIG. 6F) by body weight dose of the mRNA.

Example 6: Lung Fibrosis Treatment in Mice with TERT mRNA LNPs

Figures 7A, 7B, 7C:
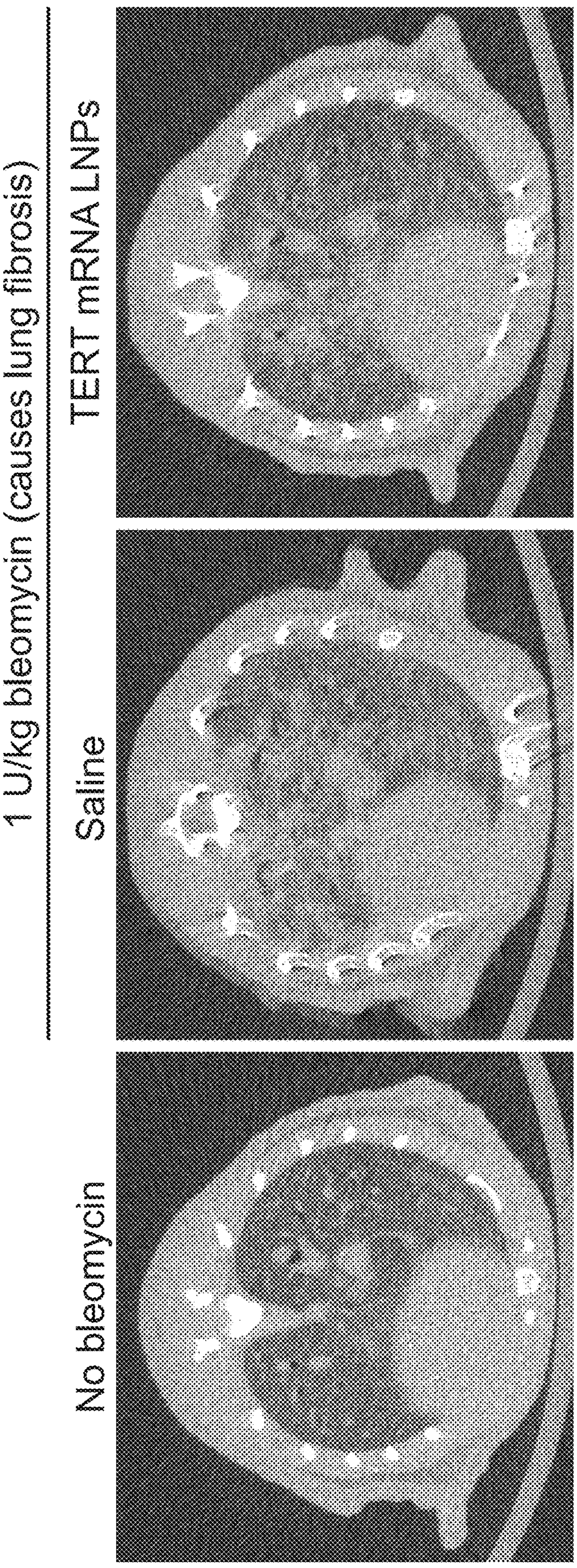
FIGS. 7A-7C depict computed tomography (CT) X-ray scans of mouse lungs tested for lung fibrosis.
Figure 7D:
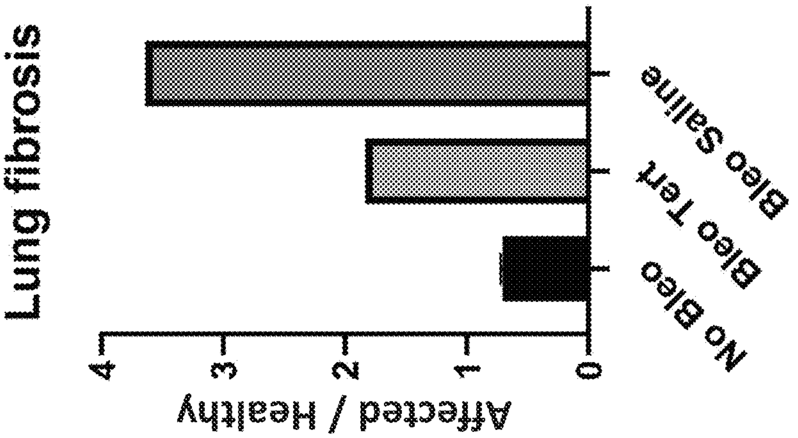
FIG. 7D is a bar graph quantifying the results shown in FIGS. 7A-7C.

FIGS. 7A-7C depict computed tomography (CT) X-ray scans of mouse lungs tested for lung fibrosis. Mice were instilled intratracheally with 1 U/kg of bleomycin on day 0 and injected intravenously with 0.6 mg/kg TERT mRNA LNPs or saline on days 4, 7, and 11. CT images were acquired two weeks later. FIG. 7A depicts a control with no bleomycin treatment, and FIGS. 7B-7C depict use of 1 U/kg bleomycin for inducing lung fibrosis. FIGS. 7B-7C were treated with saline and TERT mRNA LNPs, respectively. Healthy lung tissue appears darker, and fibrotic lung tissue appears lighter. Less fibrosis is shown in the TERT mRNA LNP-treated mouse than in the saline-treated control. These figures demonstrate the effect of treatment with TERT mRNA LNPs on fibrosis reduction in the bleomycin mouse model of pulmonary fibrosis.

Example 7: Reduction of Toxicity with Use of SS-OP DOTAP in Mice

Figure 8:
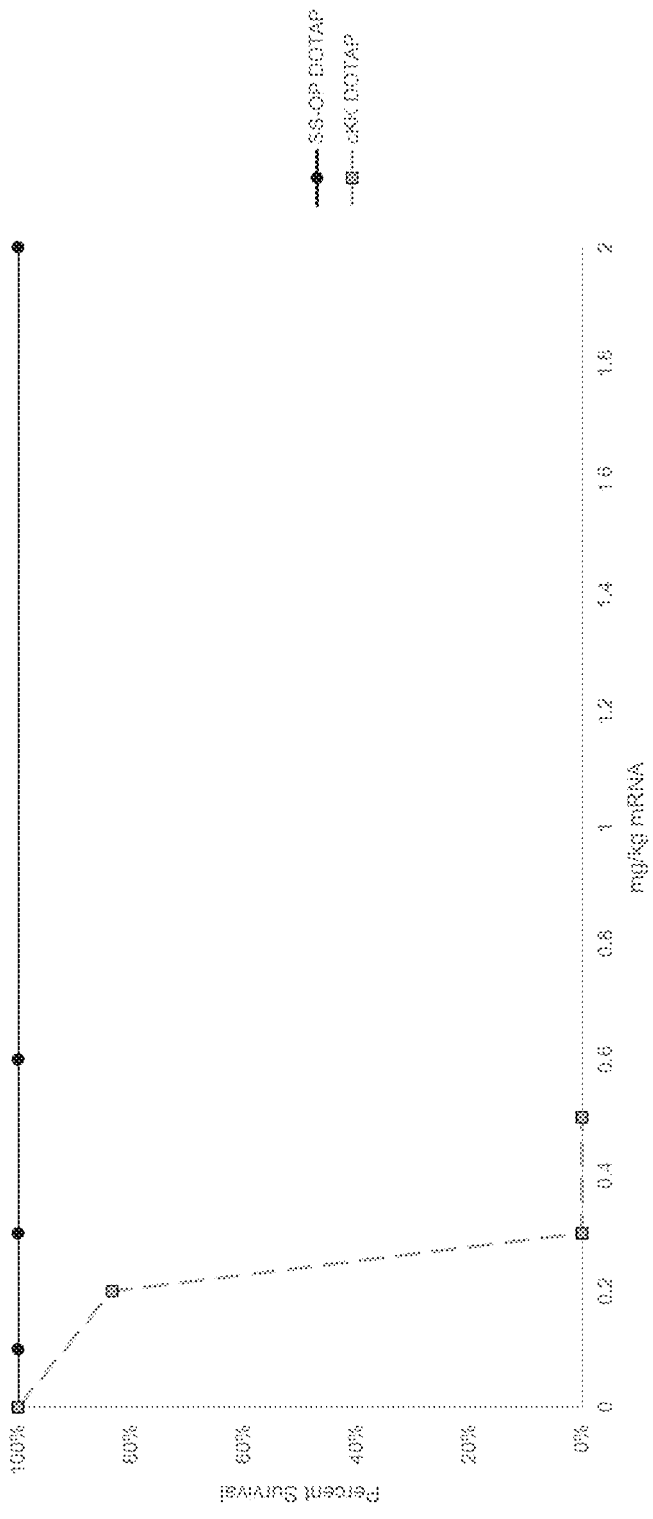
FIG. 8 depicts a graph showing the mortality of mice dosed with the formulation of Table 6A compared to other formulations of lung-targeted LNPs.
Figure 9A:
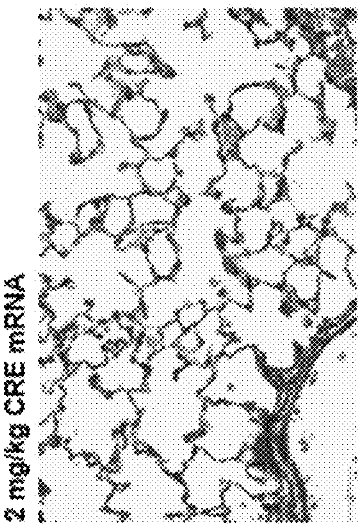
FIGS. 9A-9D depict various lung samples from mice treated with bleomycin for inducing lung fibrosis, and treated with CRE mRNA or saline to show delivery of the mRNA to alveolar cells.
Figure 9B:
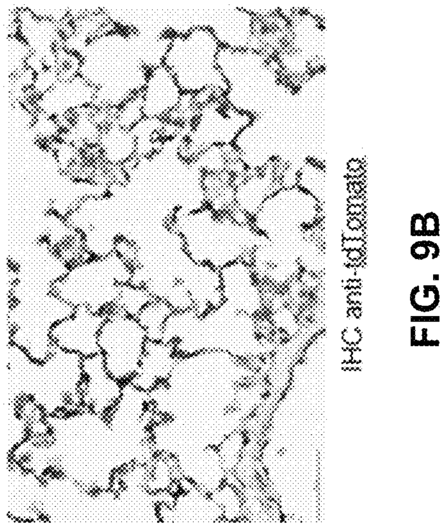
Figure 9C:
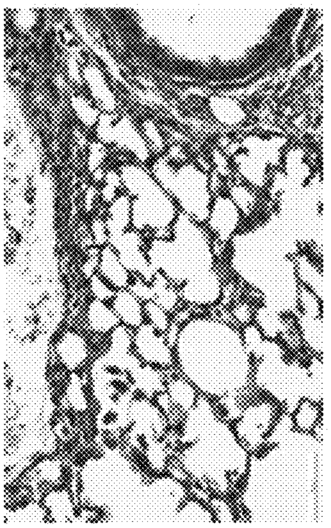
Figure 9D:
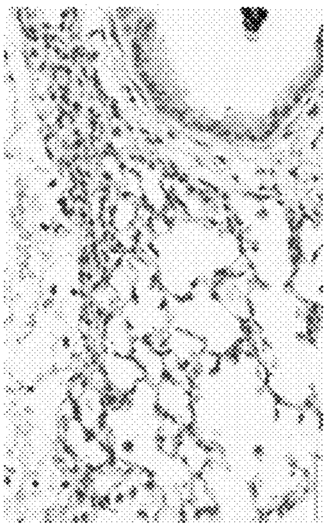

FIG. 8 depicts a graph showing the mortality of mice dosed with various formulations of lung-targeted LNPs. The C57Bl/6 mice were dosed with formulations of lung-targeted LNPs containing SS-OP and DOTAP, according to the exemplary formulation of Table 6A (N=2-12 per time point), or formulations of lung-targeted LNPs containing cKK DOTAP (N=2-4 per time point), according to the exemplary formulation of Table 6B. Mortality is shown as percent of mice that survived the acute treatment. Mice were dosed based on mg/kg of total reporter mRNA. These results demonstrate the improved tolerability and reduced toxicity rate of the exemplary formulation of Table 6A using SS-OP and DOTAP.

Example 8: Delivery of mRNA to Alveolar Cells in Mouse Fibrosis Model

FIGS. 9A-9D depict various lung samples from mice treated with bleomycin for inducing lung fibrosis, and treated with CRE mRNA or saline to show delivery of the mRNA to alveolar cells. Briefly, Ail4 (ROSA26 Lox-stop-lox tdTomato) mice were given 1 U/kg bleomycin via oral aspiration (OA) to induce fibrosis. On day 21 post-bleomycin, mice were dosed with saline or 2 mg/kg Cre mRNA, translation of which allows for tdTomato expression. At 3 days post-dosing (day 24), mice were sacrificed and the lungs were fixed by inflation with PFA. Lung sections were stained with anti-tdTomato antibody and trichrome. These results demonstrate that the Cre mRNA can be successfully delivered to alveolar cells even in mice with lung fibrosis, which can address the question of whether shunting of the LNP in a disease context affects mRNA delivery.

Example 9: Lung Delivery of mRNA by SS-OP DOTAP IV and OA Routes

Figure 10:
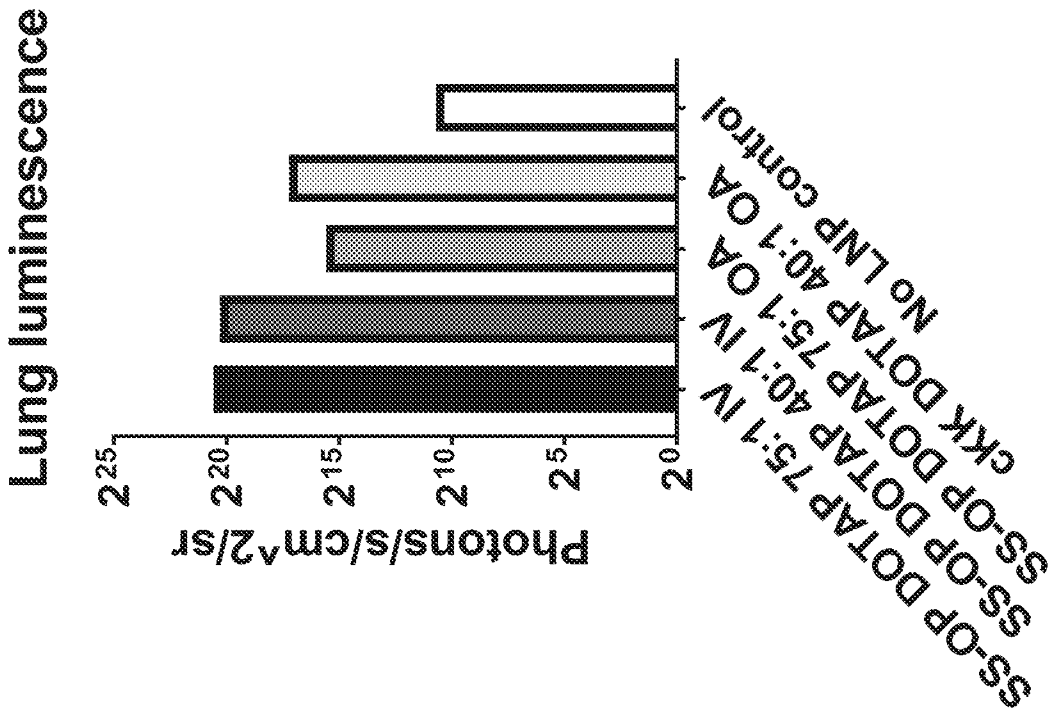
FIG. 10 shows the lung luminescence from intravenous (IV) and tracheal (OA) delivery of luciferase mRNA to the lung with SS-OP DOTAP and cKK DOTAP LNP formulations.
Figure 11:
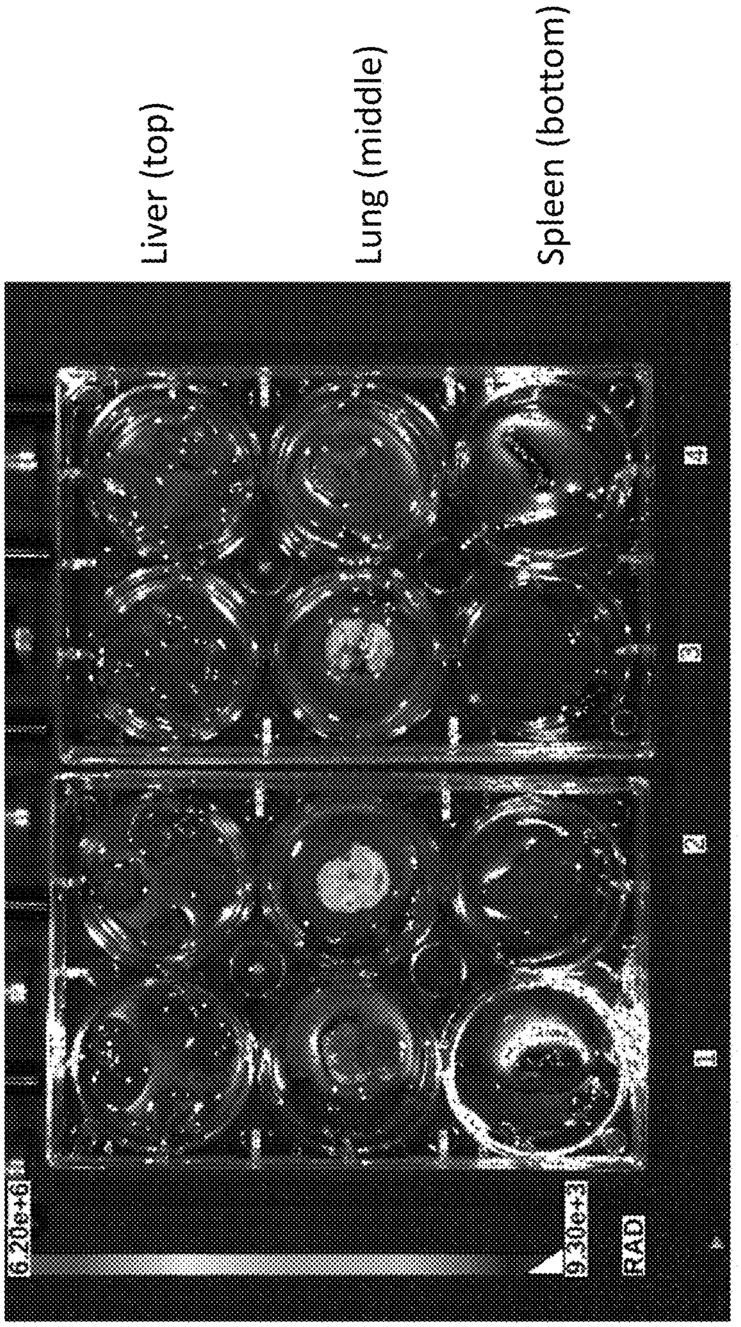
FIG. 11 shows preferential delivery to the lung of the SS-OP DOTAP formulation administered intravenously. From left to right the LNP formulations of the dish are (1) SS-OP DOTAP 75:1 delivered orally; (2) SS-OP DOTAP 75:1 delivered intravenously; (3) PBS control (no LNP); and (4) cKK DOTAP 40:1 delivered orally.

To compare intravenous and oral administration of SS-OP DOTAP LNP formulations, lipid nanoparticles (LNP) compositions encapsulating firefly luciferase (Luc) mRNA were formulated according to Tables 2A and 2B. The lipid to mRNA ratios (wt/wt) used in these experiments were 75:1 and 40:1. C57Bl/6 mice were dosed with the LNP-mRNAs at 0.5 mg/kg via intravenous injection (IV) or 0.2 mg/kg via oropharyngeal aspiration (OA). Lungs were imaged ex vivo 24 hours later. FIG. 10 shows the mean radiance of luciferase in the lung (photons/s/cm2/sr). Intravenous administration of the SS-OP DOTAP formulation provided significantly higher lung transfection (FIGS. 10 and 11) than through oral administration. Further, SS-OP DOTAP LNPs with a lipid:RNA ratio of either 75:1 or 40:1 lipid:RNA exhibited similar transfection efficiencies when dosed intravenously.

Example 10: Positively Charged Lipids Targeted mRNA to the Lung

Figure 12:
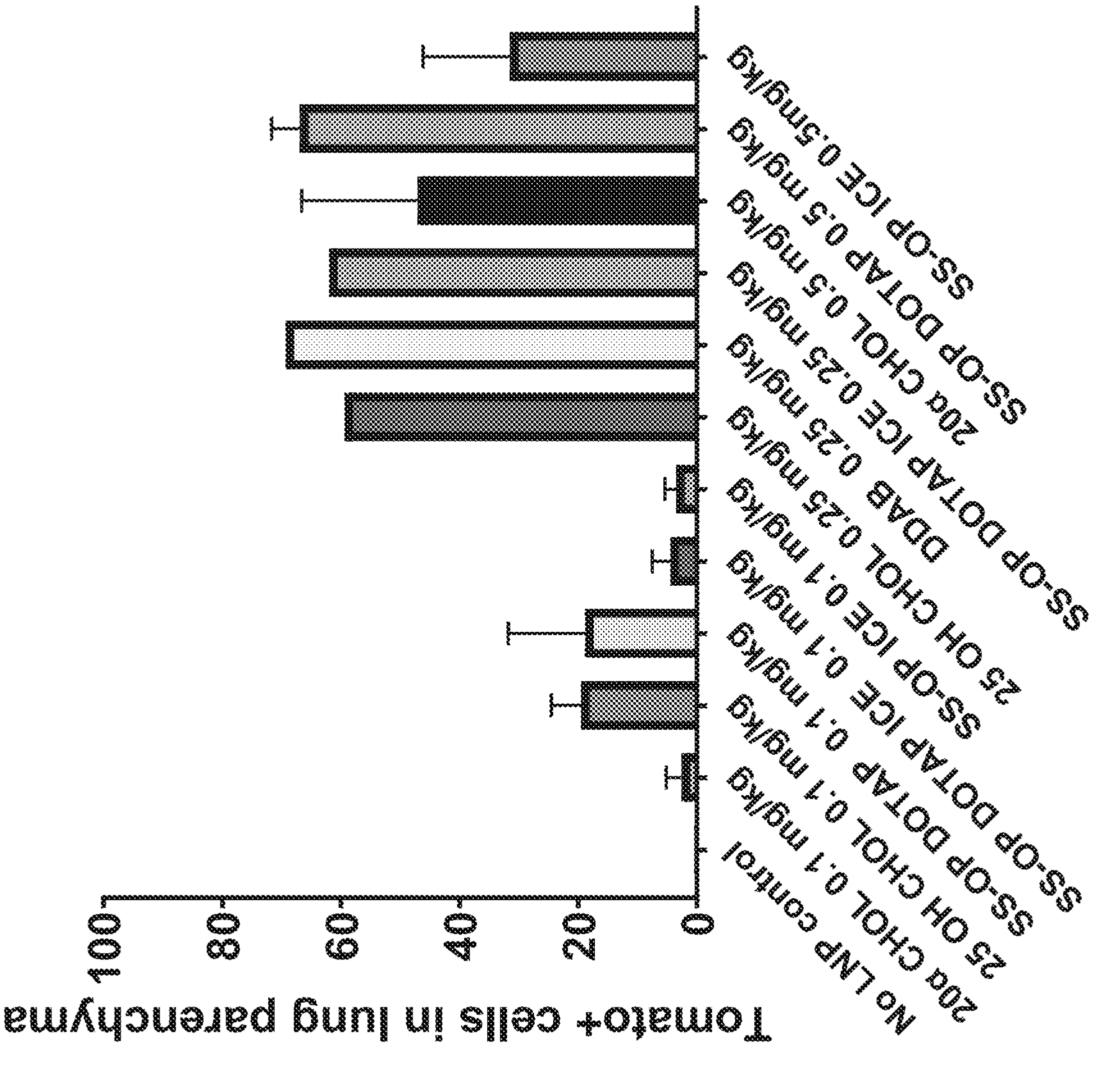
FIG. 12 shows the percentage of Tomato (+) cells in lung parenchyma with intravenous delivery of LNP formulations containing CRE mRNA.

To compare SS-OP LNP formulations with other cationic lipids, Tomato fl/fl mice were dosed with various LNP formulations encapsulating Cre mRNA, delivered intravenously in a range of 0.1-0.5 mg/kg, as shown in FIG. 12. The lipid to mRNA ratio for the SS-OP DOTAP formulation, the SS-OP 20α Chol formulation, the SS-OP DDAB formulation, and the 25 OH Chol was 80 μmol lipid: 1 mg mRNA. The lipid to mRNA ratio for SS-OP ICE was 50:1. The lipid to mRNA ratio for the SS-OP DOTAP ICE formulation was 70:1. Lungs were harvested 3 days later and processed via formalin fixation and paraffin embedding. Positive cells were labeled with anti-tdTomato antibody. FIG. 12 shows the percent positive Tomato cells in the lung parenchyma.

The results of the transfection are shown in FIG. 12 Notably, other cationic lipids with a net positive charge at physiological pH (7.4) may be substituted for DOTAP, including positively charged forms of cholesterol (ICE) in an SS-OP LNP formulation. The tested LNP formulations are shown below in Tables 7-12.

TABLE 7

| SS-OP DOTAP | | |
|---|---|---|
| Compound | Molar Ratio | Percent |
| SS-OP | 55 | 27.2 |
| DOPC | 5 | 2.5 |
| Cholesterol | 40 | 19.8 |
| DMG-PEG2000 | 2.5 | 1.2 |
| DOTAP | 100 | 49.4 |

TABLE 8

| SS-OP ICE | | |
|---|---|---|
| Compound | Molar Ratio | Percent |
| SS-OP | 55 | 54.2 |
| DOPC | 5 | 4.9 |
| Cholesterol | 0 | 0 |
| ICE | 40 | 39.4 |
| DMG-PEG2000 | 1.5 | 1.5 |

TABLE 9

| SS-OP 20α Chol | | |
|---|---|---|
| Compound | Molar Ratio | Percent |
| SS-OP | 55 | 27.2 |
| DOPC | 5 | 2.5 |
| 20α Chol | 40 | 19.8 |
| DMG-PEG2000 | 2.5 | 1.2 |
| DOTAP | 100 | 49.4 |

TABLE 10

| SS-OP DDAB | | |
|---|---|---|
| Compound | Molar Ratio | Percent |
| SS-OP | 55 | 27.2 |
| DOPC | 5 | 2.5 |
| Cholesterol | 40 | 19.8 |
| DMG-PEG2000 | 2.5 | 1.2 |
| DDAB | 100 | 49.4 |

TABLE 11

| SS-OP 25 OH Chol | | |
|---|---|---|
| Compound | Molar Ratio | Percent |
| SS-OP | 55 | 27.2 |
| DOPC | 5 | 2.5 |
| 25 OH Chol | 40 | 19.8 |
| DMG-PEG2000 | 2.5 | 1.2 |
| DOTAP | 100 | 49.4 |

TABLE 12

| SS-OP DOTAP ICE | | |
|---|---|---|
| Compound | Molar Ratio | Percent |
| SS-OP | 55 | 30.2 |
| DOPC | 5 | 2.7 |
| ICE | 40 | 22 |
| Cholesterol | 20 | 11 |
| DMG-PEG2000 | 2.2 | 1.2 |
| DOTAP | 60 | 32.9 |

Figure 13:
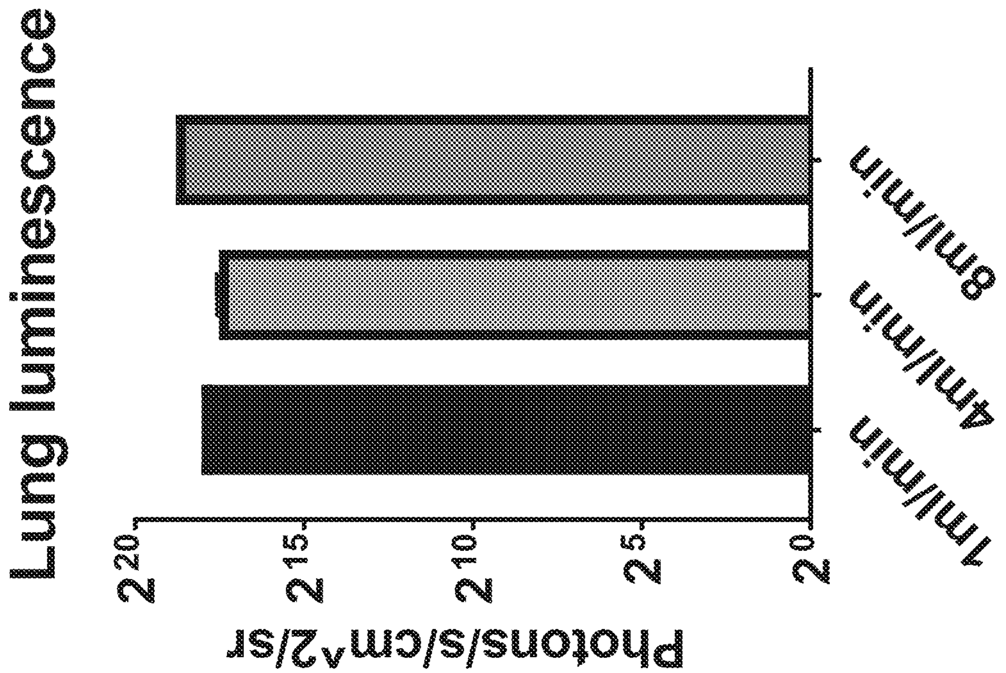
FIG. 13 shows lung luminescence relative to the flow rates used to formulate the LNP-compositions delivering firefly luciferase mRNA.

Example 11: Different Flow Rates for Formulation of mRNA LNP for Lung Delivery To compare flow rates for formulation of the SS-OP DOTAP LNP (Table 6A) encapsulation of mRNA, SS-OP DOTAP LNPs encapsulating luciferase mRNA were formulated per the ratios in Table 6A. The lipid:mRNA wt/wt ratio was 50:1. The aqueous (mRNA) to ethanol (lipid) flow ratio was 3:1. The overall flow rate was varied as shown in FIG. 13. C57Bl/6 mice were dosed at 0.1 mg/kg via intravenous injection, and lungs were imaged ex vivo 20 hours later. Shown is mean radiance of the lungs (photons/s/cm2/sr). The highest signal for SS OP DOTAP formulation was found with 8 ml/minute flow rate for LNP mRNA encapsulation (FIG. 13). Table 13 compares the flow rate to particle size, zeta potential and encapsulation efficiency of the SS OP DOTAP formulation of Table 6A.

TABLE 13

| Flow rate versus particle size, zeta potential and encapsulation efficiency | | | |
|---|---|---|---|
| Flow rate | Particle size | Zeta potential | Encapsulation |
| 1 ml/min | 69 | 41.8 | 95 |
| 4 ml/min | 73 | 30.8 | 96 |
| 8 ml/min | 52 | 17.3 | 95 |
| 12 ml/min | 54 | −2.6 | 94 |

Figure 14:
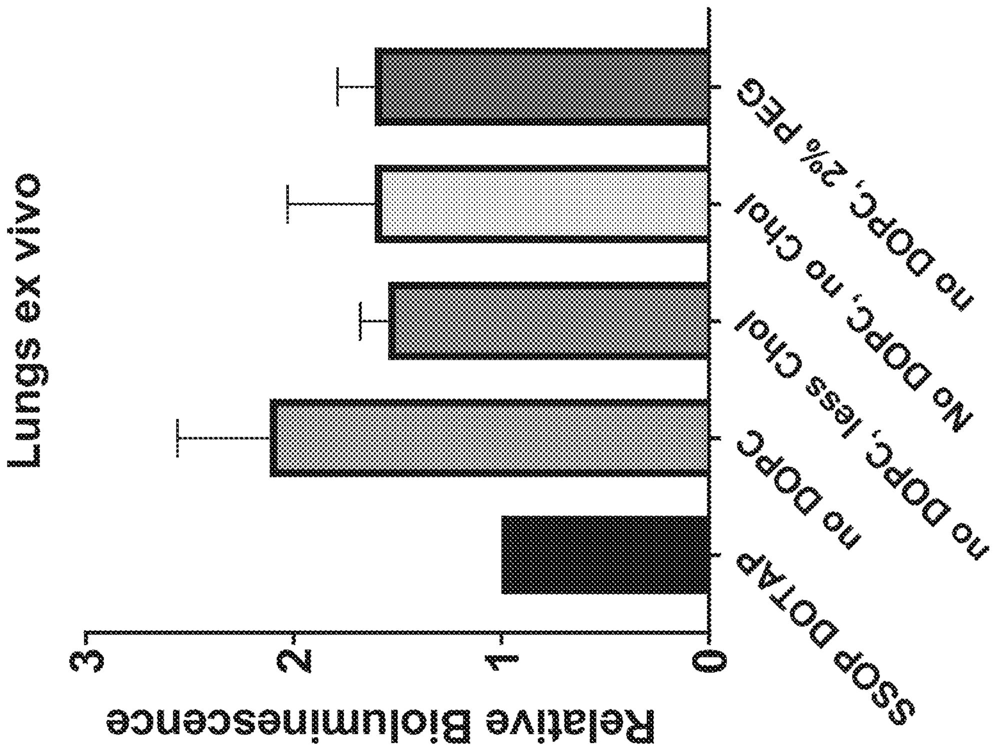
FIG. 14 shows the ex vivo bioluminescence of the LNP formulations delivering luciferase RNA, wherein no structural lipid or cholesterol was required for RNA delivery.

Example 12: DOPC and Cholesterol were not Required for SS-OP DOTAP LNP mRNA Delivery To determine the components of the SS-OP DOTAP LNPs necessary to transfect the lung, the SS-OP DOTAP LNP formulation of Table 6A was varied according to the formulas presented in Table 14 below. C57Bl/6 mice were dosed with the LNP formulations of Table 14, comprising luciferase mRNA, via intravenous injection, and lungs were imaged ex vivo 16 hours later. FIG. 14 shows the mean radiance of Luciferase activity in the lungs (photons/s/$cm^2$/sr) per the formulation. Notably, neither a neutral lipid, e.g., DOPC nor cholesterol were required for lung transfection with an SS-OP DOTAP LNP formulation. Table 14 shows the tested SS-OP DOTAP formulations, with and without DOPC and/or cholesterol.

TABLE 14

| SS-OP DOTAP formulations without DOPC and/or cholesterol | | | | | | | | |
|---|---|---|---|---|---|---|---|---|
| Mix No. | SS-OP | DOPC | Cholesterol | DMG-PEG2000 | DOTAP | Name | DOTAP % | PEG % |
| 1 | 55 | 5 | 40 | 2.5 | 100 | SSOP DOTAP | 49.4% | 1.2% |
| 2 | 55 | 0 | 40 | 2.5 | 95 | no DOPC | 49.4% | 1.3% |
| 3 | 55 | 0 | 20 | 2.5 | 75 | no DOPC, less Chol | 49.2% | 1.6% |
| 4 | 55 | 0 | 0 | 2.5 | 55 | no DOPC, no Chol | 48.9% | 2.2% |
| 5 | 55 | 0 | 40 | 4 | 95 | no DOPC, 2% PEG | 49.0% | 2.1% |

Example 13: Varying mRNA:Lipid Ratio Showed Differential Activity

Figure 15:
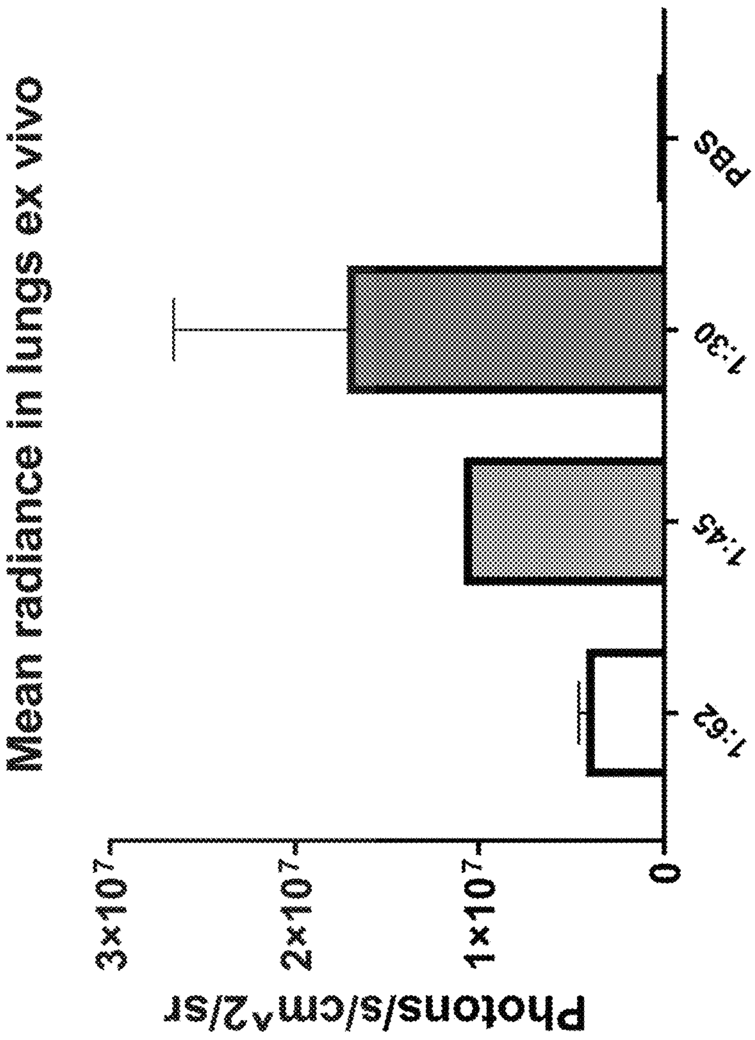
FIG. 15 shows the ex vivo lung mean radiance of LNP formulations delivering luciferase mRNA, wherein the RNA to LNP ratio was varied according to the ratios shown.

To determine the association of mRNA delivery with the ratio of mRNA to lipids, SS-OP DOTAP LNPs according to the formulation of Table 6A, and comprising the luciferase mRNA in an mRNA:lipid ratio (wt/wt) of 1:62, 1:45, and 1:30 were dosed intravenously in C57Bl/6 mice. Mice were dosed via intravenous injection at 1.5 mg/kg, and lungs were imaged ex vivo 26 hours later. FIG. 15 shows that mRNA:lipid ratios of 1:30 through 1:62 were the best performing mRNA:lipid ratios, with 1:30 exhibiting the highest bioluminescence.

SS-OP DOTAP LNPs without DOPC and comprising firefly luciferase (Luc) mRNA at varied ratios were injected intravenously in C57Bl/6 mice at a dose of 1.5 mg/kg. Lungs were imaged ex vivo 26 hours later. Shown is mean radiance of the lungs (photons/s/cm2/sr).

Figure 16:
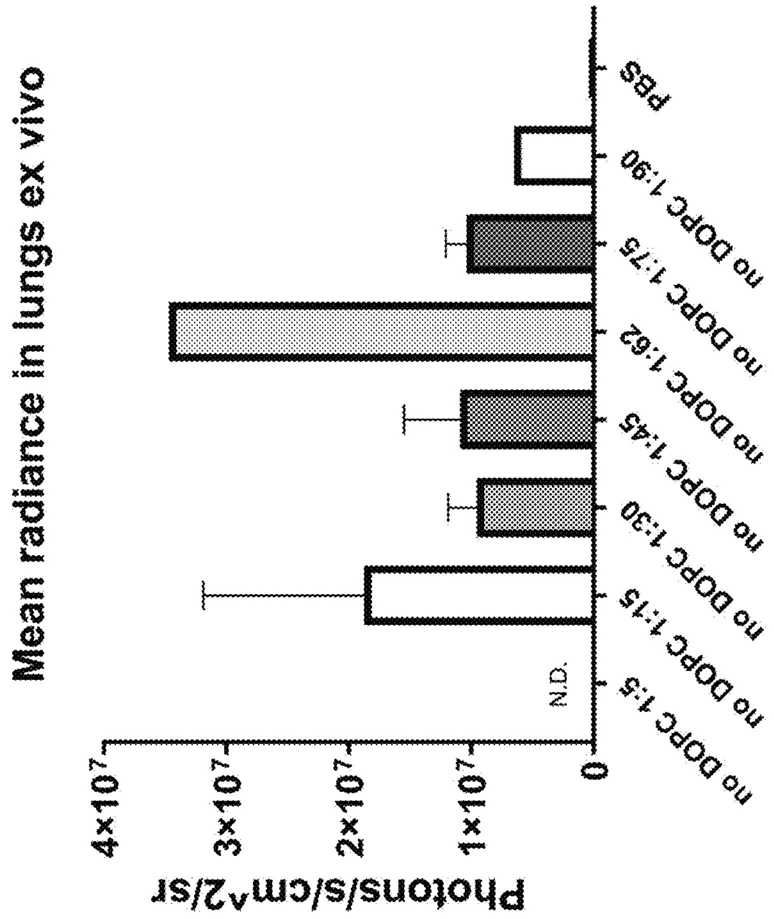
FIG. 16 shows the ex vivo lung mean radiance of LNP formulations delivering luciferase mRNA, wherein the RNA to LNP ratio was varied according to the ratios shown, and no DOPC structural lipid was used in the formulation.

LNPs were not formed with an mRNA:lipid ratio of 1:5 (N.D. refers to not dosed). In these SS-OP DOTAP LNP formulations without DOPC, the mRNA:lipid ratio of 1:62 exhibited the highest luciferase signal (FIG. 16).

Example 14: Varying PEGylated Lipid Percent Showed Differential Activity

Figure 17B:
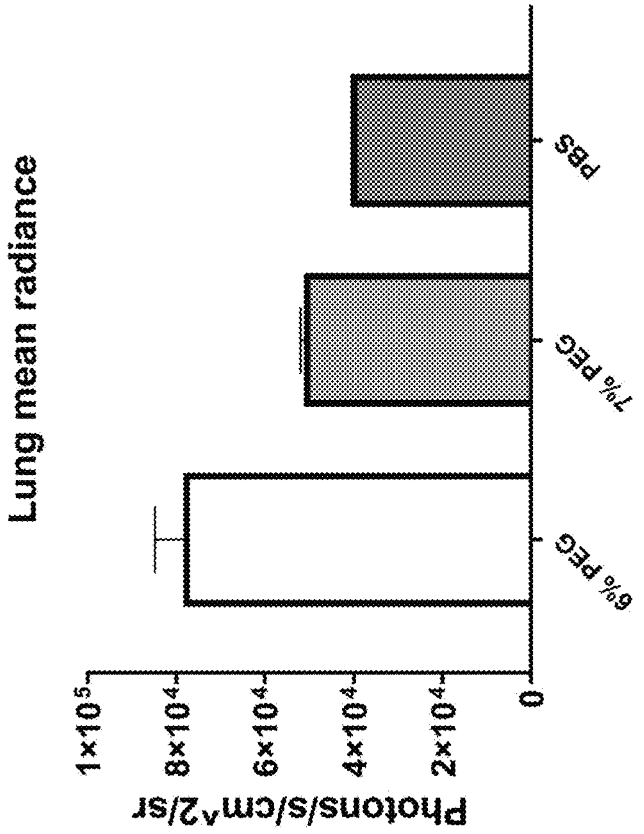
FIGS. 17A and 17B show the ex vivo lung mean radiance of the LNP formulations delivering luciferase mRNA, wherein the percentage of PEGylated lipid is varied in the formulation.
Figure 17A:
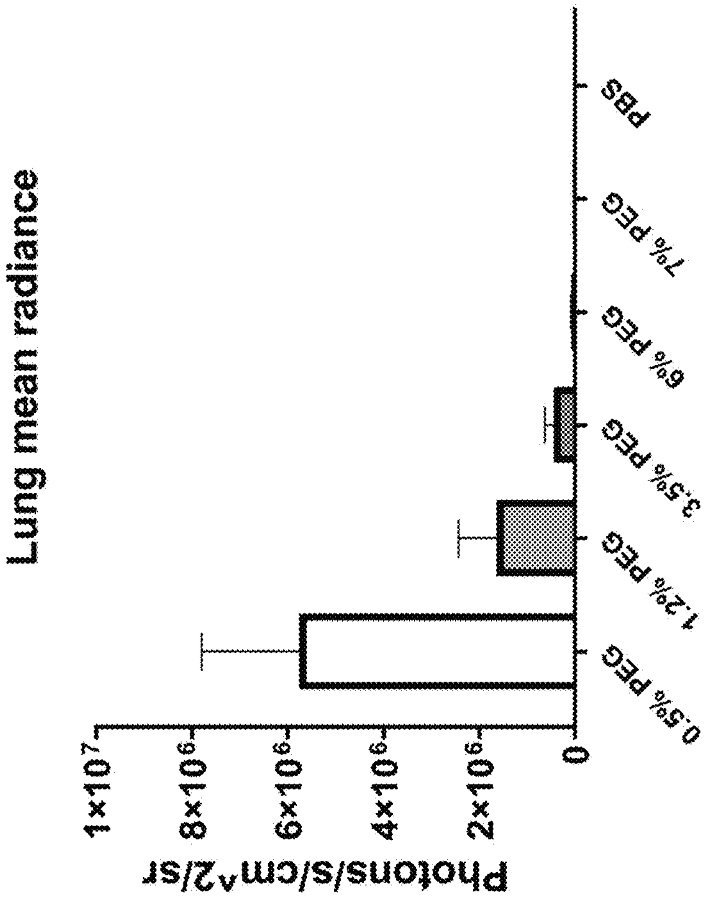

To determine the effects of the percent PEGylated lipid on SS-OP DOTAP LNPs delivery of mRNA, LNPs were formulated per the ratios in Table 15 below with luciferase mRNA and were administered intravenously to C57Bl/6 mice in a dose of 1.5 mg/kg. Lungs were imaged ex vivo 19 hours later. FIGS. 17A and 17B show the mean radiance of the lungs (photons/s/$cm^2$/sr). It was observed that the bioluminescence signal decreased as PEG signal increased.

The optimal PEGylated lipid range for SS-OP DOTAP LNPw was found to be 0-3%, with 0.5% providing the best LNP delivery of mRNA (FIGS. 17A and 17B). Table 15 shows the SS-OP DOTAP formulations with varied percentage of PEGylated lipid.

TABLE 15

SS-OP DOTAP formulations with varied percentage of PEGylated lipid

| Name | SS-OP | DOPC | Cholesterol | DMG-PEG2000 | DOTAP | DOTAP % | PEG % | Lipid:mRNA wt/wt |
|---|---|---|---|---|---|---|---|---|
| 0.5% PEG | 55 | 5 | 40 | 1.0 | 100 | 50% | 0.5% | 62 |
| 1.2% PEG | 55 | 5 | 40 | 2.5 | 100 | 49% | 1.2% | 62 |
| 3.5% PEG | 55 | 5 | 40 | 7.3 | 100 | 48% | 3.5% | 63 |
| 6% PEG | 55 | 5 | 40 | 12.8 | 100 | 47% | 6.0% | 65 |
| 7% PEG | 55 | 5 | 40 | 15.0 | 100 | 47% | 7.0% | 66 |

Example 16: PEGylated Lipid is not Required for Lung Targeting

Figure 18B:
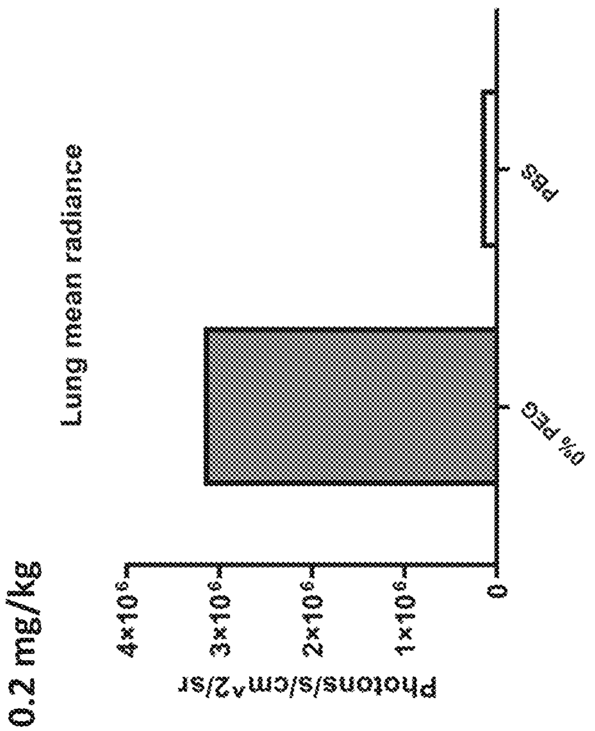
FIGS. 18A and 18B show the ex vivo lung mean radiance of the LNP formulations delivering luciferase mRNA, wherein the percentage of PEGylated lipid is below 1.5%, or not present in the formulation.
Figure 18A:
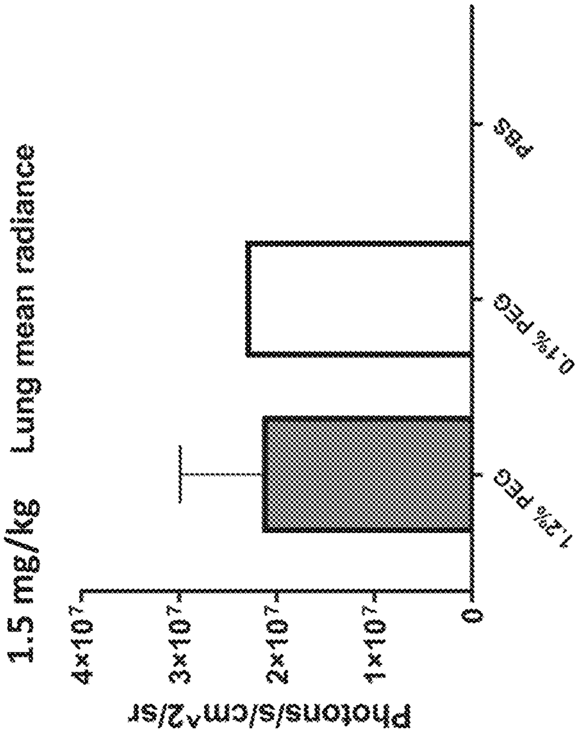

To determine whether PEGylated lipids were even required for SS-OP DOTAP LNP mRNA delivery, LNPs were formulated per the ratios in Table 16 below with luciferase mRNA. C57Bl/6 mice were dosed via intravenous injection and lungs were imaged ex vivo 21 hours later. The LNP-mRNA dose was 1.5 mg of mRNA per kg of animal mass for the 1.2% PEG and 0.10% PEG conditions. The lipid to mRNA ratio was 63. For the 0% PEG condition, the mice were dosed at 0.2 mg/kg. FIGS. 18A and 18B show the mean radiance of the lungs (photons/s/cm2/sr). These results demonstrate that SS-OP DOTAP LNP formulation containing 0.1-1.2% of a PEGylated may be optimal. However, LNP formulation without a PEGylated lipid successfully delivered mRNA to the lung. Table 16 shows the low and no PEGylated lipid SS-OP DOTAP formulations.

TABLE 16

Low and no PEGylated lipid SS-OP DOTAP formulations

| Lipid Mix | SSOP % | DOPC % | Cholesterol % | DMG-PEG2000 % | DOTAP % |
|---|---|---|---|---|---|
| 1.2% PEG | 38% | 3% | 27% | 1.2% | 30% |
| 0.1% PEG | 38% | 3% | 28% | 0.1% | 30% |
| 0% PEG | 38% | 3% | 28% | 0.0% | 30% |

Example 15: Varying DOTAP Percentage Shows Differential Lung Activity

Figure 19:
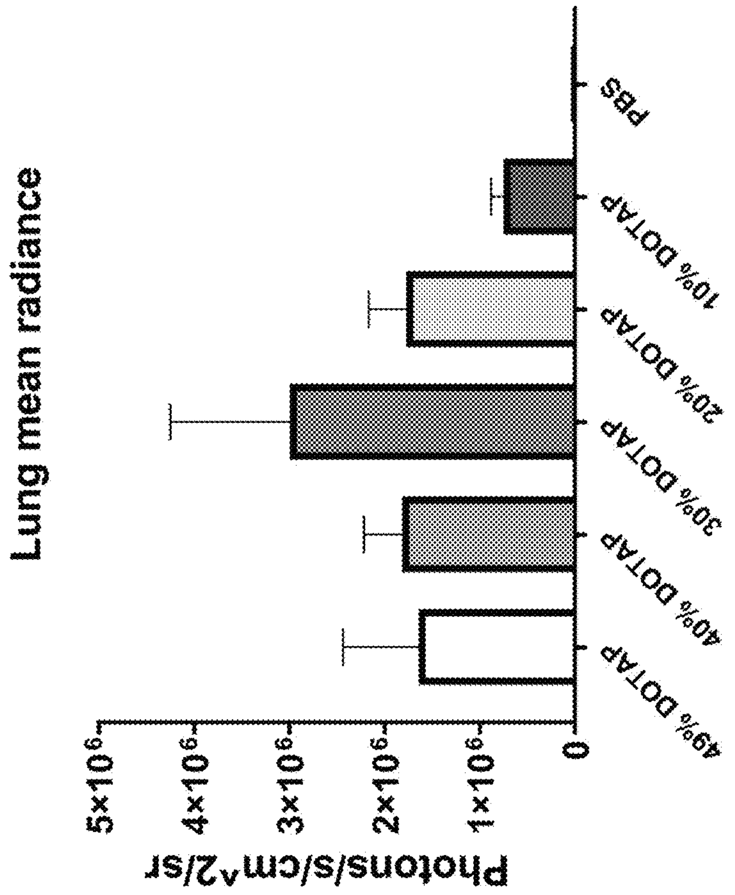
FIG. 19 shows the ex vivo lung mean radiance of the LNP formulations delivering luciferase mRNA, wherein the percentage of DOTAP is varied in the formulation.
Figure 20B:
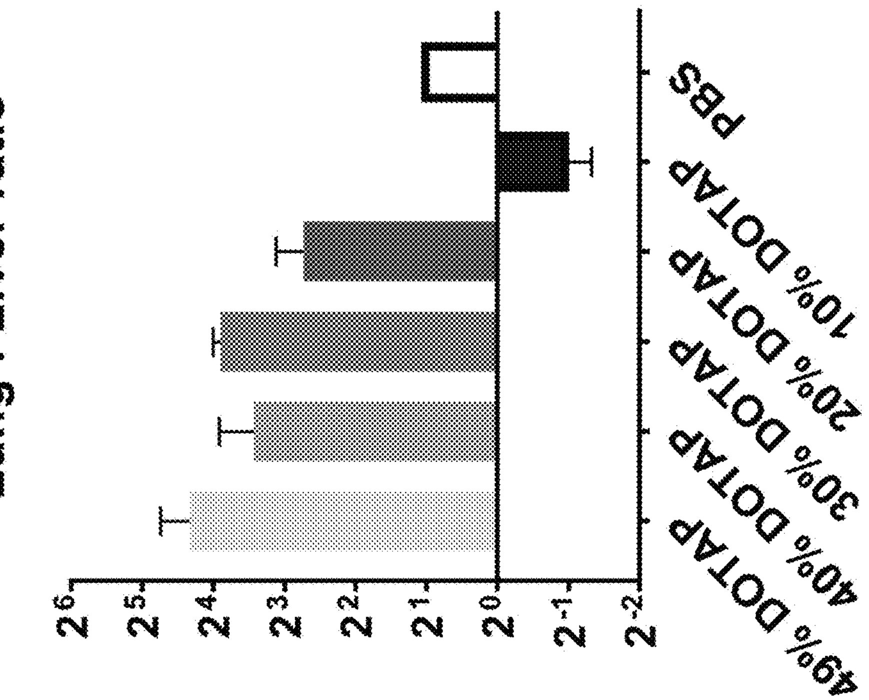
FIGS. 20A and 20B show the ex vivo preferential delivery to lung of example LNP formulations, wherein the percentage of DOTAP is varied.
Figure 20A:
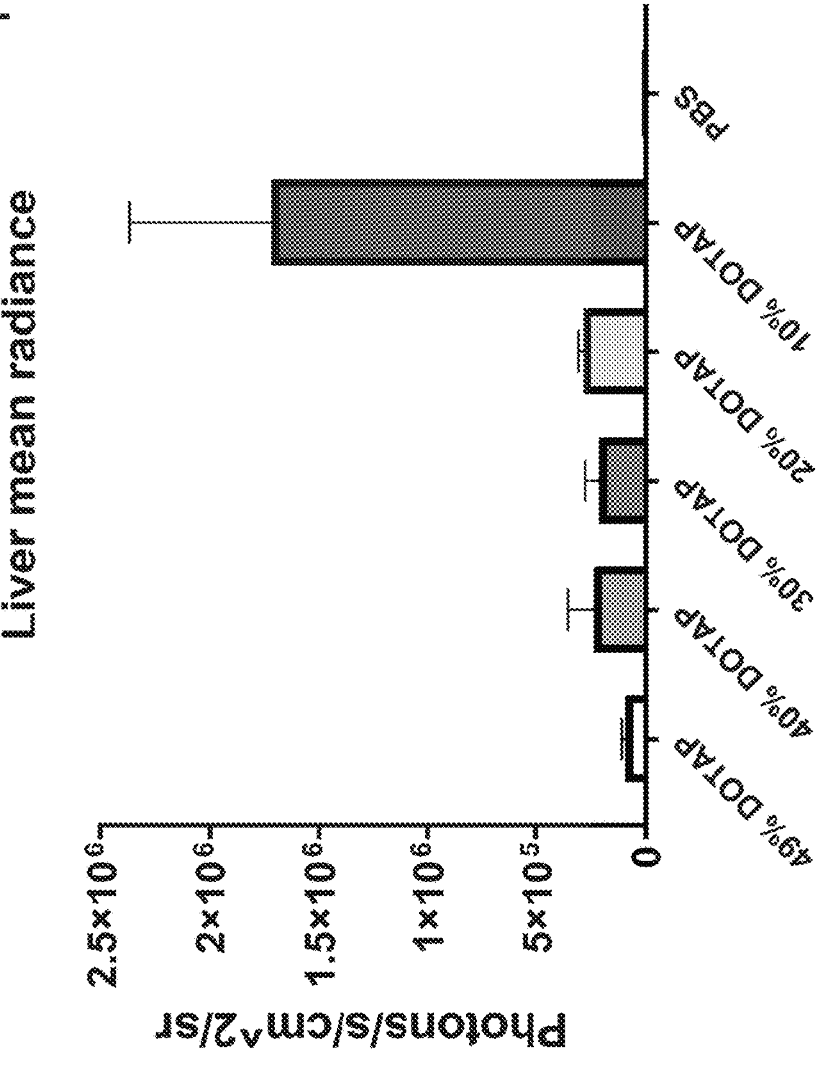

To determine the effects of varying DOTAP percentage on SS-OP DOTAP LNPs, SS-OP DOTAP LNPs were formulated with firefly luciferase (Luc) mRNA per the ratios in Table 17. C57Bl/6 mice were dosed via intravenous injection at 1.5 mg/kg, and lungs were imaged ex vivo 19 hours later. FIG. 19 shows the mean radiance of the lungs (photons/s/$cm^2$/sr) relative to the percentage of DOTAP in the LNP. The most effective delivery of SS-OP DOTAP LNPs to the lung, among the formulas in Table 17, was 30% DOTAP. Minimum liver targeting was observed for LNPs have 20% or greater DOTAP; whereas strong liver signal was seen with 10% DOTAP (FIGS. 20A and 20B). Table 17 shows the SS-OP DOTAP formulations with varied DOTAP percentage.

TABLE 17

| SS-OP DOTAP formulations with varied DOTAP percentage | | | | | | | | |
|---|---|---|---|---|---|---|---|---|
| Name | SS-OP | DOPC | Cholesterol | DMG-PEG2000 | DOTAP | DOTAP % | PEG % | Lipid:mRNA wt/wt |
| 49% DOTAP | 55 | 5 | 40 | 2.5 | 100 | 49% | 1.2% | 62 |
| 40% DOTAP | 55 | 5 | 40 | 2.5 | 69 | 40% | 1.5% | 53 |
| 30% DOTAP | 55 | 5 | 40 | 2.5 | 44 | 30% | 1.7% | 45 |
| 20% DOTAP | 55 | 5 | 40 | 2.5 | 26 | 20% | 1.9% | 39 |
| 10% DOTAP | 55 | 5 | 40 | 2.5 | 11 | 10% | 2.2% | 35 |

Figure 21B:
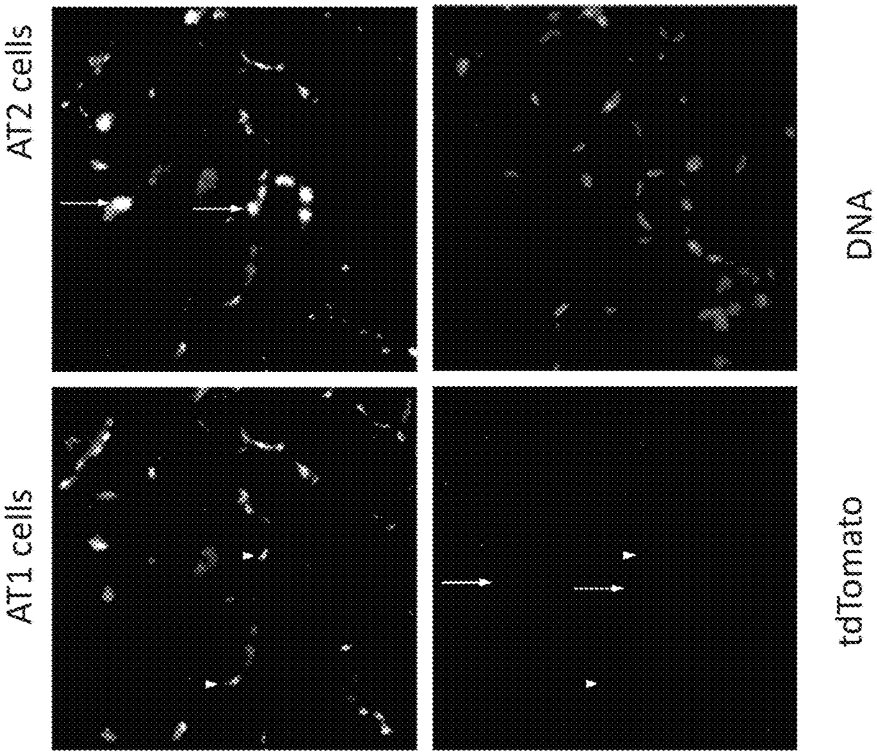
FIGS. 21A and 21B show transfection of the LNP formulations in alveolar epithelial cells. Shown are immunofluorescence staining of tdTomato expression, as induced in tomato fl/fl mice dosed with LNPs comprising Cre mRNA. AT1 and AT2 lung epithelial cell markers were also stained.
Figure 21A:
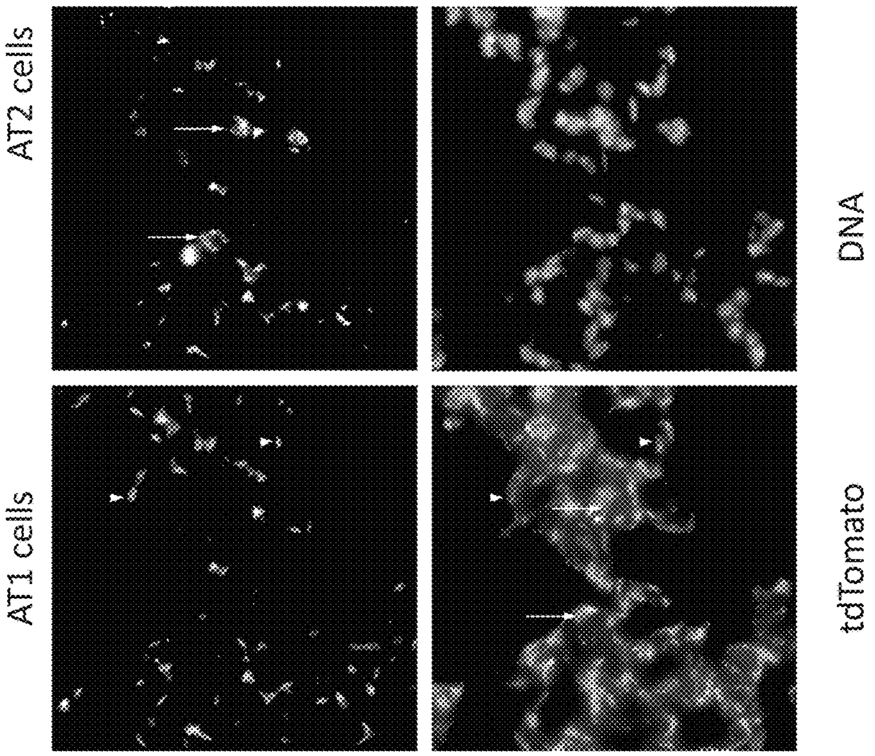

Example 17: Delivery of LNP-mRNAs to the Lung Transfects Alveolar Epithelial Cells To observe the cell types transfected by SS-OP DOTAP LNP per the formula of Table 6A, LNPs were formulated with Cre mRNA and administered to tomato fl/fl mice at 2.0 mg/kg (FIG. 21A). FIG. 21B shows a PBS negative control. Lungs were harvested 3 days later and processed via formalin fixation and paraffin embedding. 4 μm sections were stained with:

Anti-IGFBP2, a marker of AT1 alveolar epithelial lung cells, Anti-Prosurfactant Protein C (SPC) a marker of AT2 alveolar epithelial lung stem cells, Anti-tdTomato, and DAPI as a marker of DNA to identify cells. Cells positive for both SPC and tdTomato demonstrated that the LNP formulation successfully transfected lung AT2 alveolar epithelial stem cells. Cells positive for both IGFBP2 and tdTomato demonstrated that the LNP formulation successfully transfected lung AT1 alveolar epithelial cells. Absence of tdTomato staining in the control showed that the anti-tdTomato staining was specific.

Example 18: TERT mRNA Delivery in KO Mice with SS-OP DOTAP

Figure 22:
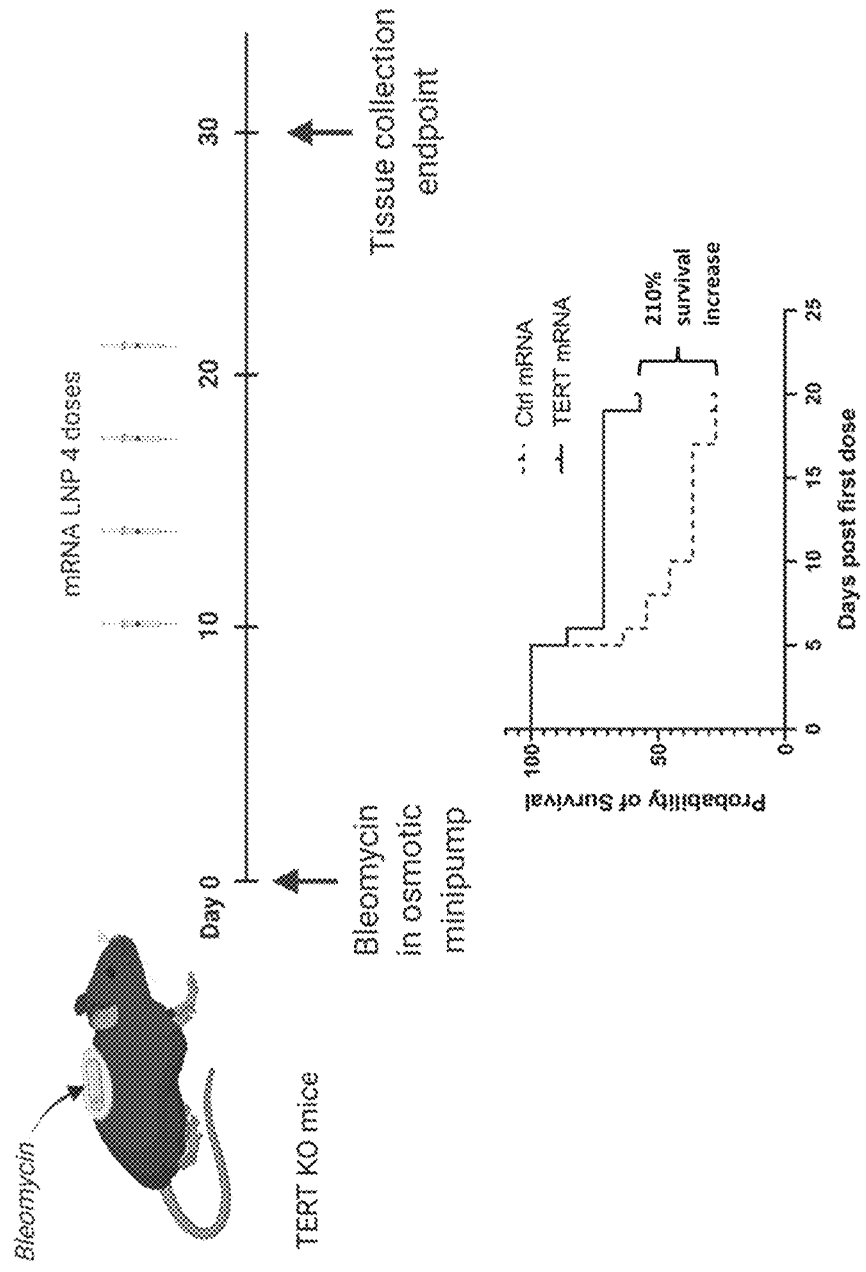
FIG. 22 shows SS-OP DOTAP delivery of a therapeutic mRNA as a disease treatment, using the SS-OP DOTAP LNPs of Table 6A, comprising TERT mRNA. The LNP TERT mRNA formulations were delivered to a lung fibrosis model mouse, induced by bleomycin at Day 0. Relative to the control mRNA, delivery of the TERT mRNA extended the survival rate of the mouse by 210% at the endpoint.

To determine SS-OP DOTAP delivery of therapeutic mRNA as a disease treatment, SS-OP DOTAP LNPs encapsulating TERT mRNA were administered to a lung fibrosis model mouse. The timeline of the mouse lung fibrosis model lung and treatment are shown in FIG. 22. Lung fibrosis was induced in third generation (G3) TERT knock-out (KO) mice, which have telomere lengths that are similar to those of humans. Bleomycin was administered continuously via subcutaneously implanted osmotic minipump. Total dose delivered was 100 U/kg. TERT mRNA encapsulated in the SS-OP DOTAP LNP formulation of Table 6A, was administered intravenously four times beginning on day 10, as shown. Relative to the control, which was firefly Luciferase mRNA, delivery of the TERT mRNA extended the survival rate of the mouse by 210% at the endpoint.

While preferred embodiments of the instant disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

The invention claimed is:

1. A method of delivering a polynucleotide to the lung of a subject, comprising administering to a lung tissue cell a pharmaceutical lipid nanoparticle (LNP) composition comprising RNA, the LNP comprising a total lipid amount including:
(a) a structural lipid at a molar percentage of between at or about 0% to 1% of the total lipid in the LNP;
(b) an insulator lipid at a molar percentage of between at or about 0.1% to 6% of the total lipid in the LNP;
(c) a cholesterol lipid at a molar percentage of between at or about 0% to 40% of the total lipid in the LNP;
(d) an ionizable lipid comprising SS-OP or an SS-OP analog, at a molar percentage of between at or about 30% to 60% of the total lipid in the LNP; and
(e) a permanently cationic lipid at a molar percentage of between at or about 20% to 80% of the total lipid in the LNP;
wherein the liposomal pKa of the LNP is between at or about 5.5 to 7.2; and
wherein the RNA is encapsulated in the LNP and encodes telomerase reverse transcriptase (TERT) mRNA having one or more modified nucleotides, wherein the LNP preferentially delivers to the lung compared to liver or transfects lung tissue cells compared to liver tissue cells, and wherein telomeres are extended within the lung tissue cells.

2. The method of claim 1, wherein the insulator lipid comprises a PEGylated lipid, the cationic lipid comprises DOTAP, and the molar percentage of structural lipid is 0%.

3. The method of claim 1, wherein the cationic lipid is one or more of 2-Dioleoyl-3-Trimethylammonium-Propane (DOTAP), Dimethyldioctadecylammonium bromide (DDAB), Imidazole Cholesterol Ester (ICE), 25-Hydroxycholesterol (25 OH Chol), 20α-hydroxycholesterol 5-cholestene-3α, 20α-diol (20a Chol), or combinations thereof.

4. The method of claim 1, wherein the cationic lipid comprises DOTAP at a molar percentage of between about 20% and about 35%, the ionizable lipid comprises SS-OP at a molar percentage of between about 30% and about 50%, the insulator lipid comprises an PEGylated lipid at a molar percentage of between about 0.1% and about 3%, the cholesterol is included at a molar percentage of between about 30% and about 40%, and the structural lipid is at a molar percentage of 0%.

5. The method of claim 1, wherein the LNP comprises: about 15% to about 40% cholesterol.

6. The method of claim 1, wherein the insulator lipid comprises a PEGylated lipid.

7. The method of claim 1, wherein the polynucleotide is a synthetic ribonucleic acid (RNA).

8. The method of claim 7, wherein the TERT mRNA comprises a nucleic acid sequence at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NOS: 38-40.

9. A method of treating a lung disease and/or lung fibrosis in a subject in need thereof, comprising administering an effective amount of: a composition comprising a lipid nanoparticle (LNP) wherein the LNP comprising a total lipid amount including:
(a) an insulator lipid at a molar percentage of between at or about 0.1% to 26% of the total lipid in the LNP;
(b) a cholesterol lipid at a molar percentage of between at or about 30% to 40% of the total lipid in the LNP;
(c) an ionizable lipid comprising SS-OP or an SS-OP analog, at a molar percentage of between at or about 30% to 50% of the total lipid in the LNP; and
(d) a permanently cationic lipid at a molar percentage of between at or about 15% to 25% of the total lipid in the LNP;
wherein the liposomal pKa of the LNP is between at or about 5.5 to 7.2;
wherein the composition is substantially free of structural lipids; and
wherein the RNA is encapsulated in the LNP and encodes telomerase reverse transcriptase (TERT) mRNA having one or more modified nucleotides, wherein the LNP preferentially delivers to the lung compared to liver or transfects lung tissue cells compared to liver tissue cells, and wherein telomeres are extended within the lung tissue cells.

10. The method of claim 9, wherein the TERT mRNA comprises a nucleic acid sequence at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NOS: 38-40.

11. The method of claim 9, wherein the TERT synthetic mRNA comprises an untranslated region (UTR).

12. The method of claim 9, wherein the TERT synthetic mRNA comprises a poly-adenosine (poly-A) nucleotide sequence 3' to the encoding region.

13. The method of claim 9, wherein the TERT synthetic mRNA is codon optimized.

14. The method of claim 9, wherein the lung disease is associated with lung fibrosis.

15. The method of claim 14, wherein the lung disease is selected from the group consisting of: pulmonary fibrosis, familial pulmonary fibrosis, idiopathic pulmonary fibrosis, pulmonary fibrosis associated with dyskeratosis congenita, an interstitial lung disease, pneumonia, interstitial pneumonia, emphysema, chronic obstructive pulmonary disease, cystic fibrosis, an infectious disease, a coronavirus disease, and lung cancer.

16. The method of claim 14, wherein the lung fibrosis is associated with a TERT mutation.

17. The method of claim 9, wherein the composition is administered to the subject via intravenous injection and/or via inhalation.

18. A composition, comprising a lipid nanoparticle (LNP) comprising a total lipid amount including:
(a) an insulator lipid at a molar percentage of between at or about 0.1% to 2% of the total lipid in the LNP;
(b) a cholesterol lipid at a molar percentage of between at or about 30% to 40% of the total lipid in the LNP;
(c) an ionizable lipid comprising SS-OP or an SS-OP analog, at a molar percentage of between at or about 30% to 60% of the total lipid in the LNP; and
(d) a permanently cationic lipid at a molar percentage of between at or about 15% to 25% of the total lipid in the LNP;
wherein the liposomal pKa of the LNP is between at or about 5.5 to 7.2;
wherein the composition is substantially free of structural lipids; and
wherein the RNA is encapsulated in the LNP and encodes telomerase reverse transcriptase (TERT) mRNA having one or more modified nucleotides.

19. The composition of claim 18, wherein the TERT RNA comprises a nucleic acid sequence at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NOS: 38-40.

20. A pharmaceutical composition comprising the composition of claim 19 and a pharmaceutically acceptable solvent or excipient.

21. The method of claim 1, wherein the LNP composition comprises a single type of ionizable lipid and a single type of permanently cationic lipid.

22. The method of claim 1, wherein the LNP composition comprises a single type of structural lipid, a single type of insulator lipid, a single type of cholesterol lipid, a single type of ionizable lipid, and a single type of permanently cationic lipid.

23. The method of claim 9, wherein the LNP composition comprises a single type of ionizable lipid and a single type of permanently cationic lipid.

24. The method of claim 9, wherein the LNP composition comprises a single type of insulator lipid, a single type of cholesterol lipid, a single type of ionizable lipid, and a single type of permanently cationic lipid.

25. The method of claim 18, wherein the LNP composition comprises a single type of ionizable lipid and a single type of permanently cationic lipid.

26. The method of claim 18, wherein the LNP composition comprises a a single type of insulator lipid, a single type of cholesterol lipid, a single type of ionizable lipid, and a single type of permanently cationic lipid.

27. The method of claim 1, wherein the cationic lipid comprises DOTAP at a molar percentage of between about 15% and about 20%, the ionizable lipid comprises SS-OP at a molar percentage of between about 40% and about 50%, the insulator lipid comprises an PEGylated lipid at a molar percentage of 2%, the cholesterol is included at a molar percentage of between about 35% and about 40%, and the structural lipid at a molar percentage of 0%.

28. The method of claim 1, wherein the composition is administered to the subject via intravenous injection.

29. The method of claim 9, wherein the composition is administered to the subject via intravenous injection.

30. The method of claim 1, wherein the RNA comprises a self-replicating RNA or a circular RNA.

31. The method of claim 9, wherein the RNA comprises a self-replicating RNA or a circular RNA.

32. The composition of claim 18, wherein the RNA comprises a self-replicating RNA or a circular RNA.

* * * * *